United States Patent [19]

Martel et al.

[11] Patent Number: 5,663,151

[45] Date of Patent: Sep. 2, 1997

[54] SULFATED α-GLYCOLIPID DERIVATIVES AS CELL ADHESION INHIBITORS

[75] Inventors: Alain Martel, Delson; Jacques Banville, St. Hubert, both of Canada; Alejandro A. Aruffo, Edmonds, Wash.

[73] Assignee: Bristol-Myers Squibb Company, Princeton, N.J.

[21] Appl. No.: 379,381

[22] Filed: Jan. 27, 1995

Related U.S. Application Data

[63] Continuation of Ser. No. 205,928, Mar. 4, 1994, abandoned.

[51] Int. Cl.⁶ .......................... A61K 31/70; C07H 15/00
[52] U.S. Cl. .......................... 514/25; 536/17.5; 536/17.6
[58] Field of Search .................. 536/17.6, 17.5; 514/25

[56] References Cited

U.S. PATENT DOCUMENTS

| | | | |
|---|---|---|---|
| 4,937,328 | 6/1990 | Schmidt et al. | 536/18.6 |
| 4,952,683 | 8/1990 | Tschannen et al. | 536/18.6 |
| 5,519,007 | 5/1996 | Della Valle et al. | 514/23 |

FOREIGN PATENT DOCUMENTS

| | | |
|---|---|---|
| WO92/01718 | 2/1992 | WIPO. |
| WO93/05803 | 4/1993 | WIPO. |
| WO93/10796 | 6/1993 | WIPO. |

OTHER PUBLICATIONS

Hsu–Lin, S., et al., *J. Biol. Chem.*, 259, 9121–9126 (1984).
Stenberg, P.E., *J. Cell Biol.*, 101, 880–886 (1985).
McEver, R.P., et al., *J. Clin. Invest.*, 84, 92–99 (1989).
Bonfanti, R., et al., *Blood*, 73, 1109–1112 (1989).
Hattori, R., et al., *J. Biol. Chem.*, 264, 7768–7771 (1989).
Hattori, R., et al., *J. Biol. Chem.*, 264, 9053–9060 (1989).
Patel, K.D., et al., *J. Cell. Biol.*, 112, 749–759 (1991).
Larsen, E., et al., *Cell*, 63, 467–474 (1990).
Erbe, V.E., et al., *J. Cell Biol.*, 119, 215–217 (1992).
Skinner, M.P., et al., *Biochem. Biophys. Res. Commun.*, 164, 1373–1379 (1989).
Aruffo, A., et al., *Cell*, 67, 35–44 (1991).
Y. Suzuki, et al., *Biochem. Biophys. Res. Commun.*, 190, 426–434 (1993).
M.S. Mulligan, et al., *Nature*, 364, 149–151 (1993).
Radin, N.S., *Handbook of Neurochemistry*, 3, 415–424 (1969).
Sweeley, C.C., *Pure and Appl. Chem.*, 61(7) 1307–1312 (1989).

*Primary Examiner*—Elli Peselev
*Attorney, Agent, or Firm*—Aldo A. Algieri

[57] ABSTRACT

There is provided novel sulfated α-glycolipid compounds of the formula

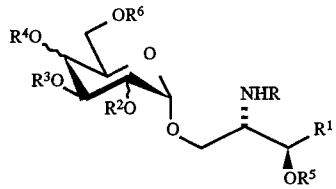

wherein

R is an acyl residue of a fatty acid;

$R^1$ is —$(CH=CH)_m$—$(CH_2)_n$—$CH_3$;

$R^2$, $R^3$, $R^4$ and $R^6$ are independently at least two —$SO_3H$;

$R^2$, $R^3$, $R^4$ $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof which are inhibitors of selectin-mediated cellular adhesion and are useful in the treatment or prevention of inflammatory diseases and other pathological conditions in mammals.

42 Claims, No Drawings

SULFATED α-GLYCOLIPID DERIVATIVES AS CELL ADHESION INHIBITORS

CROSS-REFERENCE TO RELATED APPLICATION(S)

This is a continuation of U.S. Ser. No. 08/205,928, filed Mar. 4, 1994, now abandoned.

FIELD OF THE INVENTION

The present invention provides a novel series of sulfated α-glycolipid compounds, pharmaceutically acceptable salts and pharmaceutical compositions thereof as inhibitors of selectin-mediated cellular adhesion which are useful in the treatment or prevention of inflammatory disease processes and other pathological conditions mediated by the binding of selectins involved in intercellular adhesion.

BACKGROUND Of THE INVENTION

P-selectin (CD62, GMP140, PADGEM) is a membrane glycoprotein of ~140 kDa expressed by activated platelets and vascular endothelial cells. In resting platelets and vascular endothelial cells P-selectin is sequestered in α granules [Hsu-Lin, S., et al., *J. Biol. Chem.*, 259, 9121–9126 (1984); and Stenberg, P. E., *J. Cell Biol.*, 101, 880–886 (1985)] and Weibel-Palade bodies [McEver, R. P., et al., *J. Clin. Invest.*, 84, 92–99 (1989); and Bonfanti, R., et al., *Blood*, 73, 1109–1112 (1989)], respectively. In response to inflammatory mediators such as thrombin [Hsu-Lin, S., et al., *J. Biol. Chem.*, 259, 9121–9126 (1984); and Stenberg, P. E., *J. Cell Biol.*, 101, 880–886 (1985)], histamine [Hattori, R., et al., *J. Biol. Chem.*, 264, 7768–7771 (1989)], complement components [Hattori, R., et al., *J. Biol . Chem.*, 264, 9053–9060 (1989)], or peroxides [Patel, K. D., et al., *J. Cell Biol.*, 112, 749–759 (1991)] and cytokines such as interleukin-1 and tumor necrosis factor, P-selectin is rapidly mobilized from these intracellular stores to the cell surface where it mediates the initial binding interactions of activated platelets with leukocytes and the vascular wall, and of leukocytes with activated vascular endothelial cells. P-selectin is a member of a family of adhesion molecules which includes E-selectin (ELAM-1), which is expressed by activated vascular endothelial cells, and L-selectin (Leu 8, LAM-1, LECAM), which is expressed by leukocytes. These proteins are type I membrane proteins and are composed of an amino terminal lectin domain followed by an epidermal growth factor (EGF) like domain, a variable number of complement receptor related repeats (CR), a hydrophobic membrane spanning region and a cytoplasmic domain. As indicated by high sequence homology, these proteins are not only structurally but also functionally related, modulating the trafficking of peripheral blood leukocyte by permitting adhesive interactions between leukocytes and endothelial cells. These binding interactions are predominately mediated by contacts between the lectin domain of the selectin and various carbohydrate ligands.

Although it is now widely accepted that a lectin domain/carbohydrate interaction is primarily responsible for mediating P-selectin/myeloid cell binding, the exact molecular nature of the P-selectin ligand is not known. Binding of P-selectin to myeloid cells is $Ca^{2+}$ dependent as well as neuraminidase and protease sensitive. The binding of P-selectin to myeloid cell lines can be inhibited by growing the cells in the presence of sodium selenate and inhibitor of sulfation. P-selectin has been shown to bind to the carbohydrate Le$^x$ (CD15) [Larsen, E., et al., *Cell*, 63, 467–474 (1990)] and its sialylated form, sialyl-Le$^x$ (sLe$^x$) [Erbe, V. E., et al., *J. Cell Biol.*, 119, 215–217 (1992)], and there is evidence that these carbohydrates and/or others like them are presented to P-selectin by a discrete number of cell surface proteins including L-selectin. Various anionic polymers, including heparin, fucoidan, and dextran sulfate have also been shown to inhibit P-selectin mediated adhesion [Skinner, M. P., et al., *Biochem. Biophys. Res. Commun.*, 164, 1373–1379 (1989); and *J. Biol. Chem.*, 266, 5371–5374 (1991)]. In addition, P-selectin has been shown to bind 3-sulfated galactosyl ceramides (sulfatides) [Aruffo, A., et al., *Cell*, 67, 35–44 (1991)]. Although the physiological relevance of this interaction remains to be elucidated, it is known that myeloid cells can excrete large quantities of sulfatides on activation. This suggests that sulfatides might participate in leukocyte extravasation at sites of inflammation by displacing the adhesion-mediating leukocyte surface ligand(s), thereby permitting the efficient exit of leukocytes from the blood stream at sites of inflammation.

A number of publications have appeared which describe new agents as inhibitors of cellular adhesion. Some of these publications, but not limited to, include the use of peptides and carbohydrate structures in International patent application WO 92/01718 published Feb. 6, 1992; the use of substituted lactose and lactosamine derivatives in International patent application WO 93/10796 published Jun. 10, 1993; the use of glycoconjugates in International patent application WO 93/05803 published Apr. 1, 1993; the use of sulfated glycolipid derivatives by Y. Suzuki, et al., *Biochem. Biophys. Res. Commun.*, 190, 426–434 (1993) and the use of oligosaccharides by M. S. Mulligan, et al., *Nature*, 364, 149–151 (1993).

However, there are many situations in which the recruitment of leukocytes by adhesion to the endothelial cells is abnormal or in excess, and the end result is tissue damage instead of repair. Thus, there is a need to develop specific and potent compounds which can inhibit the initial cellular adhesion process. It is the object of the present invention to provide new sulfated glycolipids which are inhibitors of cell adhesion and, therefore, useful in man for the treatment and/or prevention of acute or chronic inflammatory diseases such as rheumatoid arthritis, asthma, allergy conditions, psoriasis, septic shock and other indications such as reperfusion injury, adult respiratory distress syndrome, ischemia, ulcerative colitis, vasculitides, atherosclerosis and inflammatory bowel disease, multiple sclerosis and tumor metastases.

SUMMARY OF THE INVENTION

The present invention provides novel sulfated α-glycolipids having the formula

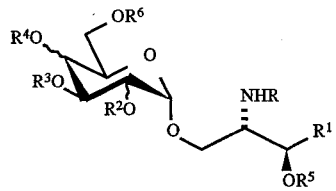

wherein R, $R^1$, $R^2$, $R^3$, $R^4$, $R^5$ and $R^6$ are as defined below, or a non-toxic pharmaceutically acceptable salt, solvate or hydrate thereof which are inhibitors of selectin-mediated cellular adhesion. The present invention also provides pharmaceutical compositions comprising said sulfated α-glycolipids and to the method of treatment or prevention of conditions characterized by selectin-mediated cellular adhesion such as inflammatory diseases and other pathological conditions in mammals.

DESCRIPTION OF THE INVENTION

The present invention provides novel sulfated α-glycolipid compounds which are inhibitors of P-selectin mediated cellular adhesion and which have the formula

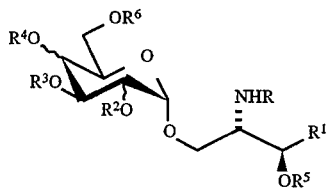

I wherein

R is an acyl residue of a fatty acid;

$R^1$ is —(CH=CH)$_m$—(CH$_2$)$_n$—CH$_3$;

$R^2$, $R^3$, $R^4$ and $R^6$ are independently at least two —SO$_3$H;

$R^2$, $R^3$, $R^4$ $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof.

The present invention also provides a method for the treatment or prevention of inflammatory diseases and other pathological conditions characterized by selectin-mediated cellular adhesion, which comprises administering a therapeutically effective amount of a compound of formula I or a non-toxic pharmaceutically acceptable salt, solvate or hydrate thereof.

The terms "$C_{1-4}$ alkyl", and "$C_{1-4}$ alkoxy" as used herein and in the claims (unless the context indicates otherwise) mean straight or branched chain alkyl or alkoxy groups such as methyl, ethyl, propyl, isopropyl, butyl, isobutyl, t-butyl. Preferably, these groups contain from 1 to 2 carbon atoms. The term "arylalkyl" as used herein and in the claims means a phenyl group attached via an alkyl moiety containing from 1 to 4 carbon atoms such as methyl, ethyl, propyl, butyl and the like, and most preferably means benzyl or phenylethyl. Unless otherwise specified, the term "halogen" as used herein and in the claims is intended to include bromine, chlorine, iodine and fluorine while the term "halide" is intended to include bromide, chloride and iodide anion. Preferably, halogen is chlorine or fluorine. The term "alkanoyl" as used herein and in the claims means acetyl, propionyl and the like.

The term "independently at least two —SO$_3$H" as used herein and in the claims means than a minimum of any two substituents selected from $R^2$, $R^3$, $R^4$ and $R^6$ must be —SO$_3$H as well as any three substituents and including all four substituents to provide a disulfated, trisulfated or tetrasulfated glycolipid. The wavy bond "⌇" in the structural formula to which $R^2O$ and $R^4O$ is attached as used herein and in the claims means that the bond may be either in the axial or equatorial configuration as occurs in the monosaccharides selected from galactose, glucose and mannose.

The term "non-toxic pharmaceutically acceptable salt" as used herein and in the claims is intended to include non-toxic base addition salts with inorganic and organic bases. Suitable inorganic bases such as alkali and alkaline earth metal bases include metallic cations such as sodium, potassium, magnesium, calcium and the like. Suitable organic bases include amines such as ammonium, trialkyl amines, pyridine, ethanolamine, N-methylglucamine, N-methylmorpholine, lysine, arginine and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

The compounds of the present invention contain a monosaccharide selected from galactose, glucose and mannose. The natural occurring sulfatides from brain tissue are part of a class of compounds known as sulfated cerebrosides [N. S. Radin *Handbook of Neurochemistry*, Vol. 3 415–424 (1969)]. The commercially available sulfatides are a mixture of compounds in which the hexose moiety is mainly galactose and the configuration of the hexose in the natural sulfatides is in the β-anomeric form. [C. C. Sweeley, *Pure and Appl. Chem.*, 61 (7) 1307–1312 (1989)]. In contrast, the compounds of the present invention are in the α-anomeric form of the carbohydrate portion as indicated in the chemical structure by an axial bond in the 1-position.

In the method of the present invention, the term "therapeutically effective amount" means the total amount of each active component of the method that is sufficient to show a meaningful patient benefit, i.e., healing of chronic conditions characterized by selectin-mediated cellular adhesion or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with selectin-mediated cellular adhesion.

The term "acyl residue of a fatty acid" as used herein and in the claims means the acyl residue of a naturally occurring saturated or unsaturated fatty acid or a fatty acid derived therefrom. Suitable saturated fatty acids are those described herein and other known fatty acids such as butyric, isovaleric, caproic, caprylic, capric, lauric, myristic, palmitic, stearic, arachidic, behenic, lignoceric, cerotic and the like. Suitable unsaturated fatty acids include the cis and trans isomers of fatty acids such as $\Delta^9$-decylenic, stillingic, $\Delta^9$-dodecylenic, palmitoleic, oleic, ricinoleic, petroselinic, vaccenic, linoleic, linolenic, eleostearic, punicic, licanic, parinaric, gadoleic, arachidonic, 5-eicosenic, 5-docosenic, cetoleic, erucic, 5,13-docosadienic, nervonic and the like.

Hydroxy-protecting groups which can be employed in the present invention to block or protect the hydroxyl group are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Hydroxy-protecting (blocking) groups which are advantageously used are those which are common in carbohydrate chemistry especially for primary alcohols, secondary alcohols and vicinal cis and trans diols.

Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$–$C_6$) alkylsilyl (e.g., trimethylsilyl, triethylsilyl, triisopropylsilyl, isopropyldimethylsilyl, t-butydimethylsilyl, methyldiisopropylsilyl or methyldi-t-butylsilyl), t-butyl-diphenylsilyl, triarylsilyl (e.g. triphenylsilyl, tri-p-xylylsilyl) or trialkylsilyl (e.g. tribenzylsilyl). Examples of these and other suitable hydroxy-protecting groups and methods for their formation and removal are known in the art, e.g., see *Protective Groups in Organic Synthesis*, second ed., T. W. Greene and P. G. M. Wuts, John Wiley & Sons, New York, 1991, Chapter 2 and references therein.

The compounds of Formula I may be prepared by various procedures such as those illustrated herein in the examples, in the reaction schemes and variations thereof which would be evident to those skilled in the art. The various sulfate substituted glycolipid compounds of Formula I wherein the carbohydrate moiety is galactose, glucose and mannose are advantageously prepared from the intermediates of Formula Va, Vb or Vc as generally illustrated in Reaction Schemes 3, 4, 5, 6 and 7.

The preparation of a generic azido diol lipid of Formula II (occasionally referred to as azidosphingosine) wherein $R^1$ is as previously defined is illustrated in the process shown in Reaction Scheme 1. Thus, 2,4-O-benzylidene-D-threose is advantageously reacted with the desired phosphonium salt in a Wittig reaction by the general procedures described by P. Zimmerman, et al., *Liebigs Ann. Chem.*, 663–667 (1988) to produce the desired trans olefin wherein n=5–14. The olefin moiety may be retained in the process to provide compounds of Formula I wherein m=1 in the definition of $R^1$ or, if desired, the olefin may be reduced by conventional hydrogenation procedures to eventually provide compounds of Formula I wherein m=0 in the definition of $R^1$. The hydroxy function of the intermediate is treated with triflic anhydride and sodium azide to produce the cyclic azido intermediate with inversion of configuration followed by acid treatment to remove the benzylidene blocking group to produce the desired azido diol intermediate of Formula II wherein $R^1$ is —(CH=CH)$_m$—(CH$_2$)$_n$—CH$_3$. It is advantageous in the present process to block (protect) the secondary alcohol or allylic alcohol as the case may be in the compound of Formula II by first readily blocking the primary alcohol by conventional blocking (protecting) groups with an organosilyl group such as t-butyldimethylsilyl followed by the reaction with the desired $R^5$ substituent, as previously defined and wherein X is a conventional leaving group well-known in the art such as chloro, bromo, iodo, fluorosulfonyl and the like. After the displacement is completed, the silyl blocking group may readily be removed such as with tetrabutylammonium fluoride to give the desired compound of Formula III which is now suitable for use in the coupling reaction with a carbohydrate moiety, as illustrated in Reaction Scheme 2.

Reaction Scheme 1

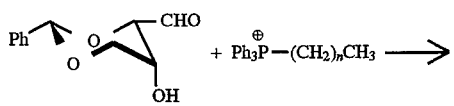

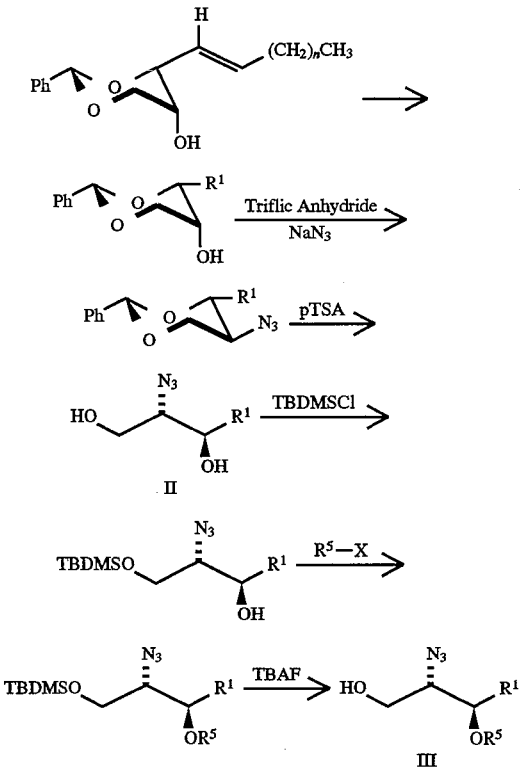

There are various processes which are useful for the preparation of compounds of Formula Va, Vb and Vc having the galactose, glucose and mannose, respectively with the α-anomeric configuration in the 1-position and these are exemplified in the examples. However, the preferred process for the preparation of the α-anomeric glycolipids of the present invention are illustrated in Reaction Scheme 2.

Reaction Scheme 2 a) Galactose/Glucose

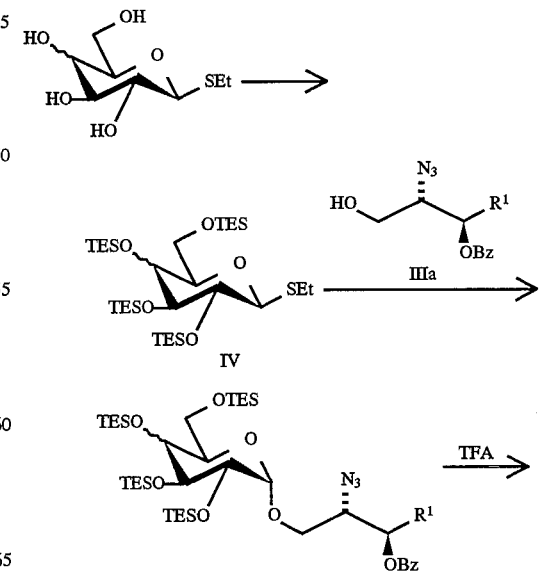

-continued
Reaction Scheme 2

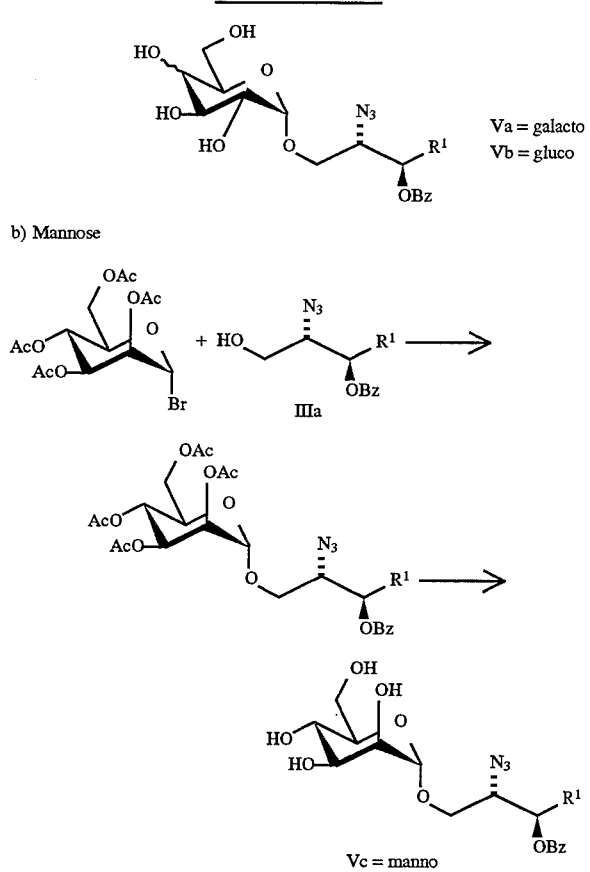

b) Mannose

The preparation of either the α-galacto or α-gluco intermediate of Formula Va or Vb, respectively is advantageously carried out by the coupling of the galactopyranoside or glucopyranoside of Formula IV with the azido alcohol of Formula IIIa and removal of the silyl blocking groups with an acid such as trifluoroacetic acid and the like as shown in Reaction Scheme 2 Part (a). In a preferred embodiment, the azido alcohol of Formula III wherein $R^5$ is benzoyl is illustrated in Reaction Scheme 2 and in subsequent Reaction Schemes 3, 4, 5, 6 and 7. The use of $R^5$ being benzoyl is for illustration purposes only and is not intended to be limiting. The fully protected (blocked) pyranoside of Formula IV is readily prepared from the corresponding 1-ethylthio-β-galacto- or β-gluco-pyranoside with chlorotriethylsilane in an inert organic solvent in the presence of a mild organic base.

The preparation of the α-manno intermediate of Formula Vc is readily carried out by the reaction of an azido alcohol of Formula IIIa and tetra-O-acetyl-α-D-mannopyranosyl bromide by well-known coupling procedures. The resulting intermediate is hydrolyzed under controlled conditions to remove the acetyl blocking groups to produce the desired α-manno intermediate of Formula Vc as shown in Reaction Scheme 2 Part (b).

The process for the preparation of sulfated α-glycolipids of Formula I are conveniently illustrated and summarized in Reaction Schemes 3, 4, 5, 6 and 7. When it is desired to prepare a disulfated carbohydrate glycolipid of Formula I, the possible combinations of the instant invention are set forth in Reaction Schemes 3, 4 and 5. It should be appreciated by those skilled in the art that selective blocking and deblocking of carbohydrates which are used to prepare the various positional sulfated isomers as well-known in the art such as those illustrated herein and in *Protective Groups in Organic Synthesis*, second ed., T. W. Greene and P. G. M. Wuts, John Wiley & Sons, New York, 1991, Chapter 2 and references therein. It should further be appreciated by those skilled in the art that the specific blocking group to be used will vary with the axial or equatorial position of the hydroxyl groups in the preferred carbohydrate moiety of the instant invention. Thus, Reaction Scheme 3 exemplifies the preparation of the 2,4-disulfate, 2,3-disulfate and 4,6-disulfate glycolipids of galacto, gluco and manno pyranosides of Formula I, respectively. The sequence in Reaction Scheme 4 exemplifies the preparation of 3,4-disulfate, 2,6-disulfate and 3,6-disulfate glycolipids of galacto pyranosides of Formula I and Reaction Scheme 5 exemplifies the preparation of 3,4-disulfate, 3,6-disulfate and 2,6-disulfate glycolipids of gluco and manno pyranosides of Formula I, respectively. Moreover, the preparation of the trisulfated glycolipids of Formula I are illustrated in Reaction Scheme 6 for the preparation of 3,4,6-trisulfate and 2,4,6-trisulfate glycolipids of galacto, gluco and manno pyranosides of Formula I and Reaction Scheme 7 exemplifies the preparation of 2,3,4-trisulfate and 2,3,6-trisulfate glycolipids of galacto, gluco and manno pyranosides of Formula I. The fully tetrasulfated glycolipids of Formula I are prepared as described in the examples herein.

In the process for the preparation of sulfated α-glycolipids of Formula I several known procedures are contemplated which generally follow the sequence of reaction steps as illustrated in Reaction Schemes 3, 4, 5, 6 and 7. Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction scheme by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

As used herein and in the reaction schemes the term "reduction" is intended to include well-known reduction procedures for the azido group such as hydrogenolysis with hydrogen and palladium; hydrogen transfer reactions with cyclohexane/formic acid/palladium, and preferably with hydrogen sulfide in aqueous pyridine.

As used herein and in the reaction schemes the term "acylation" is intended to include conventional and well-known acylation procedures for the preparation of amides such as the use of leaving groups and activating groups on the acyl portion of the fatty acid. For example, the use of acid chlorides and carbodiimide as activating groups in an organic solvent such as tetrahydrofuran, dichloromethane or mixture of aqueous-organic solvents in the presence of a base such as triethylamine, pyridine, dimethylaminopyridine and 50% sodium acetate.

As used herein and in the reaction schemes the term "sulfation" is intended to include conventional sulfation procedures with sulfur trioxide and usually as a complex with trimethylamine or pyridine in a solvent such as dimethylformamide, pyridine and the like. Advantageously, an excess of sulfur trioxide is utilized to sulfate the desired hydroxy groups while the hydroxy groups to be retained are blocked (protected).

As used herein and in the reaction schemes the terms "blocking" and "protecting" are intended to include conventional and well-known protecting groups in the art such as those illustrated herein and in *Protective Groups in Organic Synthesis*, second ed., T. W. Greene and P. G. M. Wuts, John Wiley and Sons, New York, 1991, Chapter 2 and references therein. For example, the use of acetals and ketals with an acid catalyst; the use of trisubstituted organosilyl reagents such as tert-butyldimethylsilyl chloride and triethylsilyl chloride; methoxymethyl bromide; benzyl bromide; benzoyl chloride and the like. The reaction may be carried out in tetrahydrofuran, dichloromethane, dimethyl formamide and the like in the presence of a base such as triethylamine, dimethylaminopyridine, pyridine, sodium hydride and the like, and optionally with imidazole as a catalyst.

As used herein and in the reaction schemes, the term "hydrolysis" is intended to include conventional hydrolysis procedures well-known to those skilled in the art. For example, the hydrolysis of benzylidene, isopropylidene, p-methoxybenzyl (PMB), methoxymethyl (MOM) and the like may be carried out under acidic conditions such as 90% trifluoroacetic acid, 3N hydrochloric acid, p-toluene sulfonic acid and the like in solvents such as dichloromethane and tetrahydrofuran. Also, p-methoxybenzyl may be removed with the use of dichlorodihydroxyquinone. Furthermore, organosilyl blocking groups such as tert-butyldimethylsilyl and triethylsilyl may advantageously be removed by the use of tetrabutylammonium fluoride (TBAF) in tetrahydrofuran and acetic acid. Still further, benzoate and acetate blocking groups may also be removed by the use of sodium or potassium alkoxides.

The compounds of Formula Ia to Ii wherein R, $R^1$, $R^2$, $R^3$, $R^4$, $R^5$ and $R^6$ are as previously defined may be prepared from the α-pyranosides of Formula Va, Vb, or Vc following the sequence of reactions illustrated in Reaction Scheme 3. It should be appreciated by those skilled in the art that the choice of reaction route will depend on the desired compounds of Formula I to be prepared and the appropriate selection of the corresponding starting material. To elaborate on the processes of Reaction Scheme 3, the α-galacto compound of Formula Va is treated with benzaldehyde dimethylacetal and an acid catalyst to block and protect the 4 and 6-position hydroxy moieties to give the corresponding α-galacto pyranoside of Formula VI.

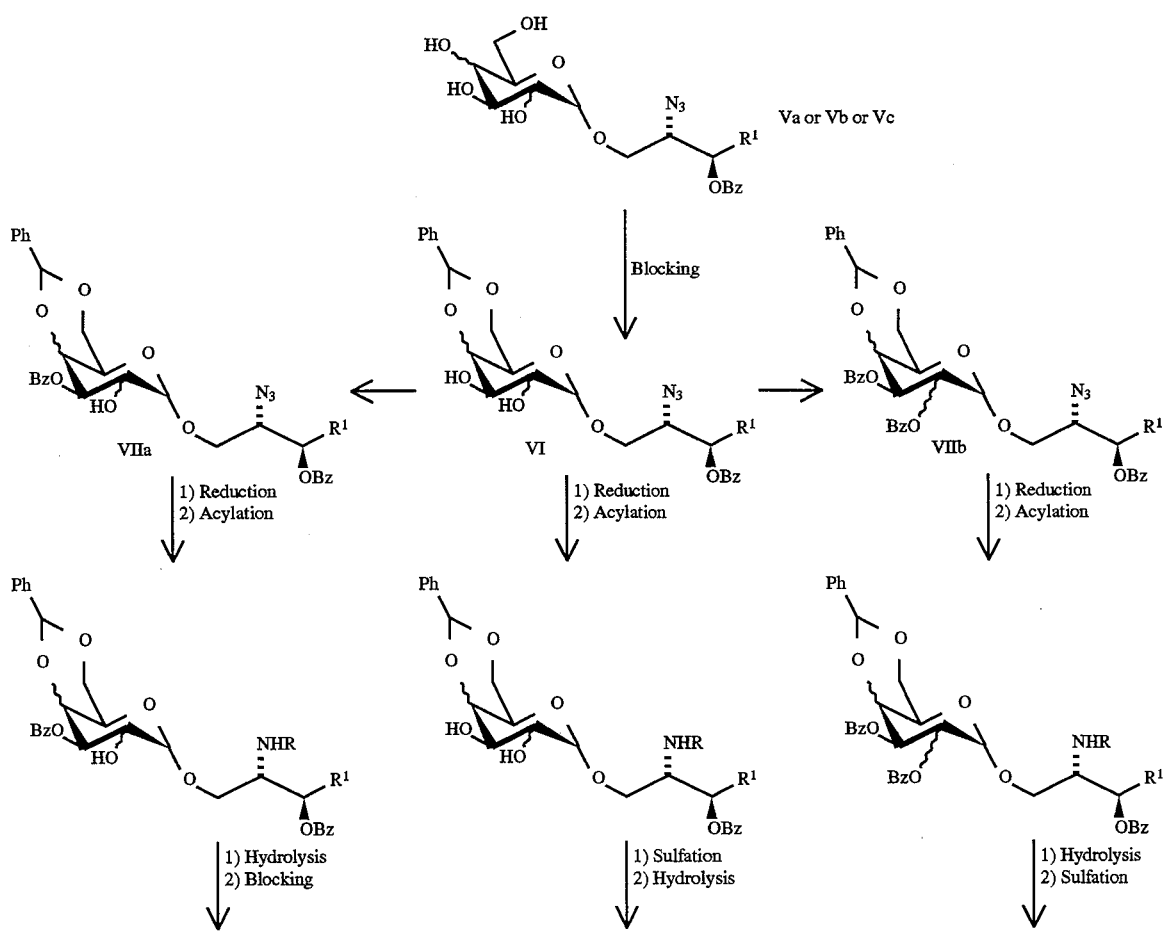

Reaction Scheme 3

-continued
Reaction Scheme 3

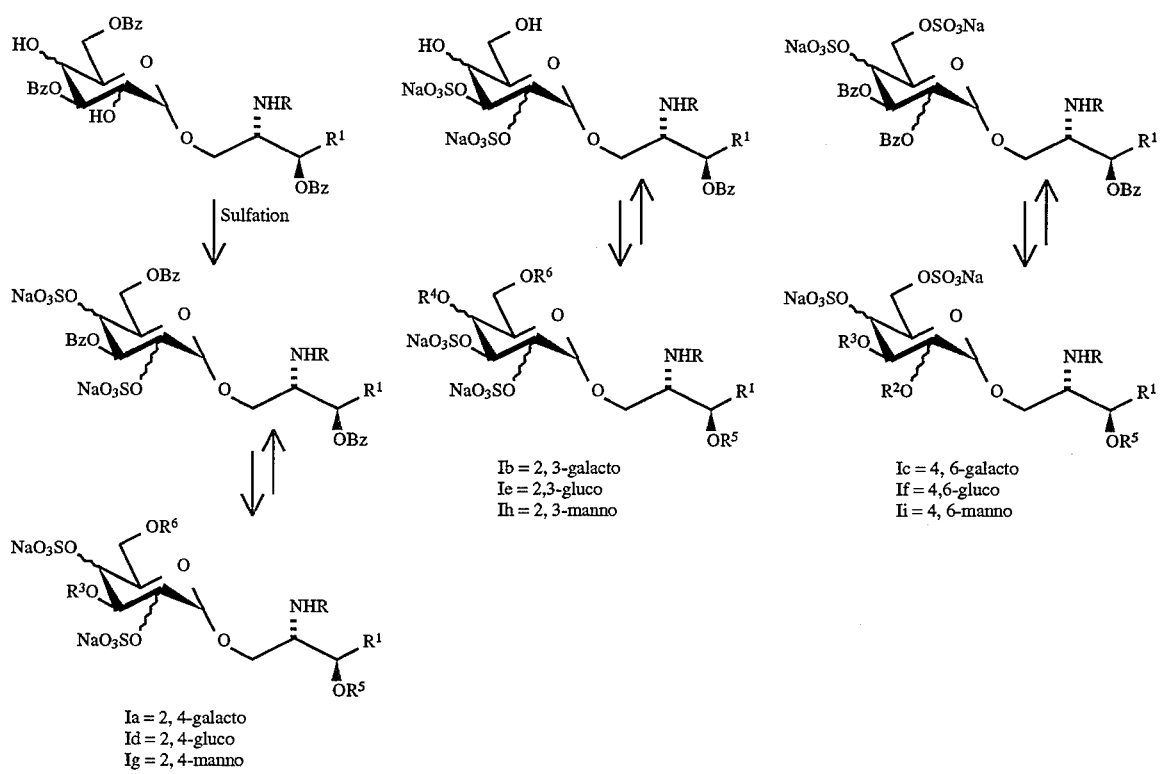

Ia = 2, 4-galacto
Id = 2, 4-gluco
Ig = 2, 4-manno

Ib = 2, 3-galacto
Ie = 2,3-gluco
Ih = 2, 3-manno

Ic = 4, 6-galacto
If = 4,6-gluco
Ii = 4, 6-manno

When it is desired to prepare the 2,3-disulfate galacto compound of Formula Ib, the intermediate of Formula VI is subjected to reduction of the azido group and then the acylation of the resulting amino group with the desired activated acyl residue of a fatty acid having the definitions of R as defined herein. The resulting pyranoside is then sulfated in the 2 and 3-position of the carbohydrate moiety by treatment with an excess of sulfur trioxide trimethylamine complex and then basified with an inorganic base such as sodium bicarbonate, potassium bicarbonate, calcium carbonate and the like. The resulting sodium salt of the sulfated and protected intermediate is subjected to conventional hydrolysis to remove the benzylidene protecting group and, if desired, the benzoyl protecting group. It should be appreciated by those skilled in the art that the removal and insertion of the desired $R^4$, $R^5$ and $R^6$ moieties in the compound of Formula Ib can be interchanged, or left untouched depending on the particular substituent which is desired in the preparation of compounds having the sulfate moiety in the 2 and 3-position of the α-galacto compounds of Formula Ib. It should be understood that by following the general sequence steps outlined above the compounds of Formula Ie and Ih can be prepared from the corresponding α-gluco pyranoside Vb and α-manno pyranoside Vc, respectively.

To prepare the 2,4-disulfated compounds of Formula Ia, Id and Ig, the corresponding pyranoside of Formula VI is selectively blocked with a protecting group and preferably with a benzoyl moiety by known methods and methods described by K. Jansson et al in *J. Org. Chem.*, 53, 5629–5647 (1988) to give compounds of Formula VIIa. The azido group of compound VIIa is reduced and then acylated with the desired fatty acid residue as described herein. The benzylidene moiety of the resulting intermediate is hydrolyzed and the resulting primary alcohol is blocked by esterification with a benzoyl group. The 3,6-blocked pyranoside is then subjected to sulfation of the remaining 2,4-dihydroxy groups and then, if desired, hydrolyzed to remove one or more of the blocking groups to produce the corresponding 2,4-disulfated galacto, gluco and manno compounds of Formula Ia, Id and Ig, respectively.

To prepare the 4,6-disulfated compounds of Formula Ic, If and Ii, the corresponding pyranoside of Formula VI is blocked with a protecting group and preferably with a benzoyl moiety to produce a compound of Formula VIIb. The azido group of the protected pyranoside of Formula VIIb is reduced and the resulting amino group acylated with the desired activated acyl residue of a fatty acid. The resulting pyranoside is subjected to conventional hydrolysis to remove the benzylidene protecting group and the 4 and 6-position hydroxy groups are then sulfated as described herein to produce the desired inhibitor of selectin-mediated cell adhesion. The resulting sodium salt of the sulfated and blocked α-glycolipid may, if desired, be hydrolyzed to selectively remove the $R^2$, $R^3$ and $R^5$ blocking groups and then replaced with other substituents by methods known in the art in the preparation of compounds having the sulfate moiety in the 4 and 6-position of the α-galacto compounds of Formula Ic. Similarly, by following the general sequence steps outlined above, the compounds of Formula If and Ii can be prepared from the corresponding α-gluco pyranoside Vb and α-manno pyranoside Vc, respectively.

To elaborate on the process of Reaction Scheme 4, the α-galacto compound of Formula Va is treated with 2,2-dimethoxypropane and an acid catalyst to protect and block the 3 and 4-position hydroxy moieties to give the corresponding α-galacto pyranoside of Formula VIII.

Reaction Scheme 4

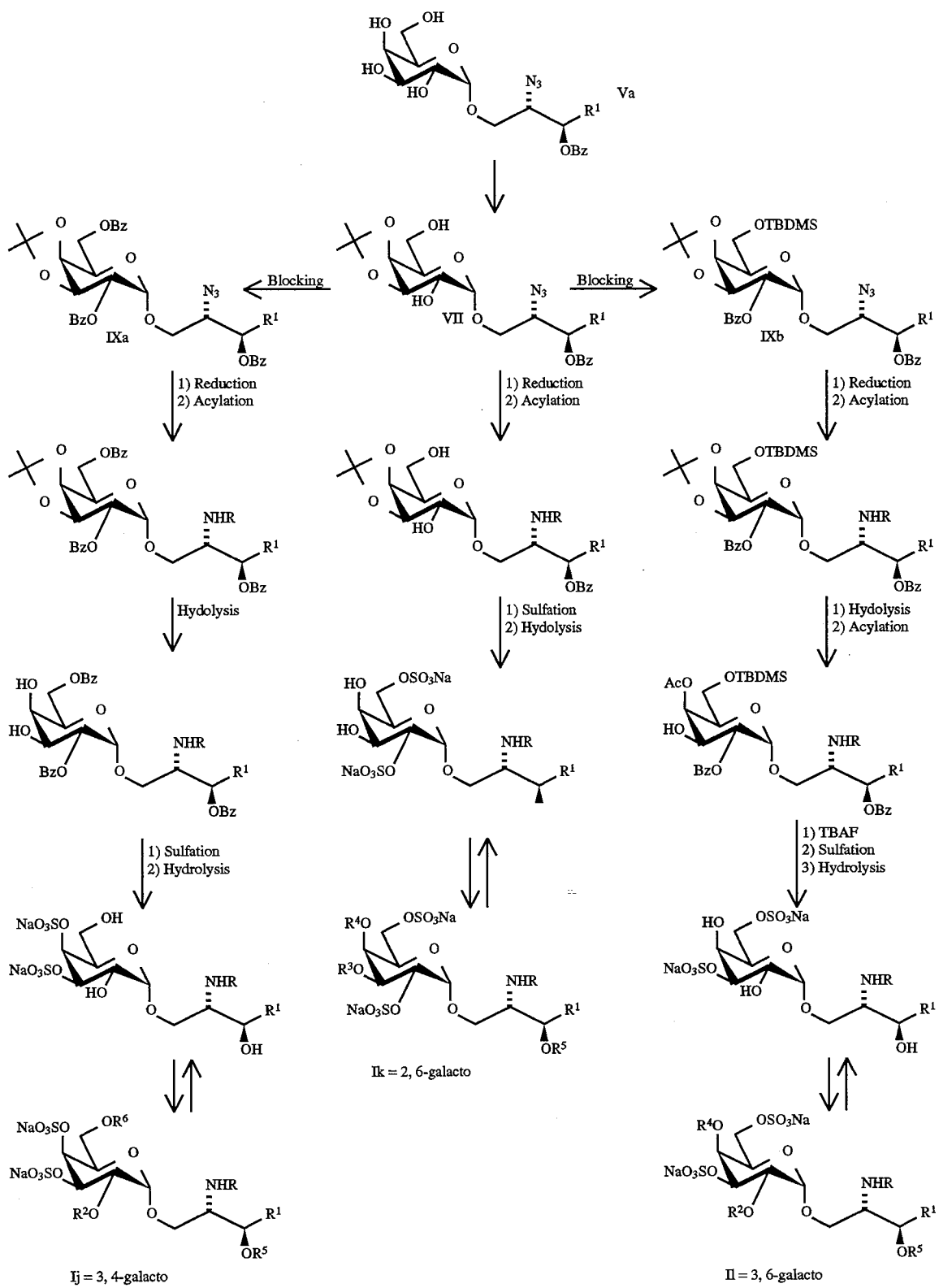

When it is desired to prepare the 2,6-disulfate galacto compound of Formula Ik, the intermediate of Formula VIII is subjected to reduction of the azido group and then acylation to incorporate the desired acyl residue of a fatty acid wherein R is as defined above. The α-glycolipid is sulfated in the 2 and 6-position of the carbohydrate moiety by treatment with excess sulfur trioxide pyridine complex and the resulting salt is subjected to conventional hydrolysis to remove the isopropylidene protecting group. It should be appreciated by those skilled in the art that the desired $R^3$, $R^4$ and $R^5$ substituents may then be inserted in the compounds having the sulfate moiety in the 2 and 6-position to produce the α-galacto compounds of Formula Ik.

To prepare the 3,4-disulfate galacto compounds of Formula Ij, the intermediate of Formula VIII is treated with a blocking group and preferably with a benzoyl moiety by known methods to give compounds of Formula IXa. The azido group is reduced and then acylated as previously described and the resulting pyranoside is subjected to selective hydrolysis to remove the isopropylidene group. The resulting unblocked 3 and 4-position hydroxy groups are sulfated and the remaining blocked hydroxy groups may, if desired, be removed or exchanged for other $R^2$, $R^5$ and $R^6$ substituents which is desired in the compounds having a sulfate moiety in the 3 and 4-position to produce the α-galacto compounds of Formula Ij.

To prepare the 3,6-disulfated galacto compounds of Formula Il, the intermediate of Formula VIII is selectively treated with two different blocking groups. It is advantageous to first block the primary alcohol group in the 6-position with a triorganosilyl group such as tri ($C_1$–$C_6$) alkylsilyl and triarylsilyl and, preferably, with a t-butyldimethylsilyl group. The secondary hydroxy group may then be advantageously blocked with other conventional groups such as a benzoyl group to produce the compound of Formula IXb. The azido group is reduced and then acylated with the desired acyl residue of a fatty acid and the resulting fully protected glycolipid is selectively hydrolyzed to remove the isopropylidene protecting group. The 4-position hydroxy group is selectively blocked by acetylation and the 6-position silyl protecting group is then removed by standard procedures such as with tetrabutylammonium fluoride. The available 3,6-dihydroxy moieties are now advantageously sulfated by the general procedures described herein and the resulting 3,6-disulfated galacto compound may, if desired, be hydrolyzed to produce a compound wherein $R^2$, $R^4$ and $R^5$ are hydrogen or $R^2$, $R^4$ and $R^5$ may be acylated to produce the 3,6-disulfated galacto compounds of Formula II.

Alternatively, the preparation of gluco and manno compounds of 3,4-disulfate, 3,6-disulfate and 2,6-disulfate of Formula I may be carried out from the corresponding α-gluco pyranoside of Formula Vb or α-manno pyranoside of Formula Vc following the reaction sequences outlined in Reaction Scheme 5. To elaborate on the processes of Reaction Scheme 5, the α-gluco or the α-manno compound of Formula Vb or Vc, respectively is treated with a blocking group and advantageously with benzaldehyde dimethylacetal to block the 4 and 6-position hydroxy groups and give the corresponding pyranoside intermediate of Formula X. The partially blocked intermediate of Formula X is then selectively blocked with a protecting group and preferably with a benzoyl moiety by methods similar to the procedure described by K. Jansson et al in *J. Org. Chem.*, 53, 5629–5647 (1988) to give compounds of Formula XIa and XIb.

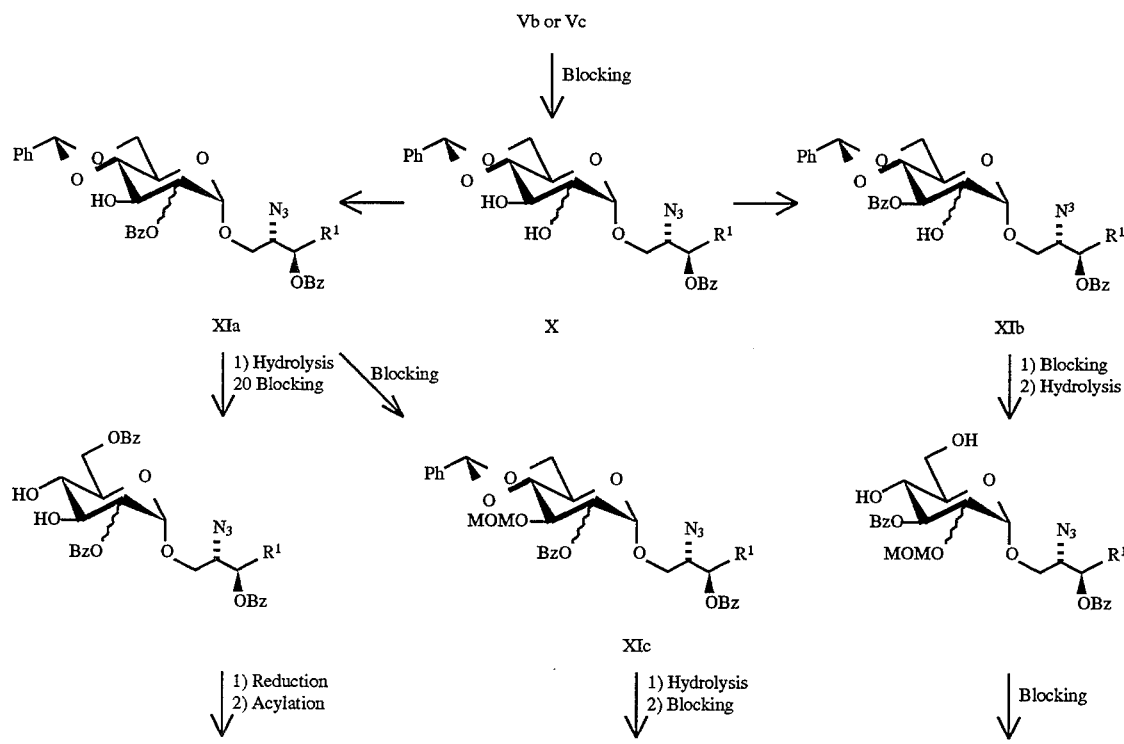

Reaction Scheme 5

-continued
Reaction Scheme 5

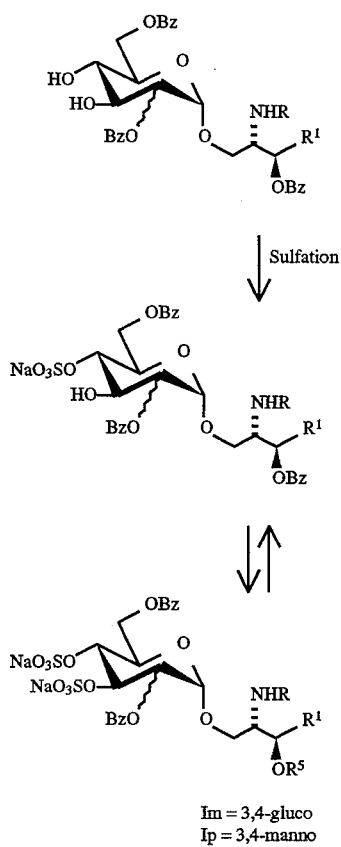

Im = 3,4-gluco
Ip = 3,4-manno

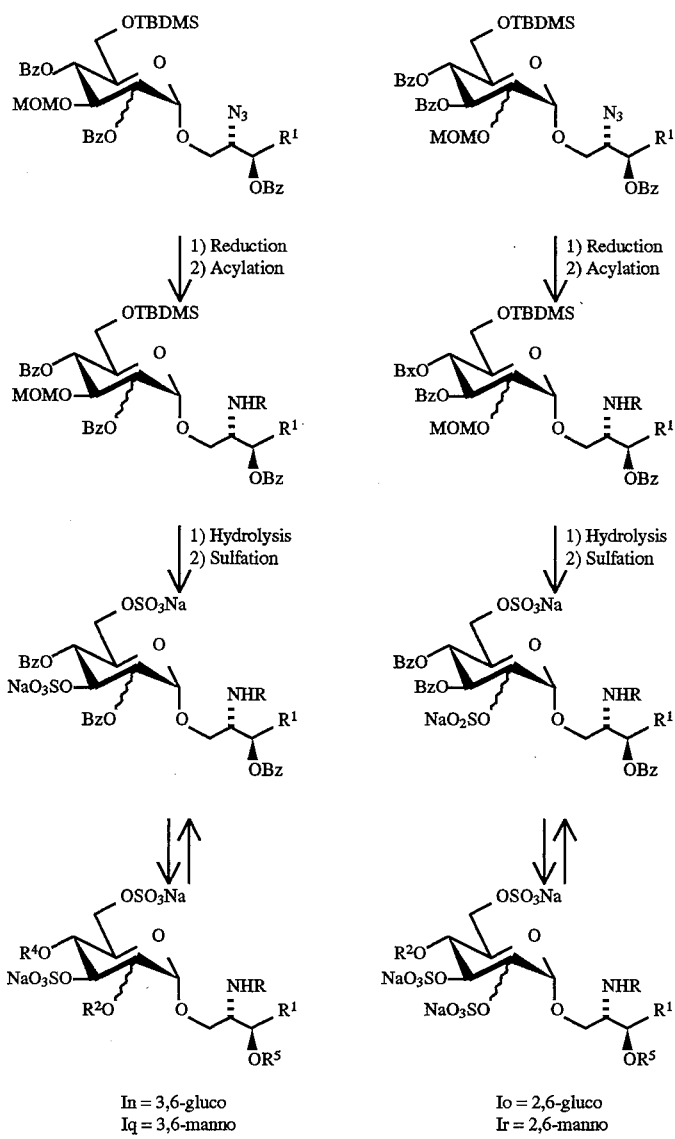

In = 3,6-gluco
Iq = 3,6-manno

Io = 2,6-gluco
Ir = 2,6-manno

When it is desired to prepare the 2,6-disulfated gluco compound of Formula Io, the corresponding gluco intermediate of Formula XIb is first blocked with a different blocking group such as a methoxymethyl group before the benzylidene moiety is hydrolyzed. The resulting intermediate is then sequentially treated with blocking groups wherein the primary alcohol is first blocked with an organosilyl group such as t-butyldimethylsilyl and then the secondary alcohols are blocked by esterification with a benzoyl group. The azido group of the fully protected pyranoside is reduced and then acylated with the desired fatty acid residue as described herein. The resulting protected glycolipid is subjected to selective hydrolysis to remove both the silyl and methoxymethyl protecting groups by known procedures and those described herein. The 3,4-blocked pyranoside is then sulfated in the 2 and 6-position as described previously and then, if desired, hydrolyzed to remove one or more of the blocking groups to produce the corresponding 2,6-disulfated gluco compounds of Formula Io. It should be understood and appreciated by those skilled in the art that the general synthetic steps outlined above may be used to prepare the 2,6-manno pyranoside of Formula Ir from the corresponding manno pyranoside of Formula XIb and preferably by the procedures described in Example 25.

To prepare the 3,4-disulfated gluco compounds of Formula Im, the corresponding gluco intermediate of Formula XIa is hydrolyzed to remove the benzylidene blocking group and then the resulting primary alcohol in the 6-position is blocked by selective esterification with a benzoyl group. The azido group is reduced and then acylated with the desired fatty acid residue and the resulting intermediate is subjected to treatment with sulfur trioxide complex to sulfate the 3 and 4-position and, if desired, optionally hydrolyzed to remove one or more of the blocking groups to produce the 3,4-disulfated gluco compounds of Formula Im. It should be appreciated by those skilled in the art that by following the general synthetic steps outlined above the 3,4-disulfated manno compounds of Formula Ip may be produced from the corresponding manno pyranoside intermediate of Formula XIa.

To prepare the 3,6-disulfated gluco compounds of Formula In, the corresponding gluco intermediate of Formula XIa is further blocked with a different blocking group such as a methoxymethyl group to produce the compound of Formula XIc. Hydrolysis of the benzylidine group followed by the sequential protection of the primary and secondary alcohol groups with an organosilyl and then a benzoyl group as described above and illustrated in Reaction Scheme 5 will produce a fully protected pyranoside compound in which the azido group is reduced and then acylated with the desired fatty acid residue. The fully protected glycolipid is subjected to selective hydrolysis to remove both the silyl and methoxymethyl groups by known procedures and the resulting 3 and 4-position hydroxy groups are sulfated with sulfur trioxide complex as generally described herein. The 3,6-disulfated gluco is optionally hydrolyzed to give the 3,6-disulfated gluco compounds of Formula In. It should be understood that by following the same general procedures outlined above, the 3,6-manno compounds of Formula Iq may be prepared from the corresponding manno pyranoside intermediate of Formula XIc.

The general processes for the preparation of trisulfated galacto, gluco and manno compounds of Formula Is to Ix and Formula Iy to Iad from the appropriate starting materials are illustrated in Reaction Schemes 6 and 7. In Reaction Scheme 6, the preparation of 3,4,6-trisulfate and 2,4,6-trisulfate compounds for the galacto, gluco and manno glycolipids of Formula Is to Ix wherein R, $R^1$, $R^2$, $R^3$ and $R^5$ are as previously defined may be prepared from the compound of Formula XII following the general sequence of reactions outlined in Reaction Scheme 6. The preparation of the 3,4,6-trisulfate galacto compounds of Formula Is may be prepared from the corresponding galacto intermediates of Formula XII by the procedures described herein in Examples 19 and 21. The corresponding 3,4,6-trisulfate gluco compounds of Formula Iu and 3,4,6-trisulfate manno compounds of Formula Iw may be prepared from the corresponding gluco and manno intermediates of Formula XII by following the general procedures used for the preparation of compounds of Formula Is.

Reaction Scheme 6

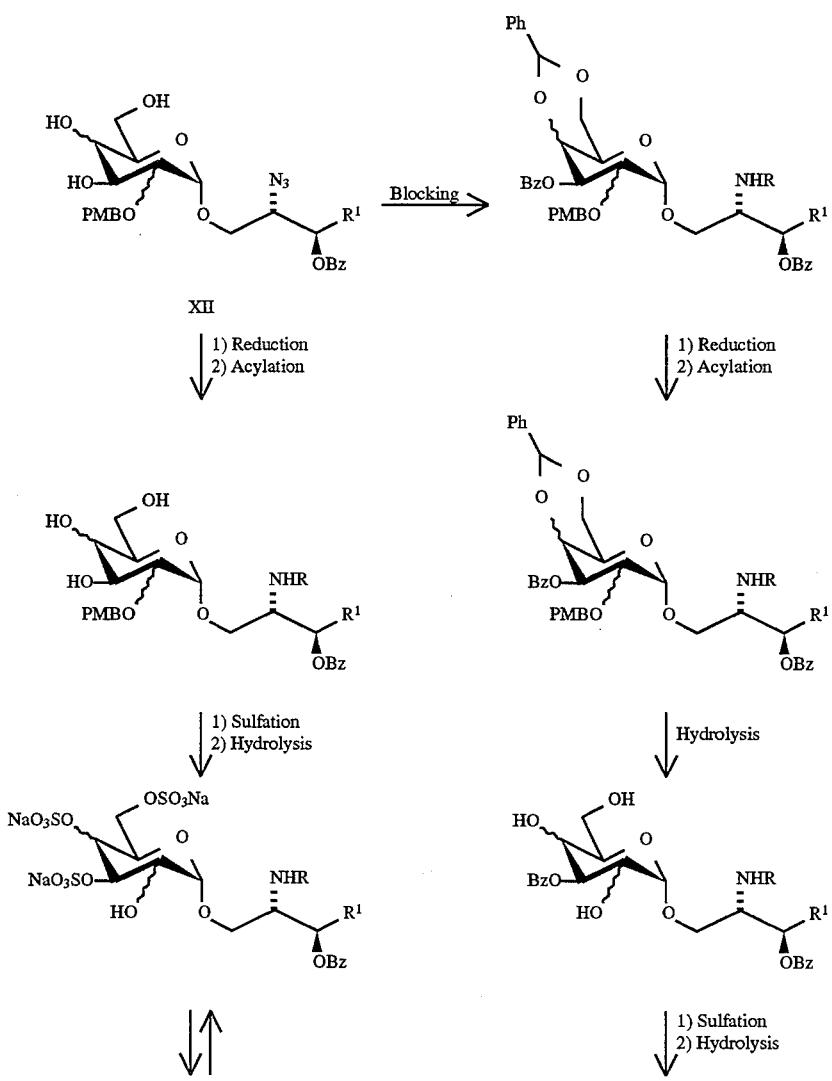

-continued
Reaction Scheme 6

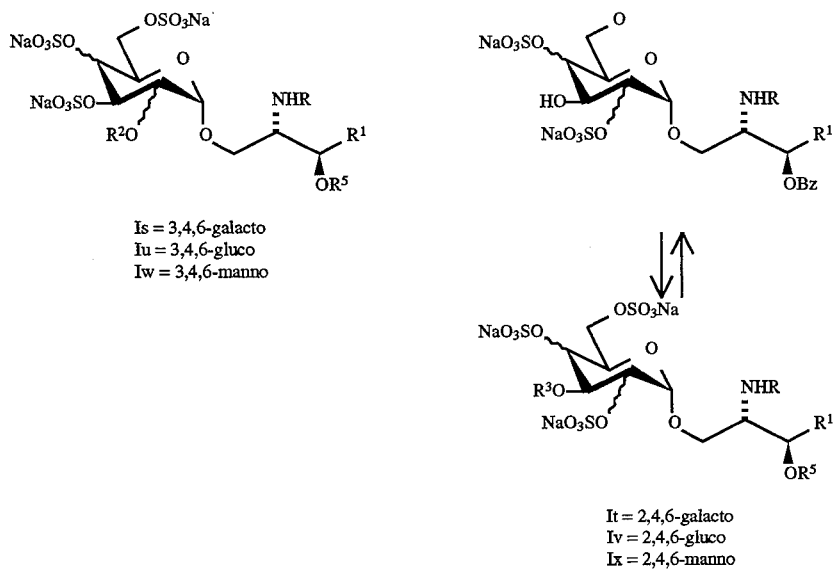

Is = 3,4,6-galacto
Iu = 3,4,6-gluco
Iw = 3,4,6-manno

It = 2,4,6-galacto
Iv = 2,4,6-gluco
Ix = 2,4,6-manno

To prepare the 2,4,6-trisulfate compounds of Formula It, Iv and Ix, the corresponding galacto, gluco or manno compound of Formula XII is selectively treated with two different blocking groups. It is advantageous to first treat the compound of Formula XII with a blocking group such as benzaldehyde dimethylacetal to block the 4 and 6-position hydroxy groups and then with a second blocking group such as benzoyl group by methods previously described. The azido group of the protected pyranoside is reduced and then acylated with the desired fatty acid residue as described herein. The resulting pyranoside is subjected to hydrolysis to remove both the benzylidene and p-methoxybenzyl blocking groups by procedures known in the art. The unblocked pyranoside is then treated with an excess of sulfur trioxide pyridine complex and then basified with an inorganic base such as sodium bicarbonate. The resulting 2,4,6-trisulfate compound may, if desired, be subjected to conventional hydrolysis to remove the blocking groups to produce compounds of the Formula It, Iv or Ix.

In Reaction Scheme 7, the preparation of 2,3,4-trisulfate and 2,3,6-trisulfate compounds for the galacto, gluco or manno glycolipids of Formula Iy to Iad wherein R, $R^1$, $R^4$, $R^5$ and $R^6$ are as previously defined may be prepared from the corresponding compounds of Formula Va, Vb or Vc, respectively by the general procedures outlined in Reaction Scheme 7.

When it is desired to prepare the 2,3,4-trisulfate compounds of Formula Iy, Iaa or Iac, the primary alcohol of the compound of Formula Va, Vb or Vc is first esterified with a blocking group such as benzoyl and then the azido group is reduced and acylated with a fatty acid. The resulting pyranoside which is blocked in the 6-position is treated with sulfur trioxide pyridine complex and then basified with sodium bicarbonate to give a 2,3,4-trisulfate pyranoside which is then optionally hydrolyzed to produce 2,3,4-trisuflate compounds of Formula Iy, Iaa or Iac.

Reaction Scheme 7

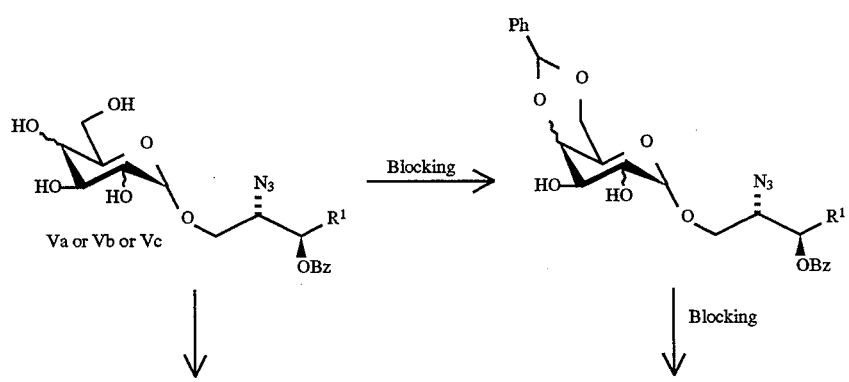

-continued
Reaction Scheme 7

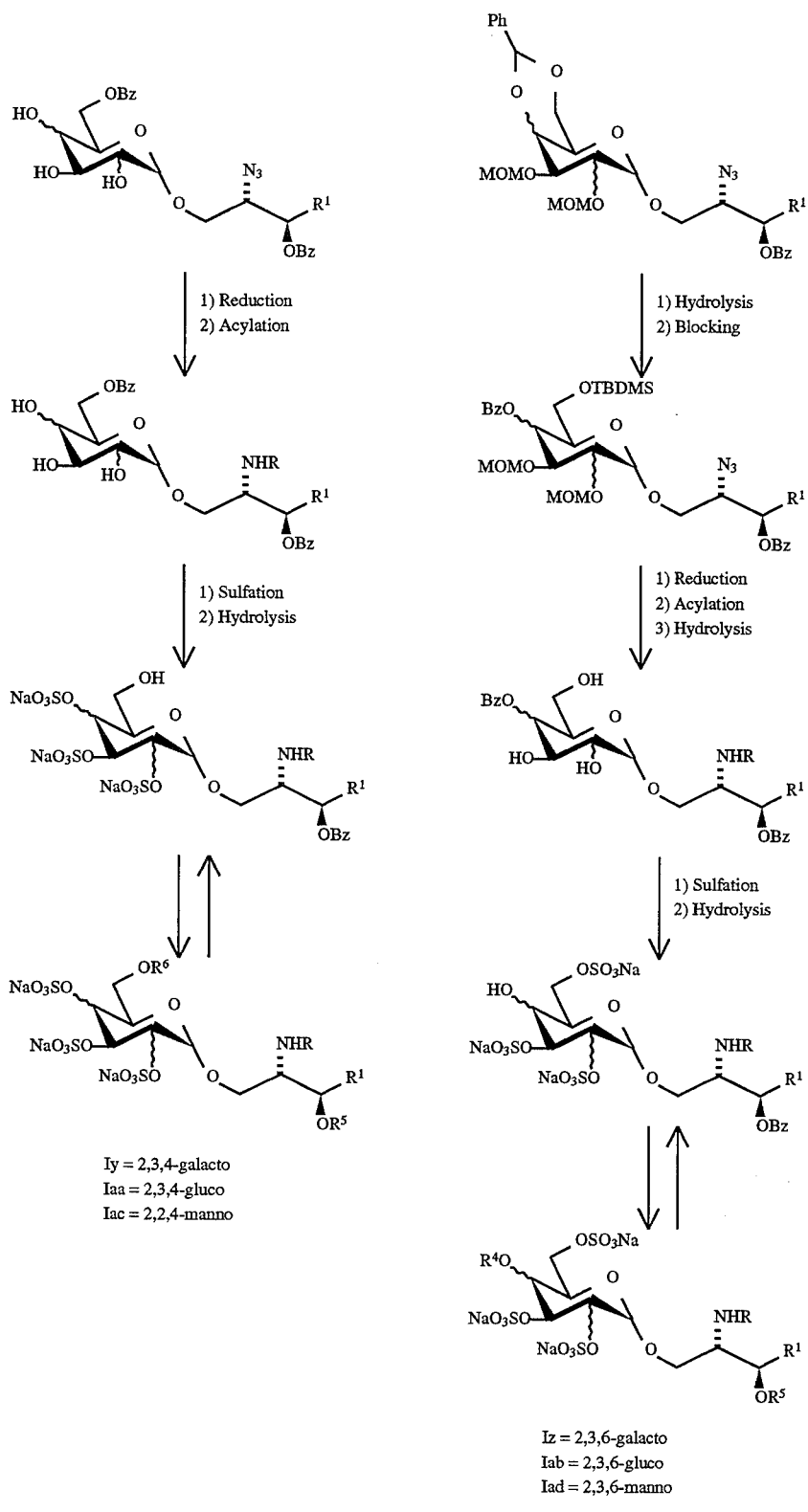

Iy = 2,3,4-galacto
Iaa = 2,3,4-gluco
Iac = 2,2,4-manno

Iz = 2,3,6-galacto
Iab = 2,3,6-gluco
Iad = 2,3,6-manno

To prepare the 2,3,6-trisulfate compounds of Formula Iz, Iab or Iad, the corresponding galacto, gluco or manno intermediates of Formula Va, Vb or Vc is selectively treated with two different blocking groups such as with benzylidene and then methoxymethyl blocking moieties. The resulting protected pyranoside is selectively hydrolyzed to remove the benzylidene blocking group and then the primary alcohol is protected with an organosilyl protecting group while the hydroxy in the 4-position is blocked with a benzoyl moiety. The azido group is then reduced and acylated with the desired fatty acid residue as previously described. Once the hydroxy group in the 4-position is selectively blocked by a group which is different from the other hydroxy blocking groups, the blocking groups such as the t-butyldimethylsilyl and the methoxymethyl groups are removed by known procedures. The resulting pyranoside is treated with excess sulfur trioxide complex and then optionally hydrolyzed as shown in Reaction Scheme 7 to produce compounds of the Formula Iz, Iab or Iad.

The process for the preparation of tetrasulfate galacto, gluco and manno compounds of Formula I wherein R, $R^1$ and $R^5$ are as previously described may be prepared from the corresponding intermediates of Formula Va, Vb or Vc by the general procedures described in Examples 23 and 24 and other procedures described herein.

In a preferred embodiment of the invention the compounds of Formula I have the formula

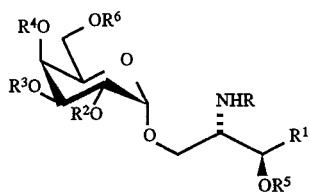

wherein R is an acyl residue of a fatty acid; $R^1$ is —(CH=CH)$_m$—(CH$_2$)$_n$—CH$_3$; $R^2$, $R^3$, $R^4$ and $R^6$ are independently at least two —SO$_3$H; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; or a non-toxic pharmaceutically acceptable salt, solvate or hydrate thereof. In a particularly preferred embodiment, $R^2$, $R^3$, $R^4$ and $R^6$ are independently two —SO$_3$H. In a further particularly preferred embodiment, $R^2$, $R^3$, $R^4$, $R^5$ and $R^6$ each are independently hydrogen or benzoyl.

In another preferred embodiment of the invention the compounds of Formula I have the formula

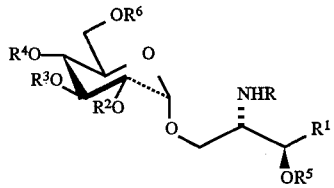

wherein R is an acyl residue of a fatty acid; $R^1$ is —(CH=CH)$_m$—(CH$_2$)$_n$—CH$_3$; $R^2$, $R^3$, $R^4$ and $R^6$ are independently at least two —SO$_3$H; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; or a non-toxic pharmaceutically acceptable salt, solvate or hydrate thereof. In a particularly preferred embodiment, $R^2$, $R^3$, $R^4$ and $R^6$ are independently two —SO$_3$H. In a further particularly preferred embodiment, $R^2$, $R^3$, $R^4$, $R^5$ and $R^6$ each are independently hydrogen or benzoyl.

In still another preferred embodiment of the invention the compounds of Formula I have the formula

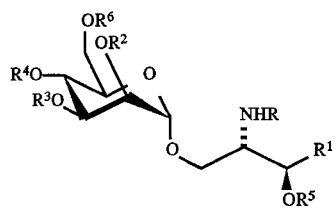

wherein R is an acyl residue of a fatty acid; $R^1$ is —(CH=CH)$_m$—(CH$_2$)$_n$—CH$_3$; $R^2$, $R^3$, $R^4$ and $R^6$ are independently at least two —SO$_3$H; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; or a non-toxic pharmaceutically acceptable salt, solvate or hydrate thereof. In a particularly preferred embodiment, $R^2$, $R^3$, $R^4$ and $R^6$ are independently two —SO$_3$H. In a further particularly preferred embodiment, $R^2$, $R^3$, $R^4$, $R^5$ and $R^6$ each are independently hydrogen or benzoyl.

In another aspect, this invention provides a method for the treatment or prevention of diseases mediated by the inhibition of selectin-mediated cellular adhesion in a mammal in need thereof, which comprises administering to said mammal a therapeutically effective amount of a compound of Formula I or a non-toxic pharmaceutically acceptable salt, solvate or hydrate thereof. In a particularly preferred embodiment, this invention provides a method for the treatment of inflammatory related diseases or other pathological conditions in a mammal in need thereof, which comprises administering to said mammal a therapeutically effective amount of a compound of Formula I or a non-toxic pharmaceutically acceptable salt, solvate or hydrate thereof.

In still another aspect, this invention provides pharmaceutical compositions comprising at least one compound of Formula I in combination with a pharmaceutical carrier or diluent.

CELL ADHESION ACTIVITY

1. P-Selectin Adhesion Receptor Binding

P-selectin (GMP140, granule membrane protein-140, PADGEM, or CD62) is a calcium-dependent transmembrane protein found in alpha granules of endothelial cells and platelets. It is an inducible selectin produced on activated endothelium and platelets which recognize alpha(2–3) sialylated and alpha(1–3)fucosylated lactosaminoglycans which include the sequence: Lewis x (Zhou et al., *J. Cell. Biol.*, (1991) 115 (2): 557–564) and sulfatides (3-sulfated galactosyl ceramides, Aruffo, et al., *Cell* (1991) 67: 35–44). P-selectin may be responsible for the initial adhesion events between endothelium and neutrophils as evidenced by leukocyte rolling induced by P-selectin in flow cells (Lawrence, M., and T. Springer, *Cell* (1991) 65: 859–873).

Based on the availability of soluble forms of P-selectin prepared as described by Aruffo, A., et al., *Cell*, 67, 35-44 (1991), a binding ELISA based assay modified from Foxall, et al., *J., Cell Biol.*, 117, 895–902 (1992) was developed to measure inhibitors of P-selectin binding to immobilized sulfatides. Such inhibitors were tested in the assay described below.

0.1 ml of sulfatide (SIGMA) or lysosulfatide (SIGMA) each at 1 µg/ml in MeOH were added to the wells of a 96-well ELISA plate (ProBind, Falcon) and allowed to dry overnight at room temperature. The next day the antigen coated plates were blocked for 1.5 hours at room temperature with 5% BSA (ICN) in buffer containing 20 mM Hepes and 0.15M NaCl, pH 8.0. Wild type P-selectin and mutants thereof were first mixed with HRP-conjugated goat anti-human IgG (Fisher Scientific), serially diluted and then incubated for 30 minutes at 37° C. in buffer containing 20 mM Hepes, 0.15M NaCl, 1% BSA and 0.8 mM $CaCl_2$, pH 8.0 prior to addition to the BSA blocked plates. Following the 30 minute preincubation, the fusion protein-HRP conjugate immunocomplexes were incubated on the blocked antigen coated plates for 45 minutes at 37° C. in the presence or absence of the test compounds and then washed to remove any unbound proteins. Bound complexes were detected by addition of substrate buffer (95 mM $NaOAc.3H_2O$, 5 mM citric acid monohydrate, 1.4 mM urea/$H_2O_2$) containing 3, 3', 5, 5' Tetramethylbenzidine (SIGMA). Reactions were stopped by the addition of 3N sulfuric acid and the absorbance read on an ELISA reader at dual wavelengths 450 and 630 nm. The efficacy of these compounds was compared to that of sulfatide (positive control) or to lysosulfatide (negative control). The data is obtained as percent inhibition of specific binding $$\% \text{ Inhibition} = \left[ 1 - \left( \frac{\text{Specific binding: Test Compound}}{\text{Specific binding: Vehicle}} \right) \right] \times 100$$

and a plot of dose vs. percent inhibition of Rg binding is generated in which $IC_{50}$ (μM) is calculated and reported as cell free data in Table 1.

2. HL-60 Cell Binding to P- and E-Selectin RG

Receptor globulin (Rg) Construction

The chimeric P- and E-selectin receptor globulin (Rg) consists of the human lectin domain, the EGF domain, and two complement repeats of the human selectins fused to the hinge, CH1 and CH2 domains of human IgG1. These proteins were prepared as described by Aruffo, et al., *Cell* (1991) 67: 35–44; Walz, et al., *Science* (1990) 250, 1132–1135.

Cell binding assay for Rg

The HL-60 cell line, obtained from the American Type Culture Collection, ATCC No. CCL240, was employed to investigate P-selectin Rg binding. Assays were done in 96-well tissue culture dishes. The wells were first coated with 0.5 ug goat anti-human Fc antiserum overnight, and nonspecific binding sites were blocked by incubation of the wells with 1% nonfat dry milk in phosphate buffered saline (PBS containing 0.9 mM $CaCl_2$ and 0.8 mM $MgSO_4$) for 30 minutes. The Rg was then bound to the anti Fc-coated wells by incubating 50 ng in 50 ul of PBS for two hours. Cells, washed twice and resuspended in PBS to remove traces of medium components, were labeled with 10 uM calcein acetoxy methyl ester for 30 minutes at $3 \times 10^7$ cells per ml at room temperature. Serum-containing medium (RPMI with 20% fetal calf serum) was added, and the cells washed, followed by resuspension in PBS and a further spin. The labeled cells, resuspended in PBS, were added to twice washed Rg-containing wells at 200,000 per well. Following a 30 minute incubation with slow shaking, the wells were aspirated and washed three times with PBS to remove unbound cells. To certain wells were added known numbers of cells for determination of a standard curve of fluorescent units per cell. The fluorescence on the plate was quantitated using a fluorescent plate reader. Following subtraction of a blank representing the binding of cells to non-Rg containing wells (<5000 cells), the specific binding to P- or E- selectin was determined.

Inhibitors of cell binding

Test compounds were prepared by dissolution to a final concentration of 20 mg/ml in dimethyl sulfoxide (DMSO), diluted in PBS to 2 mg/ml, and briefly sonicated prior to use. The Rg coated wells were preincubated at room temperature for 15 minutes with the inhibitor, and 200,000 cells were added to yield the final indicated inhibitor concentration in 160 ul of PBS. The data is obtained as percent inhibition of specific binding:

$$\% \text{ Inhibition} = \left[ 1 - \left( \frac{\text{Specific binding: Test Compound}}{\text{Specific binding: Vehicle}} \right) \right] \times 100$$

and a plot of dose vs. percent inhibition of Rg binding is generated in which $IC_{50}$ (μM) is calculated and reported in Table 1.

3. Reverse Passive Arthus Reaction in Rats

The reverse passive Arthus reaction in rats is a modification of the method by Mulligan et al., as described in *J. Clin. Invest.* (1991) 88: 1396–1406. This is an experimental model in which the interaction of antigen-antibody complexes and complement leads to a severe vasculitis that is associated with edema, induration, erythema and hemorrhage. The interaction between the antigen-antibody complexes and complement leads to a localized influx of neutrophils. These neutrophils release a variety of mediators that are associated with tissue damage and vascular permeability. The localized inflammatory reaction is measured using different techniques i.e., vascular permeability and neutrophil influx which is evaluated both biochemically and microscopically.

Male Sprague Dawley specific pathogen-free rats with jugular vein cannulae (280–320 g, Hill Top Labs, Pa.) are used in these studies. Animals are acclimated for at least 1 day and individually housed in stainless steel cages. The dorsal region of the rats is closely clipped 2 days prior to the experiments and divided into 4 sites on each side of the midline. Prior to all injections the rats are sedated with 0.4 ml per 300 gm rat of ketamine/rompun [1000 mg (10 ml) of ketamine HCL is mixed with 40 mg (2.0 ml) Rompun] administered IP and or inhalation anesthesia with metafane (methoxyflurane).

Bovin Serum Albumin (BSA) and rabbit polyclonal IgG rich in anti-BSA are purchased from Sigma Chemical Co. (St. Louis, Mo.). Radiolabelled $^{125}$I-BSA (spAct 1–5 μCi/μg) is purchased from Dupont NEN (Boston, Mass.).

Each rat is administered intradermal (ID) injection of (0.4 mg, 0.6 mg and 0.8 mg) anti-BSA in a volume of 100 μl per injection in normal saline. The ID injections are randomized near the mid dorsal region on both sides of the back bone. Immediately after the ID injections of the anti-BSA, the rats are administered intravenous (IV) injections of BSA (10 mg in 1.0 ml) in normal saline containing $^{125}$I labeled BSA (1 μCi/ml BSA or 5.0 μCi/kg body wt) for quantification of dermal vascular injury. Anti-inflammatory agents such as inhibitors of adhesion molecules of the present invention are administered IV at a single dose of 3 mg immediately after BSA. Four (4) hours after the IV injection of BSA, the rats are anesthetized with metafane and 2 to 3 ml of blood is withdrawn via the cannula into an anticoagulant containing (EDTA or Heparin) tube and plasma separated and saved for neutrophil and albumin quantitation. The rats are killed and the skin surrounding the injection site (15 mm diameter) is punched out and weighed. The skin samples and a fixed volume of plasma (0.1 to 1.0 ml) is analyzed in a gamma-counter for $^{125}$I content. Skin samples from the contralateral side are processed and analyzed for myeloperoxidase activity (MPO) as a measure of neutrophil accumulation. As needed, samples are also processed for histological evaluation of the reacted sites.

Vascular Permeability (VP)

The calculation of the plasma protein exudation into skin is made by determining the radioactivity in the tissue and relating this to the level of radioactive albumin in the blood at the time of sacrifice. The equation below shows the calculation for microliter plasma extravasated (Issekutz and Issekutz, Pharmacological methods in the control of inflammation, (1989) 129–150).

$$\mu l \text{ plasma extravasated} = \frac{CPM \text{ in tissue}}{CPM/\mu l \text{ plasma}}$$

Percent inhibition of the test compound at 3 mg was determined as follows:

$$\% \text{ Inhibition} = \left[1 - \left(\frac{\mu l \text{ plasma extravasated with test compound}}{\mu l \text{ plasma extravasated with vehicle}}\right)\right] \times 100$$

Myeloperoxidase (MPO)

MPO is located in the azurophil granules of polymorphonuclear leukocytes (PMN). Because of its abundance in these cells (5% dry weight), this enzyme is used as a marker for tissue neutrophil content. For tissue MPO content, the method of Bradley, et al., was used as described in *J. Invest. Dermatol.* (1982) 78: 206–209. Biopsies from each treatment group were placed in plastic tubes (15×100 mm) containing 10 ml of 0.5% hexadecyltrimethylammonium bromide (HTAB) in 0.05M potassium phosphate buffer pH 6.0. The tissue was then homogenized with a Brinkmann Polytron homogenizer (10s). The supernatant (0.05 ml) was assayed by mixing with 0.150 ml o-dianisidine (0.334 mg/ml) and 0.0005% hydrogen peroxide in 0.05M potassium phosphate buffer pH 6.0 in a 96-well microtiter plate. Change in absorbance at 450 nm was measured at room temperature using a $V_{max}$ kinetic plate reader (Molecular Devices, Palo Alto, Calif., USA). Percent inhibition of the test compound at 3 mg dose was determined as follows:

$$\% \text{ Inhibition} = \left[1 - \left(\frac{\text{Absorbance of test compound treated Biopsies}}{\text{Absorbance of vehicle treated Biopsies}}\right)\right] \times 100$$

The in vivo experimental results as measured by vascular permeability (VP) and myeloperoxidase (MPO) at a single dose of the test compound are shown in Table 1.

TABLE 1

| | P-Selectin | | RPA | |
|---|---|---|---|---|
| Example No. | Cell Free $IC_{50}$ (µM) | HL-60 $IC_{50}$ (µM) | VP % Inhib.* | MPO % Inhib.* |
| 1 | 0.3 | 8.3 | 68 | 97 |
| 2 | 0.2 | 17 | 14 | 0 |
| 4 | 9 | 8 | NA** | NA** |
| 7 | −0.4 | 11 | 88 | 97 |
| 10 | >6.1 | 8 | 11 | 71.6 |
| 11 | 1.7 | 8.9 | 32 | 53.7 |
| 15 | 2.2 | 5.2 | 50 | 0 |
| 23 | >8 | 2.6 | 0 | 26.4 |

*% Inhibition at 3 mg
**not available

The biological results of representative compounds according to this invention are shown in Table 1. Both the cell and cell-free in vitro assays and the in vivo tests carried out in the RPA rat model show that the compounds of Formula I are inhibitors of P-selectin mediated binding and, more importantly, confirm that the compounds of the instant invention are selectin inhibitors useful to treat inflammatory conditions in a mammal.

Therefore, the compounds of Formula I or pharmaceutical compositions thereof are useful in the treatment and/or prevention of diseases or other pathological conditions which are mediated by the binding of selectins in cellular adhesion. Such diseases and conditions include acute or chronic inflammatory diseases such as rheumatoid arthritis, asthma, allergy conditions, psoriasis, septic shock, adult respiratory distress syndrome, inflammatory bowel disease and opthalmic inflammatory diseases; autoimmune diseases; thrombosis or inappropriate platelet aggregation conditions, and cardiovascular disease; reperfusion injury; multiple sclerosis and neoplastic disease including metastasis conditions.

In another embodiment, this invention includes pharmaceutical compositions comprising at least one compound of Formula I in combination with a pharmaceutical carrier or diluent.

In still another embodiment, this invention relates to a method of treatment or prevention of diseases or other pathological conditions characterized by selectin-mediated cellular adhesion in a mammal in need thereof, which comprises administering to said mammal a therapeutically effective amount of a compound of Formula I or a non-toxic pharmaceutically acceptable salt, solvate or hydrate thereof.

In yet another embodiment, this invention relates to a method for inhibiting or reducing inflammatory disease processes in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, bronchial, rectal, topical, ophthalmic, intraarticular or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in transdermal formulations with permeation enhancers such as DMSO and iontophoresis. Other topical compositions well-known in the art can be administered to treat dermal inflammation. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of cell adhesion inhibition desired and the potency of the particular compound being utilized for the particular disorder of disease concerned. It is also contemplated that the treatment and dosage of the particular compound may be similar to the treatment and dosage used with dexamethasone phosphate and that the dosage would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention for the satisfactory inhibition or reduction of selectin-mediated cell adhesion.

A suitable dose of a compound of Formula I or pharmaceutical composition thereof for a mammal suffering from, or likely to suffer from any condition as described herein is an amount of active ingredient from 0.1 μg/kg to 100 mg/kg body weight. For systemic administration, the dose may be in the range of 0.1 to 100 mg/kg body weight to the active ingredient, and preferably, in the range of 0.1 to 50 mg/kg body weight. For topical administration, for example to the skin or eye, a suitable dose of active ingredient may be in the range of 0.1 μg to about 100 mg/ml of liquid carrier or excipient, and preferably, about 0.1 mg to 10 mg/ml. For oral dosing including the treatment of prophylaxis of inflammatory diseases or conditions, a suitable dose may be in the range of about 1 mg to 100 mg/kg of mammal body weight, and preferably, from about 1 mg to about 50 mg/kg body weight. The active ingredient will preferably be administered in equal doses from one to four times a day. However, usually a small dosage is administered, and the dosage is gradually increased until the optimal dosage for the host under treatment is determined.

The following examples are given by way of illustration and are not to be construed as limiting the invention in any way inasmuch as many variations of the invention are possible within the spirit of the invention.

DESCRIPTION OF SPECIFIC EMBODIMENTS

EXAMPLE 1

(2S,3R,4E)-3-Benzoyloxy-2-hexadecanoylamino-1-[2,3-di-O-benzoyl-4,6-di-O-(sodium oxysulfonyl)-α-D-galactopyranosyloxy]-4-octadecene A. Ethyl 3,4-O-isopropylidene-1-thio-β-D-galactopyranoside

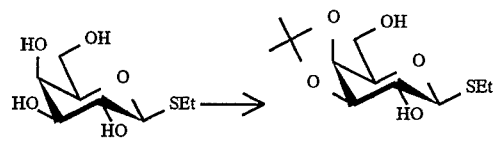

A mixture of ethyl 1-thio-β-D-galactopyranoside (24.86 g, 0.111 mol) [prepared as described by R. U. Lemieux in *Can. J. Chem.*, 29, 1079 (1951)] and 2,2-dimethoxypropane (500 mL) was treated with p-toluenesulfonic acid (0.625 g) and stirred at 22° C. for 24 hours. Water (80 mL) was added and after 15 minutes the reaction mixture was cooled in an ice water bath and stirred for another 30 minutes. Then triethylamine (5 mL) was added and the mixture was stirred for 20 minutes. The solvent was evaporated under vacuum and the residue was purified by silica gel chromatography (9-×12 cm, 50% to 70% ethyl acetate/toluene) to give the title compound (25.5 g, 87%) as a white solid. Recrystallization from ethyl acetate and hexane gave white prisms.

m.p.=90°–93° C.; $[\alpha]_D^{22}$: +20.8° (c=2.8, CHCl$_3$);

IR (KBr) $\lambda_{max}$ (cm$^{-1}$): 3200 (broad, OH);

$^1$H NMR 400 MHz (CDCl$_3$) δ(ppm): 1.33 (3H, t, J=7.3 Hz, —SCH$_2$CH$_3$), 1.36 and 1.52 (2×3H, 2s, —CH$_3$ of isopropylidene), 2.2 and 2.5 (broad, OH), 2.75 (2H, m, —SCH$_2$CH$_3$), 3.57 (1H, dd, J=10.2 and 7.0 Hz, H-2), 3.81 (1H, dd, J=11.5 and 4.0 Hz, H-6), 3.89 (1H, m, H-5), 3.98 (1H, J=11.5 7.2 Hz, H-6), 4.09 (1H, dd, J=7.0 and 5.6 Hz, H-3), 4.21 (1H, dd, J=5.6 and 2.2 Hz, H-4 ), 4.27 (1H, d, J=10.2 Hz, H-1);

Anal. Calcd. for C$_{11}$H$_{20}$O$_5$S: C, 49.98; H, 7.63; S, 12.13. Found: C, 49.89; H, 7.49; S, 12.33.

B. Ethyl 6-O-t-butyldimethylsilyl-3,4-O-isopropylidene-1-thio-β-D-galactopyranoside

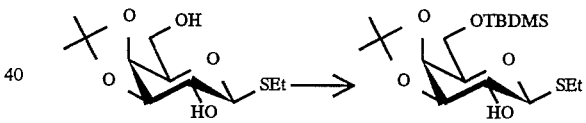

A solution of ethyl 3,4-O-isopropylidene-1-thio-β-D-galactopyranoside (8.65 g, 32.7 mmol) in dry pyridine (125 mL) was treated at 0°–5° C. with tert-butyldimethylsilyl chloride (5.92 g, 39.2 mmol) and the resulting mixture was stirred for 5 hours. Methanol (15 mL) was then added and the solution was stirred for another 15 minutes. The solvent was then evaporated under vacuum and the residue was diluted with ethyl acetate (500 mL) washed with cold 2N hydrochloric acid, saturated sodium bicarbonate, brine and dried over anhydrous magnesium sulfate. Evaporation of the solvent under vacuum gave an oil which was purified by chromatography on silica gel (9×11 cm, 10% to 20% ethyl acetate/toluene) and afforded the title compound (12.4 g, 100%) as an oil.

$[\alpha]_D^{22}$: +2.8° (c=1.0, CHCl$_3$);

$^1$H NMR 400 MHz (CDCl$_3$) δ ppm: 0.08 (6H, s, SiCH$_3$), 0.9 (9H, s, Si-t-Bu), 1.32 (3H, t, J=7.5 Hz, —SCH$_2$CH$_3$) 1.35 and 1.53 (2×3H, 2s, —CH$_3$ of isopropylidene), 2.7 (2H, m, —SCH$_2$CH$_3$), 3.56 (1H, dd, J 10.2 and 7.0 Hz, H-2), 3.8–3.9 (3H, m, H-5 and H-6), 4.05 (1H, dd, J=7.0 and J=5.5 Hz, H-3), 4.24 (1H, d, J=10.2 Hz, H-1) 4.26 (1H, dd, J=5.5 and 2.0 Hz, H-4).

C. Ethyl 6-O-t-butyldimethylsilyl-3,4-O-isopropylidene-2-O-p-methoxybenzyl-1-thio-βD-galactopyranoside

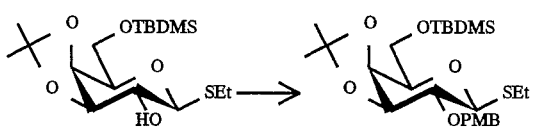

A solution of ethyl 6-O-t-butyldimethylsilyl-3,4-O-isopropylidene-1-thio-β-D-galactopyranoside (12.4 g, 32.7 mmol) in N,N-dimethylformamide (45 mL) was added to a suspension of sodium hydride (1.35 g of 80% in mineral oil, 45.0 mmol) in N,N-dimethylformamide (90 mL) and the resulting mixture was stirred at 22° C. for 2 hours. The reaction mixture was then cooled to 0°-5° C., treated dropwise with p-methoxybenzyl chloride (8.1 mL, 59.8 mmol) and stirred at 22° C. for 2 hours. The reaction mixture was cooled again in an ice bath and treated dropwise with water (20 mL). The reaction mixture was then diluted with water (300 mL) and extracted with ether (3×300 mL). The combined extracts were washed with brine, dried over anhydrous magnesium sulfate and evaporated. The residual oil was purified on silica gel chromatography (9×12 cm, 0 to 10% ethyl acetate/toluene) and gave the title compound (10.5 g, 64%) as an oil.

IR (NaCl, film) $\lambda_{max}$ (cm$^{-1}$): 1612 (aromatic) and 1516;
$^1$H NMR 200 MHz (CDCl$_3$) δ(ppm): 0.06 (6H, s, SiCH$_3$), 0.88 (9H, s, Si t-Bu), 1.29 (3H, t, J=7.4 Hz, —SCH$_2$CH$_3$), 1.34 and 1.44 (2×3H, 2s, —CH$_3$ of isopropylidene), 2.7 (2H, m, —SCH$_2$CH$_3$), 3.41 (1H, dd, J=6.1 and 9.9 Hz, H-2), 3.79 (3H, s, —OCH$_3$), 3.7–3.9 (3H, m, H-5 and H-6), 4.15–4.25 (2H, m, H-3 and H-4 overlapping), 4.39 (1H, d, J=9.9 Hz, H-1), 4.70 (1H, d, J$_{AB}$=11.0 Hz, —OCH$_2$ of 4-methoxybenzyl), 4.74 (1H, d, J$_{AB}$=11.0 Hz, —OCH$_2$ of 4-methoxybenzyl), 6.86 (2H, d, J=8.7 Hz, H-3 of 4-methoxybenzyl) and 7.35 (2H, d, J=8.7 Hz, H-2 of 4-methoxybenzyl).

D. Ethyl 2-O-p-methoxybenzyl-1-thio-β-D-galactopyranoside

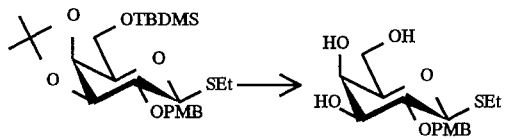

A solution of ethyl 6-O-t-butyldimethylsilyl-3,4-O-isopropylidene-2-O-p-methoxybenzyl-1-thio-β-D-galactopyranoside (10.50 g, 21.05 mmol) in 80% aqueous acetic acid (100 mL) was heated at 60° C. for 1.5 hours. The cooled mixture was evaporated under vacuum and the last traces of acetic acid removed by co-evaporation with toluene. Chromatography of the residue on silica gel (7×13 cm, 0 to 10% methanol/chloroform) gave the title compound (5.67 g, 78%) as a solid. Recrystallization from dichloromethane gave a white solid.

m.p.=131°-132° C. [α]$_D^{22}$: +22.7° (c=1.0, CHCl$_3$);
IR (KBr) ν$_{max}$ (cm$^{-1}$): 3500 and 3300 (broad, OH) and 1605 (aromatic);
$^1$H NMR 400 MHz (CDCl$_3$) δ(ppm): 1.35 (3H, t, J=7.5 Hz, —SCH$_2$CH$_3$), 2–2.8 (broad, OH and —SCH$_2$CH$_3$), 3.5–3.6 (2H, m, H-2 and H-5 overlapping), 3.61 (1H, dd, J=3.0 and 8.9 Hz, H-3), 3.81 (3H, s, —OCH$_3$), 3.84 (1H, dd, J=4.3 and 12.0 Hz, H-6), 3.95 (1H, dd, J=6.0 and 12.0 Hz, H-6), 4.03 (1H, d, J=3.0 Hz, H4), 4.44 (1H, d, J=9.5 Hz, H-1), 4.62 and 4.91 (2H, 2d, J=10.8 Hz, —CH$_2$ of 4-methoxybenzyl), 6.91 (1H, d, J=8.6 Hz, H-3 of 4-methoxybenzyl) and 7.34 ppm (1H, d, J=8.6 Hz, H-2 of 4-methoxybenzyl);

Anal. Calcd. for C$_{16}$H$_{24}$O$_6$S: C, 55.80; H, 7.02; S, 9.31. Found: C, 55.64; H, 6.78; S, 9.23.

E. Ethyl 2-O-p-methoxybenzyl-3,4,6-tri-O-acetyl-1-thio-β-D-galactopyranoside

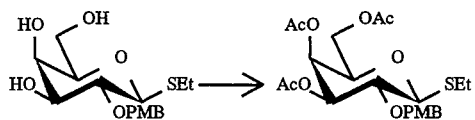

A solution of ethyl 2-O-p-methoxybenzyl-1-thio-β-D-galactopyranoside (5.67 g, 16.46 mmol) in a mixture of pyridine (100 mL) and acetic anhydride (50 mL) was stirred at 22° C. for 3 hours. The excess reagents were evaporated under vacuum and the last traces co-evaporated with toluene. The residue was purified by silica gel chromatography (7×13 cm, 0% to 20% ethyl acetate/toluene) and gave the title compound (7.29 g, 94%) as an oil.

IR (NaCl, film) ν$_{max}$ (cm$^{-1}$): 1750 (C=O of acetate);
$^1$H NMR 200 MHz (CDCl$_3$) δ(ppm): 1.34 (3H, t, J=7.4 Hz, —SCH$_2$CH$_3$), 1.97, 1.03 and 2.13 (3×3H, 3s, —OAc), 1.97, 2.03 and 2.13 (3×3H, 3s, —OAc), 2.7–2.8 (2H, m, —SCH$_2$CH$_3$), 3.64 (1H, t, J=9.8, H-2), 3.79 (3H, s, —OCH$_3$), 3.86 (1H, m, H-5), 4.53 (2H, d, J=9.8 Hz, H-1 and —CH$_2$OPMB overlapping), 4.78 (1H, d, J=10.4 Hz, —CH$_2$OPMB), 4.98 (1H, dd, J=3.4 and 9.7 Hz, H-3), 5.4 (1H, d, J=3.4 Hz, H-4), 6.86 (1H, d, J=8.5 Hz, H-3 of 4-methoxybenzyl) and 7.24 ppm (1H, d, J=8.5 Hz, H-2 of 4-methoxybenzyl).

F. (2S,3R,4E)-2-Azido-3-benzoyloxy-1-(2-O-p-methoxybenzyl-3,4,6-tri-O-acetyl-α-D-galactopyranosyloxy)-4-octadecene and (2S,3R,4E)-2-azido-3-benzoyloxy-1-(2-O-p-methoxybenzyl-3,4,6-tri-O-acetyl-β-D-galactopyranosyloxy)-4-octadecene

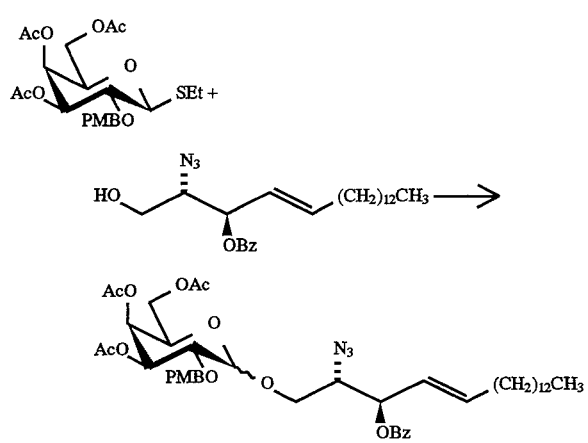

Procedure A.

A solution of (2S,3R,4E)-2-azido-3-benzoyloxy-4-octadecen-1-ol (1.11 g, 2.58 mmol) [prepared by general procedure described by P. Zimmerman et al, Liebigs Ann. Chem., 663–667 (1988)], ethyl 2-O-p-methoxybenzyl-3,4,6-tri-O-acetyl-1-thio-β-D-galactopyranoside (1.62g, 3.44 mmol) and 2,6-di-tert-butyl-4-methylpyridine (1.10 g, 5.37 mmol) in a mixture of ethyl ether (20 mL) and dichloromethane (20 mL) was stirred for 30 minutes at 22° C. with powdered 4 Å molecular sieves. Then dimethyl(methylthio)sulfonium triflate (1.30g, 5.03 mmol) [described by P. Fugedi et al, Carbohydr. Res., 149 (1986) C9–C12] was added and the resulting mixture was stirred for 3.2 hours. Triethylamine (2 mL) was then added and the reaction mixture was stirred for another 30 minutes. The reaction mixture was then filtered through Celite, diluted with ethyl acetate, washed with an aqueous solution of sodium bicarbonate and brine, dried over anhydrous magnesium sulfate and concentrated. Chromatography of the residue on a silica gel pad (5×11 cm, 0% to 20% ethyl acetate/toluene) gave the title material (1.86 g, 86%) as a clear oil. By $^1$H NMR, this product was a mixture of α and β anomers in about a 86:14 ratio.

Purification of a sample on preparative plates gave the pure α anomer as a syrup having the following characteristics.

$[α]_D^{22}$: +22.2° (c=1.0, CHCl$_3$).

IR (NaCl, film) $v_{max}$ (cm$^{-1}$): 2105 (N3), 1753 (C=O of acetate) and 1735.

$^1$H NMR 400 MHz (CDCl$_3$) δ(ppm): 0.89 (3H, t, J=7.0 Hz, —CH$_3$), 1.2–1.4 (22H, broad, —(CH$_2$)$_{11}$—), 1.99, 2.00 and 2.11 (3×3H, 3s, —OAc), 2.08 (2H, m, =CH—CH$_2$—), 3.50 (1H, dd, J=11.0 and 7.9 Hz, H-1), 3.76 (1H, dd, J=11.0 and 4.0 Hz, H-1), 3.79 (3H, s, —OCH$_3$), 3.83 (1H, dd, J=10.6 Hz, H-2'), 3.98 (1H, m, H-2), 4.05 (2H, d, J=6.5 Hz, H-6'), 4.21 (1H, t, J=6.5 Hz, H-5'), 4.56 (1H, d, J$_{AB}$=11.9 Hz, —CH$_2$ of 4-methoxybenzyl), 4.86 (1H, d, J=3.6 Hz, H-1'), 5.29 (1H, dd, J=10.6 and 3.4 Hz, H-3'), 5.44 (1H, broad d, J=3.4 Hz, H-4'), 5.58 (1H, dd, J=14.3 and 7.9 Hz, H-4), 5.62 (1H, dd, J=7.9 and 4.0 Hz, H-3), 5.95 (1H, dt, J=14.3 and 6.7 Hz, H-5), 6.85 (2H, d, J=8.7 Hz, H-3 of 4-methoxybenzyl), 7.26 (2H, d, J=8.7 Hz, H-2 of 4-methoxybenzyl), 7.46, 7.6 and 8.06 (5H, 3m, benzoate).

Procedure B.

On a large scale, the two anomers are better separated as tetra-acetates as described below.

(2S,3R,4E)-2-Azido-3-benzoyloxy-1-(2,3,4,6-tetra-O-acetyl-α-D-galactopyranosyloxy)-4-octadecene and (2S,3R,4E)-2-azido-3-benzoyloxy-1-(2,3,4,6-tetra-O-acetyl-β-D-galactopyranosyloxy)-4-octadecene

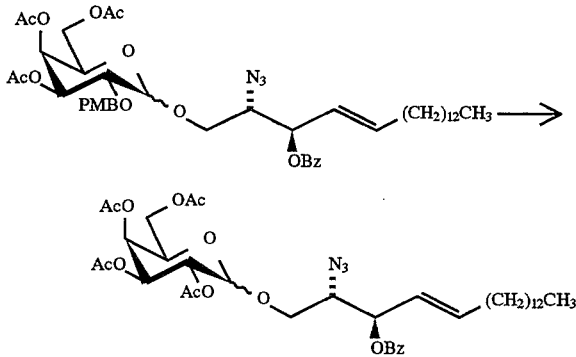

A solution containing a mixture of (2S,3R,4E)-2-azido-3-benzoyloxy-1-(2-O-p-methoxybenzyl-3,4,6-tri-O-acetyl-α-D-galactopyranosyloxy)-4-octadecene and (2S,3R,4E)-2-azido-3-benzoyloxy-1-(2-O-p-methoxybenzyl-3,4,6-tri-O-acetyl-β-D-galactopyranosyloxy)-4-octadecene (0.163 g, 0.191 mmol, ratio α and β=86:14) in dry dichloromethane (10 mL) was cooled down to 0°–5° C. and treated with trifluoroacetic acid (5 mL). After 2 hours at 0°–5° C., the solvent was evaporated under vacuum and the residue was diluted with pyridine (5 mL) and acetic anhydride (5 mL) and stirred at 22° C. for 2 hours. The excess reagents were evaporated under vacuum. The residue was purified by silica gel chromatography (0 to 5% ethyl acetate/toluene) and gave the pure two anomers (combined yield 83%).

IR (CH$_2$Cl$_2$) $v_{max}$ (cm$^{-1}$) α-anomer: 3050, 2930 (C—H), 2100 (N$_3$), 1750 (C=O), 1228 (C—O);

IR (CH$_2$Cl$_2$) $v_{max}$ (cm$^{-1}$) β-anomer: 3050, 2930, 2955 (C—H), 2130 (N$_3$), 1750 (C=O), 1220 (C—O);

$^1$H NMR 400 MHz (CDCl$_3$) δ(ppm) α-anomer: 0.89 (3H, t, J=7.0 Hz, —CH$_3$), 1.25 (20H, br s, —(CH$_2$)$_{10}$—), 1.39 (2H, m, —CH$_2$—), 2.00, 2.01, 2.09, 2.15 (4×3H, 4s, 4×—OCOCH$_3$), 2.09 (2H, m, =CH—CH$_2$—), 3.52 (1H, dd, J=10.7 and 7.7 Hz, H-1), 3.88 (1H, dd, J=10.7 and 3.5 Hz, H-1), 3.91–3.95 (1H, m, H-2), 4.09–4.10 (2H, m, H-6'), 4.24 (1H, td, J=6.5 and 1.1 Hz, H-5'), 5.14–5.17 (2H, m, H-1' and H-2'), 5.34–5.39 (1H, m, H-3'), 5.49 (1H, dd, J=3.3 and 1.1 Hz, H-4'), 5.53–5.60 (2H, m, H-3 and H-4), 5.93–5.99 (1H, m, H-5), 7.45–8.06 (5H, 3m, —C$_6$H$_5$).

$^1$H NMR 400 MHz (CDCl$_3$) δ(ppm) β-anomer: 0.89 (3H, t, J=7.0 Hz, —CH$_3$), 1.25 (20H, br s, —(CH$_2$)$_{10}$—), 1.39 (2H, m, —CH$_2$—), 2.00, 2.03, 2.11, 2.16 (4×3H, 4s, 4×—OCOCH$_3$), 2.09 (2H, m, =CH—CH$_2$), 3.58–3.63 (1H, m, H-1), 3.89–3.97 (3H, m, H-1, H-5' and H-2), 4.11 (1H, dd, J$_{AB}$=11.2 and J$_{AX}$=6.7 Hz, H-6'), 4.14 (1H, dd, J$_{AB}$=11.2 and J$_{BX}$=6.7 Hz, H-6'), 4.51 (1H, d, J=7.9 Hz, H-1'), 5.02 (1H, dd, J=10.5 and 3.4 Hz, H-3'), 5.42 (1H, dd, J=10.5 and 7.9 Hz, H-2'), 5.39 (1H, d, J=3.4 Hz, H-4'), 5.53–5.62 (2H, m, H-3 and H-4), 5.94 (1H, dt, J=14.3 and 6.9 Hz, H-5), 7.45–8.08 (5H, 3m, —C$_6$H$_5$).

G. (2S, 3R, 4E)-2-Azido-3-benzoyloxy-1-(α-D-galactopyranosyloxy)-4-octadecene

Procedure A.

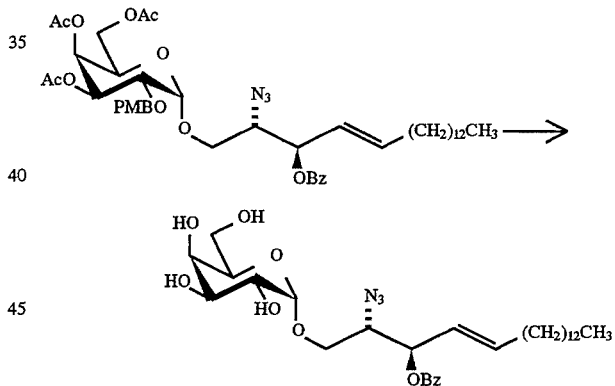

A solution of (2S, 3R, 4E)-2-azido-3-benzoyloxy-1-(2-O-p-methoxybenzyl-3,4,6-tri-O-acetyl-α-D-galactopyranosyloxy)-4-octadecene (1.27 g, 1.52 mmol) in methanol (25 mL) and dry dichloromethane (10 mL) in methanol (25 mL) and dry dichloromethane (10 mL) was treated with a solution of sodium methoxide (0.8 mL, 0.16 mmol, 0.2M) at 0°–5° C. and under argon. The mixture was stirred for 7 hours then Dowex 50W-X resin (≈2 g) was added and stirred until the pH reached ≈7. The resin was filtered and the mixture was evaporated under vacuum. The resulting residue was dissolved in dichloromethane (40 mL) and this solution was treated with trifluoroacetic acid (5 mL) at 0°–5° C. for 30 minutes. The mixture was evaporated under vacuum and co-evaporated with toluene. The residue was purified by silica gel chromatography (3×12 cm, 50% to 100% ethyl acetate/toluene) and afforded the title compound (0.782 g, 87%).

Procedure B.

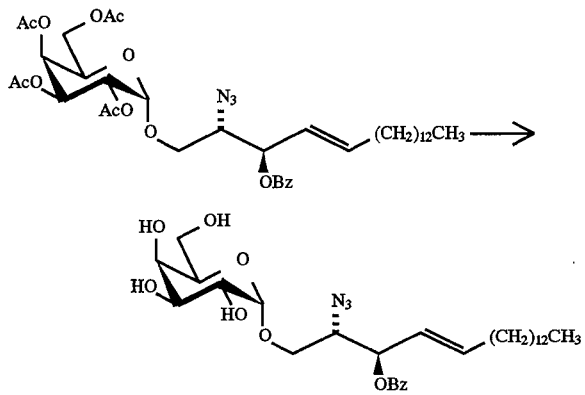

A solution of (2S,3R,4E)-2-azido-3-benzoyloxy-1-(2,3,4,6-tetra-O-acetyl-α-D-galactopyranosyloxy)-4-octadecene (1.0 g, 1.32 mmol) in dichloromethane (10 mL) was added slowly to a freshly prepared solution of sodium (0.608 g, 26.4 mmol) in methanol (15 mL) at −40° C. and under argon. The temperature of the cooling bath was allowed to reach −25° C. over a 1.5 hours period. The reaction mixture was cooled down to −40° C. and neutralized with a solution of acetic acid (1.5 mL, 26.4 mmol) in dichloromethane (2 mL). The mixture was concentrated under vacuum, giving a residue which was dissolved in dichloromethane (25 mL). The residual solid (sodium acetate) was filtered and washed with dichloromethane (5×10 mL) The combined filtrate and washings were evaporated and the residue was purified by silica gel chromatography (20 g, 0% to 35% methanol/dichloromethane) and afforded the title compound (0.545 g, 85%).

IR (nujol) $v_{max}$ (cm$^{-1}$): 3600–3060 (O—H), 2930, 2860 (C—H), 2100 (—N$_3$).

$^1$H NMR 400 MHz (CDCl$_3$), δ(ppm): 0.89 (3H, t, J=6.8 Hz, —CH$_3$), 1.2–1.4 (22H, broad, —(CH$_2$)$_{11}$—), 2.09 (2H, m, =CH—CH$_2$—), 2.50 (broad, —OH), 3.57 (1H, dd, J=10.4 and 6.2 Hz, H-1), 3.7–4.1 (7H, m, H-2', H-3', H-5', H-6', H-2 and H-1), 4.15 (1H, s, H-4'), 4.94 (1H, s, H-1'), 5.61 (1H, dd, J=15.3 and 8.0 Hz, H-4), 5.72 (1H, dd, J=8.0 and 6.0 Hz, H-3), 5.98 (1H, dt, J=15.3 and 7.0 Hz, H-5), 7.45–8.07 (5H, 3m, benzoate).

Procedure C.

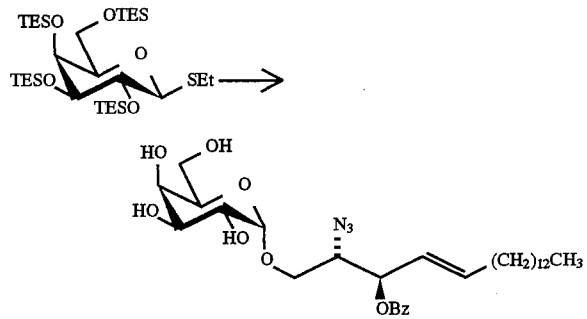

A solution of ethyl 1-thio-β-D-galactopyranoside (4.48 g, 19.98 mmol) in dry N,N-dimethylformamide (200 mL) was treated with imidazole (6.8 g, 99.88 mmol), chlorotriethylsilane (16.8 ml, 99.88 mmol), and 4-N,N-dimethylaminopyridine (80 mg) and stirred at 22° C. for 72 hours. The reaction mixture was then diluted with cold water (200 ml) and extracted with hexane (700 ml). The organic phase was washed with cold water (500 ml), brine, dried over anhydrous magnesium sulfate and evaporated. The residual oil was purified by chromatography on silica gel (6.5×12.5 cm, 0–50% toluene/hexane) to give 11.81 g (87%) of ethyl 2,3,4,6-tetra-O-triethylsilyl-1-thio-β-D-galactopyranoside as an oil.

[α]$_D^{22}$: −21° (c 1.0, CHCl$_3$)

IR (Na Cl film) $v_{max}$ (cm$^{-1}$): 1100 (broad, Si—O).

$^1$H NMR 200 MHz (CDCl$_3$) δ(ppm): 0.4–0.8 (24H, m, SiCH$_2$), 0.8–1.1 (36H, m, SiCH$_2$CH$_3$), 1.23 (3H, t, J=7.4 Hz, SCH$_2$CH$_3$), 2.65 (2H, m, SCH$_2$CH$_3$), 3.34 (1H ,m, H-6), 3.42 (1H, dd, J=2.1 and J=8.5 Hz, H-3), 3.65 (2H, m, H-5 and H-6 overlapping) 3.82 (1H, t, J=8.5 Hz, H-2), 3.93 (1H, broad s, H-4), 4.2 (1H, d, J=8.5 Hz, H-1).

A solution of (2S,3R,4E)-2-azido-3-benzoyloxy-4-octadecen-1-ol (83 mg, 0.19 mmol), ethyl 2,3,4,6-tetra-O-triethylsilyl-1-thio-β-D-galactopyranoside (171 mg, 0.25 mmol) and 2,6-di-tert-butyl-4 methylpyridine (119 mg, 0.577 mmol) in a mixture of ethyl ether (1.5 mL) and dichloromethane (1.5 mL) was stirred for 30 minutes at 22° C. with powdered 4A molecular sieves (100 mg). Then dimethyl(methylthio)-sulfonium triflate (95 mg, 0.366 mmmol)was added and the resulting mixture was stirred for 1 hour. Triethylamine (0.5 mL) was added and stirring was continued for another 20 minutes. The reaction mixture was then filtered, diluted with hexane, washed with diluted sodium bicarbonate, brine, dried over anhydrous magnesium sulfate and concentrated. Filtration of the residue on silica-gel (0–80% toluene-hexane) gave the intermediate tetrasilyl derivative (0.2 g). This material was dissolved in dichloromethane (5 mL) and treated with 90% aqueous trifluoroacetic acid (0.25 mL) at 22° C. for 1 hour. After dilution with dichloromethane, the reaction mixture was washed with saturated sodium bicarbonate, brine, dried over anhydrous magnesium sulfate and evaporated. $^1$H NMR of this crude material indicated a mixture of α and β anomers in a 93:7 ratio. Chromatography on silica gel (1.4×8 cm, elution 0–10 % methanol-dichloromethane) gave the title compound (85 mg, 75%) as a glassy solid which was identical by $^1$H NMR to the product prepared in the above Procedure B.

H. (2S,3R,4E)-2-Azido-3-benzoyloxy-1-(4,6-O-benzylidene-α-D-galactopyranosyloxy)-4-octadecene

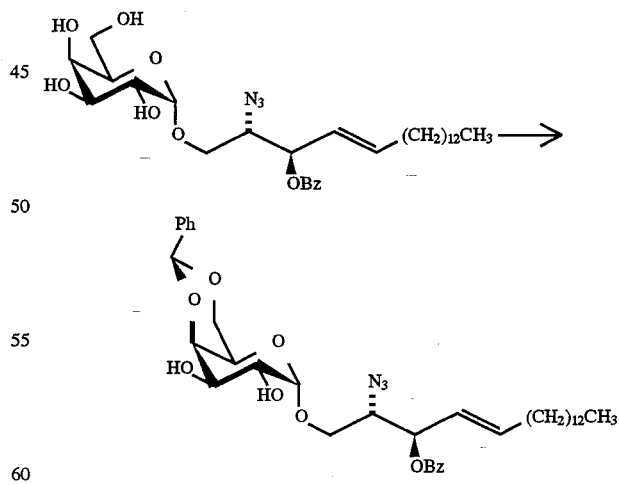

Benzaldehyde dimethylacetal (0.28 mL, 1.87 mmol) followed by para-toluenesulfonic acid (15 mg) were added to a stirred solution of (2S,3R,4E)-2-azido-3-benzoyloxy-1-(α-D-galactopyranosyloxy)-4-octadecene (0.549 g, 0.928 mmol) in acetonitrile (15 mL) at 22° C. The mixture was stirred for 45 minutes, then triethylamine (≈0.5 mL) was added and the mixture was evaporated under vacuum. The residue was purified by silica gel chromatography (72 g, 20% acetone/toluene) and afforded the title compound (0.512 g, 81%) as a solid.

$[\alpha]_D^{22}$: +36.0 (c=1.0, CHCl$_3$).

IR (KBr) $v_{max\ (cm^{-1})}$: 3380–3280 (N—H and O—H), 2925, 2860 (C—H), 2130 (N$_3$), 1710 (C=O ester);

$^1$H NMR 400 MHz (CDCl$_3$) δ(ppm): 0.89 (3H, t, J=76.9 Hz, —CH$_3$), 1.26–1.42 (22H, br s,—(CH$_2$)$_{11}$—), 2.11 (2H, m, =CH—C$\underline{H}_2$—), 3.59 (1H, dd, J=10.4 and 76.3 Hz, H-1), 3.82 (1H, br s, H-5'), 3.88 (1H, m, H-2), 3.93–3.98 (3H, m, H-1, H-2' and H-3'), 4.11 (1H, dd, J=12.6 and 1.5 Hz, H-6'), 4.28–4.32 (2H, m, H-4' and H-6'), 5.02 (1H, s, H-1'), 5.58 (1H, s, —O—CH—O—), 5.62 (1H, dd, J=15.2 and 8.1 Hz, H-4), 5.73 (1H, dd, J=8.1 and 5.7 Hz, H-3), 5.98 (1H, dt, J=15.2 and 6.9 Hz, H-5), 7.37–8.08 (10H, 4m, 2×—C$_6$H$_5$).

I. (2S,3R,4E)-2-Azido-3-benzoyloxy-1-(2,3-di-O-benzoyl-4,6-O-benzylidene-α-D-galactopyranosyloxy)-4-octadecene

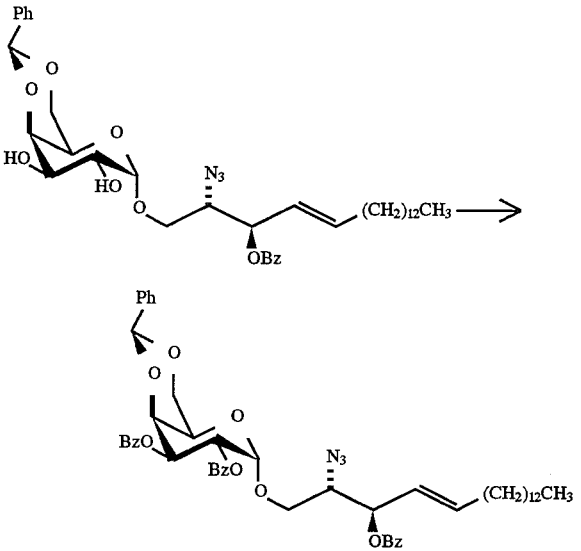

A solution of (2S,3R,4E)-2-azido-3-benzoyloxy-1-(4,6-O-benzylidene-α-D-galactopyranosyloxy)-4-octadecene (1.26 g, 1.85 mmol) in pyridine (15 mL) was cooled down to 5° C. under argon. Benzoyl chloride (0.8 mL, 6.89 mmol) was added dropwise to this solution followed by 4-dimethylaminopyridine (=40 mg) and this mixture was stirred at 5° C. for 18 hours. The mixture was treated with methanol (5 mL) at 5° C. and stirred for 0.5 hour. This reaction mixture was diluted with ethyl acetate (300 mL), washed with a 1M cold aqueous solution of sodium bicarbonate, water and brine. The organic layer was dried over anhydrous magnesium sulfate, filtered and concentrated. The residue was purified by silica gel chromatography (80 g, 0% to 2% ethyl acetate/toluene) and afforded the title compound (1.64 g, 100%) as a pale yellow oil.

IR (CH$_2$Cl$_2$) $v_{max}$ (cm$^{-1}$): 3050, 2930, 2855 (C—H), 2100 (—N$_3$), 1730 (C=O), 1265 (C—O);

$^1$H NMR 400 MHz (CDCl$_3$) δ(ppm): 0.89 (3H, t, J=7.0 Hz, —CH$_3$), 1.25 (20 H, br s, —(CH$_2$)$_{10}$—), 1.37 (2H, m, —CH$_2$—), 2.06 (2H, m, =CH—C$\underline{H}_2$—), 3.59 (1H, dd, J=10.4 and 7.4 Hz, H-1), 3.91–3.99 (3H, m, H-1, H-5' and H-2), 4.16 (1H, dd, J=12.6 and 1.6 Hz, H-6'), 4.36 (1H, dd, J=12.6 and 1.5 Hz, H-6'), 4.70 (1H, dd, J=3.2 and 1.0 Hz, H-4'), 5.43 (1H, d, J=3.3 Hz, H-1'), 5.53–5.61 (3H, m, H-3, H-4 and —O—CH—O—), 5.79 (1H, dd, J$_{AB}$=10.8 and J$_{AX}$=3.3 Hz, H-2' or H-3'), 5.84 (1H, dd, J$_{AB}$=10.8 and J$_{BX}$=3.3 Hz, H-2' or H-3'), 5.92 (1H, dt, J=14.4 and 6.9 Hz, H-5), 7.33–8.03 (20H, 2m, 4×—C$_6$H$_5$).

J. (2S,3R,4E)-3-Benzoyloxy-2-hexadecanoylamino-1-(2,3-di-O-benzoyl-4,6-O-benzylidene-α-D-galactopyranosyloxy)-4-octadecene

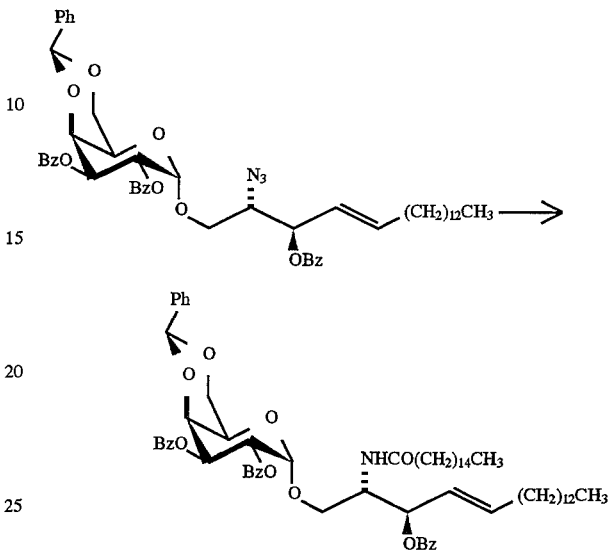

Hydrogen sulfide was bubbled into a solution of (2S,3R,4E)-2-azido-3-benzoyloxy-1-(2,3-di-O-benzoyl-4,6-O-benzylidene-α-D-galactopyranosyloxy)-4-octadecene (300 mg, 0.34 mmol) in pyridine (13 mL) and water (4 mL) at 22° C. for 15 minutes. The mixture was then tightly closed and stirred for 6 hours. Hydrogen sulfide was again bubbled in for 15 minutes and the mixture was stirred at 22° C. overnight. The next day, the same procedure is repeated with a stirring of 7 hours. The solvents were then evaporated and the residue was dissolved in toluene. This solution was evaporated and the residue was dissolved in tetrahydrofuran (15 mL). To this stirred solution was added an aqueous solution of sodium acetate (50%, 1.8 mL) followed by the dropwise addition of a solution of hexadecanoyl chloride (0.1 mL, 0.34 mmol) in tetrahydrofuran (0.5 mL) at room temperature. Since the reaction seemed to be stopped, the same procedure was repeated with a solution of sodium acetate in water (50% 0.6 mL) and hexadecanoyl chloride (33 mL, 0.11 mmol). The mixture was stirred at 22° C. for 0.5 hour, then diluted with ethyl acetate (45 mL) and washed with a cold aqueous solution of sodium bicarbonate (1M, 2×15 mL), water (2×15 mL) and brine (2×15 mL). The organic layer was dried over anhydrous magnesium sulfate, filtered and concentrated. The residue was purified by silica gel chromatography (20 g, 0% to 35% ethyl acetate/hexane) and afforded the title compound (345 mg, 92%) as a white solid. IR (CH$_2$Cl$_2$)$v_{max}$ (cm$^{-1}$): 3050, 2930, 2855 (C—H), 1720 (C=O esters), 1675 (C=O amide), 1265 (C—O);

$^1$H NMR 400 MHz (CDCl$_3$) δ(ppm): 0.89 (6H, t, J=7.0 Hz, 2×—CH$_3$), 1.23–1.30 (44H, m, —(CH$_2$)$_{10}$— and —(CH$_2$)$_{12}$—), 1.56–1.67 (4H, m, —(CH$_2$)$_2$—), 1.99 (2H, m, =CH—C$\underline{H}_2$—), 2.10–2.18 (2H, m, —NHCOC$\underline{H}_2$—), 2.36 (1H, t, J=7.5 Hz, —NH—), 3.75 (1H, dd, J=10.9 and 5.2 Hz, H-1), 3.90–3.94 (2H, m, H-1 and H-5'), 4.09 (1H, dd, J=12.6 and 1.4 Hz, H-6'), 4.32 (1H, dd, J=12.6 and 1.2 Hz, H-6'), 4.52–4.57 (1H, m, H-2), 4.66 (1H, d, J=3.3 Hz, H-4'), 5.37 (1H, d, J=3.3 Hz, H-1'), 5.46–5.56 (3H, m, H-4, H-3 and —O—CH—O—), 5.70–5.75 (1H, m overlapping H-2' and H-3', H-5), 5.79 (1H, dd, J$_{AB}$=10.8 and J$_{AX}$=3.3 Hz, H-2' or H-3'), 5.84 (1H, dd, J$_{AB}$=10.8 and J$_{BX}$=3.3 Hz, H-2' or H-3'), 7.32–8.03 (20H, 3m, 4×—C$_6$H$_5$).

K. (2S,3R,4E)-3-Benzoyloxy-2-hexadecanoylamino-1-(2,3-di-O-benzoyl-α-D-galactopyranosyloxy)-4-octadecene

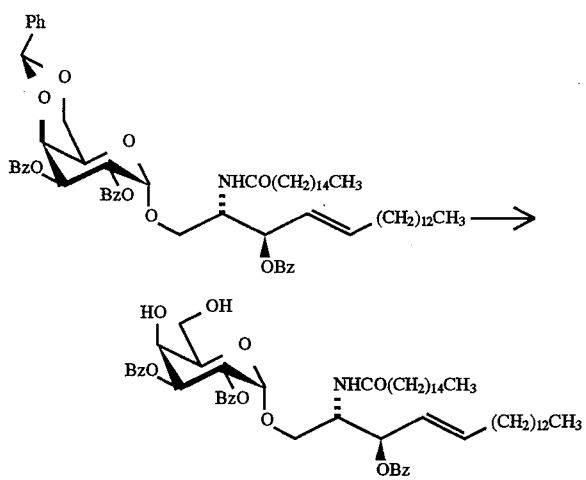

Trifluoroacetic acid (90%, 0.5 mL) was added to a stirred solution of (2S,3R,4E)-3-benzoyloxy-2-hexadecanoylamino-1-(2,3-di-O-benzoyl-4,6-O-benzylidene-α-D-galactopyranosyloxy)-4-octadecene (340 mg, 0.31 mmol) in dichloromethane (15 mL) at 5° C. The mixture was stirred for 0.5 hour at 5° C. and at 22° C. for 1 hour. Trifluoroacetic acid (same quantity) was added again and the reaction mixture was stirred for one more hour at 22° C. The mixture was diluted with ethyl acetate (30 mL) and washed with a cold aqueous solution of sodium bicarbonate (1M, 2×15 mL), water (2× 15 mL) and brine (15 mL). The organic layer was dried over anhydrous magnesium sulfate, filtered and concentrated. The residue was purified by silica gel chromatography (15 g, 0% to 60% ethyl acetate/hexane) and afforded the title compound (238 mg, 76%) as a white solid.

IR (CH$_2$Cl$_2$) $\nu_{max}$ (cm$^{-1}$): 3050, 2930, 2860 (C—H), 1725 (C=O esters), 1675 (C=O amide), 1265 (C—O);

$^1$H NMR 400 MHz (CDCl$_3$) δ(ppm): 0.89 (6H, t, J=6.8 Hz, 2× CH$_3$), 1.23–1.31 (44H, m, —(CH$_2$)$_{10}$— and —(CH$_2$)$_{12}$—), 1.56–1.61 (4H, m, —(CH$_2$)$_2$—), 1.99 (2H, m, =CH—CH$_2$—), 2.15 (2H, m, —NHCOCH$_2$—), 2.44 (1H, br s, —OH), 2.69 (1H, d, J=2.9 Hz, —OH), 3.79 (1H, dd, J=11.4 and 5.5 Hz, H-1), 3.88 (1H, dd overlapping H-6', J=11.4 and 3.9 Hz, H-1), 3.92–3.99 (2H, m, H-6'), 4.07 (1H, t, J=4.7 Hz, H-5'), 4.44 (1H, br s, H-4'), 4.53–4.60 (1H, m, H-2), 5.33 (1H, d, J=3.1 Hz, H-1'), 5.46–5.55 (2H, m, H-4 and H-3), 5.65–5.80 (4H, m, H-5, H-2', H-3' and —NH—), 7.33–8.02 (15H, 2m, 3×—C$_6$H$_5$).

L. (2S,3R,4E)-3-Benzoyloxy-2-hexadecanoylamino-1-[2,3-di-O-benzoyl-4,6-di-O-(sodium oxysulfonyl)-α-D-galactopyranosyloxy]-4-octadecene

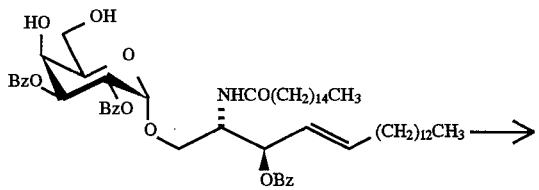

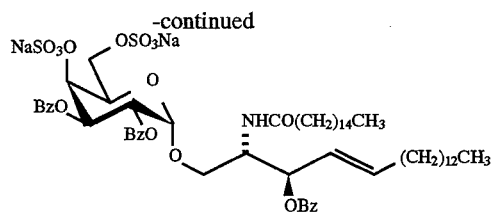

Sulfur trioxide trimethylamine complex (320 mg, 2.3 mmol) was added to a stirred solution of (2S,3R,4E)-3-benzoyloxy-2-hexadecanoylamino-1-(2,3-di-O-benzoyl-α-D-galactopyranosyloxy)-4-octadecene (230 mg, 0.23 mmol) in dry dimethylformamide (20 mL) at 22° C. and under argon. This mixture was heated up to 80°–85° C. for one hour, then sulfur trioxide trimethylamine complex (160 mg, 1.15 mmol) was added again. After 1 hour, the reaction mixture was cooled down to 5° C. and treated with an aqueous solution of sodium bicarbonate (1M, until the pH raises 8–9) and this solution was stirred for 0.75 hour. The solvents were evaporated under vacuum and the residue was dissolved in dichloromethane/methanol (8:2). Sodium bicarbonate was filtered on Celite and the filtrate was evaporated. The residue was purified by silica gel column chromatography (25 g, 0% to 30% methanol/chloroform) and further on silica gel plate (chloroform/methanol, 8:2) and afforded the title compound (233 mg, 83%) as a pale beige solid.

IR (nujol) $\nu_{max}$ (cm$^{-1}$): 3700–3200 (N—H), 2920, 2850 (C—H), 1720 (C=O esters), 1655 (C=O amide);

$^1$H NMR 400 MHz (DMSO-d$_6$) δ(ppm): 0.84 (6H, t, J=6.8 Hz, 2×—OH$_3$), 1.13–1.52 (48H, m, —(CH$_2$)$_{11}$— and —(CH$_2$)$_{13}$—), 1.79–2.00 (4H, 2m, =CH—CH$_2$— and —NHCOCH$_2$—), 3.55 (1H, dd, J=10.5 and 7.1 Hz, H-1), 3.84–3.91 (1H, m overlapping H-6', H-5'), 3.87 (1H, dd, J=12.1 and 8.4 Hz, H-6'), 4.10 (1H, dd, J=12.1 and 2.3 Hz, H-6'), 4.27–4.33 (1H, m overlapping H-1, H-2), 4.32 (1H, d, J=7.1 Hz, H-1), 4.75 (1H, d, J=3.1 Hz, H-4'), 5.13 (1H, d, J=3.4 Hz, H-1'), 5.40–5.58 (4H, m, H-2', H-3', H-3 and H-4), 5.71 (1H, dt, J=15.1 and 6.7 Hz, H-5), 7.35–7.93 (15H, 3m, 3×—C$_6$H$_5$).

EXAMPLE 2

(2S,3R,4E)-3-Hydroxy-2-hexadecanoylamino-1-[4,6-di-O-(sodium oxysulfonyl)-α-D-galactopyranosyloxy]-4-octadecene

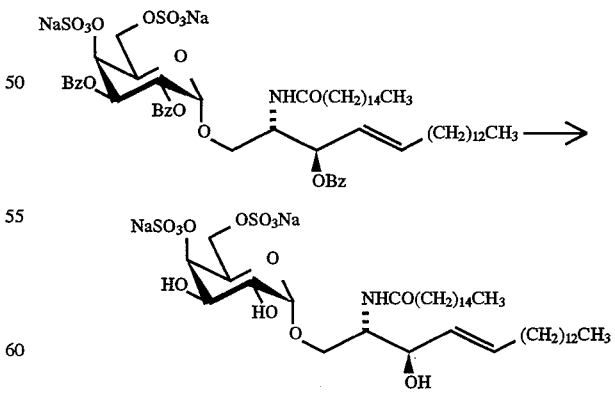

A freshly prepared solution of sodium methoxide in methanol (0.98M, 2 mL, 1.96 mmol) was added to a stirred solution of (2S,3R,4E)-3-benzoyloxy-2-hexadecanoylamino-1-[2,3-di-O-benzoyl-4,6-di-O-(sodium oxysulfonyl)-α-D-galactopyranosyloxy]-4-octadecene (120 mg, 0.098 mmol) in dichloromethane (1 mL) and methanol (5 mL) at 22° C. The reaction mixture was stirred for 1 hour then the same quantity of sodium methoxide was added again and this mixture was stirred for one more hour. After neutralization with Dowex 50W8 (H⁺) resin, water, the mixture was filtered and the resin was washed with a mixture of dichloromethane/methanol (1:1, 3×5 mL). This solution was treated with Rexyn 102 (Na⁺) resin over a period of 1 hour, then filtered and the solvents were evaporated under vacuum. The same procedure previously described was applied two more times on the residue obtained. Finally, the residue was purified on silica gel plates (20% to 30% methanol/water/chloroform 35:5:60) and afforded the title compound (19 mg, 21%), as an off-white solid.

IR (nujol) $v_{max}$ (cm$^{-1}$): 3600–3100 (N—H and O—H), 2930, 2860 (C—H), 1630 (C=O amide);

$^1$H NMR 400 MHz (DMSO-d$_6$) δ(ppm): 0.84 (6H, t, J=6.8 Hz, 2×—CH$_3$), 1.22–1.44 (48H, m, —(CH$_2$)$_{11}$— and —(CH$_2$)$_{13}$—), 1.92 (2H, m, =CH—CH$_2$—), 2.04 (2H, t, J=7.3 Hz, —NHCOCH$_2$—), 3.41 (1H, ddd, H-2'), 3.49 (1H, dd, J=10.5 and 3.3 Hz, H-1), 3.61 (1H, dd, J=10.5 and 3.5 Hz, H-1), 3.68 (1H, dd, J=10.2 and 3.9 Hz, H-3'), 3.72 (1H, dd, J=11.4 and 8.5 Hz, H-6'), 3.86 (1H, dd, J=11.4 and 2.4 Hz, H-6'), 3.89–3.95 (2H, m, H-3 and H-5'), 4.10 (1H, br s, —OH), 4.38 (1H, d, J=2.9 Hz, H-4'), 4.67 (1H, d, J=3.6 Hz, H-1'), 4.84 (1H, br s, —OH), 4.91 (1H, d, J=7.4 Hz, —OH), 5.33 (1H, dd, J=15.3 and 6.9 Hz, H-4), 5.51 (1H, dt, J=15.3 and 6.7 Hz, H-5), 7.43 (1H, d, J=9.3 Hz, —NH—).

EXAMPLE 3

(2S,3R, 4E)-3-Benzoyloxy-2-(cis-15-tetracosenoylamino)-1-[2,3-di-O-benzoyl-4,6-di-O-(sodium oxysulfonyl]-α-D-galactopyranosyloxy)-4-octadecene A. (2S,3R,4E)-3-Benzoyloxy-2-(cis-15-tetracosenoylamino)-1-(2,3,4,6-tetra-O-acetyl-α-D-galactopyranosyloxy)-4-octadecene

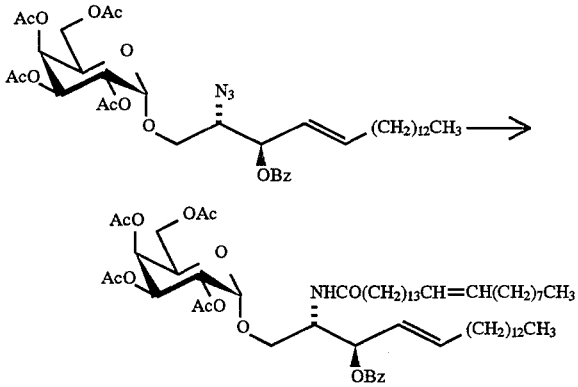

A solution of (2S,3R,4E)-2-azido-3-benzoyloxy-1-(2,3,4, 6-tetra-O-acetyl-α-D-galactopyranosyloxy)-4-octadecene described in Example 1-F procedure B (1.5 g, 2.0 mmol) in pyridine (85 mL) and water (17 mL) was saturated with hydrogen sulfide and stirred at 22° C. for 24 hours. The solvents were evaporated under vacuum and the residue dried by co-evaporation with toluene. The residue obtained was dissolved in dichloromethane (170 mL) under argon and treated with nervonic acid (1.47 g, 4.0 mmol) and 1-ethyl-3-(3-dimethylaminopropyl)carbodiimide hydrochloride (1.17 g, 6.1 mmol) at room temperature. The resulting mixture was stirred for 18 hours, then diluted with dichloromethane (1.3 L) and washed with water (650 mL) and brine (650 mL). The organic phase was dried over anhydrous magnesium sulfate, filtered and concentrated. The residue was purified by silica gel chromatography (180 g, 0% to 20% ethyl acetate/toluene) and afforded the title compound (1.58 g, 73%) as a colorless oil.

[α]$_D^{22}$: +66.2° (c=1.0, CHCl$_3$).

IR (neat) $v_{max}$ (cm$^{-1}$): 3500–3150 (O—H and N—H), 2930, 2860 (C—H), 1740 (C=O esters), 1650 (C=O amide).

$^1$H NMR (CDCl$_3$) δ(ppm): 0.89 (6H, t, J=6.7 Hz, 2×—CH$_3$), 1.24–1.36 (54H, m, —(CH$_2$)$_{10}$—, —(CH$_2$)$_{11}$— and —(CH$_2$)$_6$—), 1.60–1.66 (2H, m, —CH$_2$—), 2.01, 2.03, 2.11 and 2.14 (4×3H, 4s, 4×—OCOCH$_3$), 2.00–2.09 (6H, m overlapping —OCOCH$_3$, 3×=CH—CH$_2$—), 2.16–2.30 (2H, m, —NHCOCH$_2$—), 3.65 (1H, dd, J=10.6 and 3.2 Hz, H-1), 3.79 (1H, dd, J=10.6 and 3.3 Hz, H-1), 4.02 (1H, dd, J=11.2 and 7.1 Hz, H-6'), 4.10 (1H, dd, J=11.2 and 5.8 Hz, H-6'), 4.17 (1H, brt, H-5'), 4.54 (1H, m, H-2), 4.98 (1H, d, J=3.7 Hz, H-1'), 5.15 (1H, dd, J=11.0 and 3.7 Hz, H-2'), 5.32–5.40 (3H, m, cis-CH=CH— and H-3'), 5.45 (1H, d, J=2.5 Hz, H-4'), 5.48–5.59 (2H, m, H-3 and H-4), 5.73 (1H, d, J=9.4 Hz, —NH—), 5.91 (1H, dt, J=14.8 and 6.8 Hz, H-5), 7.43–8.02 (5H, 3m, —C$_6$H$_5$).

Anal. Calcd. for C$_{63}$H$_{103}$NO$_{13}$: C, 69.90; H, 9.59; N, 1.29. Found: C, 69.83; H, 9.47; N,1.51.

B. (2S,3R,4E)-3-Benzoyloxy-2-(cis-15-tetracosenoylamino)-1-(α-D-galactopyranosyloxy)-4-octadecene

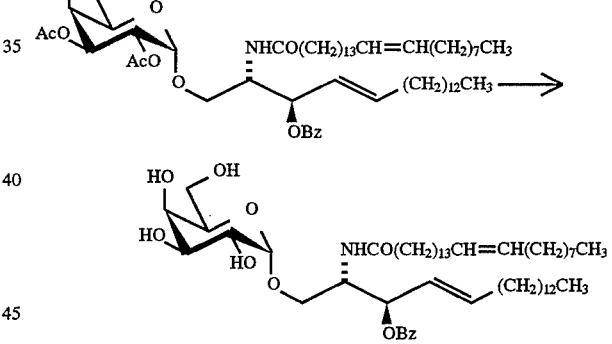

A solution of sodium methoxide in methanol (0.2M, 0.73 mL) was added to a stirred solution of (2S,3R,4E)-3-benzoyloxy-2-(cis-15-tetracosenoylamino)-1-(2,3, 4,6-tetra-O-acetyl-α-D-galactopyranosyloxy)-4-octadecene (1.58 g, 1.46 mmol) in methanol (36 mL) at 5° C. and under argon. The solution was stirred for 5 hours at 5° C. Amberlite IRC-50 (H⁺) resin was added to this mixture and the stirring was continued until the pH of the solution became neutral. The reaction mixture was filtered and concentrated under vacuum. The residue was purified by silica gel chromatography (135 g, 0% to 20% methanol/chloroform) and afforded the title compound (1.20 g, 84%) as an oil.

[α]$_D^{22}$: +42.8° (c=1.0, CHCl$_3$).

IR (KBr) $v_{max}$ (cm$^{-1}$): 3600–3200 (O—H and N—H), 2930, 2860 (C—H), 1725 (C=O esters), 1650 (C=O amide).

$^1$H NMR (CDCl$_3$) δ(ppm): 0.89 (6H, t, J=6.7 Hz, 2×—CH$_3$), 1.26–1.28 (54H, m, —(CH$_2$)$_{10}$—, —(CH$_2$)$_{11}$— and —(CH$_2$)$_6$—), 1.60–1.63 (2H, m, —CH$_2$—), 2.00–2.08 (6H, m, 3×=CH—CH$_2$—), 2.18–2.22 (2H, m, —NHCOC $H_2$—), 3.64 (1H, dd, J=10.6 and 5.4 Hz, H-1), 3.79–3.97 (6H, 2m, H-1, H-6', H-5', H-3' and H-2'), 4.10 (1H, br s, H-4'), 4.50–4.57 (1H, m, H-2), 4.88 (1H, br s, H-1'), 5.32–5.40 (2H, m, cis-CH=CH—), 5.53 (1H, dd, J=15.3 and 7.2 Hz, H-4), 5.64 (1H, t, J=7.2 Hz, H-3), 5.89 (1H, dt, J=15.3 and 6.8 Hz, H-5), 5.96 (1H, br s, —NH—), 7.45–8.04 (5H, 3m, —$C_6H_5$).

Anal. Calcd. for $C_{55}H_{95}NO_9$: C, 72.25; H, 10.47; N, 1.53. Found: C, 72.01; H, 10.38; N, 1.79.

C. (2S,3R,4E)-3-Benzoyloxy-2-(cis-15-tetracosenoylamino)-1-(4,6-O-benzylidene-α-D-galactopyranosyloxy)-4-octadecene

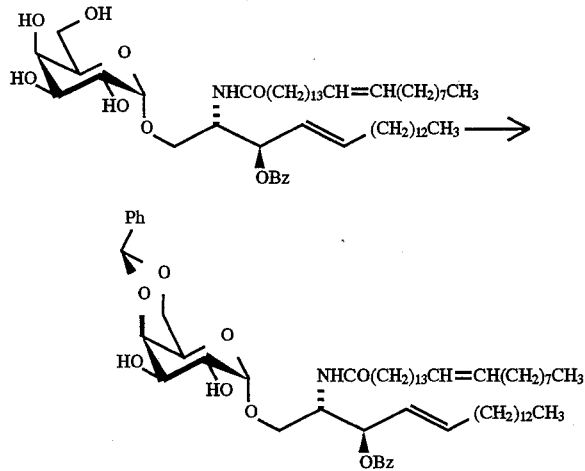

Benzaldehyde (6 mL, large excess) was added to a solution of (2S,3R,4E)-3-benzoyloxy-2-(cis-15-tetracosenoyl-amino)-1-(α-D-galactopyranosyloxy)-4-octadecene (555 mg, 0.607 mmol) in formic acid (6 mL) at 22° C. and under argon. This mixture was stirred for 1.75 hours, then diluted with chloroform (60 mL) and washed with a cold saturated solution of sodium bicarbonate (70 mL) and brine (30 mL). The organic layer was dried over anhydrous magnesium sulfate, filtered and concentrated. The residue was purified by silica gel chromatography (36 g, 50% to 80% ethyl acetate/toluene) and afforded the title compound (461 mg, 76%) as a white solid.

$[\alpha]_D^{22}$: −15.1° (c=1.0, CHCl$_3$).

IR (KBr) $\nu_{max}$ (cm$^{-1}$): 3600–3200 (O—H and N—H), 2930, 2860 (C—H), 1725 (C=O esters), 1630 (C=O amide).

$^1$H NMR (CDCl$_3$) δ(ppm): 0.89 (6H, t, J=6.7 Hz, 2×—CH$_3$), 1.25–1.64 (58H, m, —(CH$_2$)$_{11}$—, —(CH$_2$)$_{11}$—, —(CH$_2$)$_6$— and =CH—CH$_2$—), 2.00–2.08 (4H, m, 2×=CH—CH$_2$—), 2.15–2.23 (2H, m, —NHCOCH$_2$—), 2.43 and 2.52 (2×1H, 2 br s, 2×—OH), 3.65 (1H, dd, J=10.7 and 5.6 Hz, H-1), 3.75 (1H, s, H-5'), 3.93–3.96 (3H, m, H-1, H-2' and H-3'), 4.07 (1H, dd, J=12.5 and 1.2 Hz, H-6'), 4.26 (1H, dd overlapping H-4', J=12.5 and 3.1 Hz, H-6'), 4.24–4.28 (1H, br s, H-4'), 4.55 (1H, m, H-2), 4.96 (1H, s, H-1'), 5.36 (2H, m, cis-CH=CH—), 5.51–5.56 (1H, m, overlapping —O—CH—O—, H-4), 5.55 (1H, s, —O—CH—O—), 5.64 (1H, t, J=6.9 Hz, H-3), 5.81 (1H, d, J=9.1 Hz, —NH—), 5.89 (1H, dt, J=15.3 and 6.9 Hz, H-5), 7.36–8.04 (10H, 4m, 2×—C$_6$H$_5$).

Anal. Calcd. for $C_{62}H_{99}NO_9$: C, 74.29; H, 9.95; N, 1.40. Found: C, 73.94; H, 9.81; N, 1.50.

D. (2S,3R,4E)-3-Benzoyloxy-2-(cis-15-tetracosenoylamino)-1-(2,3-di-O-benzoyl-4,6-O-benzylidene-α-D-galactopyranosyloxy)-4-octadecene

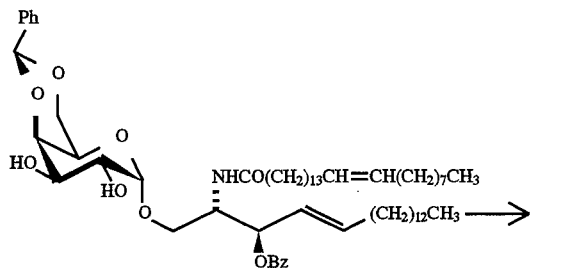

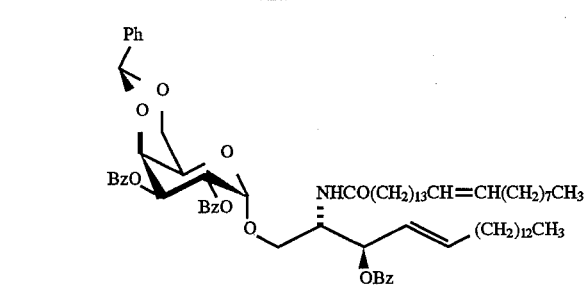

(2S,3R,4E)-3-Benzoyloxy-2-(cis-15-tetracosenoyl-amino)-1-(4,6-O-benzylidene-α-D-galactopyranosyloxy)-4-octadecene (425 mg, 0.42 mmol) was reacted by the general procedure as described in Example 1-I and afforded the title compound (332 mg, 65%) as an oil.

$[\alpha]_D^{22}$: +87.0° (c=1.0, CHCl$_3$).

IR (KBr) $\nu_{max}$ (cm$^{-1}$): 3600–3200 (O—H and N—H), 2930, 2860 (C—H), 1720 (C=O esters), 1640 (C=O amide).

$^1$H NMR (CDCl$_3$) δ(ppm): 0.89 (6H, t, J=6.7 Hz, 2×—CH$_3$), 1.23–1.28 (54H, m, —(CH$_2$)$_{11}$—, —(CH$_2$)$_{11}$— and —(CH$_2$)$_5$—), 1.56–1.61 (2H, m, —CH$_2$—), 1.96–2.04 (6H, m, 3×=CH—CH$_2$—), 2.14 (2H, m, —NHCOCH$_2$—), 3.79 (1H, dd, J=10.9 and 5.2 Hz, H-1), 3.91 (1H, dd, J=10.9 and 3.9 Hz, H-1), 3.92 (1H, s, H-5'), 4.09 (1H, dd, J=12.6 and 1.0 Hz, H-6'), 4.32 (1H, dd, J=12.6 and 0.9 Hz, H-6'), 4.55 (1H, m, H-2), 4.66 (1H, d, J=3.0 Hz, H-4'), 5.32–5.39 (3H, m, H-1' and cis-CH=CH—), 5.46–5.56 (2H, m, H-4 and H-3), 5.56 (1H, s, —O—CH—O—), 5.70–5.75 (2H, m, H-4 and —NH—), 5.77 (1H, dd, J$_{AB}$=10.8 and J$_{AX}$=3.2 Hz, H2' or H-3'), 5.80 (1H, dd, J$_{AB}$=10.8 and J$_{BX}$=3.4 Hz, H-2' or H-3'), 7.32–8.03 (10H, 3m, 2×—C$_6$H$_5$).

Anal. Calcd. for $C_{76}H_{107}NO_{11}$: C, 75.40; H, 8.91; N, 1.16. Found: C, 75.34; H, 8.81; N, 1.36.

E. (2S,3R,4E)-3-Benzoyloxy-2-(cis-15-tetracosenoyl-amino)-1-(2,3-di-O-benzoyl-α-D-galactopyranosyloxy)-4-octadecene.

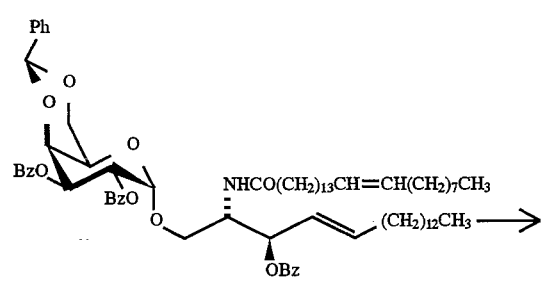

-continued

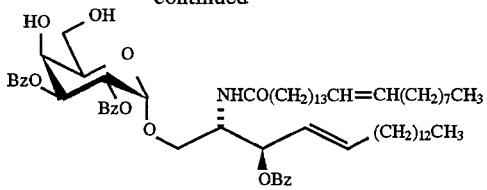

(2S,3R,4E)-3-Benzoyloxy-2-(cis-15-tetracosenoyl-amino)-1-(2,3-di-O-benzoyl-4,6-O-benzylidene-α-D-galactopyranosyloxy)-4-octadecene (317 mg, 0.262 mmol) was reacted by the general procedure as described in Example 1-K and afforded the title compound (215 mg, 74%) as an oil.

$[α]_D^{22}$: +74.0° (c=1.0, CHCl$_3$).

IR (KBr) $v_{max}$ (cm$^{-1}$): 3650–3150 (O—H and N—H), 2930, 2860 (C—H), 1725 (C=O esters), 1645 (C=O amide).

$^1$H NMR (CDCl$_3$) δ(ppm): 0.89 (6H, t, J=6.7 Hz, 2×—CH$_3$), 1.23–1.28 (54H, m, —(CZH$_2$)$_{11}$—, —(CH$_2$)$_{11}$— and —(CZH$_2$)$_5$—), 1.58–1.62 (2H, m, —CH$_2$—), 1.97–2.05 (6H, m, 3×=CH—CH$_2$—), 2.16 (2H, m, —NHCOCH$_2$—), 2.57 (1H, br s, —OH), 3.79 (1H, dd, J=11.2 and 5.5 Hz, H-1), 3.88 (1H, dd, J=11.2 and 4.0 Hz, H-1), 3.91 (1H, dd, J=11.8 and 4.2 Hz, H-6'), 3.98 (1H, dd, J=11.8 and 5.4 Hz, H-6'), 4.08 (1H, br t, H-5'), 4.45 (1H, br s, H-4'), 4.57 (1H, m, H-2), 5.33 (1H, d, J=3.1 Hz, H-1'), 5.36 (2H, m, cis-CH=CH—), 5.49 (1H, dd, J=14.5 and 7.4 Hz, H-4), 5.54 (1H, t, J=7.4 Hz, H-3), 5.68 (1H, dd, $J_{AB}$=10.7 and $J_{AX}$=2.5 Hz, H-2' or H-3'), 5.71 (1H, dd, $J_{AB}$=10.7 and $J_{BX}$=3.2 Hz, H-2' or H-3'), 5.76 (1H, dt, J=14.5 and 6.7 Hz, H-5), 5.81 (1H, d, J=9.1 Hz, —NH—), 7.33–8.02 (15H, 3m, 3×—C$_6$H$_5$).

Anal. Calcd. for C$_{69}$H$_{103}$NO$_{11}$: C, 73.83; H, 9.25; N, 1.25. Found: C, 73.61; H, 9.14; N, 1.45.

F. (2S,3R,4E)-3-Benzoyloxy-2-(cis-15-tetracosenoyl-amino)-1-[2,3-di-O-benzoyl-4,6-di-O-(sodium oxysulfonyl]-α-D-galactopyranosyloxy)-4-octadecene

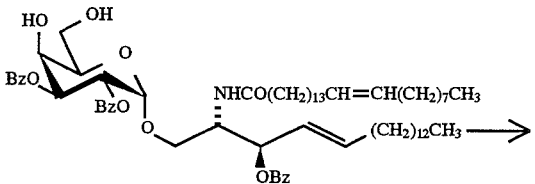

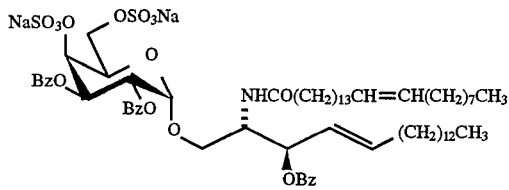

Sulfur trioxide pyridine complex (0.115 g, 0.72 mmol) was added in a solution of (2S,3R,4E)-3-benzoyloxy-2-(cis-15-tetracosenoylamino)-1-[2,3-di-O-benzoyl-α-D-galactopyranosyloxy]-4-octadecene (200 mg, 0.18 mmol) in pyridine (5 mL) at 22° C. and under argon. The reaction mixture was stirred for 2 hours at 40° C. and for 3.5 hours at 50° C., then water (5 mL) was added followed by solid sodium bicarbonate (0.2 g). The solvents were evaporated under vacuum and the residue was purified by silica gel chromatography (15 g, 5% to 20% methanol/chloroform) to give the title compound (0.222 g, 93%) as a colorless solid.

$[α]_D^{22}$: +44.2° (c=1.0, CHCl$_3$/MeOH 9:1).

IR (KBr) $v_{max}$ (cm$^{-1}$): 3700–3150 (O—H and N—H), 2930, 2860 (C—H), 1730 (C=O esters), 1640 (C=O amide).

$^1$H NMR (DMSO-d$_6$) δ(ppm): 0.82–0.89 (6H, m, 2×—CH$_3$), 1.13–1.22 (56H, m, —(CH$_2$)$_{11}$—, —(CH$_2$)$_{11}$— and —(CH$_2$)$_6$—), 1.82–1.99 (8H, 2m, 3×=CH—CH$_2$— and —NHCOCH$_2$—), 3.55 (1H, dd, J=10.3 and 7.1 Hz, H-1), 3.86–3.91 (2H, m, H-1 and H-6'), 4.12 (1H, dd, J=11.9 and 2.4 Hz, H-6'), 4.30–4.33 (2H, m, H-2 and H-5'), 4.77 (1H, d, J=2.5 Hz, H-4'), 5.13 (1H, d, J=3.3 Hz, H-1'), 5.31 (2H, m, cis-CH=CH—), 5.42 (1H, dd, $J_{AB}$=10.8 and $J_{AX}$=3.3 Hz, H-2' or H-3'), 5.49 (1H, dd, $J_{AB}$=10.8 and $J_{BX}$=3.0 Hz, H-2' or H-3'), 5.41–5.57 (1H, m overlapping H-2' and H-3', H-3), 5.54 (1H, dd, J=15.1 and 7.5 Hz, H-4), 5.72 (1H, dt, J=15.1 and 6.7 Hz, H-5), 7.35–7.92 (16H, 3m, 3×—C$_6$H$_5$ and —NH—).

EXAMPLE 4

(2S,3R,4E)-3-Hydroxy-2-(cis-15-tetracosenoylamino)-1-[4,6-di-O-(sodium oxysulfonyl)-α-D-galactopyranosyloxy]-4-octadecene

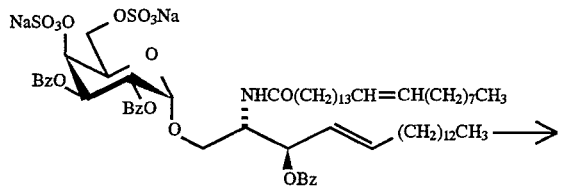

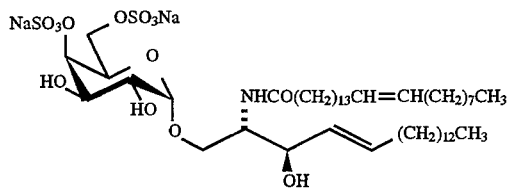

(2S,3R,4E)-3-Benzoyloxy-2-(cis-15-tetracosenoyl-amino)-1-(2,3-di-O-benzoyl-4,6-di-O-(sodium oxysulfonyl)-α-D-galactopyranosyloxy)-4-octadecene (122 mg, 0.092 mmol) was reacted by the general procedure as described in Example 2-A and afforded the title compound (71 mg, 76%) as a white solid.

IR (KBr) $v_{max}$ (cm$^-$1): 3600–3150 (O—H and N—H), 2930, 2860 (C—H), 1650 (C=O amide).

$^1$H NMR (DMSO-d$_6$) δ(ppm): 0.84 (6H, t, J=6.7 Hz, 2×—CH$_3$), 1.2–1.47 (56H, m, —(CH$_2$)$_{11}$—, —(CH$_2$)$_{11}$— and —(CH$_2$)$_6$—), 1.91–2.05 (8H, 2m, 3×=CH—CH$_2$— and —NHCOCH$_2$—), 3.41 (1H, br ddd, J=10.1 and 3.6 Hz, H-2'), 3.49 (1H, dd, J=10.5 and 3.5 Hz, H-1), 3.62 (1H, dd, J=10.5 and 3.4 Hz, H-1), 3.71 (1H, dd, J=11.4 and 8.5 Hz, H-6'), 3.65–3.73 (2H, m, overlapping H-1 and H-6', H-5' and H-3'), 3.85 (1H, dd, J=11.4 and 2.2 Hz, H-6'), 3.91–3.96 (2H, m, H$_2$ and H-3), 4.31 (1H, d, J=9.0 Hz, —OH), 4.38 (1H, d, J=2.4 Hz, H-4'), 4.68 (1H, d, J=3.6 Hz, H-1'), 4.83 (1H, d, J=6.0 Hz, —OH), 4.91 (1H, d, J=7.4 Hz, —OH), 5.27–5.35 (3H, m, cis-CH=CH— and H-4), 5.50 (1H, dt, J=15.3 and 6.7 Hz, H-5), 7.42 (1H, d, J=9.2 Hz, —NH—).

EXAMPLE 5

(2S,3R)-3-Benzoyloxy-2-hexadecanoylamino1-[2,3-di-O-benzoyl-4,6-di-O-(sodium oxysulfonyl)-α-D-galactopyranosyloxy]-octadecane A. (2R,3R)-1,3-O-Benzyilidene-octadecane-1,2,3-triol

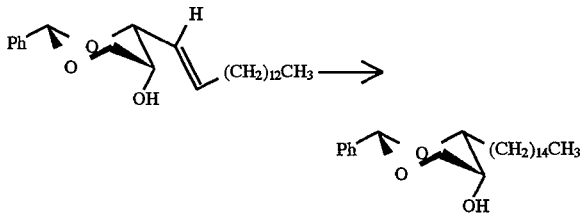

A solution of (2R,3R,4E)-1,3-O-benzylidene-4-octadecen-1,2,3-triol [prepared by general procedure described by P. Zimmerman et al, *Liebigs Ann. Chem.*, 663–667 (1988)] (3.00 g, 7.72 mmol) in a mixture of ethyl acetate (100 mL) and 0.02M sodium methoxide in methanol (100 mL) was hydrogenated over 0.35 g of 10% Pd on activated carbon at 22° C. and under 1 atm of hydrogen for 1 hour. Acetic acid (0.2 mL) was added and the catalyst was filtered. The filtrate was evaporated under vacuum and the residue was filtered on a silica gel pad using a mixture of ethyl acetate and toluene (5:95) as eluent to give 2.88 g (95%) of the title material as a white solid.

m.p.=64°–65° C. (hexane). $[\alpha]_D^{22}$: +6.0° (c=1.0, CHCl$_3$).

IR (KBr) $\nu_{max}$ (cm$^{-1}$): 3450 (OH).

$^1$H NMR 400 MHz (CDCl$_3$) δ(ppm): 0.89 (3H, t, J=7.0 Hz, —CH$_3$), 1.2–1.8 (28H, m, —(CH$_2$)$_{14}$—) 3.48 (1H, broad s, H-2), 3.87 (1H, broad t, J=7 Hz, H-3), 4.06 (1H, dd, J=1.06 and 11.8 Hz, H-1), 4.24 (1H, dd, J=1.85 and 11.8 Hz, H-1), 5.58 (1H, s, —O—CH—O—), 7.3–7.5 (5H, m, —C$_6$H$_5$).

Anal. Calcd. for C$_{25}$H$_{42}$O$_3$: C, 76.87; H, 10.84. Found: C, 75.93; H, 10.58.

B. (2S,3R)-2-Azido-1,3-O-benzylidene-octadecane-1,3-diol

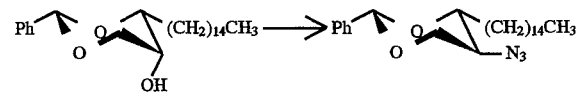

A solution of (2R,3R)-1,3-O-benzylidene-octadecane-1,2,3-triol (2.780 g, 7.11 mmol) in dichloromethane (25 mL) was cooled to −15° C. and treated successively with pyridine (1.16 mL, 14.3 mmol) and triflic anhydride (1.5 mL, 8.9 mmol). After 15 minutes at −15° C., a suspension of powdered sodium azide (2.12 g, 32.7 mmol) in N,N-dimethylformamide (80 mL) was added and the resulting mixture was stirred at 22° C. for 4 hours. The reaction mixture was then diluted with hexane (300 mL) and cold water (200 mL). The aqueous phase was extracted with hexane (2×100 mL) and the combined organic extracts were washed with brine and dried over anhydrous magnesium sulfate. Evaporation of the solvent gave an oil which was diluted with chloroform (50 mL) and methanol (50 mL), treated with p-toluenesulfonic acid (0.080 g) and stirred at 22° C. for 45 minutes. Solid sodium bicarbonate (500 mg) was added and after 15 minutes, the solution was filtered and concentrated under vacuum. Chromatography of the residual oil on silica gel (3×9 cm) using a mixture of hexane and toluene (6:4) gave 2.20 g (74%) of the title material as white needles.

m.p.=53°–53.5° C. (hexane). $[\alpha]_D^{22}$: +32.5° (c=1.0, CHCl$_3$).

IR (KBr) $\nu_{max}$ (cm$^{-1}$): 2118.

$^1$H NMR 400 MHz (CDCl$_3$) δ(ppm): 0.9 (3H, t, J=6.9 Hz, —CH$_3$), 1.2–1.9 (28H, m, —(CH$_2$)$_{14}$—), 3.41 (1H, ddd, J=5.2, 11.0 and 11.0 Hz, H-2), 3.58 (1H, ddd, J=2.6, 11.0 and 11.0 Hz, H-3), 3.68 (1H, dd, J=11.0 Hz, H-1ax), 4.38 (1H, dd, J=5.2 and 11.0 Hz, H-1eq), 5.47 (1H, s, —O—CH—O—), 7.3–7.5 (5H, m, —C$_6$H$_5$).

Anal. Calcd. for C$_{25}$H$_{41}$N$_3$O$_2$: C, 72.25; H, 9.94; N, 10.11. Found: C, 72.17; H, 9.93; N, 10.28.

C. (2S,3R)-2-Azido-octadecane-1,3-diol

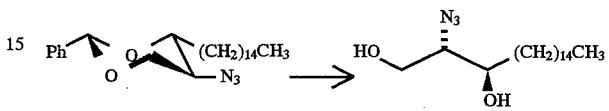

A solution of (2S,3R) 2-azido-1,3-O-benzylidene-octadecane-1,3-diol (2.15 g, 5.17 mmol) in a mixture of chloroform (70 mL) and methanol (70 mL) was treated with p-toluenesulfonic acid (0.080 g) and the resulting mixture was stirred at 22° C. for 70 hours. The resulting mixture was then stirred with sodium bicarbonate (0.5 g) filtered and evaporated. Chromatography of the residue on silica gel using a gradient of methanol in dichloromethane gave 1.38 g (81%) of the title material as a white solid.

m.p.=75°–75.5° C. (hexane). $[\alpha]_D^{22}$: +9.0° (c=1.0, CHCl$_3$).

IR (KBr) $\nu_{max}$ (cm$^{-1}$): 3340 (OH), 2150 (N$_3$).

$^1$H NMR 200 MHz (CDCl$_3$) δ(ppm): 0.87 (3H, t, J=6.4 Hz, —CH$_3$), 1.15–1.7 (28H, m, —(CH$_2$)$_{14}$)—, 2.0 (1H, broad, —OH), 3.43 (1H, dt, J=5.0 and 5.0 Hz, H-2), 3.77 (1H, m, H-3), 3.89 (2H, d, J=5.0 Hz, CH$_2$—1).

Anal. Calcd. for C$_{18}$H$_{37}$N$_3$O$_2$: C, 66.01; H, 11.39; N, 12.83. Found: C 65.84; H, 11.44; N, 12.92.

D. (2S,3R)-2-Azido-1-t-butyldimethylsilyl-octadecane-1,3-diol

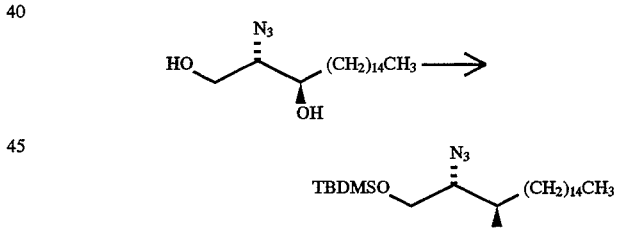

A solution of (2S,3R) 2-azido octadecane-1,3-diol (1.332 g, 4.06 mmol) in pyridine (15 mL) was treated with tert-butyldimethylsilyl chloride (0.736 g, 4.88 mmol) and the resulting mixture was stirred at 22° C. for 18 hours. Methanol (1 mL) was added and the solvent was evaporated under vacuum. The residue was purified by silica gel chromatography (2×12 cm) using a mixture of ethyl acetate and toluene (2:98) and gave 1.63 g (90%) of the title material as an oil.

$[\alpha]_D$: +15° (c=1.0, CHCl$_3$).

IR (NaCl, film) $\nu_{max}$ (cm$^{-1}$): 3450 (OH), 2100 (N$_3$).

$^1$H NMR 200 MHz (CDCl$_3$) δ(ppm): 0.11 (6H, s, SiCH$_3$), 0.88 (3H, t, J=6.7 Hz, —CH$_3$), 0.91 (9H, s, Si-t-Bu), 1.1–1.8 (29H, m, —(CH$_2$)$_{14}$— and —OH), 3.35 (1H, dt, J=5.4 and J=5.4 Hz, H-2), 3.7 (1H, m, H-3), 3.89 (2H, d, J=5.4 Hz, CH$_2$—1).

Anal. Calcd. for C$_{24}$H$_{51}$N$_3$O$_2$Si: C, 65.25; H, 11.64; N, 9.51. Found: C, 65.22; H, 11.44; N, 9.65.

E. (2S,3R)-2-Azido-3-benzoyl-octadecane-1,3-diol

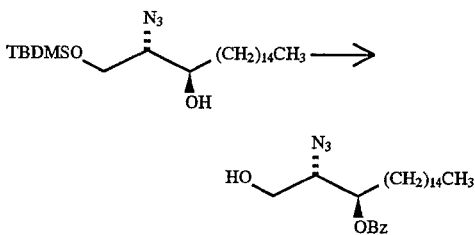

A solution of (2S,3R) 2-azido-1-t-butyldimethylsilyl-octadecane-1,3-diol (1.63 g, 3.69 mmol) in a mixture of toluene (12 mL) and pyridine (12 mL) was treated at 0°–5° C. with benzoyl chloride (1.037 g, 7.38 mmol) and a crystal of 4-dimethylaminopyridine and the resulting mixture was stirred at 0°–5° C. for 48 hours. Methanol (2 mL) was added and the solvent was evaporated under vacuum. The residue was diluted with ethyl acetate (200 mL), washed with cold 0.1N hydrochloric acid, saturated sodium bicarbonate, brine and dried over magnesium sulfate. Evaporation of the solvent gave an oil (2.4 g) which was dissolved in tetrahydrofuran (50 mL) cooled to 0°–5° C. and treated successively with acetic acid (1.38 g) and a 1M solution of tetrabutylammonium fluoride (11 mL, 11.0 mmol) in tetrahydrofuran. After 18 hours at 15° C., the reaction mixture was diluted with ethyl acetate (200 mL) washed with a saturated solution of sodium bicarbonate, brine and dried over anhydrous magnesium sulfate. Evaporation of the solvent under vacuum gave an oil which was purified by silica gel chromatography (3×12 cm). Elution with a mixture of ethyl acetate in toluene (2:98) gave 1.525 (95%) of the title material as an oil.

$[\alpha]_D^{22}$: −16° (c=1.0, CHCl$_3$).

IR (NaCl, film) $v_{max}$ (cm$^{-1}$): 3450 (OH), 2110 (N$_3$) and 1722 (C=O of benzoate).

$^1$H NMR 400 MHz (CDCl$_3$) δ(ppm): 0.89 (3H, t, J=6.8 Hz, —CH$_3$), 1.15–1.5 and 1.7–1.9 (28H, 2m, —(CH$_2$)$_{14}$—), 2.2 (broad, OH exchanged D$_2$O), 3.65–3.75 and 3.8–3.85 (2H and 1H, 2m, CH$_2$—1 and H-2), 5.28 (1H, m, H-3), 7.47, 7.6 and 8.07 (2H, 1H and 2H, 3m, —C$_6$H$_5$).

Anal. Calcd. for C$_{25}$H$_{41}$N$_3$O$_3$: C, 69.57; H, 9.57; N, 9.74. Found: C, 69.37; H, 9.53; N, 9.64.

F. (2S,3R)-2-Azido-3-benzoyloxy-1-(2-O-p-methoxybenzyl-3,4,6-tri-O-acetyl-α-D-galactopyranosyloxy)-octadecane

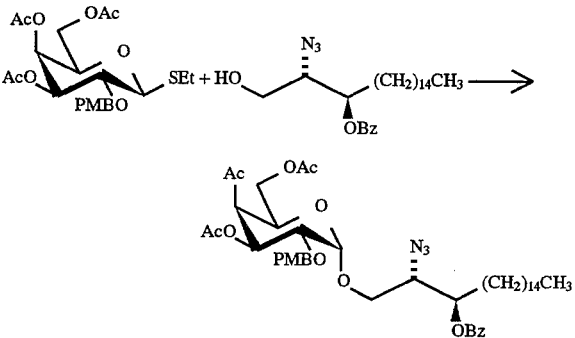

(2S,3R,)-2-Azido-3-benzoyl-octadecane-1,3-diol (3.11 g, 7.21 mmol) and ethyl 2-O-p-methoxy-benzyl-3,4,6-tri-O-acetyl-1-thio-β-D-galactopyranoside described in Example 1-E (4.52 g, 9.61 mmol) were reacted by the general procedure as described in Example 1-F and gave 5.47 g (90%) of a 83:17 mixture of α:β anomers which were separated by chromatography. The pure α-anomer was obtained as an oil.

$[\alpha]_D^{22}$: +24° (c=1.0, CHCl$_3$).

IR (NaCl, film) $v_{max}$ (cm$^{-1}$): 2105 (N$_3$), 1742 and 1725 (C=O ester).

$^1$H NMR 400 MHz (CDCl$_3$) δ(ppm): 0.86 (3H, t, J=6.8 Hz, —CH$_3$), 1.1–1.5 (26H, broad, —(CH$_2$)$_{13}$—), 1.36 and 1.40 (2H, 2m, —CH$_2$—4), 1.96, 1.99 and 2.11 (3×3H, 3s, —COCH$_3$), 3.54 (1H, dd, J=8.07 and 10.7 Hz, H-1), 3.79 (3H, s, —OCH$_3$), 3.83 (1H, dd, J=3.6 and 10.7 Hz, H-1'), 3.85 (1H, dd, J=10.1 and 3.56 Hz, H-2'), 3.94 (1H, m, H-2), 4.03 (2H, d, J=6.6 Hz, —CH$_2$OAc), 4.18 (1H, t, J=6.6 Hz, H-5'), 4.57 (1H, d, J$_{AB}$=11.9 Hz, CH$_2$ of p-methoxybenzyl), 4.63 (1H, d, J$_{AB}$=11.9 Hz, CH$_2$ of p-methoxybenzyl), 4.88 (1H, d, J=3.56 Hz, H-1'), 5.25–5.3 (2H, m, H-3 and H-3' overlapping), 5.44 (1H, broad d, J=2.5 Hz, H-4'), 6.85 and 8.3 (2×2H, 2d, J=8.5 Hz, H-2 and H-3 of p-methoxybenzyl), 7.47, 7.58 and 8.06 (2H, 1H and 2H, 3m, —C$_6$H$_5$).

Anal. Calcd. for C$_{45}$H$_{65}$N$_3$O$_{12}$: C, 64.34; H, 7.80; N, 5.0. Found: C, 64.13; H, 7.66; N, 5.05.

G. (2S,3R)-2-Azido-3-benzoyloxy-1-(α-D-galactopyranosyloxy)-octadecane

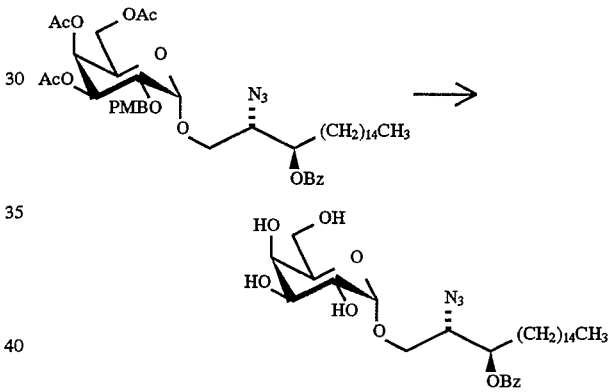

(2S,3R)-2-Azido-3-benzoyloxy-1-(2-O-p-methoxybenzyl-3,4,6-tri-O-acetyl-α-D-galactopyranosyloxy)-octadecane (4.30 g, 5.12 mmol) was reacted by the general procedure as described in Example 1-G procedure A and gave 2.50 g (82%) of the title material as a white glass.

$[\alpha]_D^{22}$: +52° (c=1.0, CHCl$_3$).

IR (NaCl, film) $v_{max}$ (cm$^{-1}$): 3400 (OH), 2105 (N$_3$),1720 (C=O ester).

$^1$H NMR 400 MHz (CDCl$_3$) δ(ppm): 0.89 (3H, t, J=6.8 Hz, —CH$_3$), 1.3–1.5 (26H, broad, —(CH$_2$)$_{13}$—), 1.8 (2H, m, —CH$_2$—4), 2.7 (4H, br s, —OH), 3.60 (1H, dd, J=5.7 and 10.5 Hz, H-1), 3.76 (1H, m, H-2), 3.85 (2H, m, H-6'), 3.86–3.98 (3H, m, H-2', H-3' and H-5'), 4.01 (1H, dd, J=3.2 and 10.5 Hz, H-1), 4.13 (1H, br s, H-4'), 4.90 (1H, br s, H-1'), 5.4 (1H, m, H-3), 7.47, 7.61 and 8.05 (2H, 1H and 2H, 3m, —C$_6$H$_5$).

Anal. Calcd. for C$_{31}$H$_{51}$N$_3$O$_8$: C, 62.71; H, 8.66; N, 7.08. Found: C, 62.62; H, 8.60; N, 7.08.

H. (2S,3R)-2-Azido-3-benzoyloxy-1-(4,6-O-benzylidene-α-D-galactopyranosyloxy)-octadecane

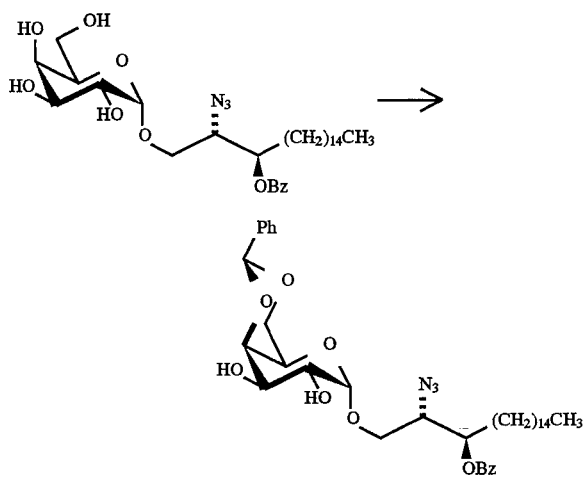

(2S,3R)-2-Azido-3-benzoyloxy-1-(α-D-galactopyranosyloxy)-octadecane (0.50 g, 0.84 mmol) was reacted by the general procedure as described in Example 3-C and afforded the title compound (0.37 g, 65%) as a thick solid.

$[\alpha]_D^{22}$: +19.7° (c=1.0, CHCl$_3$).

IR (NaCl, film) $v_{max}$ (cm$^{-1}$): 2100 (N$_3$),1715 (C=O ester).

$^1$H NMR 400 MHz (CDCl$_3$) δ(ppm): 0.89 (3H, t, J=6.8 Hz, —CH$_3$), 1.25 (26H, broad, —(CH$_2$)$_{13}$—), 1.8 (2H, m, —CH$_2$—4), 3.66 (1H, dd, J=5.8 and 10.5 Hz, H-1), 3.77 (1H, m, H-2), 3.82 (1H, br s, H-5'), 3.95 (2H, m, H-2' and H-3' overlapping), 4.02 (1H, dd, J=8.3 and 10.5 Hz, H-1), 4.11 (1H, dd, J=1.6 and 12.6 Hz, H-6'), 4.28 (1H, dd, J=1.3 and 12.6 Hz, H-6'), 4.32 (1H, br s, H-4'), 4.99 (1H, br d, J=1.9 Hz, H-1'), 5.4 (1H, m, H-3), 5.57 (1H, s, —O—CH—O—), 7.37, 7.50 7.61 and 8.06 (3H, 4H, 1H and 2H, 4m, 2×—C$_6$H$_5$).

Anal. Calcd. for C$_{38}$H$_{55}$N$_3$O$_8$: C, 66.94; H, 8.13; N, 6.16. Found: C, 66.57; H, 7.94; N, 6.05.

I. (2S,3R)-2-Azido-3-benzoyloxy-1-(2,3-di-O-benzoyl-4,6-O-benzylidene-α-D-galactopyranosyloxy)-octadecane

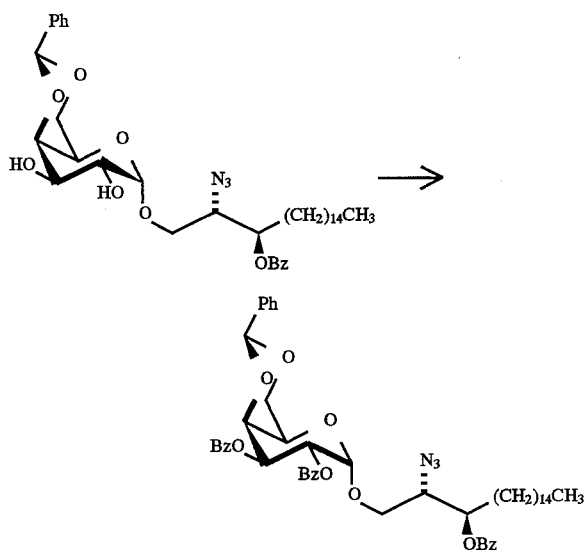

(2S,3R)-2-Azido-3-benzoyloxy-1-(4,6-O-benzylidene-α-D-galactopyranosyloxy)-octadecane (0.370 g, 0.543 mmol) was reacted by the general procedure as described in Example 1-I and gave 0.413 g (86%) of the title material as a glass.

$[\alpha]_D^{22}$: −32.5° (c=1.0, CHCl$_3$).

IR (NaCl, film) $v_{max}$ (cm$^{-1}$): 2105 (N$_3$) and 1725 (C=O ester).

$^1$H NMR 400 MHz (CDCl$_3$) δ(ppm): 0.89 (3H, t, J=6.8 Hz, —CH$_3$), 1.2–1.4 (26H, broad, —(CH$_2$)$_{13}$—), 1.65 and 1.83 (2×1H, 2m, —CH$_2$—4), 3.64 (1H, dd, J=7.9 and 10.5 Hz, H-1), 3.93 (1H, m, H-2), 3.98 (1H, br s, H-5'), 4.0 (1H, dd, J=3.25 and 10.5 Hz, H-1), 4.14 (1H, dd, J=1.2 and 12.5 Hz, H-6'), 4.33 (1H, dd, J=1.1 and 12.5 Hz, H-6'), 4.69 (1H, broad d, J≈3 Hz, H-4'), 5.43 (1H, d, J=3.3 Hz, H-1'), 5.57 (1H, s, —O—CH—O—), 5.78 (1H, dd, J=3.2 and 10.8 Hz, H-3'), 5.84 (1H, dd, J=3.3 and 10.8 Hz, H-2'), 7.36, 7.5 and 8.0 (7H, 7H and 6H, 3m, 4×—C$_6$H$_5$).

Anal. Calcd. for C$_{52}$H$_{63}$N$_3$O$_{10}$: C, 70.17; H, 7.13; N, 4.72. Found: C, 69.80; H, 7.00; N, 4.67.

J. (2S,3R)-3-Benzoyloxy-2-hexadecanoylamino-1-(2,3-di-O-benzoyl-4,6-O-benzylidene-α-D-galactopyranosyloxy)-octadecane

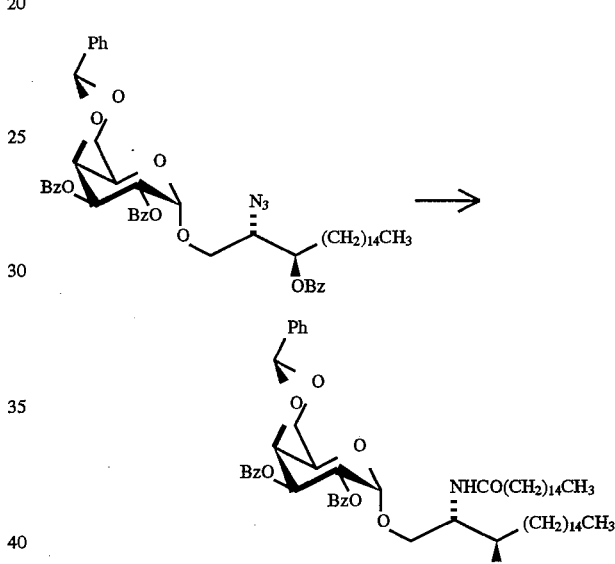

(2S,3R)-2-Azido-3-benzoyloxy-1-(2,3-O-benzoyl-4,6-O-benzylidene-α-D-galactopyranosyloxy)-octadecane (0.708 g, 0.795 mmol) was reacted by the general procedure as described in Example 1-J and gave 0.841 g (96%) of the title material as a white foam.

$[\alpha]_D^{22}$: +92.5° (c=1.0, CHCl$_3$).

IR (KBr) $v_{max}$ (cm$^{-1}$): 1720 (C=O ester) and 1652 (C=O amide).

$^1$H NMR 400 MHz (CDCl$_3$) δ(ppm): 0.89 (6H, t, J=6.8 Hz, 2×—CH$_3$), 1.2–1.9 (54H, m, —(CH$_2$)$_{14}$— and —(CH$_2$)$_{13}$—), 2.16 (2H, t, J=7.2 Hz, —NHCOCH$_2$—), 3.69 (1H, dd, J=5.6 and 10.9 Hz, H-1), 3.86 (1H, dd, J=4.6 and 10.9 Hz, H-1), 3.90 (1H, br s, H-5'), 4.02 (1H, dd, J=0.9 and 12.5 Hz, H-6'), 4.26 (1H, dd, J=0.8 and J=12.5 Hz, H-6'), 4.51 (1H, m, H-2), 4.63 (1H, br d, J=3.2 Hz, H-4'), 5.16 (1H, m, H-3), 5.38 (1H, d, J=3.3 Hz, H-1'), 5.75 (1H, dd, J=3.2 and 10.8 Hz, H-3'), 5.80 (1H, dd, J=3.3 and 10.8 Hz, H-2'), 5.97 (1H, d, J=9 Hz, —NH—), 7.3–7.6 and 7.95–8.03 (14H and 6H, 2m, 4×—C$_6$H$_5$).

Anal. Calcd. for C$_{68}$H$_{95}$NO$_{11}$: C, 74.08; H, 8.69; N, 1.27. Found: C, 74.23; H, 8.90; N, 1.41.

K. (2S,3R)-3-Benzoyloxy-2-hexadecanoylamino-1-(2,3-di-O-benzoyl-α-D-galactopyranosyloxy)-octadecane

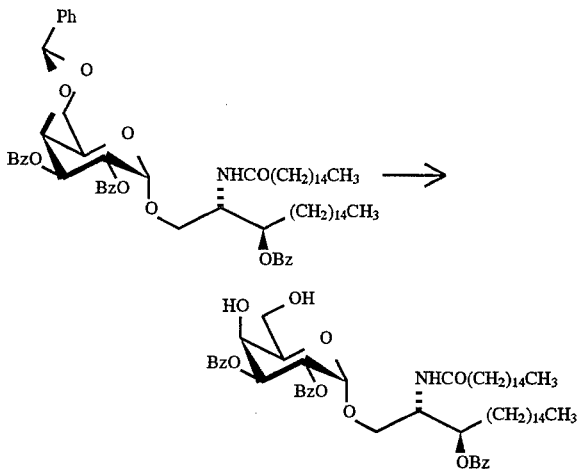

(2S,3R)-3-Benzoyloxy-2-hexadecanoylamino-1-(2,3-O-benzoyl-4,6-O-benzylidene-α-D-galactopyranosyloxy)-octadecane (0.802 g, 0.727 mmol) was treated by the general procedure as described in Example 1-K to give 0.578 g (78%) of the title material as a white glass.

[α]$_D^{22}$: +70.7° (c=1.0, CHCl$_3$).

IR (NaCl, film) $\nu_{max}$ (cm$^{-1}$): 1720 (C=O ester) and 1650 (C=O amide).

$^1$H NMR 400 MHz (CDCl$_3$) δ(ppm): 0.89 (6H, t, J=6.6 Hz, 2×—CH$_3$), 1.2–1.9 (54H, m, —(CH$_2$)$_{14}$— and —(CH$_2$)$_{13}$—), 2.18 (2H, t, J=7.5 Hz, —NHCOCH$_2$—), 3.75–3.95 (4H, m, H-1 and H-6' overlapping), 4.06 (1H, m, H-5'), 4.42 (1H, broad s, H-4'), 4.51 (1H, m, H-2), 5.17 (1H, m, H-3), 5.34 (1H, d, J=2.6 Hz, H-1'), 5.68 (2H, m, H-2' and H-3' overlapping), 6.1 (1H, d, J=9 Hz, —NH—), 7.3–7.6 and 7.9–8.0 (9H and 6H, 2m, 3×—C$_6$H$_5$).

Anal. Calcd. for C$_{61}$H$_{91}$NO$_{11}$: C, 72.23; H, 9.04; N, 1.38. Found: C, 72.40; H, 9.13; N, 1.47.

L. (2S,3R)-3-Benzoyloxy-2-hexadecanoylamino1-[2,3-di-O-benzoyl-4,6-di-O-(sodium oxysulfonyl)-α-D-galactopyranosyloxy]-octadecane

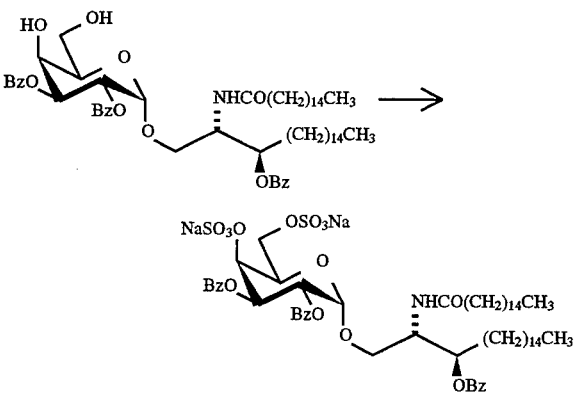

(2S,3R)-3-Benzoyloxy-2-hexadecanoylamino-1-(2,3-di-O-benzoyl-α-D-galactopyranosyloxy]-octadecane (0.543 g, 0.535 mmol) was reacted by the general procedure as described in Example 1-L and gave 0.500 g (77%) of the title material as a white solid.

[α]$_D^{22}$: +56.4° (c=1.0, CHCl$_3$/MeOH 8:2).

IR (KBr) $\nu_{max}$ (cm$^{-1}$): 1728 (C=O of ester) and 1640 (C=O of amide).

$^1$H NMR 400 MHz (DMSO-d$_6$) δ(ppm): 0.83 (6H, t, J=6.0 Hz, 2×—CH$_3$), 1.1–1.4 (52H, —(CH$_2$)$_{12}$— and —(CH$_2$)$_{13}$—), 1.65 (2H, m, —CH$_2$—4), 1.8–2.0 (2H, m, —NHCOCH$_2$—), 3.53 (1H, dd, J=6.9 and 11.0 Hz, H-1), 3.85–3.95 (2H, m, H-6'), 4.12 (1H, dd, J=2.5 and 11.0 Hz, H-1), 4.24 (1H, m, H-2), 4.31 (1H, m, H-5'), 4.77 (1H, d, J=2.8 Hz, H-4'), 5.13 (1H, d, J=3.2 Hz, H-1'), 5.16 (1H, m, H-3), 5.42 (1H, dd, J=3.2 and 10.8 Hz, H-2'), 5.47 (1H, dd, J=2.8 and 10.8 Hz, H-3'), 7.3–7.6 and 7.8–7.9 (9H and 6H, 2m, 3×—C$_6$H$_5$).

EXAMPLE 6

(2S,3R)-2-Hexadecanoylamino-3-hydroxy-1-(4,6-di-O-sodium oxysulfonyl)-α-D-galactopyranosyloxy)-octadecane

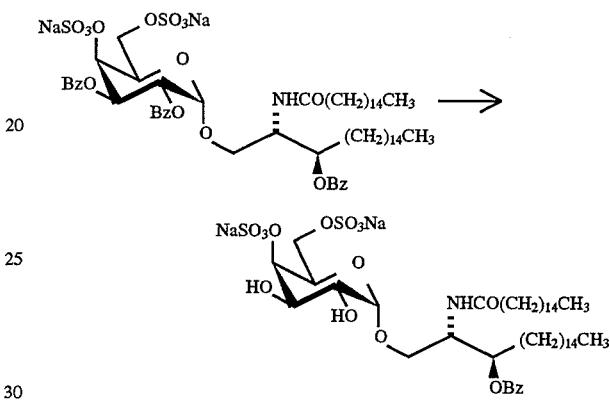

A solution of (2S,3R,4E)-2-hexadecanoylamino-3-hydroxy-1-[4,6-di-O-(sodium oxysulfonyl)-α-D-galactopyranosyloxy]-4-octadecene described in Example 2-A (0.150 g, 0.166 mmol) in a mixture of tetrahydrofuran (20 mL), water (5 mL) and ethanol (5 mL) was hydrogenated over 10% palladium over activated carbon (0.030 g) at 22° C. and under one atmosphere for 4 hours. The catalyst was filtered on a Celite pad and evaporation of the solvent gave 0.150 g (100%) of the title material as a white solid.

IR (KBr) $\nu_{max}$ (cm$^{-1}$): 1730 (C=O amide).

$^1$H NMR 400 MHz (DMSO-d$_6$) δ(ppm): 4.27 (1H, d, J=8.6 Hz, —OH), 4.49 (1H, d, J=6.5 Hz, —OH) and 4.88 (1H, d, J=7.4 Hz, —OH); (DMSO-d$_6$+D$_2$O) d (ppm): 0.84 (6H, t, J=6.8 Hz, 2×—CH$_3$), 1.1–1.6 (54H, m, —(CH$_2$)$_{14}$— and —(CH$_2$)$_{13}$—), 2.08 (2H, t, J=6.6 Hz, —NHCOCH$_2$—), 3.40 (1H, dd, J=3.6, and 10.1 Hz, H-2'), 3.46 (1H, m, H-3), 3.50 (1H, dd, J=3.4 and 10.5 Hz, H-1), 3.61 (1H, dd, J=3.6 and 10.5 Hz, H-1), 3.66 (1H, dd, J=3.0 and 10.1 Hz, H-3'), 3.66 (1H, m overlapping with H-3', H-2), 3.73 (1H, dd, J=8.3 and 11.4 Hz, H-6') 3.87 (1H, dd, J=2.2 and 11.4 Hz, H-6'), 3.96 (1H, broad d, H-5'), 4.38 (1H, d, J=3.0 Hz, H-4'), 4.68 (1H, d, J=3.6 Hz, H-1'), 7.53 (1H, d, J=9 Hz, —NH—).

EXAMPLE 7

(2S,3R,4E)-3-Benzoyloxy-2-hexadecanoylamino-1-[-2,3-di-O-benzoyl-4,6-di-O-(sodium oxysulfonyl)-α-D-glucopyranosyloxy]-4-octadecene A. (2S,3R,4E)-2-Azido-3-benzoyloxy-1-(2,3,4,6-tetra-O-acetyl-α-D-glucopyranosyloxy)-4-octadecene and (2S,3R,4E)-2-azido-3-benzoyloxy-1-(2,3,4,6-tetra-O-acetyl-β-D-glucopyranosyloxy)-4-octadecene

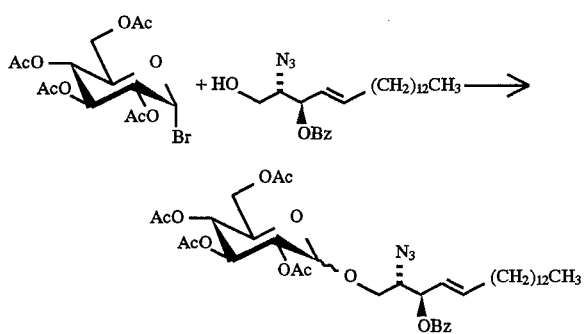

A solution of (2S,3R,4E)-2-azido-3-benzoyloxy-4-octadecen-1-ol [prepared by general procedure described by P. Zimmerman et al, *Liebigs Ann. Chem.*, 663–667 (1988)], (24.3 g, 10.0 mmol) in dry benzene (150 mL) and nitromethane (150 mL) was heated under reflux. Benzene was distilled and the solution was concentrated under vacuum to 75 mL. To this solution was added 2,3,4,6-tetra-O-acetyl-α-D-glucosyl bromide [prepared as described by C. E. Redemann et al, *Org. Synth. Coll.*, Vol. III, p. 11 (1955)], (6.2 g, 15 mmol) and mercury(II) cyanide (3.7 g, 15 mmol) at 22° C. and under argon and the resulting mixture was heated up to 80°–85° C. for 15–20 minutes. The reaction was then cooled down to 5° C. and diluted with ethyl ether/water (1:1, 150 mL). Hydrogen sulfide was bubbled in and the resulting black precipitate was filtered on Celite and washed with ethyl ether (4×150 mL). The organic phases were washed with cold aqueous sodium bicarbonate solution (1M, 4×100 mL), water (3×100 mL) and brine (100 mL), dried over anhydrous magnesium sulfate, filtered and concentrated. The black resulting residue was purified by chromatography on silica gel (65 g, 0% to 30% ethyl acetate/hexane) and afforded the β-anomer (3.90 g, 76%) as a white gummy solid and the α-anomer of the title compound (0.49 g, 9.5%) as a yellow oil.

IR (CH$_2$Cl$_2$) ν$_{max}$ (cm$^{-1}$) α-anomer: 3060, 2930 (C—H), 2100 (N$_3$), 1750 (C=O), 1225 (C—O).

IR (CH$_2$Cl$_2$) ν$_{max}$ (cm$^{-1}$) β-anomer: 3060, 2930 (C—H), 2110 (N$_3$), 1760 (C=O), 1220 (C—O).

$^1$H NMR 400 MHz (CDCl$_3$) δ(ppm) α-anomer: 0.89 (3H, t, J=6.9 Hz, —CH$_3$), 1.25 (20H, br s, —(CH$_2$)$_{10}$—), 1.40 (2H, m, —CH$_2$—), 2.03, 2.05, 2.07, 2.09 (4×3H, 4s overlapping =CH—CH$_2$—, 4×—OCOCH$_3$), 2.03–2.14 (2H, m, =CH—CH$_2$—), 3.52 (1H, dd, J=10.8 and 8.0 Hz, H-1), 3.87 (1H, dd, J=10.8 and 3.6 Hz, H-1), 3.96 (1H, dt, J=8.0 and 3.6 Hz, H-2), 4.04 (1H, ddd, J=10.2, 4.5 and 2.3 Hz, H-5'), 4.11 (1H, dd, J=12.4 and 2.3 Hz, H-6'), 4.27 (1H, dd, J=12.4 and 4.5 Hz, H-6'), 4.91 (1H, dd, J=10.2 and 3.7 Hz, H-2'), 5.08 (1H, t, J=10.2 Hz, H-4' or H-3'), 5.12 (1H, d, J=3.7 Hz, H-1'), 5.51 (1H, t, J=10.2 Hz, H-3' or H-4'), 5.54–5.61 (2H, m, H-3 and H-4), 5.92–6.00 (1H, m, H-5), 7.46–8.06 (5H, 3m, —C$_6$H$_5$).

$^1$H NMR 400 MHz (CDCl$_3$) δ(ppm) β-anomer: 0.89 (3H, t, J=6.9 Hz, —CH$_3$), 1.26–1.41 (22H, m, —(CH$_2$)$_{11}$—), 2.02, 2.04, 2.06, 2.10 (4×3H, 4s overlapping =CH—CH$_2$—, 4×—OCOCH$_3$), 2.02–2.16 (2H, m, =CH—CH$_2$), 3.61 (1H, dd, J=9.5 and 4.9 Hz, H-1), 3.70 (1H, ddd, J=9.5, 2.4 and 4.7 Hz, H-5'), 3.89–3.97(2H, m, H-1 and H-2), 4.13 (1H, dd, J=12.3 and 2.4 Hz, H-6'), 4.23 (1H, dd, J=12.3 and 4.7 Hz, H-6'), 4.56 (1H, d, J=8.0 Hz, H-1'), 5.04 (1H, dd, J=9.5 and 8.0 Hz, H-2'), 5.11 (1H, t, J=9.5 Hz, H-4' or H-3'), 5.22 (1H, t, J=9.5 Hz, H-3' or H-4'), 5.54–5.62 (2H, m, H-3 and H-4), 5.94 (1H, dt, J=14.3 and 6.8 Hz, H-5), 7.45–8.07 (5H, 3m, —C$_6$H$_5$).

B. (2S,3R,4E)-2-Azido-3-benzoyloxy-1-(α-D-glucopyranosyloxy)-4-octadecene

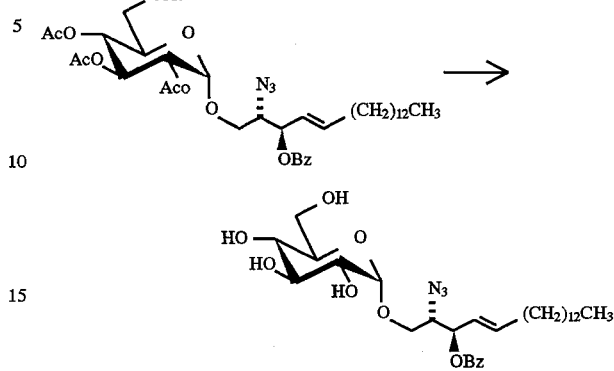

(2S,3R,4E)-2-Azido-3-benzoyloxy-1-(2,3,4,6-tetra-O-acetyl-α-D-glucopyranosyloxy)-4-octadecene (990 mg, 1.3 mmol) was reacted by the general procedure as described in Example 1-G procedure B and afforded the title compound (590 mg, 77%) as an oil.

IR (CH$_2$Cl$_2$) ν$_{max}$ (cm$^{-1}$): 3600–3150 (O—H), 3060, 2940, 2860 (C—H), 2110 (N$_3$), 1720 (C=O ester).

$^1$H NMR 400 MHz (DMSO-d$_6$) δ(ppm): 0.84 (3H, t, J=6.8 Hz, —CH$_3$), 1.19–1.33 (22H, m, —(CH$_2$)$_{11}$—), 2.02 (2H, m, =CH—CH$_2$—), 3.08 (1H, dt, J=9.3 and 5.2 Hz, H-3' or H-4'), 3.19 (1H, ddd, J=9.7, 6.1 and 3.6 Hz, H-2'), 3.36–3.48 (4H, m, H-3' or H-4', H-5', H-1 and H-6'), 3.58 (1H, ddd, J=9.8, 5.7 and 4.0 Hz, H-6'), 3.73 (1H, dd, J=10.6 and 5.3 Hz, H-1), 4.16 (1H, m, H-2), 4.43 (1H, t, J=5.7 Hz, —OH-6'), 4.64 (1H, d, J=6.1 Hz, —OH-2'), 4.70 (1H, d, J=3.6 Hz, H-1'), 4.80 (1H, d, J=4.7 Hz, —OH-3' or —OH-4'), 4.90 (1H, d, J=5.2 Hz, —OH-3' or —OH-4'), 5.56 (1H, dd, J=15.0 and 7.5 Hz, H-4), 5.62 (1H, dd, J=7.5 and 3.8 Hz, H-3), 5.86 (1H, dt, J=15.0 and 6.8 Hz, H-5), 7.52–7.99 (5H, 3m, —C$_6$H$_5$).

C. (2S,3R,4E)-2-Azido-3-benzoyloxy-1-(4,6-O-benzylidene-α-D-glucopyranosyloxy)-4-octadecene

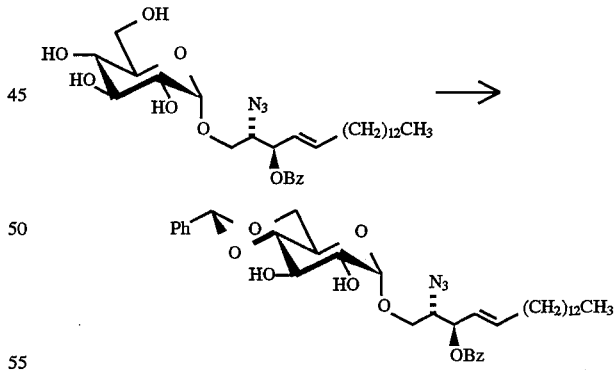

(2S,3R,4E)-2-Azido-3-benzoyloxy-1-(α-D-glucopyranosyloxy)-4-octadecene (59 mg, 0.1 mmol) was reacted by the general procedure as described in Example 1-H in tetrahydrofuran instead of acetonitrile and afforded the title compound (50 mg, 73%) as a pale yellow oil. IR (CH$_2$Cl$_2$) ν$_{max}$ (cm$^{-1}$): 3700–3580 (O—H), 3060, 2935, 2860 (C—H), 2100 (N$_3$), 1720 (C=O ester).

$^1$H NMR 400 MHz (DMSO-d$_6$) δ(ppm): 0.84 (3H, t, J=6.9 Hz, —CH$_3$), 1.25–143 (22H, m, —(CH$_2$)$_{11}$—), 2.11 (2H, m, =CH—CH$_2$—), 2.49 (1H, d, J=10.1 Hz, —OH), 2.72 (1H, s, —OH), 3.51–3.59 (2H, m, H-6' and H-5'), 3.66 (1H, m, H-2'), 3.76 (1H, t, J=10.3 Hz, H-4'), 3.88 (1H, dd, J=9.9 and 4.7 Hz, H-1), 3.91–4.03 (3H, m, H-1, H-2 and H-3'), 4.30 (1H, dd, J=10.2 and 4.8 Hz, H-6'), 4.91 (1H, d, J=3.9 Hz, H-1'), 5.56 (1H, s, —O—CH—O—), 5.62 (1H, dd, J=15.3 and 8.1 Hz, H-4), 5.72 (1H, dd, J=8.1 and 4.9 Hz, H-3), 6.00 (1H, dt, J=15.3 and 6.8 Hz, H-5), 7.37–8.08 (10H, 4m, 2×—$C_6H_5$).

D. (2S,3R,4E)-2-Azido-3-benzoyloxy-1-(2,3-di-O-benzoyl-4,6-O-benzylidene-α-D-glucopyranosyloxy)-4-octadecene

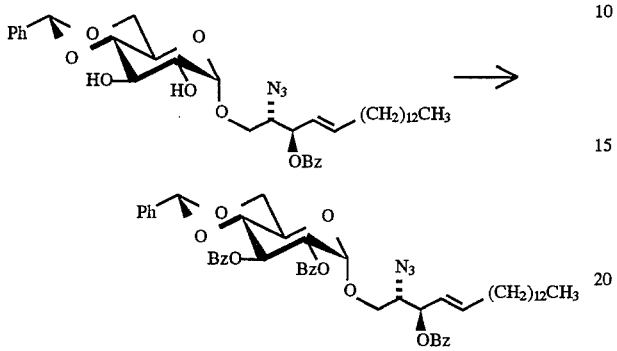

(2S,3R,4E)-2-Azido-3-benzoyloxy-1-(4,6-O-benzylidene-α-D-glucopyranosyloxy)-4-octadecene (300 mg, 0.44 mmol) was reacted by the general procedure as described in Example 1-I and afforded the title compound (404 mg, 100%) as a pale yellow oil.

IR ($CH_2Cl_2$) $v_{max}$ ($cm^{-1}$): 3060, 2930, 2860 (C—H), 2110 ($N_3$), 1725 (C=O ester).

$^1$H NMR 400 MHz ($CDCl_3$) δ(ppm): 0.89 (3H, t, J=6.9 Hz, —$CH_3$), 1.24–1.39 (22H, m, —$(CH_2)_{11}$—), 2.06 (2H, m, =CH—$CH_2$—), 3.48 (1H, dd, J=10.5 and 8.3 Hz, H-1), 3.86 (1H, t, J=9.9 Hz, H-4'), 3.90–4.00 (3H, m, H-1, H-2 and H-6'), 4.12 (1H, td, J=9.9 and 4.8 Hz, H-5'), 4.36 (1H, dd, J=10.3 and 4.8 Hz, H-6'), 5.31 (1H, dd, J=9.9 and 3.8 Hz, H-2'), 5.34 (1H, d, J=3.8 Hz, H-1'), 5.51–5.56 (2H, m, H-3 and H-4), 5.58 (1H, s, —O—CH—O—), 5.88–5.95 91H, m, H-5), 6.09 (1H, t, J=9.9 Hz, H-3'), 7.31–8.03 (20H, 2m, 4×—$C_6H_5$).

E. (2S,3R,4E)-3-Benzoyloxy-2-hexadecanoylamino-1-(2,3-di-O-benzoyl-4,6-O-benzylidene-α-D-glucopyranosyloxy)-4-octadecene

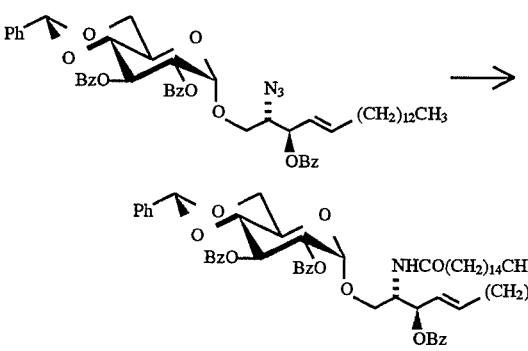

(2S,3R,4E)-2-Azido-3-benzoyloxy-1-(2,3-di-O-benzoyl-4,6-O-benzylidene-α-D-glucopyranosyloxy)-4-octadecene (100 mg, 0.11 mmol) was reacted by the general procedure as described in Example 1-H and afforded the title compound (102 mg, 84%) as a white fluffy solid.

IR ($CH_2Cl_2$) $v_{max}$ ($cm^{-1}$): 3060, 2935, 2860 (C—H), 1730 (C=O ester), 1675 (C=O amide).

$^1$H NMR 400 MHz ($CDCl_3$) δ(ppm): 0.87–0.91 (6H, m, J=6.9 Hz, 2×—$CH_3$), 1.23–1.26 (46H, m, —$(CH_2)_{11}$— and —$(CH_2)_{12}$—), 1.58–1.60 (2H, m, —$CH_2$—), 1.96 (2H, m, =CH—$CH_2$—), 2.10–2.23 (2H, m, —$CH_2$CONH—), 3.67 (1H, dd, 10.6 and 3.7 Hz, H-1), 3.83 (1H, t, J=9.9 Hz, H-4'), 3.89–3.94 (2H, m, H-1 and H-6'), 4.04 (1H, td, J=9.9 and 4.7 Hz, H-5'), 4.33 (1H, dd, J=10.3 and 4.7 Hz, H-6'), 4.50 (1H, m, H-2), 4.25 (1H, d, J=3.8 Hz, H-1'), 5.31 (1H, dd, J=9.8 and 3.8 Hz, H-2'), 5.45–5.53 (2H, m, H-3 and H-4), 5.57 (1H, s, —O—CH—O—), 5.66 (1H, dt, J=14.4 and 6.8 Hz, H-5), 5.78 (1H, d, J=8.4 Hz, —NH—), 6.07 (1H, t, J=9.9 Hz, H-3'), 7.30–8.01 (20H, 2m, 4×—$C_6H_5$).

F. (2S,3R,4E)-3-Benzoyloxy-2-hexadecanoylamino-1-(2,3-di-O-benzoyl-α-D-glucopyranosyloxy)-4-octadecene

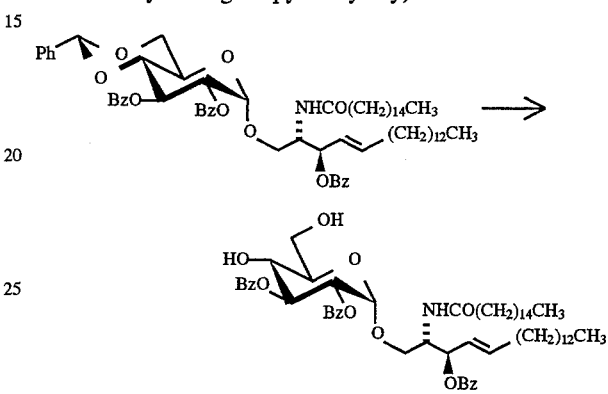

(2S,3R,4E)-3-Benzoyloxy-2-hexadecanoylamino-1-(2,3-di-O-benzoyl-4,6-O-benzylidene-α-D-glucopyranosyloxy)-4-octadecene (100 mg, 0.09 mmol) was reacted by the general procedure as described in Example 1-K and afforded the title compound (75 mg, 82%) as a white amorphous solid.

IR ($CH_2Cl_2$) $v_{max}$ ($cm^{-1}$): 3600, 3440 (O—H and N—H), 3060, 2930, 2860 (C—H), 1725 (C=O ester), 1675 (C=O amide).

$^1$H NMR 400 MHz ($CDCl_3$) δ(ppm): 0.89 (6H, t, J=6.8 Hz, 2×—$CH_3$), 1.23–1.32 (46H, m, —$(CH_2)_{11}$— and —$(CH_2)_{12}$—), 1.57–1.67 (2H, m, —$CH_2$—), 1.99 (2H, m, =CH—$CH_2$—), 2.18 (2H, m, —$CH_2$CONH—), 3.74 (1H, dd, J=10.8 and 4.8 Hz, H-1), 3.85–3.98 (4H, m, H-6', H-5' and H-1), 3.94 (1H, t, J=8.8 Hz, H-4'), 4.55 (1H, m, H-2), 5.21 (1H, d, J=3.7 Hz, H-1'), 5.28 (1H, dd, J=10.1 and 3.7 Hz, H-2'), 5.47–5.57 (2H, m, H-3 and H-4), 5.71 (1H, dd, J=10.1 and 8.8 Hz, H-3'), 5.75 (1H, dt, J=14.6 and 6.8 Hz, H-5), 5.82 (1H, d, J=9.2 Hz, —NH—), 7.33–8.01 (15H, 3m, 3×—$C_6H_5$).

G. (2S,3R,4E)-3-Benzoyloxy-2-hexadecanoylamino-1-[2,3-di-O-benzoyl-4,6-di-O-(sodium oxysulfonyl)-α-D-glucopyranosyloxy]-4-octadecene

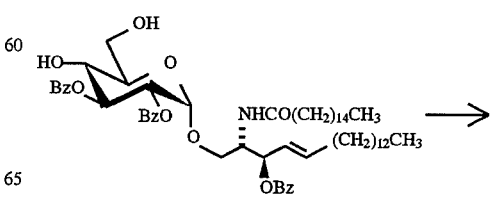

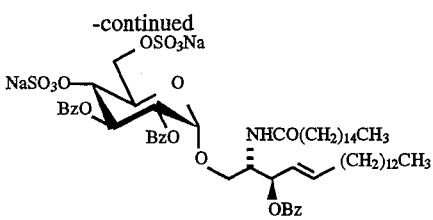

(2S,3R,4E)-3-Benzoyloxy-2-hexadecanoylamino-1-(2,3-di-O-benzoyl-α-D-glucopyranosyloxy)-4-octadecene (72 mg, 0.07 mmol) was reacted by the general procedure as described in Example 1-L and afforded the title compound (69 mg, 81%) as a beige solide.

IR (nujol) $v_{max}$ (cm$^{-1}$): 3700–3100 (O—H and N—H), 2930, 2860 (C—H), 1725 (C=O ester), 1655 (C=O amide).

$^1$H NMR 400 MHz (DMSO-d$_6$) δ(ppm): 0.84 (6H, t, J=6.7 Hz, 2×—CH$_3$), 1.06–1.38 (48H, m, —(CH$_2$)$_{11}$— and —(CH$_2$)$_{13}$—), 1.76–2.02 (4H, m =CH—C$\underline{H}_2$— and —C$\underline{H}_2$CONH—), 3.54 (1H, dd, J=10.5 and 7.3 Hz, H-1), 3.71 (1H, dd, J=11.1 and 9.5 Hz, H-6'), 3.88 (1H, dd, J=10.5 and 4.8 Hz, H-1), 3.97 (1H, br t, H-5'), 4.21 (1H, t, J=9.9 Hz, H-4'), 4.26–4.31 (1H, m, H-2), 4.37 (1H, d, J=9.5 Hz, H-6'), 5.03 (1H, dd, J=9.9 and 3.6 Hz, H-2'), 5.16 (1H, d, J=3.6 Hz, H-1'), 5.46 (1H, dd, J=7.2 and 5.0 Hz, H-3), 5.58 (1H, dd, J=15.3 and 7.4 Hz, H-4), 5.72 (1H, t overlapping H-5, J=9.9 Hz, H-3'), 5.70–5.76 (1H, m, H-5), 7.36–7.92 (16H, 4m, 3×—C$_6$H$_5$ and —NH—).

EXAMPLE 8

(2S,3R,4 E)-3-Hydroxy-2-hexadecanoylamino-1-[4,6-di-O-(sodium oxysulfonyl)-α-D-glucopyranosyloxy]-4-octadecene

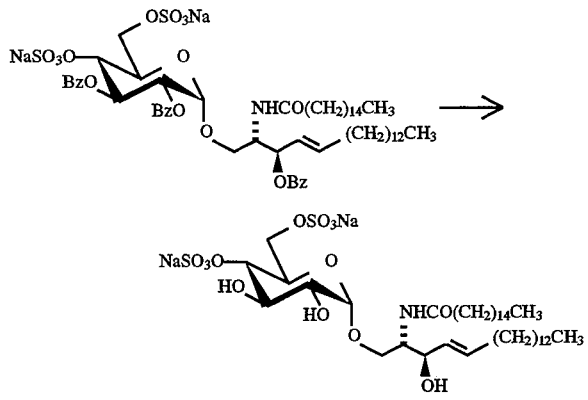

(2S,3R,4E)-3-Benzoyloxy-2-hexadecanoylamino-1-[2,3-di-O-benzoyl-4,6-di-O-(sodium oxysulfonyl)-α-D-glucopyranosyloxy]-4-octadecene is reacted as described in Example 2-A and the title compound is thereby produced.

IR (nujol) $v_{max}$ (cm$^{-1}$): 3600–3200 (OH and NH), 1640 and 1550 (C=O).

$^1$H NMR 400 MHz (DMSO-d$_6$) δ(ppm): 0.85 (6H, t, J=6.8 Hz, 2×CH$_3$), 1.24 (46H, m, —(CH$_2$)$_{11}$— and —(CH$_2$)$_{12}$—), 1.5–1.7 (2H, m, CH$_2$), 1.87–2.00 (2H, m, =CH—CH$_2$), 2.05 (2H, t, J=7.3 Hz, CH$_2$CO), 3.22 (1H, dd, J=9.3 and 3.7 Hz, H-1), 3.5–3.67 (5H, 2 sets of m, H-2', H-3', H-5', H-3, H-6'), 3.67–3.8 (1H, m, H-2), 3.72 (1H, dd, J=3.5 and 8.6 Hz, H-2, H-1), 3.93 (1H, t, J=7.8 Hz, H-4), 4.09 (1H, d, J=10.4 Hz, H-6), 4.64 (1H, d, J=3.7 Hz, H-1'), 5.32 (1H, dd, J=15.3 and 7.1 Hz, H-4) 5.52 (1H, dt, J=15.2 and 6.6 Hz, H-4), 7.45 (1H, d, J=9.2 Hz, NH), 4.6, 4.87 and 5.31 (3H, 3 sets of s, OH).

EXAMPLE 9

(2S,3R,4E)-3-Benzoyloxy-1-[2,3-di-O-benzoyl-4,6-di-O-(sodium oxysulfonyl)-α-D-glucopyranosyloxy)-2-(cis-15-tetracosenoylamino)-4-octadecene A. (2S,3R,4E)-3-Benzoyloxy-1-(2,3-di-O-benzoyl-4,6-O-benzylidene-α-D-glucopyranosyloxy)-2-(cis-15-tetracosenoylamino)-4-octadecene

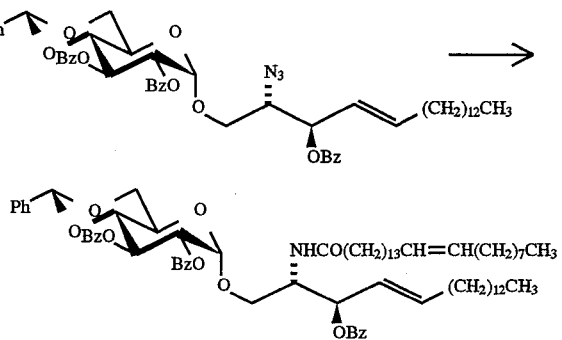

(2S,3R,4E)-2-Azido-3-benzoyloxy-1-(2,3-di-O-benzoyl-4,6-O-benzylidene-α-D-glucopyranosyl-oxy)-4-octadecene obtained in Example 7-D (150 mg, 0.17 mmol) was reacted as described in Example 3-A and afforded the title compound (190 mg, 92%) as a yellow gum.

IR (CH$_2$Cl$_2$) $v_{max}$ (cm$^{-1}$): 3420 (N—H), 3060, 2930, 2860 (C—H), 1730 and 1675 (C=O).

$^1$H NMR 400 MHz (CDCl$_3$) δ(ppm): 1.23–1.28 and 1.56–1.67 (56H, 2 sets of m, 2×—(CH$_2$)$_{11}$— and —(CH$_2$)$_6$—), 1.94–2.05 and 2.09–2.23 (8H, 2 sets of m, 3 ×=CH—CH$_2$— and —CH$_2$CONH—), 3.67 (1H, dd, J=10.7 and 3.7 Hz, H-1), 3.83 (1H, t, J=10.3 Hz, H-6'), 3.91 (1H, dt, J=10.7 and 4.3 Hz, H-1), 3.92 (1H, t, J=9.3 Hz, H-4'), 4.04 (1H, dt, J=9.7 and 4.7 Hz, H-5'), 4.33 (1H, dd, J=10.3 and 4.7 Hz, H-6'), 4.47–4.53 (1H, m, H-2), 5.25 (1H, d, J=3.8 Hz, H-1'), 5.32 (1H, dd, J=9.9 and 3.8 Hz, H-2'), 5.36 (2H, br t, J=4.7 Hz, cis)-CH=CH—), 5.45–5.53 (2H, m, H-4 and H-3), 5.57 (1H, s, —O—CH—O), 5.66 (1H, dt, J=14.4 and 6.7 Hz, H-5), 5.79 (1H, d, J=9.1 Hz, —NH—), 6.07 (1H, t, J=9.8 Hz, H-3'), 7.31–7.55 and 7.92–8.01 (20H, 2 sets of m, 4×—C$_6$H$_5$).

B. (2S,3R,4E)-3-Benzoyloxy-1-(2,3-di-O-benzoyl-α-D-glucopyranosyloxy)-2-(cis-15-tetracosenoylamino)-4-octadecene

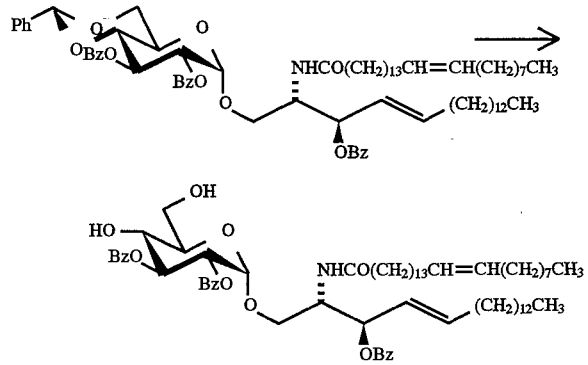

(2S,3R,4E)-3-Benzoyloxy-1-(2,3-di-O-benzoyl-4,6-O-benzylidene-α-D-glucopyranosyloxy)-2-(cis-15-tetracosenoylamino)-4-octadecene (180 mg, 0.148 mmol) was reacted as described in Example 1-K and afforded the title compound (133 mg, 80%) as a pale yellow oil.

IR (CH$_2$Cl$_2$) $v_{max}$ (cm$^{-1}$): 3600 (O—H), 3440 (N—H), 3060, 2930, 2860 (C—H), 1725 and 1675 (C=O).

$^1$H NMR 400 MHz (CDCl$_3$) δ(ppm): 0.89 (6H, t, J=6.8 Hz, 2×—CH$_3$), 1.23–1.28 (56H, m, 2×—(CH$_2$)$_{11}$— and —(CH$_2$)$_6$), 1.60–1.63 (1H, m, —OH), 1.90–2.05 (6H, m, 3×=CH—C$\underline{H}_2$—), 2.10–2.25 (2H, m, —C$\underline{H}_2$CONH—), 3.13 (1H, br s, —OH), 3.74 (1H, dd, J=10.6 and 4.6 Hz, H-1), 3.85–3.98 (5H, m, H-1, H-6', H-5' and H-4'), 4.52–4.59 (1H, m, H-2), 5.22 (1H, d, J=3.7 Hz, H-1'), 5.28 (1H, dd, J=10.1 and 3.7 Hz, H-2'), 5.36 (2H, br t, J=4.6 Hz, cis-CH=CH—), 5.51 (1H, dd, J=14.7 and 7.4 Hz, H-4), 5.55 (1H, br t, J=7.4 Hz, H-3), 5.71 (1H, dd, J=10.0 and 8.9 Hz, H-3'), 5.76 (1H, dt, J=14.7 and 6.9 Hz, H-5), 5.82 (1H, d, J=9.2 Hz, —NH—), 7.33–7.58 and 7.95–8.01 (15H, 2 sets of m, 3×—C$_6$H$_5$).

C. (2S,3R,4E)-3-Benzoyloxy-1-[2,3-di-O-benzoyl-4,6-di-O-(sodium oxysulfonyl)-α-D-glucopyranosyloxy]-2-(cis-15-tetracosenoylamino)-4-octadecene

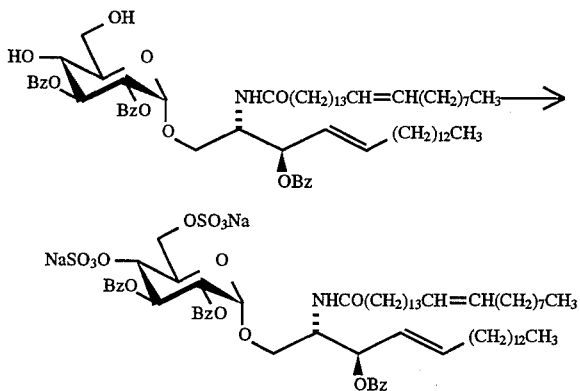

(2S,3R,4E)-3-Benzoyloxy-1-(2,3-di-O-benzoyl-1-α-D-glucopyranosyloxy)-2-(cis-15-tetracosenoylamino)-4-octadecene (129 mg, 0.115 mmol) was reacted as described in Example 1-L and afforded the title compound (149 mg, 98%) as a white solid.

IR (Nujol) $v_{max}$ (cm$^{-1}$): 3560, 3450, 3420 (N—H), 1730, 1680 and 1650 (C=O).

$^1$H NMR 400 MHz (DMSO-d$_6$) δ(ppm): 0.83 (3H, t, J=6.8 Hz, —CH$_3$), 0.83 (3H, t, J=6.8 Hz, —CH$_3$), 1.12–1.37 (56H, m, 2×—(CH$_2$)$_{11}$— and —(CH$_2$)$_6$—), 1.74–1.81 and 1.86–2.07 (8H, 2 sets of m, 3×=CH—C$\underline{H}_2$— and —C$\underline{H}_2$CONH—), 5.53 (1H, dd, J=10.5 and 7.4 Hz, H-1), 3.70 (1H, dd, J=11.1 Hz, and 9.2 Hz, H-5'), 3.87 (1H, dd, J=10.7 and 4.9 Hz, H-1), 3.95 (1H, br t, J=9.5 Hz, H-6'), 4.20 (1H, t, J=9.7 Hz, H-4'), 4.24–4.31 (1H, m, H-2), 4.36 (1H, br d, J=10.0 Hz, H-6'), 5.02 (1H, dd, J=10.3 and 3.7 Hz, H-2'), 5.14 (1H, d, J=3.6 Hz, H-1'), 5.30 (2H, br t, J=4.8 Hz, cis-CH=CH—), 5.44 (1H, dd, J=7.3 and 4.9 Hz, H-3), 5.56 (1H, dd, J=15.1 and 7.5 Hz, H-4), 5.71 (1H, d, J=9.6 Hz, H-3'), 5.73 (1H, dt, J=15.1 and 6.7 Hz, H-5), 7.34–7.39, 7.46–7.61 and 7.78–7.91 (15H, m, 3×—C$_6$H$_5$).

EXAMPLE 10

(2S,3R,4E)-1-[2,3-di-O-benzoyl-4,6-Di-O-(sodium oxysulfonyl)-α-D-galactopyranosyloxy]-3-benzoyloxy-2-hexanoylamino-4-undecene A. (2S,3R,4E)-1,3-O-Benzylidene-4-undecene-1,2,3-triol

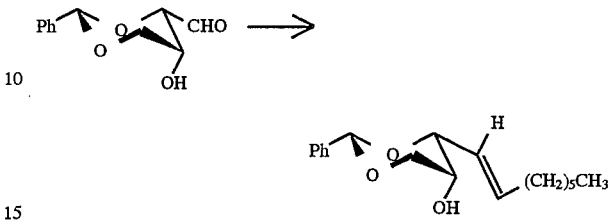

Reaction of 2,4-O-benzylidene-D-threose [as described by P. Zimmermann and R. R. Schmidt. *Liebigs Ann. Chem.*, 663–667 (1988).] (23.5 g, 0.112 mol) with n-heptyltriphenylphosphonium bromide [as described by C. F. Hauser, T. W. Brooks, M. L. Miles, M. A. Raymond and G. B. Butler, *J. Org. Chem.*, 28, 372 (1963).] (64 g, 0.145 mol) and phenyllithium (0.393 mol) using the methodology described by P. Zimmermann and R. R. Schmidt gave 15.14 g (46%) of the title material as a white solid after chromatography.

m.p. 50°–52° C.; [α]$_D^{22}$: -2° (c=0.5, CHCl$_3$).

IR (KBr) $v_{max}$ (cm$^{-1}$): 3380 (OH).

$^1$H NMR 400 MHz (CDCl$_3$) δ(ppm): 0.89 (3H, t, J=6.9 Hz, —CH$_3$), 1.2–1.45 (8H, m, —(CH$_2$)$_4$—), 2.09 (2H, m, =CHC$\underline{H}_2$—), 2.64 (1H, d, J=10.4 Hz, —OH), 3.54 (1H, m, H-2), 4.09 (1H, dd, J=1.3 and 11.8 Hz, H-1), 4.25 (1H, dd, J=1.9 and 11.8 Hz, H-1), 4.42 (1H, br d, J=6 Hz, H-3), 5.63 (1H, s, —O—CH—O—), 5.67 (1H, m, J=15.6 Hz, H-4), 5.88 (1H, m, J=15.6 Hz, H-5), 7.38 and 7.53 (3H and 2H, 2m, —C$_6$H$_5$).

Anal. Calcd. for C$_{18}$H$_{26}$O$_3$: C, 74.45; H, 9.02. Found: C, 74.47; H, 8.87.

B. (2S,3R,4E)-2-Azido-1,3-O-Benzylidene-4-undecene-1,3-diol

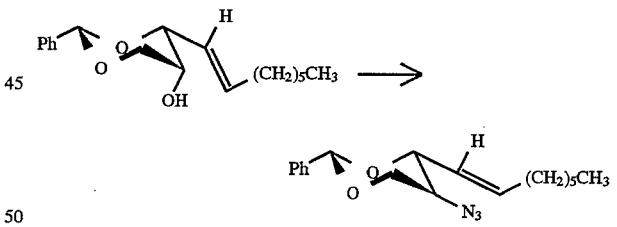

(2S,3R,4E)-1,3-O-Benzylidene-4-undecene-1,2,3-triol (9.20 g, 31.7 mmol) was reacted by the general procedure as described in Example 19-B and gave 5.32 g (53%) of the title material as an oil.

[α]$_D^{22}$: -17° (c=1.0, CHCl$_3$).

IR (NaCl, film) $v_{max}$ (cm$^{-1}$): 2105 (N$_3$).

$^1$H NMR 200 MHz (CDCl$_3$) δ(ppm): 0.89 (3H, t, J=6.5 Hz, —CH$_3$), 1.2–1.5 (8H, m, —(CH$_2$)$_4$—), 2.11 (2H, m, =CHC$\underline{H}_2$—) 3.46 (1H, ddd, J=4.7 Hz, 9.0 and 10.7 Hz, H-2), 3.62 (1H, dd, J=10.7 and 10.7 Hz, H-1), 4.05 (1H, dd, J=7.4 and 9.0 Hz, H-3), 4.34 (1H, dd, J=4.7 and 10.7 Hz, H-1), 5.49 (1H, s, —O—CH—O—), 5.59 (1H, ddt, J=7.4, 15.5 and 1.3 Hz, H-4), 6.00 (1H, dt, J=6.8 and 15.5 Hz, H-5), 7.3–7.5 (5H, m, —C$_6$H$_5$).

Anal. Calcd. for C$_{18}$H$_{25}$N$_3$O$_2$: C, 68.54; H, 7.99; N, 13.32. Found: C, 68.59; H, 7.49; N, 13.41.

C. (2S,3R,4E)-2-Azido-4-undecene-1,3-diol

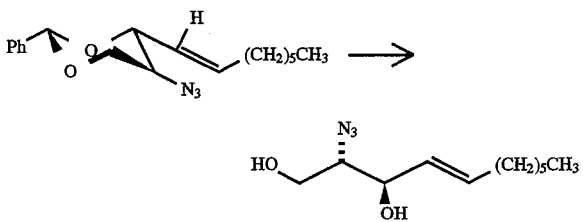

(2S,3R,4E)-2-Azido-1,3-O-benzylidene-4-undecene-1,3-diol (5.32 g, 11.9 mmol) was reacted by the general procedure as described in Example 19-C and gave 3.48 g (91%) of the title material as a white solid.

m.p. 29°–30° C. (hexane); $[\alpha]_D^{22}$: –51° (c=1.0, CHCl$_3$).
IR (NaCl, film) $v_{max}$ (cm$^{-1}$): 3350 (OH), 2100 (N$_3$).
$^1$H NMR 200 MHz (CDCl$_3$) δ(ppm): 0.88 (3H, t, J=6.5 Hz, —CH$_3$), 1.2–1.7 (8H, m, —(CH$_2$)$_4$—), 2.1 (4H, m, =CHC$\underline{H}_2$— and 2×—OH), 3.51 (1H, dt, J=5.3 and 5.3 Hz, H-2), 3.78 (2H, br d, CH$_2$—1), 4.25 (1H, br t, H-3), 5.53 (1H, ddt, J=15.4, 7.2 and 1.3 Hz, H-4), 5.82 (1H, dt, J=15.4 and 6.6 Hz, H-5).
Anal. Calcd. for: C$_{11}$H$_{21}$N$_3$O$_2$: C, 58.12; H, 9.31; N, 18.49. Found: C, 58.21; H, 9.22; N, 18.27.

D. (2S,3R,4E)-2-Azido-1-O-t-butyldimethylsilyl-4-undecene-1,3-diol

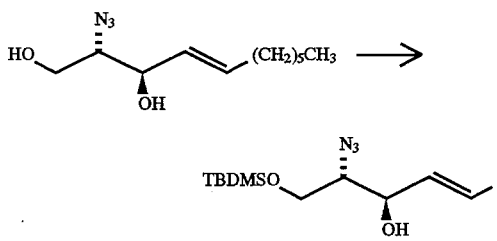

(2S,3R,4E)-2-Azido-4-undecene-1,3-diol (2.74 g, 12.06 mmol) was reacted by the general procedure as described in Example 19-D and gave 3.96 g (96%) of the title material as an oil.
$[\alpha]_D^{22}$: –3.5° (c=1.0, CHCl$_3$).
IR (NaCl, film) $v_{max}$ (cm$^{-1}$): 3440 (OH), 2100 (N$_3$).
$^1$H NMR 200 MHz (CDCl$_3$) δ(ppm): 0.09 (6H, s, —SiCH$_3$), 0.9 (12H, br s, —Si-t-Bu and —CH$_3$), 1.2–1.5 (8H, m, —(CH$_2$)$_4$—), 2.06 (2H, m, =CHC$\underline{H}_2$—), 2.32 (1H, d, J=5.0 Hz, —OH), 3.42 (1H, m, H-2), 3.80 (2H, m, CH$_2$—1), 4.21 (1H, m, H-3), 5.49 (1H, ddt, J=15.4, 7.0 and 1.3 Hz, H-4), 5.78 (1H, m, H-5).
Anal. Calcd. for C$_{17}$H$_{35}$N$_3$O$_2$Si: C, 59.78, H, 10.33; N, 12.30. Found: C, 59.71; H, 10.24; N, 12.16.

E. (2S,3R, 4E)-2-Azido-3-benzoyloxy-1-O-t-butyldimethylsilyl-4-undecene-1-ol

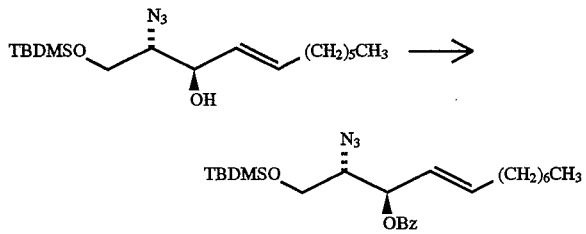

(2S,3R,4E)-2-Azido-1-O-t-butyldimethylsilyl-4-undecene-1,3 diol (3.96 g, 11.6 mmol) was reacted by the general procedure as described in Example 19-E and gave 5.2 g (100%) of the crude title material which was used as such in the next step.

IR (NaCl, film) $v_{max}$ (cm$^{-1}$): 2100 (N$_3$), 1725 (C=O ester).
$^1$H NMR 200 MHz (CDCl$_2$) δ(ppm): 0.07 (6H, s, —SiCH$_3$), 0.86 (3H, t, J=6.7 Hz, —CH$_3$), 0.91 (9H, s, —Si-t-Bu), 1.2–1.5 (8H, m, —(CH$_2$)$_4$—), 2.08 (2H, m, =CHC$\underline{H}_2$—), 3.6–3.9 (3H, m, CH$_2$—1 and H-2), 5.5–5.7 (2H, m, H-3 and H-4), 5.92 (1H, dt, J=6.7 and 14.4 Hz, H-5), 7.45, 7.56 and 8.06 (2H, 1H and 2H, 3m, —C$_6$H$_5$).

F. (2S,3R,4E)-2-Azido-3-benzoyloxy-4-undecene-1-ol

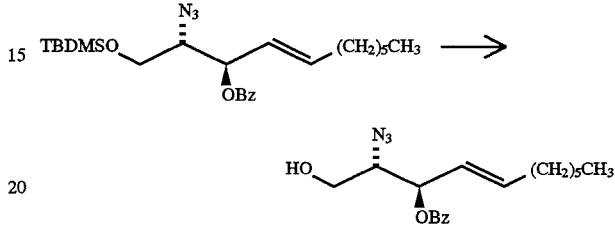

(2S,3R,4E)-2-azido-3-benzoyloxy-1-O-t-butyldimethylsilyl-4-undecene-1-ol (5.20 g, 11.6 mol) was treated by the general procedure as described in Example 19-E and gave 3.26 g (85%) of the title material as an oil.
$[\alpha]_D^{22}$: –65° (c=1.0, CHCl$_3$).
IR (NaCl, film) $v_{max}$ (cm$^{-1}$): 2105 (N$_3$), 1720 (C=O of ester).
$^1$H NMR 400 MHz (CDCl$_3$) δ(ppm): 0.87 (3H, t, J=6.8 Hz, —CH$_3$), 1.2–1.4 (8H, m, —(CH$_2$)$_4$—), 2.09 (2H, m, =CHC$\underline{H}_2$—), 3.63 (1H, dd, J=11.7 and 7.1 Hz, H-1), 3.76 (1H, dd, J=11.7 and 4.0 Hz, H-1), 3.81 (1H, m, H-2), 5.58–5.65 (2H, m, H-3 and H-4), 5.95 (1H, m, H-5), 7.44, 7.59 and 8.06 (2H, 1H and 2H, 3m, —C$_6$H$_5$).
Anal. Calcd. for C$_{18}$H$_{25}$N$_3$O$_3$·0.5 H$_2$O: C, 63.51; H, 7.70; N, 12.34. Found: C, 63.45; H, 7.45; N, 12.29.

G. (2S,3R,4E)-2-Azido-3-benzoyloxy-1-(2,3,4,6-tetra-O-acetyl-α-D-galactopyranosyloxy)-4-undecene and (2S,3R,4E)-2-azido-3-benzoyloxy-1-(2,3,4,6-tetra-O-acetyl-β-D-galactopyranosyloxy)-4-undecene

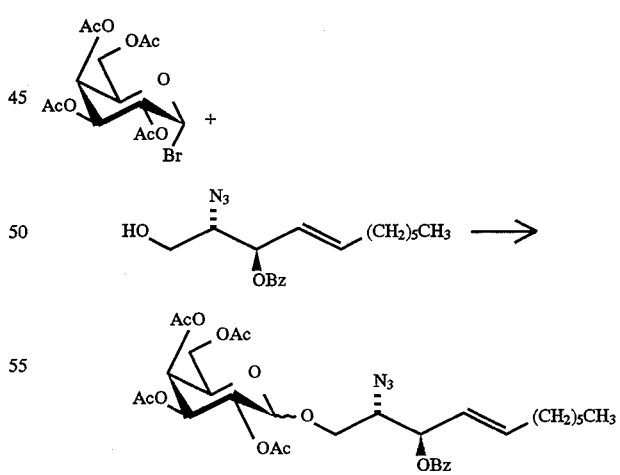

(2S,3R,4E)-2-Azido-3-benzoyloxy-4-undecene-1-ol (4.17 g, 12.58 mmol) and 2,3,4,6-tetra-O-acetyl-α-D-galactopyranosyl bromide [as described by P. Zimmermann and R. R. Schmidt. *Liebigs Ann. Chem.*, 663–667 (1988).] (8.2 g, 20.0 mmol) were reacted by the general procedure as described in Example 1-A and gave 1.11 g (13%) of the α-anomer and 5.72 g (68%) of the β-anomer.

α-anomer: Needles, m.p. 67°–68° C. (hexane).

$[\alpha]_D^{22}$: +700° (c=1.0, CHCl₃).

IR (KBr) $v_{max}$ (cm⁻¹): 2100 (N₃), 1752, 1745 and 1722 (C=O ester).

¹H NMR 400 MHz (CDCl₃) δ(ppm): 0.87 (3H, t, J=6.8 Hz, —CH₃), 1.2–1.4 (8H, m, —(CH₂)₄—), 2.0, 2.01, 2.09 and 2.15 (4×3H, 4s, 4×—OCOCH₃), 2.08 (2H, m, =CH—C$\underline{H}$₂), 3.52 (1H, dd, J=10.7 and 7.7 Hz, H-1), 3.88 (1H, dd, J=10.7 and 3.54 Hz, H-1), 3.93 (1H, m, H-2), 4.09 (2H, m, H-6'), 4.24 (1H, m H-5), 5.13–5.18 (2H, m, H-1' and H-2'), 5.34–5.39 (1H, m, H-3'), 5.49 (1H, dd, J=3.3 and 1.2 Hz, H-4'), 5.53–5.61 (2H, m, H-3 and H-4), 5.9–6.0 (1H, m, H-5), 7.47, 7.59 and 8.05 (2H, 1H and 2H, 3m, —C₆H₅).

Anal. Calcd. for C₃₂H₄₃N₃O₁₂: C, 58.03; H, 6.55; N, 6.35. Found: C, 58.14; H, 6.38; N, 6.37.

β-anomer: Clear oil.

$[\alpha]_D^{22}$: −28° (c=1.0, CHCl₃).

IR (NaCl, film) $v_{max}$ (cm⁻¹): 2108 (N₃),1750 and 1725 (C=O).

¹H NMR 400 MHz (CDCl₃) δ(ppm): 0.87 (3H, t, J=6.8 Hz, —CH₃), 1.26–1.4 (8H, m, —(CH₂)₄—), 1.99, 2.03, 2.11 and 2.16 (4×3H, 4s, 4×—OCOCH₃), 2.09 (2H, m, =CH—C$\underline{H}$₂), 3.60 (1H, m, H-1), 3.85–3.97 (2H, m, H-1 and H-2), 4.12 (2H, ABX system, $J_{AB}$=11 Hz, $J_{AX}$=5.07 Hz and $J_{BX}$=5.1 Hz, H-6'), 4.51 (1H, d, J=7.97 Hz, H-1'), 5.02 (1H, dd, J=10.54 and 3.41 Hz, H-3'), 5.25 (1H, dd, J=10.54 and 7.97 Hz, H-2'), 5.39 (1H, dd, J=3.41 and 0.87 Hz, H-4'), 5.53–5.62 (2H, m, H-3 and H-4), 5.94 (1H, dt, J=14.3 and 7.1 Hz, H-5), 7.27, 7.48 and 8.06 (2H, 1H and 2H, 3m, —C₆H₅).

Anal. Calcd. for C₃₂H₄₃N₃O₁₂: C, 58.03; H, 6.55; N, 6.35. Found: C, 57.89; H, 6.29; N, 6.30.

H. (2S,3R,4E)-2-Azido-3-benzoyloxy-1-(α-D-galactopyranosyloxy)-4-undecene

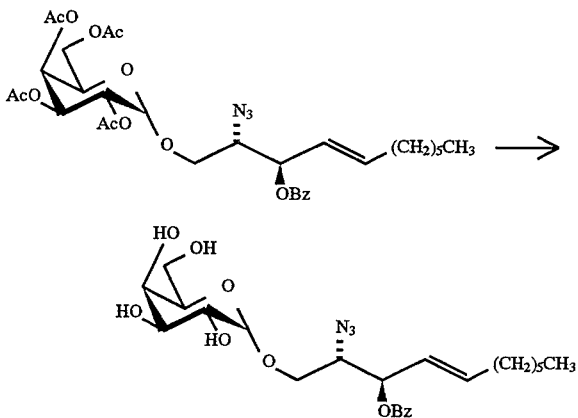

A solution of (2S,3R,4E) 2-azido-3-benzoyloxy-1-(2,3,4,6-tetra-O-acetyl-α-D-galactopyranosyloxy)-4-undecene 0.720 g, 1.09 mmol;) in a mixture of methanol (30 mL) and dichloromethane (10 mL) was treated at 0°–5° C. with 0.4 mL (0.11 mmol) of a 0.29M solution of sodium methoxide in methanol. After 2 hours at 22° C., the solution was neutralized with Dowex-50W 8% XL (H⁺), filtered, concentrated and chromatographed on silica gel (2.5×8 cm). Elution with a gradient of methanol (10–20%) in chloroform gave 0.439 g (81%) of the title material as a thick glass.

$[\alpha]_D^{22}$: +45.5° (c=1.1, CHCl₃).

IR (NaCl, film) $v_{max}$ (cm⁻¹): 2100 (N₃) and 1720 (C=O of ester).

¹H NMR 400 MHz (DMSO-d₆) δ(ppm): 0.81 (3H, t, J=6.8 Hz, CH₃), 1.2–1.4 (8H, m, (CH₂)₄), 2.03 (2H, m, =CH—C$\underline{H}$₂), 3.4–3.6 (5H, m, H-1', H-2', H-3' and C$\underline{H}$₂OH), 3.62 (1H, broad t, H-5'), 3.70 (1H, m, H-4'), 3.74 (1H, dd, J=10.8 and J=5.1 Hz, H-1), 4.15 (1H, m, H-2), 4.37 (1H, d, J=4.2 Hz, OH, exchanged D₂O ), 4.42 (1H, d, J=6.2 Hz, OH, exchanged D₂O), 4.53 (1H, t, J=5.5 Hz, OH, exchanged D₂O), 4.60 (1H, d, J=5.3 Hz, OH, exchanged D₂O), 4.70 (1H, d, J=3.34 Hz, H-1'), 5.57 (1H, dd, J=14.8 and J=7.5 Hz, H-4), 5.62 (1H, dd, J=7.5 and J=3.9 Hz, H-3), 5.85 (1H, dt, J=14.8 and J=6.8 Hz, H-5), 7.54, 7.65 and 7.98 (2H, 1H and 2H, 3m, C₆H₅).

Anal. Calcd. for C₂₄H₃₅N₃O₈·0.25 H₂O: C, 57.88; H, 7.18; N, 8.44. Found: C, 57.75; H, 6.99; N, 8.39.

I. (2S,3R,4E)-2-Azido-3-benzoyloxy-1-(4,6-O-benzylidene-α-D-galactopyranosyloxy)-4-undecene

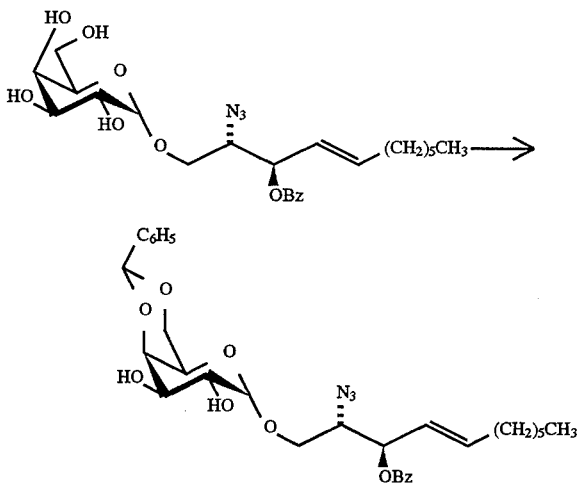

A solution of (2S,3R,4E) 2-azido-3-benzoyloxy-1-(α-D-galactopyranosyloxy)-4-undecene (0.418 g, 0.847 mmol) in 98% formic acid (3 mL) was treated at 22° C. with benzaldehyde (3 mL). After 1.5 h the reaction mixture was diluted with ethyl acetate (75 mL); washed with saturated sodium bicarbonate and dried (MgSO₄). The residue obtained after evaporation of the solvent was chromatographed on silica gel (2.5×12 cm, elution with a gradient of ethyl acetate 20–30% in toluene) and gave 0.390 g (79%) of the title material as a white solid after trituration in a mixture of ethyl acetate and hexane.

m.p.=109°–110° C.; $[\alpha]_D^{22}$: +33° (c=1.0, CHCl₃).

IR (KBr) $v_{max}$ (cm⁻¹): 2138 (N₃) and 1718 (C=O of ester).

¹H NMR 400 MHz (DMSO-d₆) δ(ppm): 0.82 (3H, t, J=6.8 Hz, CH₃), 1.2–1.4 (8H, m, (CH₂)₄), 2.05 (2H, m, =CH—C$\underline{H}$₂), 3.53 (1H, dd, J=10.7 and J=7.35 Hz, H-1), 3.65 (1H, broad s, H-5'), 3.69 (1H, m, becomes dd upon D₂O exchange J=10.3 and J=3.4 Hz, H-2'), 3.74 (1H, m overlapping with H-1, H-3'), 3.77 (1H, dd, J=10.7 and J=4.9 Hz, H-1), 4.02 (2H, AB part of ABX system, $J_{AX}$=1.0, $J_{BX}$=1.4 and $J_{AB}$=11.8 Hz, Δv=25.2 Hz, CH₂O-6'), 4.16 (2H, m, H-2 and H-4'), 4.66 (1H, d, J=6.1 Hz, OH, exchanged D₂O), 4.82 (1H, d, J=5.9 Hz, OH, exchanged D₂O), 4.84 (1H, d, J=3.4 Hz, H-1'), 5.54 (1H, s, C$\underline{H}$C₆H₅), 5.59 (1H, dd, J=14.8 and J=7.6 Hz, H-4), 5.64 (1H, dd, J=7.6 and J=3.9 Hz, H-3), 5.87 (1H, dd, J=14.8 and J=6.8 Hz, H-5), 7.35, 7.43, 7.55, 7.68 and 7.98 (3H, 2H, 2H, 1H and 2H, 5m, 2×C₆H₅).

Anal. Calcd. for C₃₁H₃₉N₃O₈: C, 64.01; H, 6.76; N, 7.22. Found: C, 63.90; H, 6.67; N, 7.23.

J. (2S,3R,4E)-2-Azido-1-(2,3-di-O-benzoyl-4,6-O-benzylidene-α-D-galactopyranosyloxy)-3-benzoyloxy-4-undecene

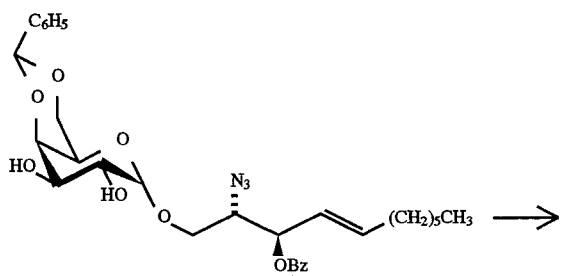

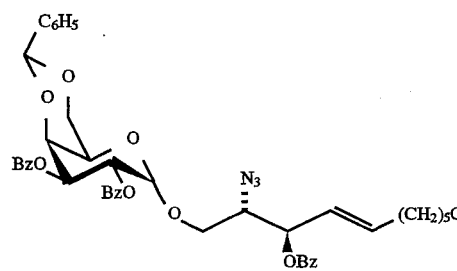

A solution of (2S,3R,4E) 2-azido-3-benzoyloxy-1-(4,6-O-benzylidene-α-D-galactopyranosyloxy)-4-undecene (0.350 g, 0.60 mmol) in dry pyridine (8 mL) was treated at 0°–5° C. with benzoyl chloride (0.34 g, 2.4 mmol) and a small crystal of 4-dimethylaminopyridine. After 16 h at 0°–5° C., methanol (2 mL) was added and the reaction mixture was evaporated under vacuum. Chromatography of the residue on silica gel (2.5×10 cm) using a gradient of ethyl acetate (0–5%) in toluene gave 0.460 g (96%) of the title material as a thick oil.

$[\alpha]_D^{22}$: +119° (c=1.0, CHCl$_3$).

IR (NaCl, film) $\nu_{max}$ (cm$^{-1}$): 2105 (N$_3$) and 1720 (C=O of ester).

$^1$H NMR 400 MHz (CDCl$_3$) δ(ppm): 0.87 (3H, t, J=6.7 Hz, CH$_3$), 1.2–1.4 (8H, m, (CH$_2$)$_4$), 2.07 (2H, m, =CH—CH$_2$), 3.58 (1H, dd, J=10.3 and J=7.5 Hz, H-1), 3.93 (1H, dd, J=10.3 and J=3.9 Hz, H-1), 3.97 (1H, m, H-2), 3.99 (1H, broad s, H-5'), 4.20 (2H, AB part of ABX system, J$_{AX}$=1.2 Hz, J$_{BX}$=1.3 Hz and J$_{AB}$=12.4 Hz, Δν=79.2 Hz, CH$_2$O-6'), 4.70 (1H, broad d, J=3 Hz, H-4'). 5.42 (1H, d, J=3.3 Hz, H-1'), 5.53–5.61 (2H, m, H-3 and H-4), 5.58 (1H, s, CHC$_6$H$_5$), 5.78 (1H, dd, J=10.8 and J=3.3 Hz, H-2'), 5.84 (1H, dd, J=10.8 and J=3.4 Hz, H-3'), 5.92 (1H, dt, J=14.2 and J=6.7 Hz, H-5), 7.34–7.6 and 8.0–8.02 (14H and 6H, 2m, 4×C$_6$H$_5$).

Anal. Calcd. for C$_{45}$H$_{47}$N$_3$O$_{10}$: C, 68.43; H, 6.0; N, 5.32. Found: C, 68.50; H, 5.97; N, 5.36.

K. (2S,3R,4E)-1-(2,3-di-O-benzoyl-4,6-di-O-benzylidene-α-D-galactopyranosyloxy)-3-benzoyloxy-2-hexanoylamino-4-undecene

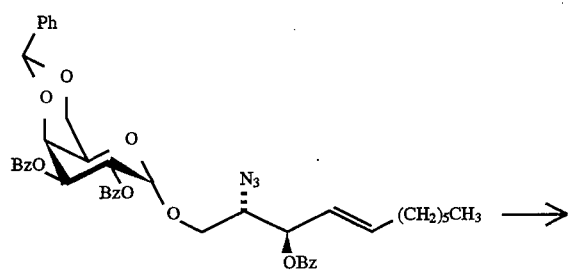

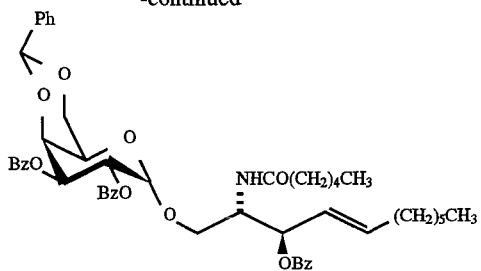

A solution of (2S,3R,4E) 2-azido-1-(2,3-di-O-benzoyl-4,6-O-benzylidene-α-D-galactopyranosyloxy)-3-benzoyloxy-4-undecene (0.450 g, 0.57 mmol) was reduced and acylated by the general procedure as described in Example 1–5 except that hexanoyl chloride (0.080 g, 0.59 mmol) was used as the acylating agent. Chromatography on silica gel (2.5×12 cm, gradient of ethyl acetate 10–20% in toluene) gave 0.413 g (84%) of the title material as an oil.

$[\alpha]_D^{22}$: +13.5° (c=1.0, CHCl$_3$).

IR (NaCl, film) $\nu_{max}$ (cm$^{-1}$): 1720 (C=O of ester) and 1660 (C=O of amide).

$^1$H NMR 400 MHz (CDCl$_3$) δ(ppm): 0.85 and 0.90 (2×3H, 2t, J=7.0 and J=6.8 Hz, 2×CH$_3$), 1.2–1.4 and 1.55–1.65 (14H, m, (CH$_2$)$_4$) and (CH$_2$)$_3$), 1.99 (2H, m, =CH—CH$_2$), 2.14 (2H, m, COCH$_2$), 3.75 (1H, dd, J=10.9 and J=5.2 Hz, H-1), 3.91 (1H, dd, J=10.9 and J=4.0 Hz, H-1), 3.91 (1H, broad s, H-5), 4.21 (2H, AB part of ABX system, J$_{AX}$=1.1 Hz, J$_{BX}$=1.3, J$_{AB}$=12.5 Hz, Δν=88.9 Hz, CH$_2$O-6'), 4.55 (1H, m, H-2), 4.66 (1H, broad d, J=3 Hz, H-4'), 5.38 (1H, d, J=3.32 Hz, H-1'), 5.49 (1H, dd, J=14.6 and J=7.41Hz, H-4), 5.53 (1H, dd, J=7.4 and J=5.3 Hz, H-3), 5.56 (1H, s, CHC$_6$H$_5$), 5.7–5.75 (2H, m, H-5 and NH), 5.76 (1H, dd, J=10.8 and J=3.3 Hz, H-2'), 5.81 (1H, dd, J=10.8 and J=3.3 Hz, H-3'), 7.3–7.6 and 7.9–8.05 (14H and 6H, 2×m, 4×C$_6$H$_5$).

Anal. Calcd. for C$_{51}$H$_{79}$NO$_{11}$: C, 71.06; H, 6.90; N, 1.62. Found: C, 70.82; H, 6.81; N, 1.81.

L. (2S,3R,4E)-1-(2,3-di-O-benzoyl-α-D-galactopyranosyloxy)-3-benzoyloxy-2-hexanoylamino-4-undecene

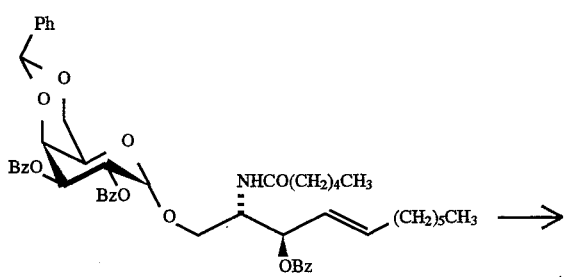

(2S,3R,4E)-1-(2,3-di-O-Benzoyl-4,6-di-O-benzylidene-α-D-galactopyranosyloxy)-3-benzoyloxy-2-hexanoylamino-4-undecene (0.410 g, 0.476 mmol) was reacted by the general procedure as described in Example I-K and gave 0.276 g (75%) of the title material as a white amorphous solid.

$[\alpha]_D^{22}$: +107° (c=1.0, CHCl$_3$).

IR (KBr) $v_{max}$ (cm$^{-1}$): 1725 (C=O of ester) and 1655 (C=O of amide).

$^1$H NMR 400 MHz (CDCl$_3$) δ(ppm): 0.85 and 0.89 (2×3H, 2s, J=7.0 and J=6.6 Hz, 2×CH$_3$), 1.23–1.35 and 1.55–1.65 (12H and 2H, 2m, (CH$_2$)$_4$ and (CH$_2$)$_3$), 1.99 (2H, m, =CH—CH$_2$), 2.15 (2H, m, COCH$_2$), 3.79 (1H, dd, J=11.2 and J=5.4 Hz, H-1), 3.88 (1H, dd, J=11.2 and J=4.0 Hz, H-1), 3.91 (1H, dd, J=11.9 and J=4.2 Hz, 1H, CH$_2$O-6'), 3.97 (1H, dd, J=11.9 and J=5.4 Hz, CH$_2$O-6'), 4.07 (1H, broad t, J=5 Hz, H-5'), 4.45 (1H, broad d, J=2 Hz, H-4'), 4.56 (1H, m, H-2), 5.3 (1H, d, J=3.2 Hz, H-1'), 5.49 (1H, dd, J=14.5 and J=7.3 Hz, H-4), 5.53 (1H, dd, J=7.3 and J=6.0 Hz, H-3), 5.67 (1H, dd, J=10.7 and J=2.6 Hz, H-3'), 5.71 (1H, dd, J=10.7 and J=3.2 Hz, H-2'), 5.76 (1H, dt, J=14.5 and J=7.0 Hz, H-5), 5.82 (1H, d, J=9.3 Hz, NH), 7.3–7.6 and 7.9–9.0 (9H and 6H, 2m, 3×C$_6$H$_5$).

M. (2S,3R,4E)-1-[2,3-di-O-benzoyl-4,6-di-O-(sodium oxysulfonyl)-β-D-galactopyranosyloxy]-3-benzoyloxy-2-hexanoylamino-4-undecene

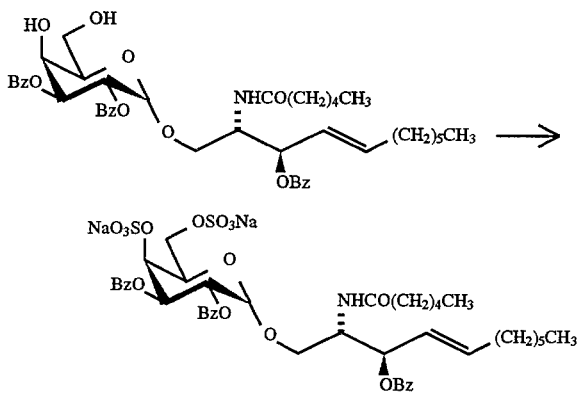

A solution of (2S,3R,4E) 1-(2,3-di-O-benzoyl-α-D-galactopyranosyloxy)-3-benzoyloxy-2-hexanoylamino-4-undecene (0.270 g, 0.35 mmol) in dry pyridine (25mL) was treated with sulfur trioxide pyridine complex (0.33 g) and the resulting mixture was maintained at 40° C. for 8 h. The cooled mixture was treated with water (5 mL) and solid sodium bicarbonate (0.5 g). After the evolution of gas has ceased, the solvent was evaporated and the residue was extracted with a mixture of chloroform and methanol (7:3). The combined extracts were concentrated and chromatographed on silica gel (3×11 cm, elution with a gradient of methanol 10–20% in chloroform) to give 0.315 g (92%) of the title material as a white amorphous solid.

$[\alpha]_D^{22}$: +99° (c=1.0, CHCl$_3$).

IR (KBr) $v_{max}$ (cm$^{-1}$): 1727 (C=O of ester) and 1640 (C=O of amide).

$^1$H NMR 400 MHz (DMSO-d$_6$) δ(ppm): 0.74 and 0.78 (2×3H, 2t, J=7.15 and J=6.5 Hz, 2×CH$_3$), 1.0–1.4 (14H, m, (CH$_2$)$_4$ and (CH$_2$)$_3$), 1.87 (2H, m, COCH$_2$), 1.98 (2H, m, =CHCH$_2$), 3.55 (1H, dd, J=10.4 and J=3.9 Hz, H-1), 3.85 (2H, m, H-1 and H-5'), 4.12 (1H, dd, J=11.9 and J=2.6 Hz, CH$_2$O-6'), 4.27 (1H, m, H-2), 4.32 (1H, broad dd, CH$_2$O-6'), 4.8 (1H, broad d, J=3 Hz, H-4'), 5.14 (1H, d, J=3.4 Hz, H-1'), 5.41 (1H, dd, J=10.8 and J=3.4 Hz, H-2'), 5.45–5.5 (2H, m, H-3 and H-3'), 5.57 (1H, dd, J=15.2 and J=7.4 Hz, H-4), 5.72 (1H, dt, J=15.2 and J=6.6 Hz, H-5), 7.35–7.4, 7.45–7.61 and 7.81–7.93 (4H, 5H and 7H, 3×m, 3×C$_6$H$_5$ and NH).

Anal. Calcd. for C$_{44}$H$_{53}$NO$_{17}$ S$_2$Na$_2$.2H$_2$O: C, 52.12; H, 5.67; N, 1.38. Found: C, 52.12; H, 5.43; N, 1.45.

EXAMPLE 11

(2S,3R,4E)-2-Hexadecanoylamino-3-benzoyloxy-1-[2,3-di-O-benzyl-4,6-di-O-(sodium oxysulfonyl)-α-D-galactopyranosyloxy]-4-octadecene A. Ethyl 4,6-O-benzylidene-1-thio-β-D-galactopyranoside

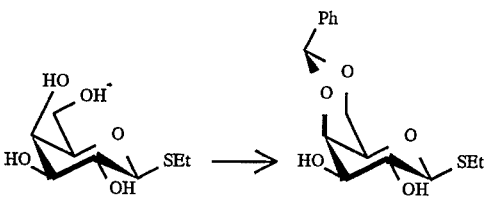

Benzaldehyde dimethylacetal (2.0 mL, 13.3 mmol) followed by para-toluenesulfonic acid (15 mg) were added to a stirred solution of ethyl 1-thio-β-D-galactopyranoside (1.3 g, 5.80 mmol) in acetonitrile (20 mL) at 22° C. The mixture was stirred for 1 hour, then triethylamine (≈3 mL) was added and the mixture was evaporated under vacuum. The residue was dissolved in ethyl acetate and washed with water and a 1M aqueous solution of sodium bicarbonate. The organic layer was dried over anhydrous magnesium sulfate, filtered and concentrated. The residue was precipitated from ethyl acetate/hexane and afforded the title compound (1.3 g, 72%) as a white solid.

$^1$H NMR 400 MHz (CDCl$_3$) δ(ppm): 1.35 (3H, t=J=7.4 Hz, —CH$_3$), 2.57 (1H, s, —OH), 2.59 (1H, d, J=10.1 Hz, —OH), 2.70–2.90 (2H, m, —SCH$_2$—), 3.54 (1H, d, J=1.3 Hz, H-5), 3.69 (1H, ddd, J=12.3, 9.1 and 3.5 Hz, H-3), 3.82 (1H, ddd, J=10.5, 9.2 and 1.4 Hz, H-2), 4.04 (1H, dd, J=12.5 and 1.8 Hz, H-6), 4.27 (1H, dd, J=3.6 and 1.0 Hz, H-4), 4.36 (1H, dd, J=12.3 and 1.8 Hz, H-6), 4.35 (1H, d, J=9.5 Hz, H-1), 3.55 (1H, s, —O—CH—O—), 7.34–7.52 (5H, m, —C$_6$H$_5$).

B. Ethyl 2,3-di-O-benzyl-4,6-O-benzylidene-1-thio-β-D-galactopyranoside

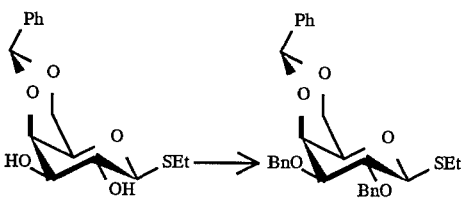

A solution of ethyl 4,6-O-benzylidene-1-thio-β-D-galactopyranoside (1.3 g, 4.17 mmol) in tetrahydrofuran (20 mL) was added to sodium hydride (980 mg, 60% suspension in oil, 24.5 mmol, washed with hexane) at 22° C. and this solution was stirred for 30 minutes. The solution was cooled down to 0° C. and a solution of benzyl bromide (≈2 mL, ≈17 mmol) in dimethylformamide (12 mL) was added. The resulting mixture was stirred at 22° C. for ≈1 hour, then poured in a cold 1M aqueous solution of sodium bicarbonate and extracted with ethyl acetate. The organic layers were washed with a 1M aqueous solution of sodium bicarbonate and water, dried over anhydrous magnesium sulfate, filtered and evaporated. The residue was purified by trituration with ethyl acetate (≈5 mL) and hexane (≈150 mL) and afforded the title compound (1.24 g, 60%) as a white solid.

$^1$H NMR 200 MHz (CDCl$_3$) δ(ppm): 1.33 (1H, t, J=6.4 Hz, —CH$_3$), 2.69–2.88 (2H, m, —CH$_2$S—), 3.36 (1H, br s, H-5), 3.59 (1H, dd, J=9.1 and 3.4 Hz, H-3), 3.89 (1H, t, J=9.4 Hz, H-2), 3.96 (1H, dd, J=12.3 and 1.8 Hz, H-6), 4.16 (1H, d, J=3.4 Hz, H-4), 4.31 (1H, dd, J=12.3 and 1.4 Hz, H-6), 4.44 (1H, d, J=9.6 Hz, H-1), 4.76 (2H, br s, CH$_2$-benzyl), 4.83 (1H, d, J$_{AB}$=10.2 Hz, CH$_2$-benzyl), 4.87 (1H, d, J$_{AB}$=10.2 Hz, CH$_2$-benzyl), 5.48 (1H, s, —O—CH—O—), 7.28–7.57 (5H, m, —C$_6$H$_5$).

C. (2S,3R,4E)-2-Azido-3-benzoyloxy-1-(2,3-di-O-benzyl-4,6-O-benzylidene-α-D-galactopyranosyloxy)-4-octadecene and (2S,3R,4E)-2-azido-3-benzoyloxy-1-(2,3-di-O-benzyl-4,6-O-benzylidene-β-D-galactopyranosyloxy)-4-octadecene

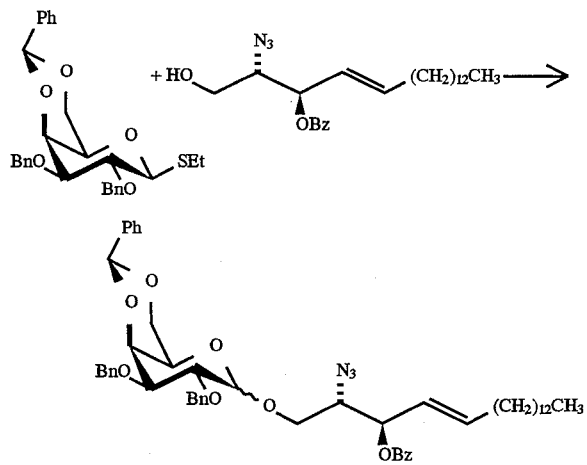

Ethyl 2,3-di-O-benzyl-4,6-O-benzylidene-1-thio-β-D-galactopyranoside (1.4 g, 2.85 mmol) and (2S,3R,4E)-2-azido-3-benzoyloxy-4-octadecen-1-ol (0.60 g, 1.40 mmol) were reacted by the general procedure as described in Example 1-F in using toluene instead of ethyl ether. The α-anomer (942 mg, 78%) and the β-anomer (257 mg, 21%) of the title compound were obtained after silica get chromatography.

IR (CH$_2$Cl$_2$) ν$_{max}$ (cm$^{-1}$) α-anomer: 3060, 2930, 2860 (C—H), 2110 (N$_3$) and 1720 (C=O).

$^1$H NMR 400 MHz (CDCl$_3$) δ(ppm) α-anomer: 0.89 (3H, t, J=6.8 Hz, —CH$_3$), 1.25–1.38 (22H, m, —(CH$_2$)$_{11}$—), 2.04–2.09 (2H, m, =CH—CH$_2$—), 3.58 (1H, dd, J=10.9 and 7.5 Hz, H-1), 3.67 (1H, br s, H-5'), 3.73 (1H, dd, J=10.9 and 4.7 Hz, H-1), 3.92–3.97 (1H, m, H-2), 4.00 (1H, dd, J=10.1 and 3.4 Hz, H-3'), 4.01 (1H, dd, J=12.5 and 1.5 Hz, H-6'), 4.09 (1H, dd, J=10.1 and 3.4 Hz, H-2'), 4.19 (1H, d, J=3.4, H-4'), 4.21 (1H, dd, J=12.5 Hz and 1.3 Hz, H-6'), 4.68 (1H, d, J$_{AB}$=12.0 Hz, CH$_2$-benzyl), 4.74 (1H, d, J$_{AB}$=12.2 Hz, CH$_2$-benzyl), 4.83 (1H, d, J$_{AB}$=12.2 Hz, CH$_2$-benzyl), 4.85 (1H, d, J$_{AB}$=12.0 Hz, CH$_2$-benzyl), 4.93 (1H, d, J=3.4 Hz, H-1'), 5.49 (1H, s, —O—CH—O—), 5.58 (1H, dd, J=14.7 and 8.1 Hz, H-4), 5.63 (1H, dd, J=8.1 and 4.1 Hz, H-3), 5.90 (1H, dt, J=14.7 and 6.7 Hz, H-5), 7.22–7.61 and 8.06–8.08 (20H, 2 sets of m, 4×—C$_6$H$_5$).

$^1$H NMR 400 MHz (CDCl$_3$) δ(ppm) β-anomer: 0.89 (3H, t, J=6.8 Hz, —CH$_3$), 1.24–1.33 (22H, m, —(CH$_2$)$_{11}$—), 1.99–2.04 (2H, m, =CH—CH$_2$—), 3.33 (1H, br s, H-5'), 3.57 (1H, dd, J=9.6 and 3.6 Hz, H-3'), 3.61 (1H, d, J=4.7 Hz, H-1), 3.89 (1H, dd, J=9.6 and 7.8 Hz, H-2'), 3.98–4.05 (3H, m, H -6', H-2 and H-1), 4.12 (1H, d, J=3.5 Hz, H-4'), 4.30 (1H, d, J=12.5 Hz, H-6'), 4.41 (1H, d, J=7.8 Hz, H-1'), 4.76 (1H, d, J$_{AB}$=12.4 Hz, CH$_2$ of benzyl), 4.78 (1H, d, J$_{AB}$=12.4 Hz, CH$_2$ of benzyl), 4.84 (1H, d, J$_{AB}$=10.8 Hz, CH$_2$ of benzyl), 4.94 (1H, d, J$_{AB}$=10.8 Hz, CH$_2$ of benzyl), 5.50 (2H, s, —O—CH—O—), 5.57 (1H, dd, J=15.4 and 7.9 Hz, H-4), 5.68 (1H, dd, J=7.9 and 3.2 Hz, H-3), 5.88 (1H, dd, J=15.3 and 6.7 Hz, H-5), 7.28–7.59 and 8.06–8.09 (20H, 3 sets of m, 4×—C$_6$H$_5$).

D. (2S,3R,4E)-2-Hexadecanoylamino-3-benzoyloxy-1-(2,3-di-O-benzyl-4,6-O-benzylidene-α-D-galactopyranosyloxy)-4-octadecene

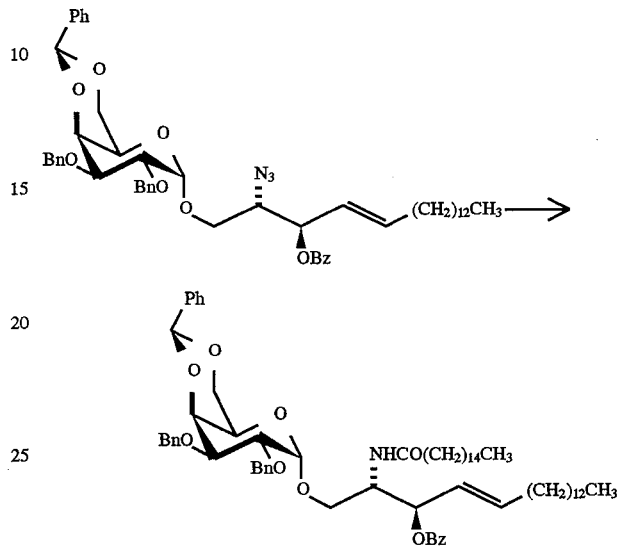

(2S,3R,4E)-2-Azido-3-benzoyloxy-1-(2,3-di-O-benzyl-4,6-O-benzylidene-α-D-galactopyranosyloxy)-4-octadecene (306 mg, 0.36 mmol) was reacted by the general procedure as described in Example 1-J and afforded the title compound (410 mg, 100%) as a white solid.

IR (CH$_2$Cl$_2$) ν$_{max}$ (cm$^{-1}$): 3440 (N—H), 3060, 2930, 2860 (C—H), 1715 and 1675 (C=O).

$^1$H NMR 200 MHz (CDCl$_3$) δ(ppm): 0.88 (6H, t, J=6.7 Hz, 2×—CH$_3$), 1.26–1.70 (48H, m, —(CH$_2$)$_{11}$— and —(CH$_2$)$_{13}$—), 1.96–2.09 (4H, m, =CH—CH$_2$— and —NHCOCH$_2$—), 3.65 (1H, br s, H-5'), 3.78 (2H, br d, J=4.3 Hz, H-6'), 3.95 (1H, dd, J=10.1 and 3.4 Hz, H-3'), 3.99 (1H, d, J=10.5 Hz, H-1), 4.08 (1H, dd, J=10.1 and 3.4 Hz, H-2'), 4.19 (1H, d, J=10.5 Hz, H-1), 4.21 (1H, d, J=3.4 Hz, H-4'), 4.40–4.52 (1H, m, H-2), 4.72 (1H, d, J$_{AB}$=11.3 Hz, CH$_2$-benzyl), 4.82 (1H, d, J$_{AB}$=11.3 Hz, CH$_2$-benzyl), 4.75–4.82 (2H, CH$_2$-benzyl), 4.95 (1H, d, J=3.4 Hz, H-1'), 5.46 (1H, dd, J=14.9 and 7.2 Hz, H-4), 5.47 (1H, s, —O—CH—O—), 5.58 (1H, br t, J=7.2 Hz, H-3), 5.76 (1H, dt, J=14.9 and 6.5 Hz, H-5), 5.89 (1H, d, J=9.1 Hz, —NH—), 7.24–7.62 and 8.01–8.05 (20H, 2 sets of m, 4×—C$_6$H$_5$).

E. (2S,3R,4E)-2-Hexadecanoylamino-3-benzoyloxy-1-(2,3-di-O-benzyl-α-D-galactopyranosyloxy)-4-octadecene

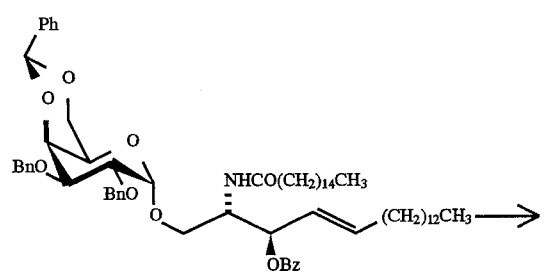

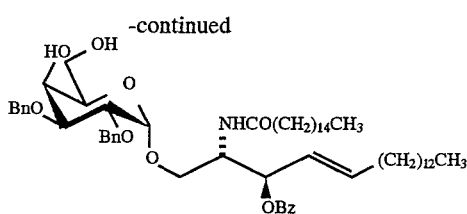

(2S,3R,4E)-2-Hexadecanoylamino-3-benzoyloxy-1-(2,3-di-O-benzyl-4,6-O-benzylidene-α-D-galactopyranosyloxy)-4-octadecene 400 mg, 0.37 mmol) was reacted by the general procedure as described in Example 1-K and afforded the title material (239 mg, 66%) as a white solid.

IR (CH$_2$Cl$_2$) v$_{max}$ (cm$^{-1}$): 3600 (O—H), 344 (N—H), 3060, 2930, 2860 (C—H), 1720 and 1670 (C=O).

$^1$H NMR 400 MHz (DMSO-d$_6$) δ(ppm): 0.85 (6H, t, J=6.8 Hz, 2×—CH$_3$), 1.19–1.28, 1.40–1.5 (48H, 2 sets of m, —(CH$_2$)$_{11}$— and —(CH$_2$)$_{13}$—), 1.95–2.16 (4H, 2 sets of m, =CH—CH$_2$ and —CH$_2$CONH—), 3.43 (1H, dd, J=10.3 and 6.2 Hz, H-1), 3.49 (1H, dd, J=11.4 and 5.1 Hz, H-6')), 3.53 (1H, dd, J=11.4 and 5.5 Hz, H-6'), 3.61 (1H, br t, J=6.2 Hz, H-5'), 3.67 (1H, dd, J=10.1 and 2.8 Hz, H-3'), 3.67 (1H, dd, J=10.3 and 5.4 Hz, H-1), 3.77 (1H, dd, J=10.1 and 3.5 Hz, H-2'), 4.01 (1H, d, J=2.6 Hz, H-4'), 4.35–4.40 (1H, m, H-2), 4.52 (1H, d, J$_{AB}$=11.9 Hz, CH$_2$-benzyl), 4.58 (1H, d, J$_{AB}$=12.2 Hz, CH$_2$-benzyl), 4.61 (1H, d, J$_{AB}$=12.2 Hz, CH$_2$-benzyl), 4.68 (1H, d, J$_{AB}$=11.9 Hz, CH$_2$-benzyl), 4.64–4.69 (1H, s, —OH), 4.88 (1H, d, J=3.5 Hz, H-1'), 5.49 (1H, dd, J=7.5 and 5.5 Hz, H-3), 5.55 (1H, dd, J=14.9 and 7.5 Hz, H-4), 5.75 (1H, dr, J=14.9 and 6.7 Hz, H-5), 7.20–7.38, 7.47–7.52, 7.61–7.66 and 7.95–7.97 (15H, 4 sets of m, 3×—C$_6$H$_5$), 7.86 (1H, d, J=8.9 Hz, —NH—).

F. (2S,3R,4E)-2-Hexadecanoylamino-3-benzoyloxy-1-[2,3-di-O-benzyl-4,6-di-O-(sodium oxysulfonyl)-α-D-galactopyranosyloxy]-4-octadecene

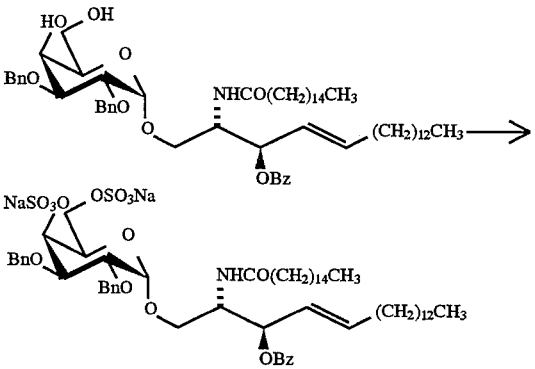

(2S,3R,4E)-2-Hexadecanoylamino-3-benzoyloxy-1-(2,3-di-O-benzyl-α-D-galactopyranosyloxy)-4-octadecene (230 mg, 0.24 mmol) was reacted by the general procedure as described in Example 1-L and afforded the title compound (142 mg, 50%) as a white fluffy solid.

IR (Nujol) v$_{max}$ (cm$^{-1}$): 3430 (N—H),1725, 1755 and 1635 (C=O).

$^1$H NMR 400 MHz (DMSO-d$_6$) δ(ppm): 0.85 (6H, t, J=6.7 Hz, 2×—CH$_3$), 1.19–1.3, 1.3–1.45 (48H, 2 sets of m, —(CH$_2$)$_{11}$— and (CH$_2$)$_{13}$—), 1.95–2.05, 2.05–2.10 (4H, 2 sets of m, =CH—CH$_2$ and —CH$_2$CONH—) 3.56 (1H, dd, J=10.7 and 6.7 Hz, H-1), 3.62 (1H, dd, J=10.0 and 3.5 Hz, H-2'), 3.77 (1H, dd, J=10.0 and 2.7 Hz, H-3'), 3.76–3.79 (1H, m, H-5'), 3.85 (1H, dd, J=11.3 and 8.7 Hz, H-6'), 4.10 (1H, br d, J=8.8 Hz, H-1), 4.10 (1H, dd, J=11.3 and 2.0 Hz, H-6'), 4.29 (1H, d, J$_{AB}$=11.2 Hz, CH$_2$-benzyl), 4.2–4.31 (1H, m, H-2), 4.55 (1H, d, J$_{AB}$=11.9 Hz, CH$_2$-benzyl), 4.59 (1H, d, J$_{AB}$=11.9 Hz, CH$_2$-benzyl), 4.67 (1H, J=2.7 Hz, H-4'), 4.92 (1H, d, J$_{AB}$=11.2 Hz, CH$_2$-benzyl), 4.92 (1H, d, J=3.6 Hz, H-1'), 5.50 (1H, dd, J=5.5 Hz, H-3), 5.58 (1H, dd, J=15.0 and 7.5 Hz, H-4), 5.72 (1H, dt, J=15.0 Hz, H-5), 7.19–7.27, 7.38–7.40, 7.47–7.51, 7.59–7.62 and 7.96–7.98 (15H, 5 sets of m, 3×—C$_6$H$_5$) and 7.83 (1H, d, J=8.7 Hz, —NH—).

EXAMPLE 12

(2S,3R,4E)-3-Benzoyloxy-2-(cis-15-tetracosenoylamino)-1-[2,6-di-O-(sodium oxysulfonyl)-α-D-galactopyranosyloxy]-4-octadecene A. (2S,3R,4E)-3-Benzoyloxy-2-(cis-15-tetracosenoylamino)-1-(3,4-O-isopropylidene-α-D-galactopyranosyloxy)-4-octadecene

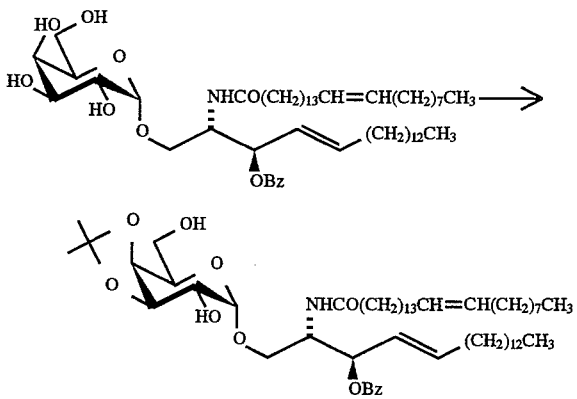

A stirred solution of (2S,3R,4E)-3-benzoyloxy-2-(cis-15-tetracosenoylamino)-1-(α-D-galactopyranosyloxy)-4-octadecene (626 mg, 0.68 mmol) described in Example 3-B in 2,2-dimethoxypropane (29 mL) was treated by p-toluenesulfonic acid (39 mg) at 22° C. and under argon. The resulting mixture was stirred for 17 hours at room temperature. Water (25 mL) was added followed by p-toluenesulfonic acid (55 mg) and this was stirred at room temperature for 2 more hours. The reaction mixture was then diluted with dichloromethane (6 mL), treated with triethylamine (0.195 mL) and stirred for 15 minutes at 22° C. The mixture was concentrated under vacuum and the residue was co-evaporated with toluene and purified by silica gel chromatography (60 g, 30% to 55% ethyl acetate/toluene) and afforded the title compound (597 mg, 92%).

[α]$_D^{22}$: +34.3° (c=1.0, CHCl$_3$).

IR (neat) v$_{max}$ (cm$^{-1}$): 3700–3150 (O—H and N—H), 3070–2700 (C—H), 1720 (C=O esters), 1650 (C=O amide).

$^1$H NMR (CDCl$_3$) δ(ppm): 0.89 (6H, t, J=6.7 Hz, 2×—CH$_3$), 1.24–1.35 (52H, m overlapping —C—(CH$_3$)$_2$, —(CH$_2$)$_{10}$—, —(CH$_2$)$_{11}$— and —(CH$_2$)$_5$—), 1.35 and 1.48 (6H, s, —C—(CH$_3$)$_2$), 1.56–1.63 (4H, m, 2×—CH$_2$—), 2.00–2.08 (6H, m, 3×=CH—CH$_2$—), 2.15–2.25 (3H, m, —NHCOCH$_2$— and —OH), 2.77 (1H, br s, —OH), 3.81 (1H, dd, J=11.1 and 5.2 Hz, H-1), 3.79–3.93 (4H, m overlapping H-1, H-1, H-6' and H-2'), 4.19 (1H, ddd, J=6.4, 4.0 and 2.1 Hz, H-5'), 4.26 (1H, dd, J=6.6 and 2.1 Hz, H-4'), 4.34 (1H, t, J=6.6 Hz, H-3'), 4.55 (1H, m, H-2), 4.82 (1H, d, J=3.8 Hz, H-1'), 5.36 (2H, m, cis-CH=CH—), 5.54 (1H, dd, J=15.3 and 7.4 Hz, H-4), 5.66 (1H, t, J=7.4 Hz, H-3), 5.88

(1H, dt, J=15.3 and 6.9 Hz, H-5), 6.16 (1H, d, J=9.4 Hz, —NH—), 7.44–8.05 (5H, 3m, —C₆H₅).

Anal. Calcd. for $C_{58}H_{99}NO_9$: C, 72.99; H, 10.45; N, 1.47. Found: C, 73.10; H, 10.35; N, 1.62.

B. (2S,3R,4E)-3-Benzoyloxy-2-(cis-15-tetracosenoylamino)-1-[3,4-O-isopropylidene-2,6-di-O-(sodium oxysulfonyl)-α-D-galactopyranosyloxy]-4-octadecene

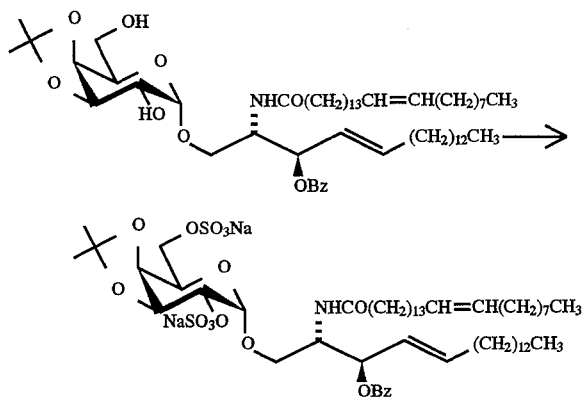

Sulfur trioxide pyridine complex (0.693 g, 4.35 mmol) was added in a solution of (2S,3R,4E)-3-benzoyloxy-1-(3,4-O-isopropylidene-α-D-galactopyranosyloxy)-2-(cis-15-tetracosenoylamino)-4-octadecene (0.575 g, 0.6 mmol) in pyridine (17 mL) at room temperature and under argon. The reaction mixture was stirred for 5 hours at room temperature, then water (10 mL) was added followed by solid sodium bicarbonate (1.46 g). The solvents were evaporated under vacuum and the resulting residue was triturated with methanol (25 mL) and filtered. The filtrate was concentrated under vacuum and the residue was purified by silica gel chromatography (130 g, 10% to 30% methanol/chloroform) to give the title material (0.695 g, 100%) as a white solid.

$[\alpha]_D^{22}$: +38.6° (c=1.0, CHCl₃/MeOH 8:2).

IR (KBr) $\nu_{max}$ (cm⁻¹): 3700–3150 (O—H and N—H), 2930, 2860 (C—H), 1720 (C=O esters), 1640 (C=O amide).

¹H NMR (DMSO-d₆) δ(ppm): 0.85 (6H, t, J=6.4 Hz, 2×—CH₃), 1.20–1.35 (57H, m overlapping —C—(CH₃)₂, —(CH₂)₁₀—, —(CH₂)₁₁—, —(CH₂)₆—, and —C—(CH₃)₂), 1.39 (3H, s, —C—(CH₃)₂), 1.39–1.46 (2H, m overlapping —C—(CH₃)₂, —CH₂—), 1.95–2.16 (8H, m, 3×=CH—CH₂— and —NHCOCH₂—), 3.40 (1H, dd, J=9.9 and 7.0 Hz, H-1), 3.78 (1H, dd, J=9.9 and 6.6 Hz, H-1), 3.82–3.88 and 4.09–4.13 (4H, 2m, H-6', H-4' and H-5'), 3.98 (1H, dd, J=8.4 and 5.0 Hz, H-3'), 4.0 (1H, dd, J=8.4 and 3.1 Hz, H-2'), 4.27 (1H, m, H-2), 5.07 (1H, d, J=3.1 Hz, H-1'), 5.32 (2H, m, cis-CH=CH—), 5.51 (1H, dd, J=7.4 and 4.6 Hz, H-3), 5.55 (1H, dd, J=14.4 and 7.4 Hz, H-4), 5.74 (1H, dt, J=14.4 and 6.9 Hz, H-5), 7.82 (1H, d, J=8.2 Hz, —NH—), 7.49–7.96 (5H, 3m, —C₆H₅).

C. (2S,3R,4E)-3-Benzoyloxy-2-(cis-15-tetracosenoylamino)-1-[2,6-di-O-(sodium oxysulfonyl)-α-D-galactopyranosyloxy]-4-octadecene

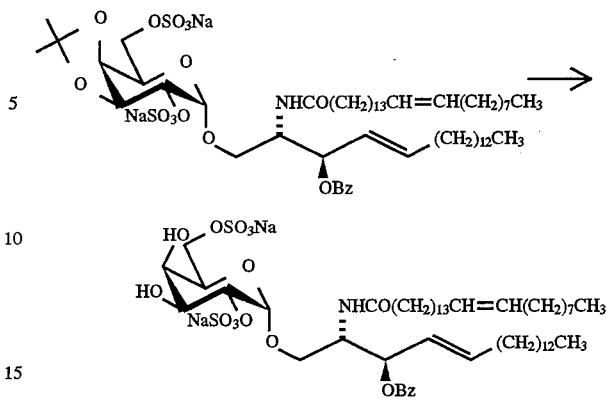

(2S,3R,4E)-3-Benzoyloxy-1-[3,4-O-isopropylidene-2,6-di-O-(sodium oxysulfonyl)-α-D-galactopyranosyloxy]-2-(cis-15-tetracosenoylamino)-4-octadecene (0.695 g, 0.6 mmol) was treated with trifluoroacetic acid (90%, 17 mL) and this resulting suspension was stirred for 30 minutes at room temperature. The mixture was concentrated under vacuum and the residue was co-evaporated with toluene (2×25 mL). The residue was then dissolved in a mixture of methanol/chloroform (2:8, 40 mL) and treated with Rexyn 102 (Na⁺) resin. The mixture was stirred for ≈15 minutes. The resin was filtered and washed with a mixture methanol/chloroform (2:8). The filtrate was finally concentrated under vacuum. The residue obtained was purified by silica gel chromatography (150 g, 10% to 30% methanol/chloroform) and afforded the title compound (0.66 g, 98%) as an off-white solid.

$[\alpha]_D^{22}$: +32.3° (c=1.0, CHCl₃/MeOH 8:2).

IR (KBr) $\nu_{max}$ (cm⁻¹): 3700–3150 (O—H and N—H), 2930, 2860 (C—H), 1685 (C=O amide), 1210 (S=O).

¹H NMR (DMSO-d₆) δ(ppm): 0.83–0.86 (6H, m, 2×—CH₃), 1.20–1.49 (56H, m, —(CH₂)₁₀—, —(CH₂)₁₂— and —(CH₂)₆—), 1.95–2.18 (8H, m, 3×=CH—CH₂— and —NHCOCH₂—), 3.39–3.43 (1H, m, H-1), 3.66–3.86 (6H, m, H-1, H-3', H-4', H-5' and H-6'), 4.23–4.30 (1H, m, overlapping H-2', H-2), 4.28 (1H, dd, J=10.0 and 3.6 Hz, H-2'), 4.62 (1H, d, J=3.7 Hz, —OH), 4.82 (1H, d, J=3.2 Hz, —OH), 4.86 (1H, d, J=3.6 Hz, H-1'), 5.31 (2H, m, cis-CH=CH—), 5.48 (1H, dd, J=7.3 and 4.8 Hz, H-3), 5.56 (1H, dd, J=15.1 and 7.3 Hz, H-4), 5.74 (1H, dt, J=15.1 and 6.8 Hz, H-5), 7.40–7.96 (5H, 3m, —C₆H₅), 7.82 (1H, d, J=8.4 Hz, —NH—).

EXAMPLE 13

(2S,3R,4E)-3-Benzoyloxy-2-(cis-15-tetracosenoylamino)-1-[3,4-di-O-benzoyl-2,6-di-O-(sodium oxysulfonyl)-α-D-galactopyranosyloxy]-4-octadecene

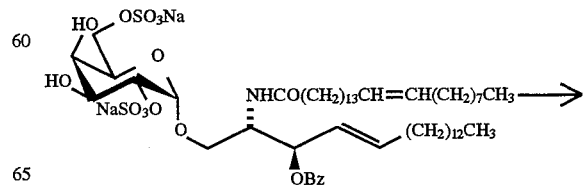

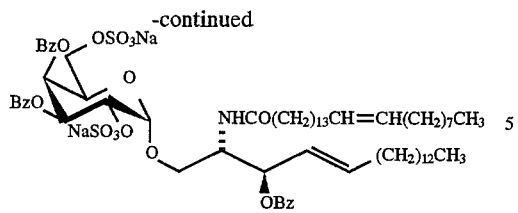

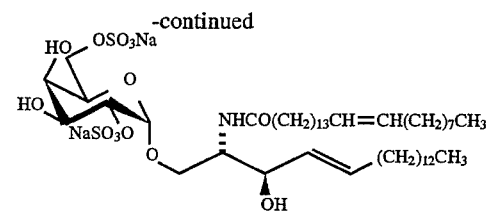

To a stirred solution of (2S,3R,4E)-3-benzoyloxy-1-[2,6-di-O-(sodium oxysulfonyl)-α-D-galactopyranosyloxy]-2-(cis-15-tetracosenoylamino)-4-octadecene (205 mg, 0.18 mmol) in pyridine (2 mL) at 0° C. was added benzoyl chloride (104 mL, 0.90 mmol) followed by dimethylaminopyridine (1 crystal). The mixture was stirred for 2 hours at 22° C. and benzoyl chloride was added again (11 μL, 0.09 mmol). The mixture was stirred for 30 more minutes at 22° C. then methanol (1.5 mL) was added and the stirring was continued for 15 minutes. The mixture was evaporated under vacuum and the resulting residue was purified by silica gel chromatography (≈130 g, 5% to 25% methanol/chloroform). The residue was dissolved in methanol/chloroform (12 mL, 2:8) and treated with Rexyn 102 (Na⁺) resin and the resulting mixture was stirred for 1 hour, filtered on microfibre paper and evaporated under vacuum. The residue was co-evaporated with toluene then purified by silica gel column chromatography (72 g, 10% to 25% methanol/chloroform) and afforded the title compound (116 mg, 49%) as a white solid.

$[\alpha]_D^{22}$: +67.6° (c=1.0, CHCl$_3$/MeOH 8:2).

IR (KBr) $v_{max}$ (cm$^{-1}$): 3700–3150 (O—H and N—H), 2930, 2860 (C—H), 1735 (C=O esters), 1640 (C=O amide), 1270 (S=O).

$^1$H NMR (DMSO-d$_6$) δ(ppm): 0.83 (6H, t, J=6.8 Hz, 2×—CH$_3$), 1.20–1.46 (56H, m, —(CH$_2$)$_{10}$—, —(CH$_2$)$_{12}$— and —(CH$_2$)$_6$—), 1.94–2.18 (8H, m, 3×=CH—C$\underline{H}_2$— and —NHCOC$\underline{H}_2$—), 3.60 (1H, dd, J=10.1 and 7.3 Hz, H-1), 3.72 (1H, dd, J=10.3 and 6.9 Hz, H-6'), 3.79 (1H, dd, J=10.3 and 6.4 Hz, H-6'), 3.86 (1H, dd, J=10.0 and 5.7 Hz, H-1), 4.33–4.40 (2H, m, H-2 and H-5'), 4.63 (1H, dd, J=10.8 and 3.4 Hz, H-2'), 5.28–5.36 (4H, m, H-1', H-3' and cis-CH=CH—), 5.54 (1H, dd, J=7.3 and 4.7 Hz, H-3), 5.62 (1H, dd, J=15.0 and 7.3 Hz, H-4), 5.67 (1H, d, J=3.0 Hz, H-4'), 5.79 (1H, dt, J=15.0 and 6.7 Hz, H-5), 7.36–9.21 (16H, 4m, 3×—C$_6$H$_5$ and —NH—).

EXAMPLE 14

(2S,3R,4E)-3-Hydroxy-2-(cis-15-tetracosenoylamino)-1-[2,6-di-O-(sodium oxysulfonyl)-α-D-galactopyranosyloxy]-4-octadecene

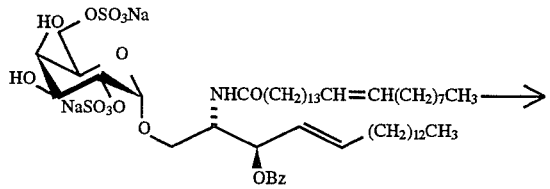

A freshly prepared solution of sodium methoxide in methanol (0.2M, 1.07 mL, 0.21 mmol) was added to a stirred solution of (2S,3R,4E)-3-benzoyloxy-1-[2,6-di-O-(sodium oxysulfonyl)-α-D-galactopyranosyloxy]-2-(cis-15-tetracosenoylamino)-4-octadecene (0.372 g, 0.33 mmol) in methanol (13 mL) and dichloromethane (13 mL) at 22° C. and under argon. The mixture was stirred for 47 hours, then Dowex-50W 8% XL 100–200 mesh resin was added until the pH of the mixture reached ≈7. The resin was filtered and washed with a mixture chloroform/methanol (7:3). The filtrate was then treated with Rexyn 102 (Na⁺) resin and stirred for ≈15 minutes. The resin was filtered and washed again with a mixture chloroform/methanol (7:3 to 1:9). The filtrate was finally concentrated under vacuum. The residue obtained was purified by silica gel chromatography (80 g, 10% to 35% methanol/chloroform) and afforded the title compound (0.157 g, 47%) as a white amorphous solid.

IR (KBr) $v_{max}$ (cm$^{-1}$): 3700–3100 (O—H and N—H), 2930, 2860 (C—H), 1735 (C=O esters): 1640 (C=O amide), 1250 and 1010 (S=O).

$^1$H NMR (DMSO-d$_6$) δ(ppm): 0.84 (6H, t, J=6.7 Hz, 2×—CH$_3$), 1.22–1.50 (56H, m, —(CH$_2$)$_{10}$—, —(CH$_2$)$_{12}$— and —(CH$_2$)$_6$—), 1.89–2.12 (8H, m, 3×=CH—C$\underline{H}_2$— and —NHCOC$\underline{H}_2$—), 3.45 (1H, dd, J=9.8 and 5.2 Hz, H-1), 3.57 (1H, dd, J=9.8 and 3.8 Hz, H-1), 3.67–3.84 (6H, m, H-6', H-4', H-3', H-2 and H-3), 3.97 (1H, br t, J=6.8 Hz, H-5'), 4.24 (1H, dd, J=10.3 and 3.6 Hz, H-2'), 4.56 (1H, d, J=4.0 Hz, —OH), 4.74 (1H, d, J=4.1 Hz, —OH), 4.84–4.86 (1H, m overlapping H-1', —OH), 4.85 (1H, d, J=3.6 Hz, H-1'), 5.27–5.33 (2H, m, cis-CH=CH—), 5.34 (1H, dd, J=8.5 Hz, —NH—).

EXAMPLE 15

(2S,3R,4E)-3-Benzoyloxy-2-hexadecanoylamino-1-[2,6-di-O-(sodium oxysulfonyl)-α-D-galactopyranosyloxy]-4-octadecene A. (2S,3R,4E)-3-Benzoyloxy-2-hexadecanoylamino-1-(α-D-galactopyranosyloxy)-4-octadecene

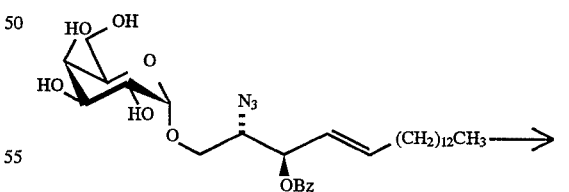

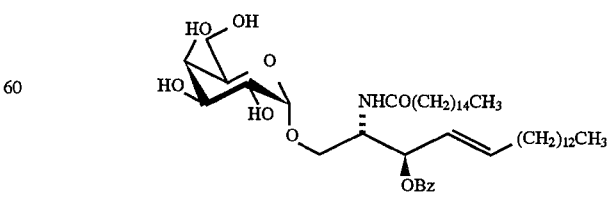

(2S,3R,4E)-2-Azido-3-benzoyloxy-1-(α-D-galactopyranosyloxy)-4-octadecene (0.729 g, 1.23 mmol)

described in Example 1-G was reacted by the general procedure as described in Example 1-J and gave 0.772 g (78%) of the title material as a white solid.

m.p.=59°–60° C. (acetone). $[\alpha]_D^{22}$: +50.5° (c=1.0, MeOH).

IR (NaCl, film) $v_{max}$ (cm$^{-1}$): 1720 (C=O ester) and 1650 (C=O amide).

$^1$H NMR 400 MHz (DMSO-d$_6$) δ(ppm): 0.85 (6H, t, J=6.8 Hz, 2×—CH$_3$), 1.2–1.6 (48H, m, —(CH$_2$)$_{11}$— and —(CH$_2$)$_{13}$—), 2.0 and 2.09 (2×2H, 2m, =CH—C$\underline{H}_2$— and —NHCOC$\underline{H}_2$—), 3.37–3.69 (8H, m, H-1, H-2', H-3', H-4', H-5' and H-6'), 4.17 (1H, d, J=7.3 Hz, —OH), 4.35 (1H, d, J=4.2 Hz, —OH), 4.36 (1H, m, overlapping with —OH, H-2), 4.50 (1H, t, J=5.5 Hz, —OH), 4.54 (1H, d, J=5.1 Hz, —OH), 4.61 (1H, d, J=2.8 Hz, H-1'), 5.47–5.55 (2H, m, H-3 and H-4 overlapping), 5.77 (1H, dt, J=6.5 and J=14.2 Hz, H-5), 7.50, 7.64 and 7.95 (2H, 1H and 2H, 3m, —C$_6$H$_5$), 7.80 (1H, d, J=9.1 Hz, —NH—).

Anal. Calcd. for C$_{47}$H$_{81}$NO$_9$: C, 70.02; H, 10.15; N, 1.74. Found: C, 70.03; H, 10.13; N, 1.96.

B. (2S,3R,4E)-3-Benzoyloxy-2-hexadecanoylamino-1-(3,4-O-isopropylidene-α-D-galactopyranosyloxy)-4-octadecene

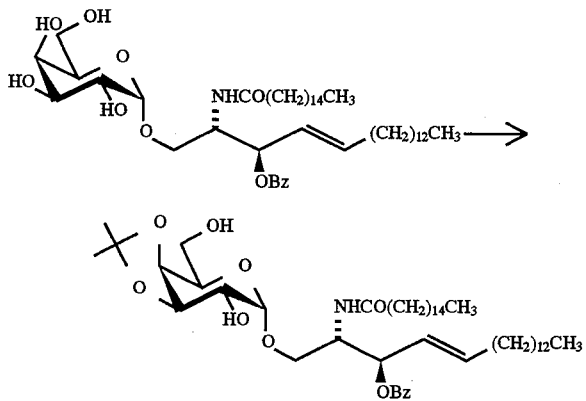

(2S,3R,4E)-3-Benzoyloxy-2-hexadecanoylamino-1-(α-D-galactopyranosyloxy)-4-octadecene (0.764 g, 0.95 mmol) was treated by the general procedure as described in Example 12-A and gave 0.793 g (99%) of the title material as a thick glass.

$[\alpha]_D^{22}$: +38° (c=1.0, CHCl$_3$).

IR (NaCl, film) $v_{max}$ (cm$^{-1}$): 1722 (C=O ester) and 1647 (C=O amide).

$^1$H NMR 400 MHz (DMSO-d$_6$) δ(ppm): 0.84 (6H, t, J=6.8 Hz, 2×—CH$_3$), 1.19 (51H, m, —(CH$_2$)$_{11}$— —(CH$_2$)$_{13}$ and —C(CH$_3$)$_2$—), 1.34 (3H, s, —C(CH$_3$)$_2$—), 1.99 and 2.07 (2×2H, 2m, =CH—C$\underline{H}_2$— and —NHCOC$\underline{H}_2$—), 3.42–3.55 (4H, m, H-1, H-2' and H-6'), 3.68 (1H, dd, J=5.7 and 10.3 Hz, H-1), 3.88 (1H, m, H-5'), 4.01 (1H, dd, J=5.8 and 7.1 Hz, H-3'), 4.10 (1H, dd, J=2.2 and 5.8 Hz, H-4'), 4.35 (1H, m, H-2), 4.6 (1H, d, J=3.45 Hz, H-1'), 4.67 (1H, t, J=5.4 Hz, —OH, exchanged with D$_2$O), 4.80 (1H, d, J=6.5 Hz, —OH, exchanged with D$_2$O), 5.47 (1H, dd, J=5.8 and 7.7 Hz, H-3), 5.51 (1H, dd, J=7.7 and 14.6 Hz, H-4), 5.76 (1H, dt, J=6.7 and 14.6 Hz, H-5), 7.48, 7.63 and 7.94 (2H, 1H and 2H, 3m, —C$_6$H$_5$), 7.80 (1H, d, J=9 Hz, —NH—).

Anal. calcd. for C$_{50}$H$_{85}$NO$_9$: C, 71.14; H, 10.15; N, 1.66. Found: C, 71.08; H, 10.14; N, 1.86.

C. (2S,3R,4E)-3-Benzoyloxy-2-hexadecanoylamino-1-[3,4-O-isopropylidene-2,6-di-O-(sodium oxysulfonyl)-α-D-galactopyranosyloxy]-4-octadecene

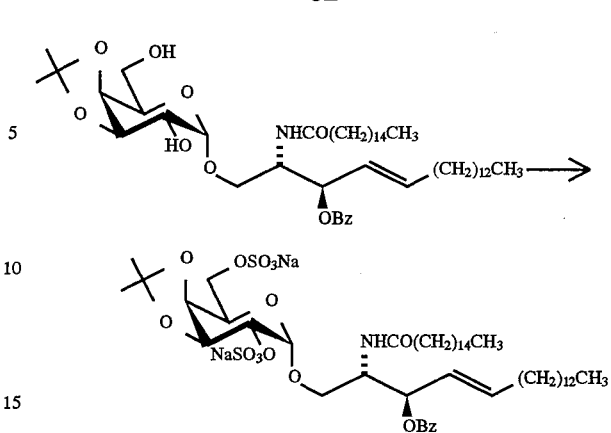

(2S,3R,4E)-3-Benzoyloxy-2-hexadecanoylamino-1-(3,4-O-isopropylidene-α-D-galactopyranosyloxy)-4-octadecene (0.757 g, 0.89 mmol) was reacted by the general procedure as described in Example 12-B and gave 0.814 g (87%) of the title material as an amorphous solid.

$[\alpha]_D^{22}$: +39° (c=1.0, MeOH).

IR (NaCl, film) $v_{max}$ (cm$^{-1}$): 1725 (C=O ester) and 1635 (C=O amide).

$^1$H NMR 400 MHz (DMSO-d$_6$) δ(ppm): 0.85 (6H, t, J=6.8 Hz, 2×—CH$_3$), 1.1–1.5 (51H, m, —C(CH$_3$)$_2$—, —(CH$_2$)$_{11}$— and —(CH$_2$)$_{13}$), 1.39 (3H, s, —C(CH$_3$)$_2$—), 1.96–2.17 (4H, m, =CH—C$\underline{H}_2$— and —NHCOC$\underline{H}_2$—), 3.40 (1H, dd, J=6.9 and 9.9 Hz, H-1), 3.78 (1H, dd, J=6.7 and 9.9 Hz, H-1), 3.87 (2H, m, H-6'), 3.99 (1H, dd, J=4.8 and 8.35 Hz, H-3'), 4.05 (1H, dd, J=3.1 and 8.4 Hz, H-2'), 4.10 (1H, d, J=4.8 Hz, H-4'), 4.11 (1H, m overlapping with H-4', H-5'), 4.27 (1H, m, H-2), 5.08 (1H, d, J=3.1 Hz, H-1'), 5.52 (1H, dd, J=4.5 and 7.4 Hz, H-3), 5.56 (1H, dd, J=7.4 and 14.4 Hz, H-4), 5.75 (1H, dt, J=6.6 and 14.4 Hz, H-5), 7.51, 7.62 and 7.95 (2H, 1H and 2H, 3m, —C$_6$H$_5$), 7.83 (1H, d, J=8.2 Hz, —NH—).

Anal. calcd. for C$_{50}$H$_{83}$NO$_{15}$S$_2$Na$_2$.3H$_2$O: C, 54.48;.H, 8.14; N, 1.27. Found: C, 54.63; H, 7.52; N, 1.44.

D. (2S,3R,4E)-3-Benzoyloxy-2-hexadecanoylamino-1-[2,6-di-O-(sodium oxysulfonyl)-α-D-galactopyranosyloxy]-4-octadecene

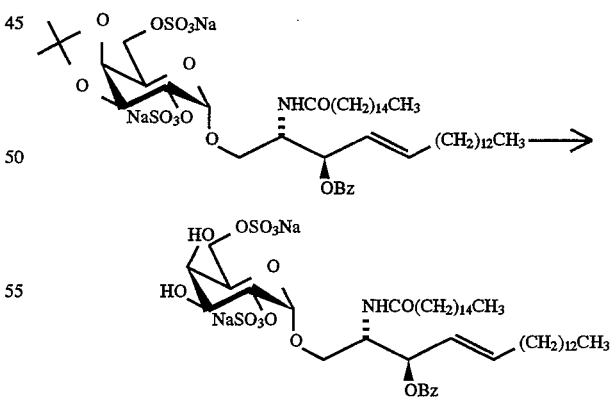

A solution of (2S,3R,4E)-3-benzoyloxy-2-hexadecanoylamino-1-[3,4-O-isopropylidene-2,6-di-O-(sodium oxysulfonyl)-α-D-galactopyranosyloxy]-4-octadecene (0.810 g, 0.773 mmol) in a mixture of tetrahydrofuran (20 mL) and 80% aqueous acetic acid (20 mL) was heated at 55° C. for 2 hours. The solvent was evaporated under vacuum and the residue was purified by silica gel chromatography (15% to 30% methanol/chloroform) to give 0.708 g (91%) of the title material as a glassy solid.

$[\alpha]_D^{22}$: +41.5° (c=1.0, MeOH ).

IR (KBr) $v_{max}$ (cm$^{-1}$): 1725 (C=O ester) and 1640 (C=O amide).

$^1$H NMR 400 MHz (DMSO-d$_6$) δ(ppm): 0.85 (6H, t, J=6.8 Hz, 2×—CH$_3$), 1.2–1.5 (48H, m, —(CH$_2$)$_{11}$— and —(CH$_2$)$_{13}$), 1.95–2.2 (4H, m, =CH—C$\underline{H}_2$— and —NHCOC$\underline{H}_2$—), 3.41 (1H, dd, J=7.1 and 10.1 Hz, H-1), 3.65–3.85 (6H, m, H-1, H-3', H-4', H-5' and H-6'), 4.25 (1H, m overlapping with H-2', H-2), 4.29 (1H, dd, J=3.6 and 9.8 Hz, H-2'), 4.62 (1H, d, J=3.7 Hz, —OH exchanged with D$_2$O), 4.83 (1H, d, J=3.4 Hz, —OH, exchanged with D$_2$O), 4.86 (1H, d, J=3.6 Hz, H-1'), 5.49 (1H, dd, J=4.7 and 7.3 Hz, H-3), 5.56 (1H, dd, J=7.3 and 15.0 Hz, H-4), 5.73 (1H, dt, J=6.6 and 15.0 Hz, H-5), 7.50, 7.62 and 7.95 (2H, 1H and 2H, 3m, —C$_6$H$_5$), 7.83 (1H, d, J=8.4 Hz, —NH—).

EXAMPLE 16

(2S,3R,4E)-3-Benzoyloxy-2-hexadecanoylamino-1-[3,4-di-O-benzoyl-2,6-di-O-(sodium oxysulfonyl)-α-D-galactopyranosyloxy]-4-octadecene

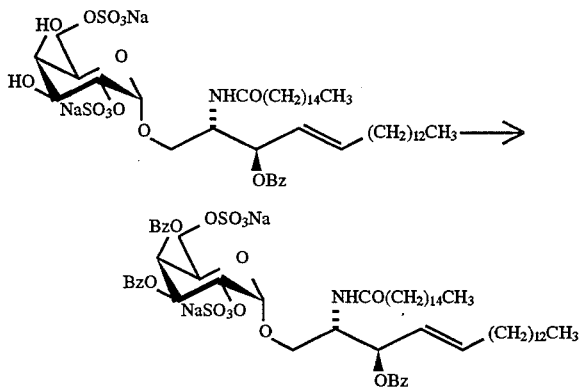

(2S,3R,4E)-3-Benzoyloxy-2-hexadecanoylamino-1-[2,6-di-O-(sodium oxysulfonyl)-α-D-galactopyranosyloxy)-4-octadecene (0.345 g, 0.342 mmol) was reacted by the general procedure as described in Example 13-A and gave 0.285 g (68%) of the title material as an amorphous solid after chromatography and lyophilization.

$[\alpha]_D^{22}$: +68° (c=1.0, MeOH).

HPLC on Zorbax Rx-C$_8$, 3.9 mm×30 cm, elution acetonitrile/0.01M aqueous ammonium acetate, 75:25, flow rate 1 mL/min, UV detector 239 nm, retention time 3.8 min, purity 94%.

IR (KBr) $v_{max}$ (cm$^{-1}$): 1730 (C=O ester) and 1660 (C=O amide).

$^1$H NMR 400 MHz (DMSO-d$_6$) δ(ppm): 0.85 (6H, t, J=6.7 Hz, 2×—CH$_3$), 1.0–1.4 (48H, m, —(CH$_2$)$_{11}$— and —(CH$_2$)$_{13}$), 1.96–2.22 (2×2H, 2m, =CH—C$\underline{H}_2$— and —NHCOC$\underline{H}_2$—), 3.71 (1H, br t, H-1), 3.80 (1H, dd, J=5.8 and 10.2 Hz, H-1), 4.0 (2H, br d, H -6'), 4.37 (1H, broad, H-5'), 4.65 (1H, dd, J=3.3 and 10.8 Hz, H-2'), 4.9 (1H, broad, H-2), 5.20 (1H, d, J=3.3 Hz, H-1'), 5.26 (1H, br d, H-3'), 5.48 (1H, dd, J=8.4 and 15.3 Hz, H-4), 5.66 (1H, br s, H-4'), 5.80 (1H, dt, J=6.6 and J=15.3 Hz, H-5), 5.92 (1H, t, H-3), 7.35–8.2 (16H, m, 3×—C$_6$H$_5$ and —NH—).

EXAMPLE 17

(2S,3R,4E)-2-Hexadecanoylamino-3-hydroxy-1-[2,6-di-O-(sodium oxysulfonyl)-α-D-galactopyranosyloxy]-4-octadecene

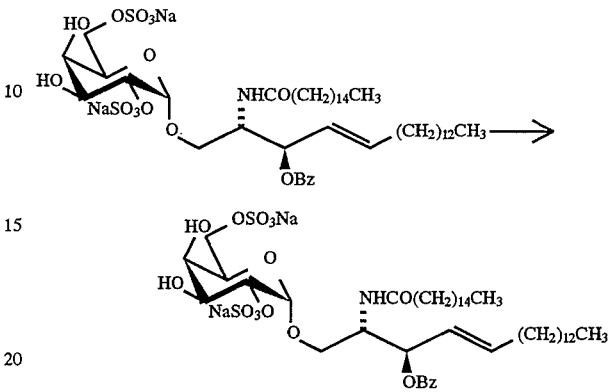

(2S,3R,4E)-3-Benzoyloxy-2-hexadecanoylamino-1-[2,6-di-O-(sodium oxysulfonyl)-α-D-galactopyranosyloxy]-4-octadecene (0.200 g, 0.198 mmol) was reacted by the general procedure as described in Example 14-A and gave 0.141 g (79%) of the title material as an amorphous solid.

$[\alpha]_D^{22}$: +40° (c=0.53, MeOH).

HPLC on Zorbax Rx-C$_8$, 4.6 mm×25 cm, elution acetonitrile/0.01M aqueous ammonium acetate, 60:40, flow rate 1 mL/min, UV detector 210 nm, retention time 4.5 min, purity 99%.

IR (KBr) $v_{max}$ (cm$^{-1}$): 1630 (C=O of amide).

$^1$H NMR 400 MHz (DMSO-d$_6$) δ(ppm): 0.84 (6H, t, J=6.8 Hz, 2×—CH$_3$), 1.1–1.5 (48H, m, —(CH$_2$)$_{11}$— and —(CH$_2$)$_{13}$), 1.42 and 1.92 (2×2H, 2m, =CH—C$\underline{H}_2$— and —NHCOC$\underline{H}_2$—), 3.46 (1H, dd, J=5.3 and J=10.0 Hz, H-1), 3.58 (1H, dd, J=3.9 and 10.0 Hz, H-1), 3.65–3.85 (6H, m, H-2, H-3', H-4', H-5' and H-6'), 3.97 (1H, m, H-3), 4.25 (1H, dd, J=3.7 and 10.3 Hz, H-2'), 4.57 (1H, d, J=4.0 Hz, —OH, exchanged D$_2$O), 4.74 (1H, d, J=4.1 Hz, —OH, exchanged D$_2$O), 4.85 (1H, d, J=1.6 Hz, —OH exchanged D$_2$O), 4.86 (1H, d, J=3.7 Hz, H-1'), 5.34 (1H, dd, J=6.8 and 15.4 Hz, H-4), 5.54 (1H, dt, J=6.7 and 15.4 Hz, H-5), 7.48 (1H, d, J=8.6 Hz, —NH—).

EXAMPLE 18

(2S,3R,4E)-3-Benzoyloxy-2-hexadecanoylamino-1-[2,3-di-O-benzoyl-4,6-di-O-(sodium oxysulfonyl)-α-D-mannopyranosyloxy]-4-octadecene A. (2S,3R,4E)-2-Azido-3-benzoyloxy-1-(2,3,4,6-tetra-O-acetyl-α-D-mannopyranosyloxy)-4-octadecene

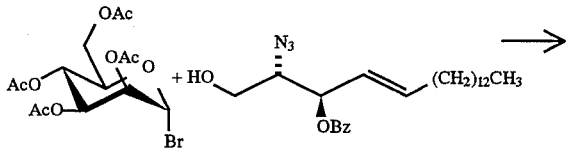

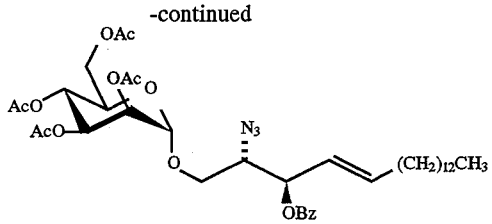

A solution of (2S,3R,4E)-2-azido-3-benzoyloxy-4-octadecene-1-ol (1.0 g, 2.43 mmol) and 2,3,4,6-tetra-O-acetyl-α-D-mannopyranosyl bromide (0.86 g, 2 mmol) in dichloromethane was cooled to −25° C. and treated with silver triflate (0.625 g, 2.43 mmol). After stirring for 1 hour, the reaction was quenched by adding collidine (0.606 g, 5 mmol). The insoluble salt was filtered through Celite. The filtrate was washed with cold diluted hydrochloric acid and then with brine. After drying over magnesium sulfate, the solvent was evaporated and the residue chromatographed on silica gel (5 to 10% ethyl acetate/hexane), and gave the title compound (0.837 g, 55%).

IR (CH$_2$Cl$_2$) $v_{max}$ (cm$^{-1}$): 2105 (—N$_3$), 1752 (—OAc), 1723 (—OBz).

$^1$H NMR 400 MHz (CDCl$_3$) δ(ppm); 0.89 (3H, t, J=6.83 Hz, —CH$_3$), 1.25 (2 OH, br s, —(CH$_2$)$_{10}$), 1.39 (2H, m, —CH$_2$—), 2.01, 2.06, 2.07, 2.17 (4×3H, 4 s, 4-OAc), 2.09 (2H, m, CH$_2$ allylic), 3.55 (1H, dd, J=10.67 and 8.28 Hz, H-1), 3.84 (1H, dd, J=10.73 and 3.85 Hz, H-1), 3.99–4.04 (2H, m, H-2, H-5'), 4.11 (1H, dd, J=12.25 and 2.33 Hz, H-6'), 4.29 (1H, dd, J=12.27 and 5.34 Hz, H-6'), 4.89 (1H, d, J=1.55 Hz, H-1'), 5.27–5.32 (2H, m-2', H-4'), 5.37 (1H, dd, J=10.02 and 3.25 Hz, H-3'), 5.56–5.62 (2H, m, H-3, H-4), 5.91–6.00 (1H, m, H-5), 7.45–8.07 (5H, 3m, —C$_6$H$_5$).

B. (2S,3R,4E)-2-Azido-3-benzoyloxy-1-(α-D-mannopyranosyloxy)-4-octadecene

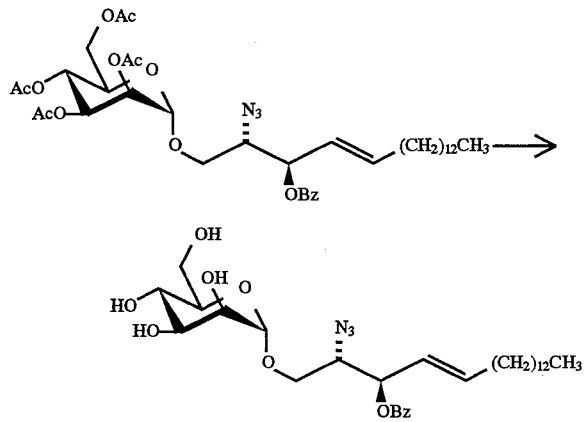

A solution of (2S,3R,4E)-2-azido-3-benzoyloxy-1-(2,3,4,6-tetra-O-acetyl-α-D-mannopyranosyloxy)-4-octadecene (0.829 g, 1.09 mmol) in ethanol (15 mL) was treated at room temperature with 1,5-diazabicyclo[4.3.0]-non-5-ene (0.135 g, 1.09 mmol). After 30 minutes some debenzoylation was apparent and the reaction mixture was cooled in ice. After an additional 180 minutes, acetic acid (0.066 g, 1.1 mmol) was added and the solvent was evaporated. The residue was purified by chromatography on silica gel (5 to 10% methanol/dichloromethane) and gave the title compound (0.51 g, 79%) as a glassy syrup.

IR (CH$_2$Cl$_2$)) $v_{max}$ (cm$^{-1}$): 3600, 3400 (—OH), 2108 (—N$_3$), 1721 (—OBz)

$^1$H NMR 400 MHz (DMSO-d$_6$) δ(ppm): 0.83 (3H, t, J=7.0 Hz, —CH$_3$), 1.10–1.40 (22H, br, s, —(CH$_2$)$_{11}$), 2.02 (2H, m, CH$_2$ allylic), 3.7–3.28 (7H, m, H-1, H-2', H-3', H-4', H-5', 2×H-6'), 3.80 (1H, dd, J=10.61 and 4.50 Hz, H-1), 4.10 (1H, m, H-2), 4.64 (1H, d, J=1.38 Hz, H-1'), 5.48–5.90 (3H, 2m, H-3, H-4, H-5), 7.48–8.0 (5H, 3m, Ar).

C. (2S,3R,4E)-2-Azido-3-benzoyloxy-1-(4,6-O-benzylidene-(α-D-mannopyranosyloxy)-4-octadecene

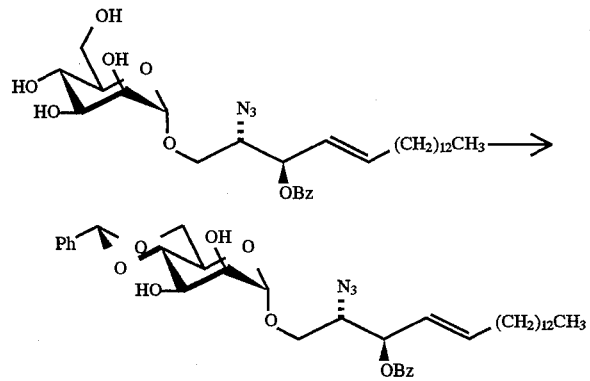

A solution of (2S,3R,4E)-2-azido-3-benzoyloxy-1-(α-D-mannopyranosyloxy)-4-octadecene (0.750 g, 1.27 mmol) and benzaldehyde dimethyl acetal (0.193 g, 1.27 mmol) in dichloromethane (10 mL) and acetonitrile (25 mL) was cooled to 5° C. and treated dropwise with trimethylsilyl-chloride (0.138 g, 1.27 mmol). After 30 minutes, additional benzaldehyde dimethyl acetal (0.097 g, 0.64 mmol) was added. After stirring for an additional 30 minutes, the solution was diluted with ethyl acetate and washed with cold sodium bicarbonate and brine. After drying (MgSO$_4$), the organic phase was evaporated and the crude product chromatographed on silica gel (10% acetonitrile in dichloromethane), and afforded the title compound (507 mg, 59%), as colorless gum.

IR (CH$_2$Cl$_2$) $v_{max}$ (cm$^{-1}$): 3595 (—OH), 2150 (—N$_3$), 1721 (C=O).

$^1$H NMR 400 MHz (DMSO) δ(ppm): 0.84 (3H, t, J=6.81 Hz, —CH$_3$), 1.10–1.40 (22H, br s, —(CH$_2$)$_{11}$), 2.04 (2H, m, OH$_2$ allylic), 3.51 (1H, dd, J=7.4 and 10.4 Hz, H-1), 3.64 (1H, m, H-5'), 3.70–3.90 (5H, 2m, H-6', H-4', H-3', H-2', H-1), 4.09 (1H, dd, J=4.62 and 9.81 Hz, H-6'), 4.18 (1H, m, H-2), 4.73 (1H, S, H-1'), 5.58–5.70 (3H, m, H-3, H-4, —OCHO—), 5.83–5.89 (1H, m, H-5), 7.34–8.0 (10H, 5m, 5-C$_6$H$_5$).

D. (2S,3R,4E)-2-Azido-3-benzoyloxy-1-(2,3-di-O-benzoyl-4,6-O-benzylidene-α-D-mannopyranosyloxy)-4-octadecene

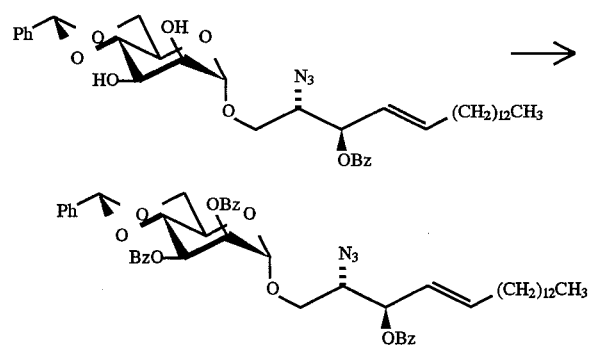

A solution of (2S,3R,4E)-2-azido-3-benzoyloxy-1-(4,6, O-benzylidene-α-D-manno-pyranosyloxy)-4-octadecene (500 mg, 0.74 mmol) in pyridine (5 mL) was cooled in ice and treated with benzoyl chloride (620 mg, 4.41 mmol) and 4-dimethylaminopyridine (10 mg). The mixture was stirred at 5° C. for 1.5 h and 20° C. for 20 hours then methanol (1 mL) was added and stirring maintained for one additional hour. The solution was diluted with ethyl acetate and washed with cold bicarbonate and brine. After drying over magnesium sulfate, the organic phase was evaporated and the crude product purified by chromatography on silica gel (10% ethyl acetate in hexane), to give 631 mg (97%) of the title compound.

IR (CH$_2$Cl$_2$) v$_{max}$ (cm$^{-1}$): 2110 (—N$_3$), 1730 (—OBz).

$^1$H NMR 400 MHz (CDCl$_3$) δ(ppm): 0.89 (3H, t, J=6.86 Hz, —CH$_3$), 1.24–1.55 (22H, br s and m, —(CH$_2$)$_{11}$), 2.10 (2H, m, CH$_2$ allylic), 3.59 (1H, dd, J=10.55 and 8.31 Hz, H-1), 3.95 (2H, dd, J=10.55 and 4.08 Hz, H-1', t, J=10.27 Hz, H-6'), 4.06–4.16 (2H, m, H-2, H-5'), 4.30–4.40 (2H, dd, J=10.10 and 4.80 Hz, H-6', t, J=9.97 Hz, H-4'), 5.09 (1H, d, J=1.83 Hz, H-1'), 5.55–5.66 (2H, m, H-3, H-4), 5.67 (1H, s, —OCHO—), 5.76 (1H, dd, J=3.53 and 1.51 Hz, H-2'), 5.83 (1H, dd, J=10.27 and 3.56 Hz, H-3'), 6.0 (1H, m H-5), 7.30–8.10 (20 H, 5 m, Ar).

E. (2S,3R,4E)-3-Benzoyloxy-2-hexadecanoylamino-1-(2,3-di-O-benzoyl-4,6-O-benzylidene-α-D-mannopyranosyloxy)-4-octadecene

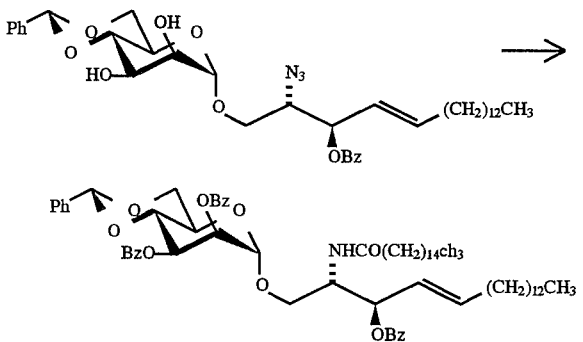

Hydrogen sulfide was bubbled for 10 minutes, into a solution of (2S,3R,4E)-2-azido-3-benzoyloxy-1-(2,3-di-O-benzoyl-4,6-O-benzylidene-α-D-mannopyranosyloxy)-4-octadecene (382 mg, 0.43 mmol) in pyridine (10 mL) and water (2 mL). The solution was stirred at room temperature for 18 hours and again treated with H$_2$S for 5 minutes. After standing for 8 hours, again more H$_2$S (5 minutes) was bubbled into the solution. The starting material disappeared after an additional period of 20 hours. The solvent was evaporated and the residue azeotroped three times with toluene. The crude amine was dissolved in a mixture of tetrahydrofuran (12 mL) and 50% aqueous sodium acetate (2 mL). Palmitoyl chloride (118 mg, 0.43 mmol) was added dropwise to that mixture. After 30 min, the reaction mixture was diluted with ethyl acetate and washed with cold sodium bicarbonate and brine. The organic phase was dried over magnesium sulfate and evaporated. The crude product was purified by chromatography on silica gel (1% acetonitrile in dichloro-methane), and afforded 240 mg (51%) of the title compound.

IR (CH$_2$Cl$_2$) v$_{max}$ (cm$^{-1}$): 1730 (—OBz), 1677 (amide), 1603 (>=<)

$^1$H NMR 400 MHz (CDCl$_3$) δ(ppm): 0.89 (6H, 2 overlapping t, 2×CH$_3$), 1.23–1.39 (46H, m, and br s, —(CH$_2$)$_{11}$— and —(CH$_2$)$_{12}$), 1.67 (2H, m, —(CH$_2$)—), 2.09 (2H, m, CH$_2$ allylic), 2.27 (2H, m, —COCH$_2$—), 3.75 (1H, dd, J=3.86 and 10.47 Hz, H-1), 3.92 (1H, t, J=10.27 Hz, H-6'), 3.96 (1H, dd, J=4.32 and 10.62 Hz, H-1), 4.05 (1H, m, H-5'), 4.30 (1H, t, J=9.61 Hz, H-4), 4.32 (1H, dd, J=4.06 and 10.33 Hz, H-6), 4.57 (1H, m, H-2), 4.96 (1H, d, J=0.94 Hz, H-1'), 5.58–5.71 (3H, m, H-3, H-4, —OCHO—), 5.73 (1H, dd, J=1.41 and 3.53 Hz, H-2'), 5.79 (1H, dd, J=3.57 and 10.23 Hz, H-3'), 5.97 (2H, m, H-5, =NH), 7.31–8.08 (20H, 6 m, Ar).

F. (2S,3R,4E)-3-Benzoyloxy-2-hexadecanoylamino-1-(2,3-di-O-benzoyl-α-D-mannopyranosyloxy)-4-octadecene

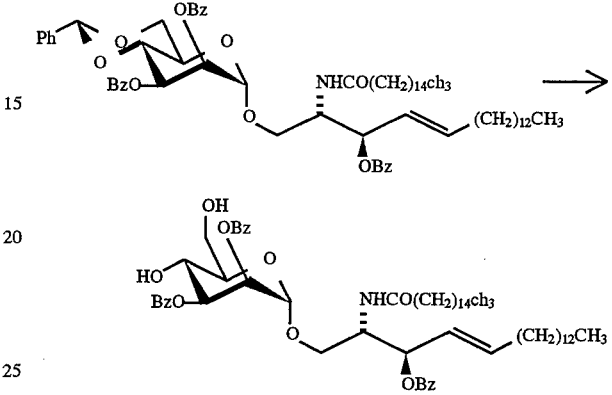

To a solution of (2S,3R,4E)-3-benzoyloxy-2-hexadecanoylamino-1-(2,3-O-benzoyl-4,6-O-benzylidene-α-D-mannopyranosyloxy)-4-octadecene (240 mg, 0.218 mmol) in dichloromethane (10 mL) was added 90% aqueous trifluoroacetic acid (0.15 mL). Since the reaction was not complete after 24 hours at room temperature, additional reagent (50% TFA-water, 0.3 mL) was again added and stirring continued for 16 more hours. The reaction mixture was then poured into saturated sodium bicarbonate and extracted with ethyl acetate. The extracts were washed with brine, dried and evaporated. The crude diol was purified by chromatography on silica gel (0–15% acetonitrile in dichloromethane), to give 176 mg (80%) of the title compound.

$^1$H NMR 400 MHz (CDCl$_3$) δ(ppm): 0.89 (6H, t; J=6.72 Hz, 2×—CH$_3$), 1.25–1.40 (46H, br s, —(CH$_2$)$_{12}$— and —(CH$_2$)$_{11}$), 1.66 (2H, m, —CH$_2$—), 2.08 (2H, m, CH$_2$ allylic), 2.25 (3H, m, N—COCH$_2$, —OH), 2.85 (1H, d, J=4.97, —OH), 3.79 (1H, dd, J=5.12 and 10.73 Hz, H-1), 3.87 (1H, m, H-5'), 3.93–4.01 (3H, m, 2 ×H-6', H-1), 4.30 (1H, dt, J=4.92 and 9.68 Hz, H-4'), 4.60 (1H, m, H-2), 4.90 (1H, d, J=1.60 Hz, H-1'), 5.51 (1H, dd, J=3.38 and 9.80 Hz, H-3'), 5.58 (1H, dd, J=1.72 and 3.28 Hz, H-2'), 5.55–5.67 (2H, m, H-3, H-4), 5.90–5.97 (2H, m, H-5, NH), 7.75–8.06 (15H, 6m, Ar).

G. (2S,3R,4E)-3-Benzoyloxy-2-hexadecanoylamino-1-[2,3-di-O-benzoyl-4,6-di-O-(sodium oxysulfonyl)-α-D-mannopyranosyloxy]-4-octadecene

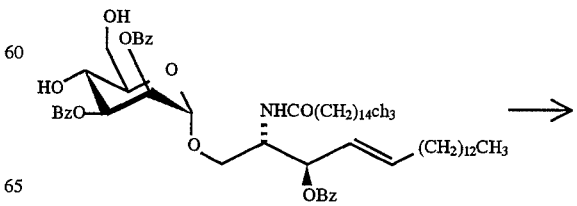

89

-continued

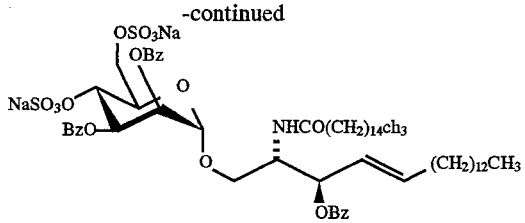

A solution of (2S,3R,4E)-3-benzoyloxy-2-hexadecanoylamino-1-(2,3-di-O-benzoyl-α-D-mannopyranosyloxy]-4-octadecene (217 mg, 0.214 mmol) and sulfur trioxide pyridine complex (136 mg, 0.851 mmol) in pyridine (15 mL) was heated at 60° C. for 16 hours. The reaction mixture was cooled (ice-water) and sodium bicarbonate (197 mg, 2.4 mmol) in water (4 mL) was added. The whole mixture was evaporated to dryness and the residue azeotroped twice with toluene. The residual solid was triturated in chloroform-methanol (4:1) and filtered. Finally the filtrate was evaporated and the crude product purified by chromatography on silica gel (5, 10, 15% methanol in chloroform), to give 235 mg of the product. This glassy product was dissolved in 20% methanol-chloroform and stirred for 1 hour in the presence of Amberlite IKF-64 resin (Na form, 850 mg). The mixture was then filtered and the resin washed with methanol-dichloromethane (1:1). The filtrate was evaporated to dryness, the disulfate redissolved in dioxane, frozen and lyophilized to give 240 mg (92%) of the title compound as a white solid.

IR (Nujol) $v_{max}$ (cm$^{-1}$): 1725 (—OBz), 1650 (N—CO), 1602 (>=<).

$^1$H NMR 400 MHz (DMSO-d$_6$) δ(ppm): 0.85 (6H, 2 overlapping t, 2×CH$_3$), 1.10–1.33 (46H, m and br s, —(CH$_2$)$_{12}$—, —(CH$_2$)$_{11}$—), 1.46 (2H, m —CH$_2$—), 2.02–2.13 (4H, m, —COCH$_2$—, CH$_2$ allylic), 3.61 (1H, dd, J=6.96 and 10.52 Hz, H-1), 3.82 (1H, dd, J=9.18 and 10.97 Hz, H-5'), 3.91 (1H, dd, J=5.23 and 10.57 Hz, H-1), 3.95 (1H, dt, J=1.32 and 9.61 Hz, H-6'), 4.35–4.46 (3H, m, H-4', H-6', H-2), 4.95 (1H, d, J=0.98 Hz, H-1'), 5.41–5.46 (2H, m, H-2', H-3'), 5.51 (1H, m, H-3), 5.61 (1H, m, H-4), 5.79 (1H, m, H-5), 7.35–8.03 (16H, series of m, N—H, 3×—At).

EXAMPLE 19

(2S,3R,4E) 1-[2-O-Benzoyl-3,4,6-tri-O-(sodium oxysulfonyl)-α-D-galactopyranosyloxy]-3-benzoyloxy-2-hexadecanoylamino-4-octadecene A. (2S,3R,4E)-3-Benzoyloxy-1-(6-O-t-butyldimethylsilyl-3,4-O-isopropylidene-α-D-galactopyranosyloxy)-2-hexadecanoylamino-4-octadecene

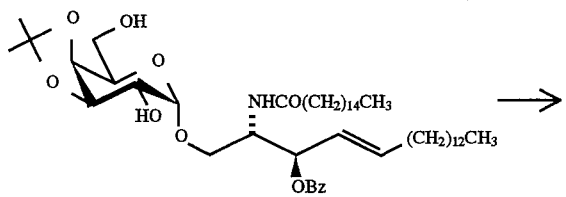

90

-continued

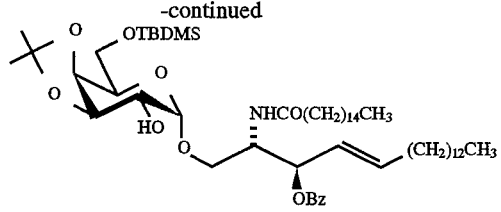

A solution of (2S,3R,4E)-3-benzoyloxy-2-hexadecanoylamino-1-(3,4-O-isopropylidene-α-D-galactopyranosyloxy)-4-octadecene (1.51 g, 1.79 mmol) in dry pyridine (25 mL) was treated at 0° C. with tert-butyldimethylsilyl chloride (0.32 g, 2.12 mmol) and the resulting mixture was stirred at 22° C. for 18 hours. Then more tert-butyldimethylsilyl chloride (0.12 g, 0.80 mmol) was added and the solution was stirred for another 6 hours. The reaction mixture was then concentrated under vacuum. The residue obtained after evaporation of the solvent was chromatographed on silica gel (elution toluene-ethyl acetate; 8:2) and gave 1.34 (78%) of the title material as a white glass.

[α]$_D^{22}$: +45° (c=1.0, CHCl$_3$).

IR (NaCl, film:) $v_{max}$ (cm$^{-1}$): 1738 (C=O of ester) and 1645 (C=O of amide).

$^1$H NMR 400 MHz (CDCl$_3$) δ(ppm): 0.07 and 0.08 (2×3H, 2s, SiCH$_3$), 0.9 (15H, m, Si-t-Bu and 2×OH$_3$), 1.3 and 1.6 (48H, m, (OH$_2$)$_{11}$ and (CH$_2$)$_{13}$) 1.34 and 1.48 (2×3H, 2s, C(CH$_3$)$_2$), 2.04 (2H, m, COCH$_2$), 2.18 (2H, m, =CHCH$_2$), 2.69 (1H, d, J=6.4 Hz, OH, exchanged D$_2$O), 3.68 (1H, dd, J=4.7 and 10.8 Hz, H-1), 3.75 (1H, dd, J=6.4 and J=10.0 Hz, H-6'), 3.75 (1H, m overlapping with H-6', H-2'), 3.84 (1H, dd, J=6.7 and J=10.0 Hz, H-6'), 3.88 (1H, dd, J=3.4 and J=10.8 Hz, H-1), 4.10 (1H, m, H-5'), 4.25 (2H, m, H-3' and H-4'), 4.51 (1H, m, H-2), 4.73 (1H, d, J=3.64 Hz, H-1'), 5.54 (dd, J=7.5 , H-4), 5.66 (1H, broad t, J=7.3 Hz, H-3), 5.88 (1H, dr, J=6.75 and J=15.3 Hz, H-5), 5.96 (1H, d, J=9.3 Hz, NH), 7.45, 7.58 and 8.03 (2H, 1H and 2H, 3m, C$_6$H$_5$).

Anal. Calcd. for C$_{56}$H$_{99}$NO$_9$Si: C, 70.17; H, 10.41; N, 1.46. Found: C, 70.25; H, 10.53; N, 1.53.

B. (2S,3R,4E)-1-(2-O-Benzoyl-6-O-t-butyldimethylsilyl-3,4-O-isopropylidene-α-D-galactopyranosyloxy)-3-benzoyloxy-2-hexadecanoylamino-4-octadecene

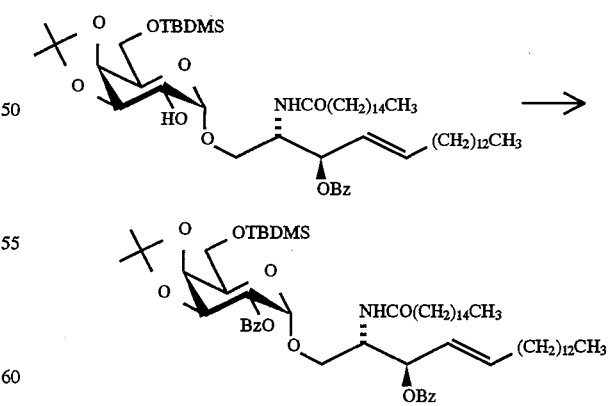

A solution of (2S,3R,4E)-3-benzoyloxy-1-(6-O-t-butyldimethylsilyl-3,4-O-isopropylidene-α-D-galactopyranosyloxy)-2-hexadecanoylamino-4-octadecene (1.29 g, 1.34 mmol) in pyridine (25 mL) was treated at 22° C. with benzoyl chloride (0.31 mL, 2.67 mmol) and 4-dimethylaminopyridine (0.020 g). After 1 hour, methanol (5 mL) was added and the solution was evaporated under vacuum. The residue was diluted with ethyl acetate (200 mL) washed with saturated sodium bicarbonate, brine and dried (MgSO$_4$). Evaporation of the solvent under vacuum gave an oil which was chromatographed on silica gel (23×13 cm). Elution with a gradient of ethyl acetate (0–6%) in toluene gave 1.35 g (94%) of the title material as a white amorphous solid.

$[\alpha]_D^{22}$: +50° (c=1.0, CHCl$_3$).

IR (KBr) $v_{max}$ (cm$^{-1}$): 1725 (C=O of ester) and 1648 (C=O of amide).

$^1$H NMR 400 MHz (CDCl$_3$) δ(ppm): 0.1 and 0.105 (2×3H, 2s, SiCH$_3$), 0.9 (15H, m, Si-t-Bu and 2×CH$_3$), 1.1–1.6 (48H, m, (CH$_2$)$_{11}$ and (CH$_2$)$_{13}$), 1.36 and 1.55 (2×3H, 2s, C(CH$_3$)$_2$), 1.95–2.08 (4H, m, COCH$_2$ and =CH—CH$_2$), 3.62 (1H, dd, J=5.2 and J=10.6 Hz, H-1), 3.8–3.9 (2H, m, H-1 and H-6'), 3.92 (1H, dd, J=6.8 and J=9.95 Hz, H-6'), 4.12 (1H, m, H-5'), 4.34 (1H, dd, J=2.3 and J=5.5 Hz, H-4'), 4.46 (1H, m, H-2), 4.50 (1H, dd, J=7.7 and J=5.5 Hz, H-3'), 5.04 (1H, d, J=3.6 Hz, H-1'), 5.19, (1H, dd, J=7.7 and J=3.6 Hz, H-2'), 5.48 (1H, dd, J=15.1 and J=7.3 Hz, H-4), 5.55 (1H, broad t, H-3), 5.63 (1H, d, J=9.2 Hz, NH), 5.78 (1H, dr, J=15.1 and J=6.7 Hz, H-5), 7.42, 7.54, 7.96 and 8.06 (4H, 2H, 2H and 2H, 4m, 2×C$_6$H$_5$).

Anal. Calcd. for C$_{63}$H$_{103}$NO$_{10}$Si: C, 71.21; H, 9.77; N, 1.32. Found: C, 71.40; H, 9.77; N, 1.42.

C. (2S,3R,4E)-1-(2-O-Benzoyl-α-D-galactopyranosyloxy-3-benzoyloxy-2-hexadecanoylamino-4-octadecene

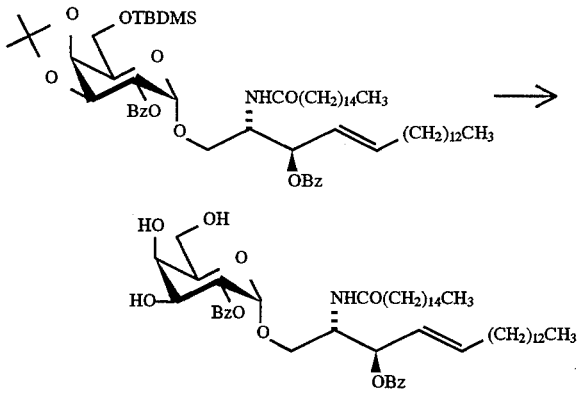

A solution of (2S,3R,4E) 1-(2-O-benzoyl-6-O-t-butyldimethylsilyl-3,4-O-isopropylidene-α-D-galactopyranosyloxy)-3-benzoyloxy-2-hexadecanoyl-amino-4-octadecene (1.31 g, 1.23 mmol) in dichloromethane (50 mL) was treated at 22° C. with 5 mL of 90% aqueous trifluoroacetic acid. After 1.5 hour, the reaction mixture was diluted with dichloromethane (200 mL) washed with saturated sodium bicarbonate, brine and dried (MgSO$_4$). The residue obtained after evaporation of the solvent under vacuum was chromatographed on silica gel (2.5×13 cm). Elution with a gradient of methanol (0–10%) in chloroform gave 0.852 g (76%) of the title material as an amorphous solid.

$[\alpha]_D^{22}$: +50.5° (c=1.0, CHCl$_3$).

IR (KBr) $v_{max}$ (cm$^{-1}$): 1722 (C=O of ester) and 1642 (C=O of amide).

$^1$H NMR 400 MHz (DMSO-d$_6$) δ(ppm): 0.844 and 0.846 (2×3H, 2t, J=6.6 and J=6.3 Hz, 2×CH$_3$), 1.1–1.4 (48H, m, (CH$_2$)$_{11}$ and (CH$_2$)$_{13}$), 1.8–2.0 (4H, m, COCH$_2$ and =CH—CH$_2$), 3.41 (1H, dd, J=10.3 and J=7.1 Hz, H-1), 3.52 (2H, m, becomes AB part of ABX system upon D$_2$O exchange, J$_{AX}$=5.75, J$_{BX}$=6.6 and J$_{AB}$=10.9 Hz, Δv=23.9 Hz, C H$_2$OH-6'), 3.71 (1H, dd, J=10.3 and J=4.5 Hz, H-1), 3.74 (1H, broad t, H-5'), 3.84 (1H, m, become d, J=3.2 Hz upon D$_2$O exchange, H-4'), 4.0 (1H, m, becomes add upon D$_2$O exchanged, J=10.3 and J=3.2 Hz, H-3'), 4.30 (1H, m, H-2), 4.60 (1H, t, J=5.5 Hz, OH, exchanged D$_2$O), 4.76 (1H, d, J=4.38 Hz, OH, exchanged D$_2$O), 4.95 (1H, d, J=3.6 Hz, H-1'), 4.97 (1H, d, J=6.6 Hz, OH, exchanged D$_2$O), 5.08 (1H, dd, J=10.3 and J=3.6 Hz, H-2'), 5.42 (1H, dd, J=7.5 and J=5.8 Hz, H-3), 5.50 (1H, dd, J=15.1 and J=7.5 Hz, H-4), 5.72 (1H, dt, J=15.1 and J=6.68 Hz, H-5), 7.81 (1H, d, J=8.9 Hz, NH), 7.46, 7.61, 7.87 and 7.97 (4H, 2H, 2H and 2H, 4m, 2×C$_6$H$_5$).

Anal. Calcd. for C$_{54}$H$_{85}$NO$_{10}$: C, 71.41; H, 9.43; N, 1.54. Found: C, 71.36; H, 9.39; N, 1.60.

D. (2S,3R,4E)-1-[2-O-Benzoyl-3,4,6-tri-O-(sodium oxysulfonyl)-α-D-galactopyranosyloxy]-3-benzoyloxy-2-hexadecanoylamino-4-octadecene

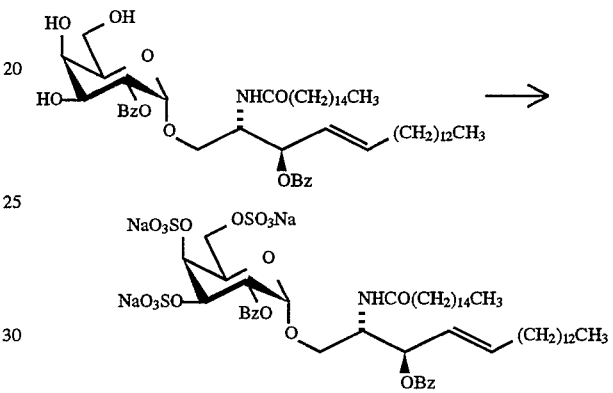

A solution of (2S,3R,4E)-1-(2-O-benzoyl-α-D-galactopyranosyloxy)-3-benzoyloxy-2-hexadecanoylamino-4-octadecene (0.80 g, 0.88 mmol) in dry pyridine (40 mL) was treated with sulfur trioxide pyridine complex (1.68 g, 10.6 mmol) and the resulting mixture was stirred at 60° C. for 24 hours. The cooled reaction mixture was then treated with water (5 mL) followed after 10 min with 2 g of solid sodium bicarbonate. After the evolution of gas has ceased, the solution was evaporated to dryness and the residue was triturated with a mixture of chloroform and methanol (7:3) and filtered. The filtrate was concentrated and chromatographed on silica gel (2.5×13 cm). Elution with a gradient of methanol—water—chloroform (from 20:0:80 to 40:10:50) gave 1.06 g (99%) of the title material as glassy solid.

$[\alpha]_D^{22}$: +68.6° (c=1.0, CHCl$_3$—MeOH; 7–3). HPLC on Zorbax RCX-8, 4.6×250 mm, elution 25% 0.01M aqueous ammonium acetate in acetonitrile, flow rate 0.5 mL/min, UV detector 239 nm, retention time 6.3 min, purity 95.5%.

IR (KBr) $v_{max}$ (cm$^{-1}$): 1725 (C=O of ester) and 1650 (C=O of amide).

$^1$H NMR 400 MHz (DMSO-d$_6$) δ(ppm): 0.84 (6H, t, J=6.7 Hz, 2×CH$_3$), 1.0–1.4 (48H, m, (CH$_2$)$_{11}$ and (CH$_2$)$_{13}$), 1.6–1.9 (2H, m, =CH—CH$_2$), 1.97 (2H, m, COCH$_2$), 3.49 (1H, dd, J=10.6 and J=8.1 Hz, H-1), 3.81 (1H, dd, J=10.6 and J=4.1 Hz, H-1), 3.85 (1H, dd, J=12.1 and J=8.6 Hz, H-6'), 4.09 (1H, dd, J=12.1 and J=2.3 Hz, H-6'), 4.18 (1H, m, H-5'), 4.2 (1H, m, H-2), 4.71 (1H, dd, J=10.6 and J=3.07 Hz, H-3'), 4.81 (1H, d, J=3.07 Hz, H-4'), 5.03 (1H, dd, J=10.6 and J=3.7 Hz, H-2'), 5.09 (1H, d, J=3.7 Hz, H-1'), 5.37 (1H, dd, J=7.4 and J=5.1 Hz, H-3), 5.50 (1H, dd, J=15.3 and J=7.4 Hz, H-4), 5.66 (1H, dt, J=15.3 and J=6.7 Hz, H-5), 7.79 (1H, d, J=8.5 Hz, NH), 7.41, 7.48, 7.59, 7.87 and 8.02 (4×2H, 4×m, 2×C$_6$H$_5$).

Anal. Calcd. for C$_{54}$H$_{82}$NO$_{19}$S$_3$Na$_3$.4H$_2$O: C, 50.42; H, 7.05; N, 1.09. Found: C, 50.35; H, 6.69; N, 1.17.

EXAMPLE 20

(2S,3R,4E)-2-Hexadecanoylamino-3-hydroxy-1-[3,4,6-tri-O-(sodium oxysulfonyl)-α-D-galactopyranosyloxy]-4-octadecene

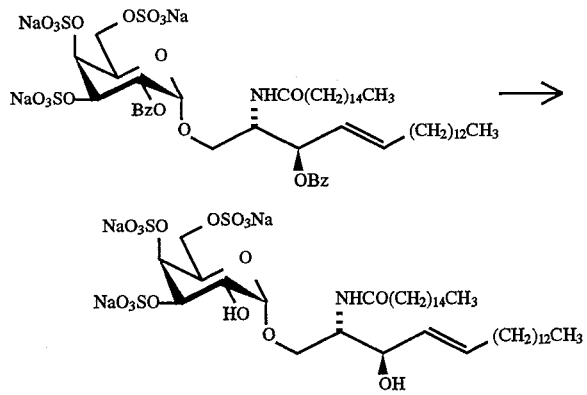

A solution of (2S,3R,4E)-1-[2-O-benzoyl-3,4,6-tri-O-(sodium oxysulfonyl)-α-D-galactopyranosyloxy]-3-benxoyloxy-2-hexadecanoylamino-4-octadecene (0.411 g, 0.339 mmol) in a mixture of methanol (25 mL) and dichloromethane (25 mL) was treated at 22° C. and under argon with 5 mL of a 0.2M solution of sodium methoxide in methanol. After 18 hours, water (5 mL) was added and the reaction mixture was neutralized with Dowex- 50W 8% XL 100 (H⁺) and filtered. The filtrate was treated with Amberlite resin IRC-50 (Na⁺) filtered and chromatographed on silica gel. Elution with a gradient of methanol—water—chloroform (from 20:0:80 to 40:10:50) gave 0.257 g (75%) of the title material as a white solid after trituration with methanol.

$[\alpha]_D^{22}$: +21° (c=1.0, $H_2O$).

IR (KBr) $\nu_{max}$ (cm$^{-1}$): 1640 (C=O of amide).

$^1$H NMR 400 MHz (DMSO-$d_6$) δ(ppm): 0.85 (6H, t, J=6.8 Hz, 2×CH$_3$), 1.2–1.5 (48H, m, (CH$_2$)$_{11}$ and (CH$_2$)$_{13}$), 1.93 (2H, m, =CH—CH$_2$), 2.06 (m, 2H, COCH$_2$), 3.56 (1H, m, H-1), 3.63 (1H, m, dd upon D$_2$O exchange J=10.1 and J=3.6 Hz, H-2'), 3.65–3.75 (2H, m, H-2 and H-5'), 3.79 (1H, dd, J=11.0 and J=7.6 Hz, H-1), 3.95 (1H, m, broad t upon D$_2$O exchange H-3), 4.0–4.1 (2H, m, CH$_2$O-6'), 4.33 (1H, dd, J=10.1 and J=3.1 Hz, H-3'), 4.47 (1H, d, J=7.8 Hz, OH, exchanged D$_2$O), 4.7(1H, d, J=3.1 Hz, H-4'), 4.77 (1H, d, J=3.7 Hz, H-1'), 4.86 (1H, d, J=5.9 Hz, OH, exchanged D$_2$O), 5.36 (1H, dd, J=15.3 and J=6.9 Hz, H-4), 5.53 (1H, dd, J=15.3 and J=6.6 Hz, H-5), 7.61 (1H, d, J=8.7 Hz, NH).

Anal. Calcd. for $C_{40}H_{74}NO_{17}S_3Na_3 \cdot 6H_2O$: C, 43.12; H, 7.78; N, 1.26. Found: C, 43.35; H, 7.02; N, 1.33.

EXAMPLE 21

(2S,3R,4E)-3-Benzoyloxy-2-hexadecanoylamino-1-[2-O-(4-methoxybenzyl)-3,4,6-tri-O-(sodium oxysulfonyl)-α-D-galactopyranosyloxy]-4-octadecene A. (2S,3R,4E)-2-Azido-3-benzoyloxy-1-[2-O-(4-methoxybenzyl)-α-D-galactopyranosyloxy]-4-octadecene

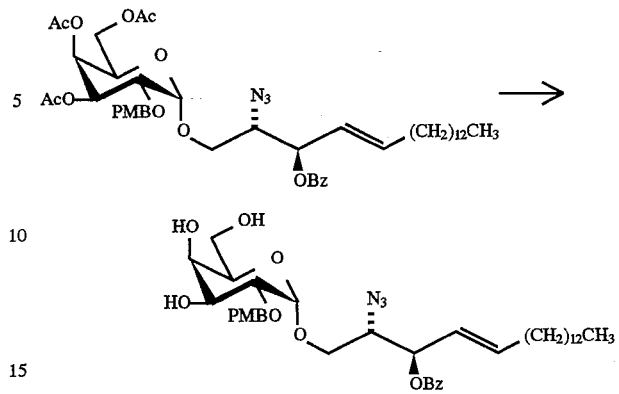

A solution of (2S,3R,4E) 2-azido-3-benzoyloxy-1-[2-O-(4-methoxybenzyl)-3,4,6-tri-O-acetyl-α-D-galactopyranosyloxy]-4-octadecene (1.30 g, 1.55 mmol described in Example 1, Step F) in a mixture of methanol (25 mL) and dichloromethane (10 mL) was treated at 0°–5° C. with 0.8 mL (0.16 mmol) of a 0.2M solution of sodium methoxide in methanol. After 7 hours, the reaction mixture was neutralized with Dowex 50-W 8% XL ion exchange resin (H⁺) filtered and concentrated. Chromatography of the residue on silica gel (3×10 cm, elution with a gradient of ethyl acetate in toluene 50 to 100%) gave 0.96 g (87%) of the title material as a thick oil.

$[\alpha]_D^{22}$: +45.4° (c=1.0, CHCl$_3$).

IR (NaCl, film) $\nu_{max}$ (cm$^{-1}$): 2110 (N$_3$), 1720 (C=O of ester).

$^1$H NMR 400 MHz (DMSO-$d_6$) δ(ppm): 0.85 (3H, t, J=6.8 Hz, CH$_3$), 1.1–1.4 (22H, m, (CH$_2$)$_{11}$), 2.03 (2H, m, =CH—CH$_2$), 3.4–3.5 (4H, m, H-1, H-3' and CH$_2$O-6'), 3.54 (1H, dd, J=9.5 and J=3.5 Hz, H-2), 3.62 (1H, broad t, H-5'), 3.7 (3H, s, OCH$_2$), 3.71 (1H, m, H-4'), 3.77 (1H, dd, J=10.7 and J=4.5 Hz, H-1), 4.09 (1H, m, H-2), 4.45–4.55 (4H, m, 2×OH and OCH$_2$Ar; 2×OH exchange D$_2$O leaving AB system $J_{AB}$=11.9 Hz, Δν=6.6 Hz, OCH$_2$Ar), 4.8 (1H, d, J=3.5 Hz, H-1'), 4.82 (1H, d, J=5.8 Hz, OH, exchange D$_2$O), 5.58 (1H, dd, J=14.5 and 7.5 Hz, H-4), 5.61 (1H, dd, J=7.5 and J=4.5 Hz, H-3), 5.85 (1H, dt, J=14.5 and J=6.7 Hz, H-5), 6.81 and 7.25 (2×2H, 2×d, J=8.6 Hz, H-2, H-2' and H-3, H-3' of p-methoxybenzyl), 7.55, 7.68 and 8.0 (2H, 1H and 2H, 3m, $C_6H_5$).

Anal. calcd. for $C_{39}H_{57}N_3O_9 \cdot 0.5H_2O$: C, 64.98; H, 8.11; N, 5.83. Found: C, 64.80; H, 7.90; N, 5.90.

B. (2S,3R,4E) 3-Benzoyloxy-2-hexadecanoylamino-1-[2-O-(4-methoxybenzyl)-α-D-galactopyranosyloxy]-4-octadecene

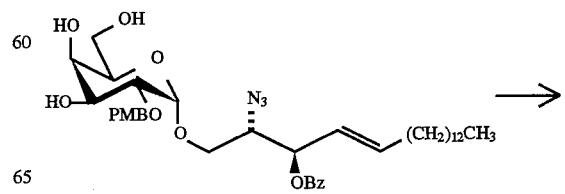

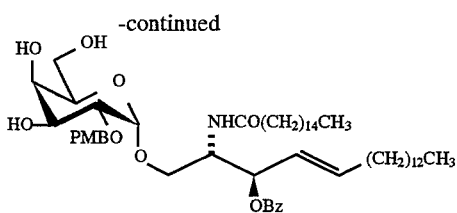

(2S,3R,4E) 2-Azido-3-benzoyloxy-1-[2-O-(4-methoxybenzyl)-α-D-galactopyranosyloxy]-4-octadecene (0.43 g, 0.60 mmol) was reduced and acylated by the general procedure as described in Example I-J and gave 0.458 g (82%) of the title material as an amorphous solid.

$[\alpha]_D^{22}$: +45° (c=1.0, CHCl$_3$).

IR (KBr) $\nu_{max}$ (cm$^{-1}$): 1722 (C=O of ester) and 1650 (C=O of amide).

$^1$H NMR 400 MHz (DMSO-d$_6$) δ(ppm): 0.85 (6H, t, J=6.7 Hz, 2×CH$_3$), 1.1–1.5 (48H, m, (CH$_2$)$_{11}$ and (CH$_2$)$_{13}$), 2.0 (2H, m, =CH—CH$_2$), 2.05 (2H, m, COCH$_2$), 3.35–3.5 (3H, m, H-1 and CH$_2$O-6'), 3.50 (1H, dd, J=10.0 and J=3.5 Hz, H-2'), 3.60 (1H, broad t, H-5'), 3.64 (1H, dd, J=10.5 and J=5.6 Hz, H-1), 3.69 (3H, s, OCH$_3$), 3.7 (1H, m, H-4'), 3.73 (1H, m, becomes dd upon D$_2$O exchange, J=10.0 and J=3.2 Hz, H-3'), 4.37 (1H, m, H-2), 4.45 (1H, d, J=4.2 Hz, exchanged D$_2$O, OH), 4.47 (2H, s, CH$_2$ of methoxybenzyl), 4.5 (1H, t, J=5.5 Hz, exchanged D$_2$O, OH), 4.73 (1H, d, J=6.0 Hz, exchanged D$_2$O, OH), 4.74 (1H, d, J=3.5 Hz, H-1'), 5.48 (1H, dd, J=7.6 and J=5.6 Hz, H-3), 5.53 (1H, dd, J=14.7 and J=7.6 Hz, H-4), 5.76 (1H, dt, J=14.7 and J=6.7 Hz, H-5), 6.79 and 7.22 (2×2H, 2d, J=8.6 Hz, H-2, H-2' and H-3, H-3' of methoxybenzyl), 7.83 (1H, d, J=9.0 Hz, NH), 7.51, 7.65 and 7.95 (2H, 1H and 2H, 3m, C$_6$H$_5$).

Anal. Calcd. for C$_{55}$H$_{89}$NO$_{10}$·0.5H$_2$O: C, 70.78; H, 9.72; N, 1.50. Found: C, 70.83; H, 9.61; N, 1.57.

C. (2S,3R,4E) 3-Benzoyloxy-2-hexadecanoylamino-1-[2-O-(4-methoxybenzyl)-3,4,6-tri-O-(sodium oxysulfonyl)-α-D-galactopyranosyloxy]-4-octadecene

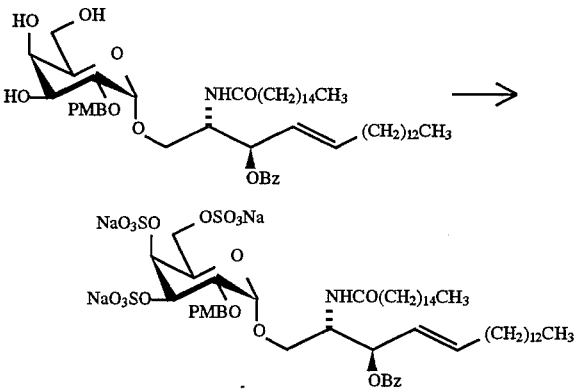

(2S,3R,4E) 3-Benzoyloxy-2-hexadecanoylamino-1-[2-O-(4-methoxybenzyl)-α-D-galactopyranosyloxy]-4-octadecene (0.419 g, 0.45 mmol) was sulfated by the general procedure as described in Example 19-D and gave 0.552 g (98%) of the title material as an amorphous solid. $[\alpha]_D^{22}$: +43° (c=1.0, CHCl$_3$—MeOH 7:3).

IR (KBr) $\nu_{max}$ (cm$^{-1}$): 1720 (C=O of ester) and 1630 (C=O of amide).

$^1$H NMR 400 MHz (DMSO-d$_6$) δ(ppm): 0.85 (6H, t, J=6.8 Hz, 2×CH$_3$), 1.1–1.5 (48H, m, (CH$_2$)$_{11}$ and (0H$_2$)$_{13}$), 1.9–2.1 (4H, m, =CH—CH$_2$ and COCH$_2$), 3.56 (1H, dd, J=10.8 and J=7.0 Hz, H-1), 3.65 (1H, dd, J=9.9 and J=3.4 Hz, H-2'), 3.69 (3H, s, OCH$_3$), 3.75 (1H, dd, J=10.8 and J=4.8 Hz, H-1), 3.82 (1H, dd, J=12.6 and J=9.3 Hz, CH$_2$O-6'), 4.05–4.1 (2H, m, H-5' and CH$_2$O-6'), (1H, m, H-2), 4.54 (2H, ABq, J$_{AB}$=11.1 Hz, Δν=24.3 Hz, CH$_2$O of methoxybenzyl), 4.57 (1H, overlapping with CH$_2$, H-3'), 4.80 (1H, d, J=2.7 Hz, H-4'), 4.91 (1H, d, J=3.4 Hz, H-1'), 5.49 (1H, dd, J=7.4 and J=5.3 Hz, H-3), 5.57 (1H, dd, J=15.1 and J=7.4 Hz, H-4), 5.72 (1H, dt, J=15.1 and J=6.63 Hz, H-5), 7.51, 7.63 and 7.97 (2H, 1H and 2H, 3m, C$_6$H$_5$), and 7.87 (1H, d, J=8.6 Hz, NH).

EXAMPLE 22

(2S,3R,4E)-2-Hexadecanoylamino-3-hydroxy-1-[2-O-(4-methoxybenzyl)-3,4,6-tri-O-(sodium oxysulfonyl)-α-D-galactopyranosyloxy]-4-octadecene

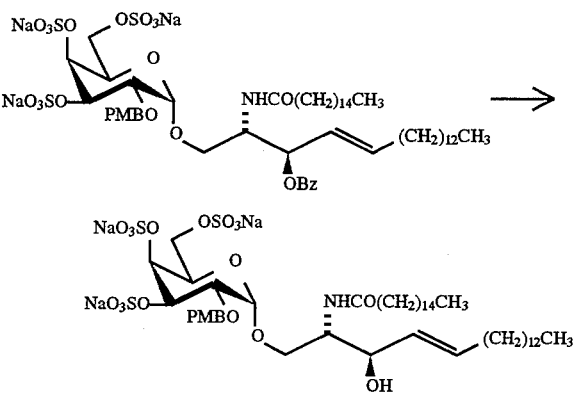

(2S,3R,4E) 3-Benzoyloxy-2-hexadecanoylamino-1-[2-O-(4-methoxybenzyl)-3,4,6-tri-O-(sodium oxysulfonyl)-α-D-galactopyranosyloxy]-4-octadecene (0.30 g, 0.244 mmol described in Example 21) was reacted by the general procedure as described in Example 24 and gave 0.241 g (87%) of the title material as a white amorphous powder after lyophilization from dioxane.

$[\alpha]_D^{22}$: +40° (c=1.0, CHCl$_3$—MeOH 7:3).

IR (KBr) $\nu_{max}$ (cm$^{-1}$): 1640 (C=O of amide).

$^1$H NMR 400 MHz (DMSO-d$_6$) δ(ppm): 0.85 (6H, t, J=6.8 Hz, 2×CH$_3$), 1.1–1.5 (48H, m, (CH$_2$)$_{11}$ and (CH$_2$)$_{13}$), 1.91 (2H, m, =CH—CH$_2$), 1.99 (m, 2H, CH$_2$), 3.61 (1H, dd, J=11.0 and J=5.9 Hz, H-1), 3.64 (1H, dd, J=10.0 and J=3.5 Hz, H-2'), 3.65–3.75 (m, 2H, H-1 and H-2), 3.73 (3H, s, OCH$_3$), 3.8 (1H, dd, J=13.0 and J=10.0 Hz, CH$_2$O-6'), 3.92 (1H, m, becomes a broad t upon D$_2$O exchange, H-3), 4.0–4.1 (2H, m, H-5' and CH$_2$O-6'), 4.56 (1H, dd, J=10.0 and J=3.2 Hz, H-3'), 4.56 (2H, ABq, J$_{AB}$=11.4 Hz and Δν=31 Hz, CH$_2$ of methoxybenzyl), 4.78 (1H, d, J=6.1 Hz, exchanged D$_2$O, OH), 4.79 (1H, d, J=3.2 Hz, H-4'), 4.90 (1H, d, J=3.5 Hz, H-1'), 5.37 (1H, dd, J=15.3 and J=6.6 Hz, H-4), 5.48 (1H, dt, J=15.3 and J=6.4 Hz, H-5), 6.84 and 7.32 (2d, J=8.7 Hz, H-2, H-2' and H-3, H-3' of methoxybenzyl), 7.48 (1H, d, J=8.5 Hz, NH).

EXAMPLE 23

(2S,3R,4E)-3-Benzoyloxy-2-hexadecanoylamino-1-[2,3,4,6-tetra-O-(sodium oxysulfonyl)-α-D-galactopyranosyloxy]-4-octadecene

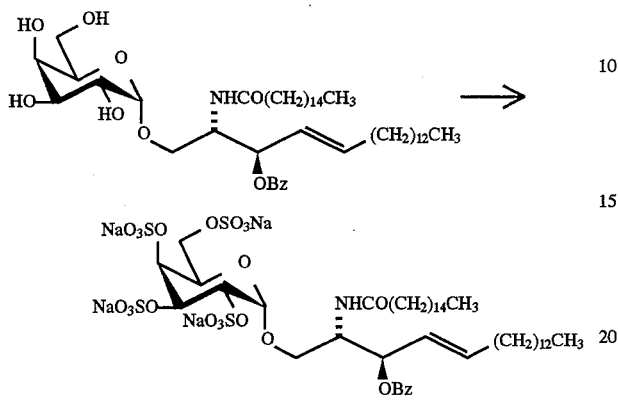

A solution of (2S,3R,4E)-3-benzoyloxy-1-(α-D-galactopyranosyloxy)-2-hexadecanoylamino-4-octadecene (0.467 g, 0.58 mmol, described in Example 15-A) in dry pyridine (25 mL) was treated with sulfur trioxide pyridine complex (1.40 g) and maintained at 60° C. for 20 hours. The cooled mixture was then treated with water (5 mL) and powdered sodium bicarbonate (2 g). The resulting mixture was stirred for 30 min, filtered and concentrated under vacuum. The residue was chromatographed on silica gel using a mixture of chloroform and methanol (7:3) followed by chloroform, methanol and water (5:4:1) as eluent and gave 0.661 g (94%) of the title material as a white amorphous solid.

$[\alpha]_D^{22}$: +43° (c=1.0, CHCl$_3$—MeOH 7:3).

HPLC on Zorbax Rx C-8, 4.6 mm×25 cm, 0.01M aqueous ammonium acetate-acetonitrile 1:1, flow rate 1 mL/min, UV detector 239 nm, retention time 5.7 min, purity 97%.

IR (KBr) $v_{max}$ (cm$^{-1}$): 1720 (C=O of ester) and 1640 (C=O of amide).

$^1$H NMR 400 MHz (DMSO-d$_6$) δ(ppm): 0.85 (6H, t, J=6.6 Hz, 2×CH$_3$), 1.1 and 1.5 (48H, m, (CH$_2$)$_{11}$ and (CH$_2$)$_{13}$), 1.9 and 2.2 (4H, m, =CH—CH$_2$ and COCH$_2$), 3.57 (1H, broad t, J=9.7 Hz, H-5'), 3.80 (1H, dd, J=11.3 and J=9.4 Hz, H-1), 3.86 (1H, dd, J=11.3 and J=4.8 Hz, H-1), 4.02 (2H, broad d, J=9.7 Hz, CH$_2$O-6'), 4.11 (1H, m, H-2), 4.29 (1H, dd, J=10.8 and J=3.0, H-2'), 4.34 (1H, dd, J=10.8 and J=2.3 Hz, H-3'), 4.85 (1H, broad s, H-4'), 5.15 (1H, d, J=3.0 Hz, H-1'), 5.57 (1H, dd, J=15.2 and J=6.9 Hz, H-4), 5.64 (1H, dd, J=6.9 and J=5.0 Hz, H-3), 5.72 (1H, dt, J=15.2 and J=6.9 Hz, H-5), 7.76 (1H, d, J=6.7 Hz, NH), 7.51, 7.62 and 7.95 (2H, 1H and 2H, 3m, C$_6$H$_5$).

Anal. Calcd. for C$_{47}$H$_{77}$NO$_{21}$S$_4$Na$_4$.6H$_2$O: C, 42.75; H, 6.79; N, 1.06. Found: C, 42.99; H, 6.12; N, 1.29.

EXAMPLE 24

(2S,3R,4E)-2-Hexadecanoylamino-3-hydroxy-1-[2,3,4,6-tetra-O-(sodium oxysulfonyl)-α-D-galactopyranosyloxy]-4-octadecene

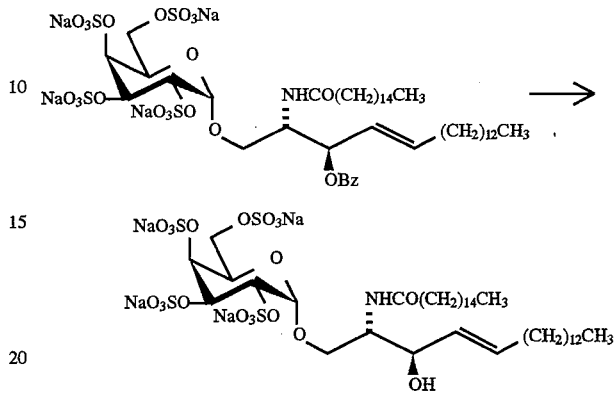

A solution of (2S,3R,4E) 3-benzoyloxy-2-hexadecanoylamino-1-[2,3,4,6-tetra-O-(sodium oxysulfonyl)-α-D-galactopyranosyloxy]-4-octadecene (0.370 g, 0.30 mmol; described in Example 23) in a mixture of methanol (25 mL) and dichloromethane (25 mL) was treated at 22° C. with 3 mL (0.6 mmol) of 0.2M solution of sodium methoxide in methanol. After 18 hours, water (5 mL) was added, the pH of the mixture was adjusted to 7 with Dowex -50W 8% XL (H$^+$) ion exchange resin and the solution was filtered. The filtrate was then treated with Amberlite IRP-64 (Na$^+$) resin, filtered, concentrated and chromatographed on silica gel (2.5×12 cm). Elution with a mixture of chloroform, methanol and water (from 7:3:0 to 5:4:1) gave 0.273 g (80%) of the title material as an amorphous solid.

$[\alpha]_D^{22}$: +38° (c=1.0, H$_2$O).

IR (KBr) $v_{max}$ (cm$^{-1}$): 1615 (C=O of amide).

$^1$H NMR 400 MHz (DMSO-d$_6$) δ(ppm): 0.85 (6H, t, J=6.8 Hz, 2×CH$_3$), 1.1–1.5 (48H, m, (CH$_2$)$_{11}$) and (CH$_2$)$_{13}$), 1.92 (2H, m, =CH—CH$_2$), 2.13 (2H, m, COCH$_2$), 3.53 (1H, m, H-5'), 3.66 (2H, m, H-1 and H-3), 3.78 (1H, dd, J=12.1 and J=9.1 Hz, H-1), 4.02 (2H, m, CH$_2$O-6'), 4.05 (1H, m, H-2), 4.30 (1H, dd, J=10.7 and J=3.56 Hz, H-2'), 4.44 (1H, dd, J=10.7 and J=2.8 Hz, H-3'), 4.88 (1H, d, J=2.8 Hz, H-4'), 5.03 (1H, d, J=6.1 Hz, exchanged D$_2$O, OH), 5.12 (1H, d, J=3.56 Hz, H-1'), 3.36 (1H, dd, J=15.3 and J=6.35 Hz, H-4), 5.56 (1H, dt, J=15.3 and J=6.7 Hz, H-5), 7.64 (1H, d, J=7.3 Hz, NH).

Anal. Calcd. for C$_{40}$H$_{73}$NO$_{20}$S$_4$Na$_4$.8H$_2$O: C, 38.36; H, 7.16; N, 1.12. Found: C, 38.25; H, 6.23; N, 1.23.

EXAMPLE 25

(2S,3R,4E)-3-Benzoyloxy-2-hexadecanoylamino-1-[3,4-di-O-benzoyl-2,6-di-O-(sodium oxysulfonyl)-α-D-mannopyranosyloxy]-4-octadecene A. (2S,3R,4E)-2-Azido-3-benzoyloxy-1-(6-O-tert-butyldimethylsilyl-α-D-mannopyranosyloxy)-4-octadecene

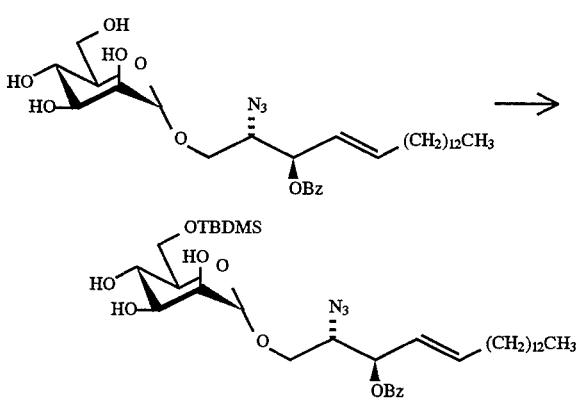

A cold (5° C.) solution of (2S,3R,4E)-2-azido-3-benzoyloxy-1-(α-D-mannopyranosyloxy)-4-octadecene described in Example 18-B (0.59 g, 1.0 mmol) in pyridine (20 mL) was treated with tert-butyldimethylsilyl chloride (0.3 g, 2.0 mmol). The solution was left in the freezer (–20° C.) over the weekend (~64 hours) and then the solvent was removed under vacuum. The residue was dissolved in ethyl acetate, washed with cold hydrochloric acid (0.1N) and brine. The organic phase was dried over anhydrous magnesium sulfate, filtered and concentrated. The residue was purified by silica get column chromatography and gave the title compound (0.606 g, 86%) as a viscous oil.

IR (CH$_2$Cl$_2$) $v_{max}$ (cm$^{-1}$): 3580 (OH), 2920, 2850 (C—H), 2090 (N$_3$), 1715 (C=O).

$^1$H NMR 200 MHz (CDCl$_3$) δ(ppm): 0.10 (6H, s, —Si(CH$_3$)$_2$), 0.88 (3H, t, J=6.7 Hz, —CH$_3$), 0.91 (9H, s, tert-butyl), 1.24–1.34 (22H, m, —(CH$_2$)$_{11}$—), 2.0–2.1 (2H, m, =CH—CH$_2$—), 2.46 (1H, d, J=3.9 Hz, —OH), 2.69 (1H, d, J=4.4 Hz, —OH), 3.25 (1H, d, J=1.3 Hz, —OH), 3.49 (1H, dd, J=10.0 and 7.3 Hz, H-1), 3.4–4.1 (8H, m, H-1, H-2, H-2', H-3', H-4', H-5' and H-6'), 4.85 (1H, d, J=1.2 Hz, H-1'), 5.5–5.6 and 5.8–6.1 (3H, 2 sets of m, H-3, H-4 and H-5), 7.4–7.6 and 8.03–8.07 (5H, 2 sets of m, —C$_6$H$_5$).

B. (2S,3R,4E)-2-Azido-8-benzoyloxy-1-(6-O-tert-butyldimethylsilyl-3-O-benzoyl-α-D-mannopyranosyloxy)-4-octadecene

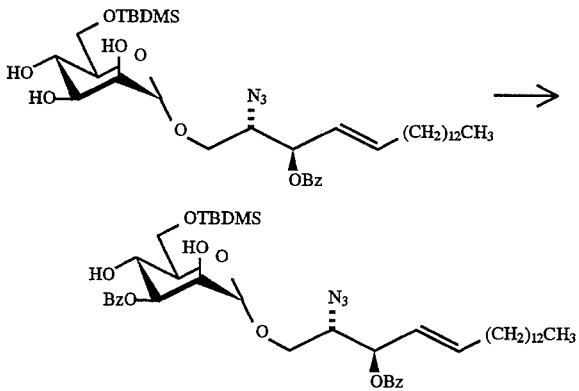

A solution of benzoyl chloride (131 mg, 0.935 mmol) in methylene chloride was added dropwise to a solution of (2S,3R,4E)-2-azido-3-benzoyloxy-1-(6-O-tert-butyldimethylsilyl-α-D-mannopyranosyloxy)-4-octadecene (0.6 g, 0.85 mmol) in pyridine (15 mL) at 0° C. The reaction mixture was allowed to stand in the freezer (–20° C.) overnight. Benzoyl chloride (24 mg, 0.17 mmol) was added again and the reaction was stirred at 0° C. for another 2 hours. This process was repeated a second time, then the solvent was evaporated and the residue was dissolved in ethyl acetate. The organic phase was washed with cold dilute hydrochloric acid, and brine, dried over anhydrous magnesium sulfate, filtered and concentrated. The residue was purified by silica gel column chromatography (0 to 5% acetonitrile/methylene chloride) and afforded the title compound (0.442 g, 64%) as a viscous oil.

IR (CH$_2$Cl$_2$) $v_{max}$ (cm$^{-1}$): 3680, 3600, 3480 (OH), 2920, 2850 (C—H), 2090 (N$_3$), 1715 (C=O).

$^1$H NMR 400 MHz (CDCl$_3$) δ(ppm): 0.11 (6H, 2s, —Si(CH$_3$)$_2$), 0.89 (3H, t, J=6.8 Hz, —CH$_3$), 0.92 (9H, s, tert-butyl), 1.2–1.45 (22H, m, —(CH$_2$)$_{11}$—), 2.03–2.16 (3H, m, —OH and =CH—CH$_2$), 3.08 (1H, d, J=3.2 Hz, —OH-4'), 3.53 (1H, dd, J=10.2 and 7.8 Hz, H-1), 3.76 (1H, td, J=9.5 and 4.8 Hz, H-5'), 3.86–4.00 (4H, m, H-1, H-6' and H-2), 4.15 (1H, td, J=9.6 and 3.1 Hz, H-4'), 4.15 (1H, br d, H-2'), 4.92 (1H, d, J=1.5 Hz, H-1'), 5.38 (1H, dd, J=9.7 and 3.2 Hz, H-3'), 5.57 (1H, dd, J=14.6 and 8.0 Hz, H-4), 5.58–5.61 (1H, m, H-3), 5.96 (1H, td, J=14.6 and 6.9 Hz, H-5), 7.45–7.49, 7.57–7.60 and 8.06–8.12 (10H, 3 sets of m, 2×—C$_6$H$_5$).

C. (2S,3R,4E)-2-Azido-3-benzoyloxy-1-(3-O-benzoyl-α-D-manno pyranosyloxy)-4-octadecene

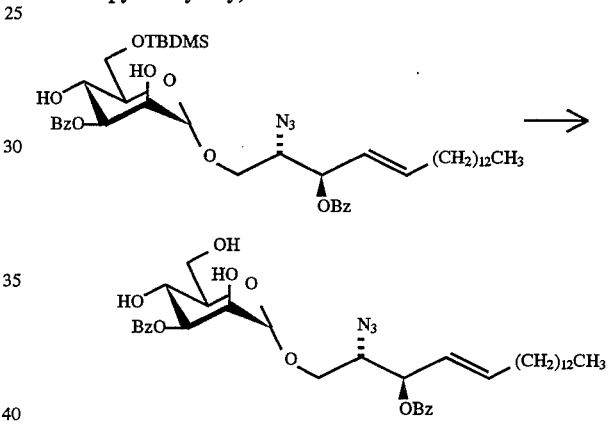

A solution of (2S,3R,4E)-2-azido-3-benzoyloxy-1-(6-O-tert-butyldimethylsilyl-3-O-benzoyl-α-D-mannopyranosyloxy)-4-octadecene (0.346 g, 0.427 mmol) in 10% aqueous acetonitrile was treated with hydrochloric acid (2N, 0.5 mL). The reaction was stirred at 22° C. for 45 minutes, then diluted with ethyl acetate and washed with cold aqueous sodium bicarbonate and brine. The organic phase was dried over anhydrous magnesium sulfate, filtered and concentrated. The residue was purified by silica gel column chromatography (30% acetonitrile/methylene chloride) and gave the title material (0.266 g, 90%) as a colorless thick oil.

IR (CH$_2$Cl$_2$) $v_{max}$ (cm$^{-1}$): 3680, 3600 (OH), 2925, 2850 (C—H), 2100 (N$_3$), 1720 (C=O).

$^1$H NMR 400 MHz (CDCl$_3$) δ(ppm): 0.89 (3H, t, J=6.8 Hz, —CH$_3$), 1.25–1.40 (22H, m, —(CH$_2$)$_{11}$—), 2.10 (2H, ap qa, =CH—CH$_2$—), 2.25 (1H, t, J=6.4Hz, —OH-6'), 2.45 (1H, d, J=4.9 Hz, —OH-2'), 2.77 (1H, d, J=5.1 Hz, —OH-4'), 3.56 (1H, dd, J=10.4 and 7.7 Hz, H-1), 3.79 (1H, dt, J=9.7 and 3.7 Hz, H-5'), 3.91–3.95 (3H, m, H-1 and H-6'), 3.97 (1H, m, H-2), 4.24 (1H, td overlapping H2', J=9.7 and 5.1 Hz, H-4'), 4.21–4.28 (1H, m, H-2'), 4.95 (1H, d, J=1.4 Hz, H-1'), 5.37 (1H, dd, J=9.8 and 3.2 Hz, H-3'), 5.57–5.64 (2H, m, H-3 and H-4), 5.98 (1H, dt, J=14.2 and 6.7 Hz, H-5), 7.45–7.49, 7.57–7.63 and 8.06–8.11 (10H, 3 sets of m, 2×—C$_6$H$_5$).

101

D. (2S,3R,4E)-2-Azido-3-benzoyloxy-1-(2-O-tert-butyldimethylsilyl-3-O-benzoyl-4,6-O-isopropylidene-α-D-mannopyranosyloxy)-4-octadecene

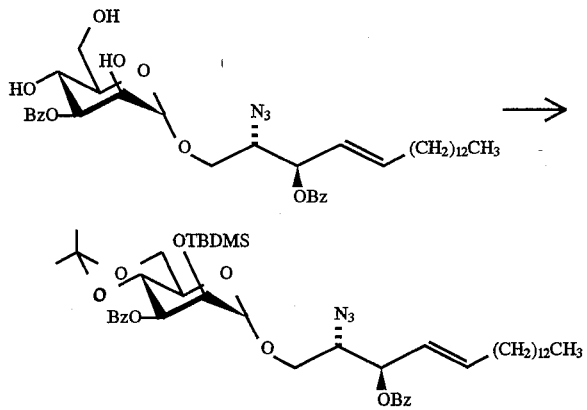

To a solution of (2S,3R,4E)-2-azido-3-benzoyloxy-1-(3-O-benzoyl-α-D-mannopyranosyloxy)-4-octadecene (0.265 g, 0.382 mmol) in 2,2-dimethoxypropane (5 mL) was added p-toluenesulfonic acid (anhydrous, 25 mg). The solution was stirred at 22° C. for 2 hours, then poured into a cold saturated solution of sodium bicarbonate. The aqueous layer was extracted with ethyl acetate and the combined organic extracts were washed with brine, dried over anhydrous magnesium sulfate, filtered and concentrated. Without purification, the crude residue was dissolved in pyridine and the resulting solution was cooled in ice and treated dropwise with tert-butyldimethylsilyl triflate (0.264 mL, 1.15 mmol). The reaction mixture was stirred at 22° C. for 24 hours, then poured into a cold solution of sodium bicarbonate. The aqueous phase was extracted with ethyl ether and the combined extracts were washed with brine, dried over anhydrous magnesium sulfate, filtered and concentrated. The residue was purified by silica gel column chromatography (2% acetonitrile/methylene chloride) and afforded the title material (0.29 g, 91%) as a colorless oil.

IR (CH$_2$Cl$_2$) $v_{max}$ (cm$^{-1}$): 2930, 2850 (C—H), 2100 (N$_3$), 1720 (C=O).

$^1$H NMR 400 MHz (CDCl$_3$) δ(ppm): −0.10 and 0.00 (6H, 2s, —Si(CH$_3$)$_2$), 0.89 (3H, t, J=7.1 Hz, —CH$_3$), 0.90 (9H, s, tert-butyl), 1.25–1.32 (20H, m, —(CH$_2$)$_{10}$—), 1.38–1.43 (2H, m, —CH$_2$—), 1.55 and 1.57 (6H, 2s, —C(CH$_3$)$_2$), 2.11 (2H, qa, J=6.8 Hz, =CH—CH$_2$—), 3.50 (1H, dd, J=10.7 and 8.3 Hz, H-1), 3.75–3.91 (4H, m, H-1, H-5' and H-6'), 4.01 (1H, dt, J=8.2 and 4.0 Hz, H-2), 4.35 (1H, d, J=2.9 Hz, H-2'), 4.36 (1H, t, J=10.1 Hz, H-4'), 4.73 (1H, d, J=1.3 Hz, H-1'), 5.32 (1H, dd, J=10.0 and 2.9 Hz, H-3'), 5.56–5.64 (2H, m, H-3 and H-4), 5.98 (1H, dt, J=14.2 and 6.8 Hz, H-5), 7.43–7.50, 7.56–7.61 and 8.05–8.09 (10H, 3 sets of m, 2×—C$_6$H$_5$).

E. (2S,3R,4E)-2-Azido-3-benzoyloxy-1-(2-O-tert-butyldimethylsilyl-3-O-benzoyl-α-D-mannopyranosyloxy)-4-octadecene

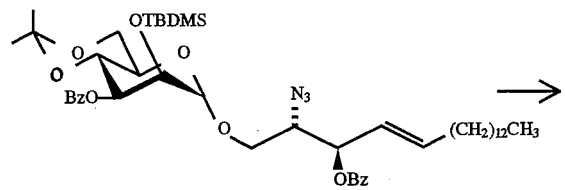

102

-continued

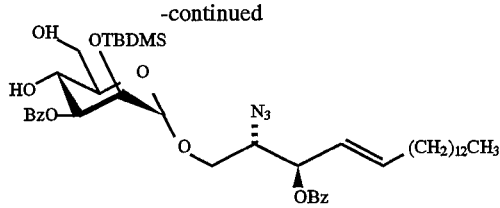

A solution of (2S,3R,4E)-2-azido-3-benzoyloxy-1-(2-O-tert-butyldimethylsilyl-3-O-benzoyl-4,6-O-isopropylidene-α-D-mannopyranosyloxy)-4-octadecene (0.280 g, 0.335 mmol) in methylene chloride (minimum amount) was added dropwise, but rapidly, to cold (5° C.) 90% aqueous trifluoroacetic acid (2 mL). The reaction mixture was stirred for 10 minutes, then diluted with methylene chloride and washed with cold brine (3×), aqueous sodium bicarbonate and brine. The organic layer was dried over anhydrous magnesium sulfate, filtered and concentrated. The residue was purified by silica gel column chromatography (5 to 10% acetonitrile/methylene chloride) to give the title compound (0.231 g, 85%) as a colorless oil.

IR (CH$_2$Cl$_2$) $v_{max}$ (cm$^{-1}$): 3600 (OH), 2925, 2850 (C—H), 2100 (N$_3$), 1718 (C=O).

$^1$H NMR 400 MHz (CDCl$_3$) δ(ppm): −0.03 and 0.03 (6H, 2s, —Si(CH$_3$)$_2$), 0.89 (3H, t, J=6.9 Hz, —CH$_3$), 0.90 (9H, s, tert-butyl), 1.25–1.29 (20H, m, —(CH$_2$)$_{10}$—), 1.40 (2H, m, —CH$_2$—), 2.02 (1H, dd, J=7.6 and 5.3 Hz, —OH-6'), 2.10 (2H, qa, J=6.9 Hz, =CH—CH$_2$—), 2.35 (1H, d, J=5.2 Hz, —OH-4'), 3.54 (1H, dd, J=10.6 and 7.9 Hz, H-1), 3.75 (1H, dt, J=9.7 and 3.8 Hz, H-5'), 3.88–3.94 (3H, m, H-6' and H-1), 3.98 (1H, dt, J=7.9 and 4.0 Hz, H-2), 4.27 (1H, td, J=9.7 and 5.2 Hz, H-4'), 4.28 (1H, br d, H-2'), 4.76 (1H, d, J=1.6 Hz, H-1'), 5.31 (1H, dd, J=9.7 and 2.9 Hz, H-3'), 5.57–5.65 (2H, m, H-3 and H-4), 5.98 (1H, dt, J=14.2 and 6.9 Hz, H-5), 7.44–7.49, 7.57–7.61 and 8.06–8.10 (10H, 3 sets of m, 2×—C$_6$H$_5$).

F. (2S,3R,4E)-2-Azido-3-benzoyloxy-1-(2,6-di-O-tert-butyldimethylsilyl-3-O-benzoyl-α-D-mannopyranosyloxy)-4-octadecene

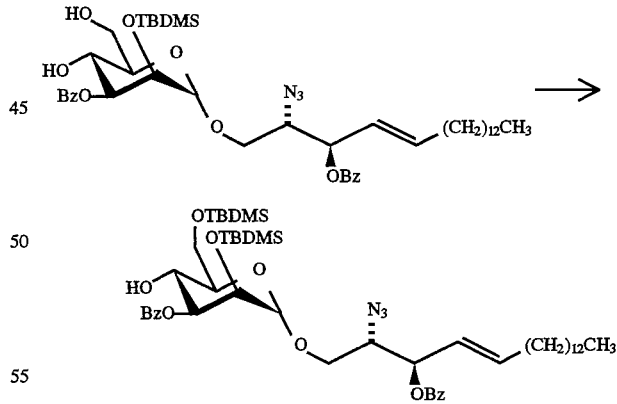

A cold (5° C.) solution of (2S,3R,4E)-2-azido-3-benzoyloxy-1-(2-O-tert-butyldimethylsilyl-3-O-benzoyl-α-D-mannopyranosyloxy)-4-octadecene (0.225 g, 0.278 mmol) in pyridine was treated with tert-butyldimethylsilyl chloride (85 mg, 0.57 mmol). The reaction mixture was left in the cold room (7° C.) for the weekend (65 hours), then poured into cold aqueous sodium bicarbonate and extracted with methylene chloride. The organic extracts were washed with brine (2×), dilute hydrochloric acid and brine again, dried over anhydrous magnesium sulfate, filtered and concentrated. The residue was purified by silica gel column chromatography (methylene chloride) and afforded the title material (0.247 g, 96%) as a colorless oil.

IR ($CH_2Cl_2$) $v_{max}$ ($cm^{-1}$): 3600 (OH), 2925, 2850 (C—H), 2100 ($N_3$), 1718 (C=O).

$^1$H NMR 400 MHz ($CDCl_3$) δ(ppm): −0.05, 0.01, 0.11 and 0.11 (12H, 4s, 2×—Si($CH_3$)$_2$), 0.89 (3H, t, J=7.0 Hz, —$CH_3$), 0.90 and 0.92 (18H, 2×tert-butyl), 1.25–1.32 (20H, m, —($CH_2$)$_{10}$—), 1.40 (2H, m, —$CH_2$—), 2.09 (2H, qa, J=6.9 Hz, =CH—C$\underline{H}_2$—), 2.71 (1H, d, J=3.7 Hz, —OH), 3.53 (1H, dd, J=10.8 and 8.2 Hz, H-1), 3.70 (1H, dt, J=9.4 and 4.7 Hz, H-5'), 3.88–3.95 (3H, m, H-6' and H-1), 3.99 (1H, m, H-2), 4.22 (1H, td, J=9.7 and 3.7 Hz, H-4'), 4.24 (1H, br d, H-2'), 4.75 (1H, d, J=1.7 Hz, H-1'), 5.33 (1H, dd, J=9.8 and 3.0 Hz, H-3'), 5.56–5.63 (2H, m, H-3 and H-4), 5.96 (1H, dt, J=14.2 and 6.9 Hz, H-5), 7.43–7.49, 7.56–7.61 and 8.0–8.12 (10H, 3 sets of m, 2×—$C_6H_5$).

G. (2S,3R,4E)-2-Azido-3-benzoyloxy-1-(2,6-di-O-tert-butyldimethylsilyl-3,4-di-O-benzoyl-α-D-mannopyranosyloxy)-4-octadecene

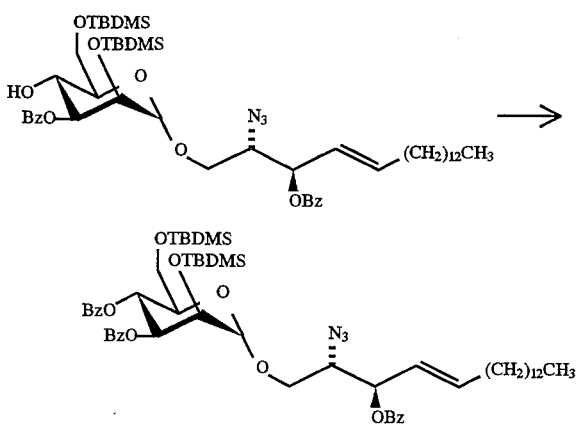

A solution of (2S,3R,4E)-2-azido-3-benzoyloxy-1-(2,6-di-O-tert-butyldimethylsilyl-3-O-benzoyl-α-D-mannopyranosyloxy)-4-octadecene (0.242 g, 0.262 mmol) in cold (5° C.) pyridine was treated with benzoyl chloride (74 mg, 0.52 mmol). The reaction mixture was stirred for 20 hours at 22° C., then poured into cold aqueous sodium bicarbonate and extracted with methylene chloride. The combined organic extracts were washed with brine (2×), dilute hydrochloric acid and brine again, dried over anhydrous magnesium sulfate, filtered and concentrated. The residue was purified by silica gel column chromatography (methylene chloride) and gave the title compound (0.233 g, 87%) as a colorless oil.

IR ($CH_2Cl_2$) $v_{max}$ ($cm^{-1}$): 2930, 2855 (C—H), 2100 ($N_3$), 1722 (C=O).

$^1$H NMR 400 MHz ($CDCl_3$) δ(ppm): −0.09, −0.01, 0.00 and 0.02 (12H, 4s, 2×—Si($CH_3$)$_2$), 0.89 and 0.92 (18H, 2s, 2×tert-butyl), 0.89–0.92 (3H, t, —$CH_3$), 1.25–1.31 (20H, m, —($CH_2$)$_{10}$—), 1.42 (2H, m, —$CH_2$—), 2.11 (2H, qa, J=6.9 Hz, =CH—C$\underline{H}_2$—), 3.58 (1H, dd, J=10.8 and 8.2 Hz, H-1), 3.77–3.84 (2H, m, H-6'), 3.97 (1H, dd, J=10.8 and 3.7 Hz, H-1), 4.00–4.03 (1H, m, H-5'), 4.06 (1H, dt, J=8.2 and 3.9 Hz, H-2), 4.38 (1H, br dd, H-2'), 4.84 (1H, d, J=1.7 Hz, H-1'), 5.54 (1H, dd, J=10.1 and 2.9 Hz, H-3'), 5.59–5.67 (2H, m, H-3 and H-4), 5.85 (1H, t, J=10.1, H-4'), 5.99 (1H, dt, J=14.2 and 6.9 Hz, H-5), 7.34–7.38, 7.46–7.51, 7.58–7.62, 7.94–7.98 and 8.08–8.10 (15H, 5 sets of m, 3×—$C_6H_5$).

H. (2S,3R,4E)-2-Hexadecanoylamino-3-benzoyloxy-1-(2,6-di-O-tert-butyldimethylsilyl-3,4-di-O-benzoyl-α-D-mannopyranosyloxy)-4-octadecene

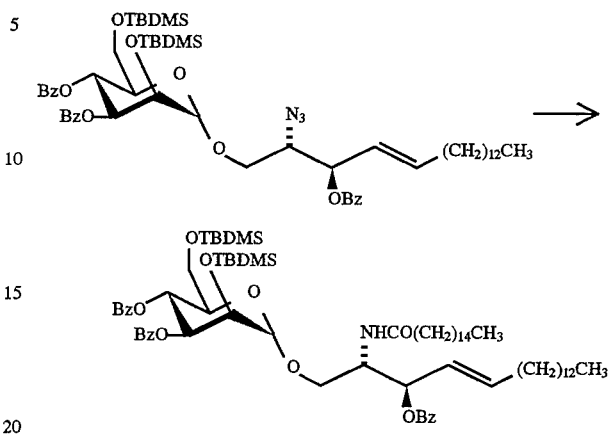

(2S,3R,4E)-2-Azido-3-benzoyloxy-1-(2,6-di-O-tert-butyldimethylsilyl-3,4-di-O-benzoyl-α-D-mannopyranosyloxy)-4-octadecene (0.23 g, 0.224 mmol) was reacted by the general procedure as described in Example 1-J and afforded the title compound (0.249 g, 90%) as a colorless oil.

IR ($CH_2Cl_2$) $v_{max}$ ($cm^{-1}$): 3680, 3600, 3430 (OH and NH), 2925, 2850 (C—H), 1728, 1675 (C=O).

$^1$H NMR 400 MHz ($CDCl_3$) δ(ppm): −0.11, −0.06, −0.05 and −0.02 (12H, 4s, 2×—Si($CH_3$)$_2$), 0.85 and 0.88 (18H, 2s, 2×tert-butyl), 0.89 (6H, t, J=6.7 Hz, 2×—$CH_3$), 1.21–1.38 (46H, m, —($CH_2$)$_{11}$— and —($CH_2$)$_{12}$—), 1.68 (2H, m, —$CH_2$—), 2.07 (2H, qa, J=7.0 Hz, =CH—C$\underline{H}_2$—), 2.27 (2H, m, —NHCOC$\underline{H}_2$—), 3.69 (1H, dd, J=10.5 and 3.5 Hz, H-1), 3.73–3.80 (2H, m, H-6'), 3.88 (1H, dd, J=10.5 and 3.9Hz, H-1), 3.95 (1H, dt, J=10.1 and 3.1 Hz, H-5'), 4.33 (1H, br dd, H-2'), 4.57 (1H, m, H-2), 4.68 (1H, d, J=1.5 Hz, H-1'), 5.51 (1H, dd, J=10.1 and 2.9 Hz, H-3'), 5.59 (1H, dd, J=15.2 and 7.6 Hz, H-4), 5.67 (1H, t, J=7.6 Hz, H-3), 5.85 (1H, t, J=10.1 Hz, H-4'), 5.92–5.99 (1H, m, H-5), 5.95 (1H, d, J=9.5 Hz, —NH—), 7.34–7.59 and 7.92–8.06 (15H, 2 sets of m, 3×—$C_6H_5$).

I. (2S,3R,4E)-2-Hexadecanoylamino-3-benzoyloxy-1-(2-O-tert-butyldimethylsilyl-3,4-di-O-benzoyl-α-D-mannopyranosyloxy)-4-octadecene

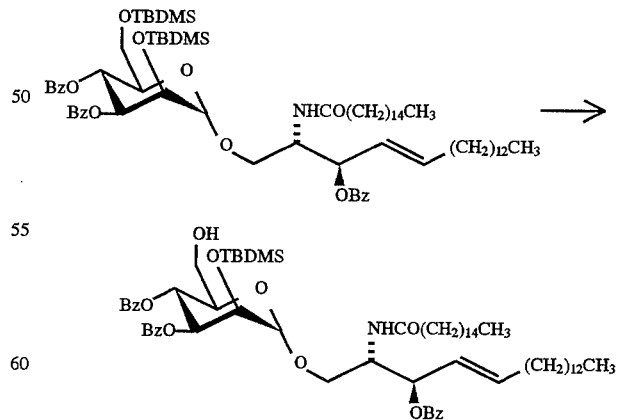

A solution of (2S,3R,4E)-2-hexadecanoylamino-3-benzoyloxy-1-(2,6-di-O-tert-butyldimethylsilyl-3,4-di-O-benzoyl-α-D-mannopyranosyloxy)-4-octadecene (0.230 g, 0.185 mmol) in methylene chloride (10 mL) was cooled in ice and treated with 90% aqueous trifluoroacetic acid (1 mL). The solution was stirred for 30 minutes at 5° C., then diluted with methylene chloride and washed successively with water, aqueous sodium bicarbonate and brine. The organic layer was dried over anhydrous magnesium sulfate, filtered and concentrated. The residue was purified by silica gel column chromatography (5 to 10% acetonitrile/methylene chloride) and afforded the title material (0.181 g, 87%) as a viscous colorless oil.

$^1$H NMR 400 MHz (CDCl$_3$) δ(ppm): −0.09 and −0.03 (6H, 2s, —Si(CH$_3$)$_2$), 0.87–0.92 (6H, m, 2×—CH$_3$), 0.89 (9H, s, overlapping —CH$_3$, tert-butyl), 1.21–1.38 (46H, m, —(CH$_2$)$_{11}$— and —(CH$_2$)$_{12}$—), 1.67 (2H, m, —CH$_2$—), 2.08 (2H, ap qa, —CH$_2$—), 2.26 (2H, m, —CH$_2$—), 2.40 (1H, br s, —OH), 3.71 (1H, dd overlapping H-6', J=10.6 and 4.0 Hz, H-1), 3.6–3.8 (2H, m, H-6'), 3.89 (1H, dd, J=10.6 and 4.0 Hz, H-1), 3.90–3.94 (1H, m, H-5'), 4.33 (1H, br dd, H-2'), 4.59 (1H, m, H-2), 4.72 (1H, d, J=1.6 Hz, H-1'), 5.57–5.62 (1H, m, H-4), 5.61 (1H, dd overlapping H-4, J=10.2 and 3.0 Hz, H-3'), 5.67 (1H, t, J=7.4 Hz, H-3), 5.77 (1H, t, J=10.0 Hz, H-4'), 5.94 (1H, d, J=9.5 Hz, —NH—), 5.95 (1H, dt, J=15.1 and 6.6 Hz, H-5), 7.35–7.59, 7.93–7.93 and 8.04–8.06 (15H, 3 sets of m, 3×—C$_6$H$_5$).

J. (2S,3R,4E)-2-Hexadecanoylamino-3-benzoyloxy-1-(3,4-di-O-benzoyl-α-D-mannopyranosyloxy)-4-octadecene

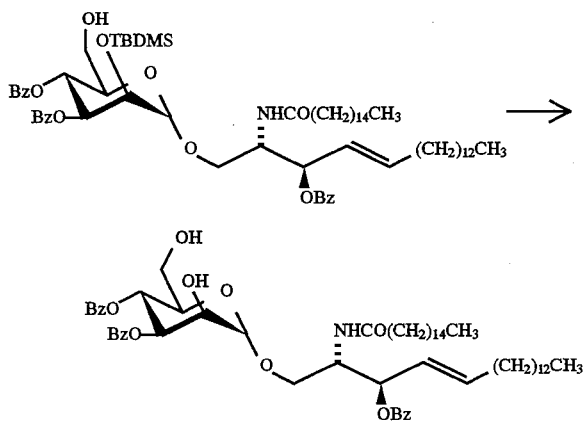

A cold (0° C.) solution of (2S,3R,4E)-2-hexadecanoylamino-3-benzoyloxy-1-(2-O-tert-butyldimethylsilyl-3,4-di-O-benzoyl-α-D-mannopyranosyloxy)-4-octadecene (0.162 g, 0.144 mmol) in tetrahydrofuran was treated with acetic acid (0.099 mL, 1.73 mmol), followed by tetrabutylammonium fluoride (1M in tetrahydrofuran, 0.863 mL, 0.863 mmol). The ice-bath was removed and the reaction was left at 22° C. for 7 days. Although a fair amount of starting material was still present, the reaction mixture was diluted with ethyl acetate and washed with cold aqueous sodium bicarbonate and brine. The organic layer was dried over anhydrous magnesium sulfate, filtered and concentrated. The residue was purified by silica get column chromatography (15% acetonitrile/methylene chloride) and the unreacted material was recovered. The same process was repeated with the unreacted material and the title compound was obtained (0.091 g, 62%) as a white solid.

IR (Nujol) ν$_{max}$ (cm$^{-1}$): 3600 (OH, NH), 2930, 2855 (C—H), 1725, 1675 (C=O).

$^1$H NMR 400 MHz (CDCl$_3$) δ(ppm): 0.89 (6H, t, J=6.8 Hz, 2×—CH$_3$), 1.23–1.50 (46H, m, —(CH$_2$)$_{11}$— and —(CH$_2$)$_{12}$—), 1.66 (2H, m, —CH$_2$—), 2.08 (2H, qa, J=7.0 Hz, =CH—CH$_2$—), 2.25 (2H, m, —NHCOCH$_2$—), 2.33 (1H, d, J=4.9 Hz, —OH), 2.61 (1H, br t, —OH), 3.66–3.78 (3H, m, H-6' and H-1), 3.92 (1H, dd, J=10.8 and 4.2 Hz, H-1), 3.93–3.97 (1H, m, H-5'), 4.30 (1H, br dd, H-2'), 4.59 (1H, m, H-2), 4.94 (1H, d, J=1.4 Hz, H-1'), 5.58 (1H, dd, J=15.1 and 7.3 Hz, H-4), 5.65 (1H, t, J=7.3 Hz, H-3), 5.69–5.75 (2H, m, H-4' and H-3'), 5.91 (1H, d, J=8.8 Hz, —NH—), 5.94 (1H, dt, J=15.1 and 7.0 Hz, H-5), 7.36–7.59 and 7.94–8.06 (15H, 2 sets of m, 3×—C$_6$H$_5$).

K. (2S,3R,4E)-2-Hexadecanoylamino-3-benzoyloxy-1-[2,6-di-O-(sodium oxysulfonyl)-3,4-di-O-benzoyl-α-D-mannopyranosyloxy]-4-octadecene

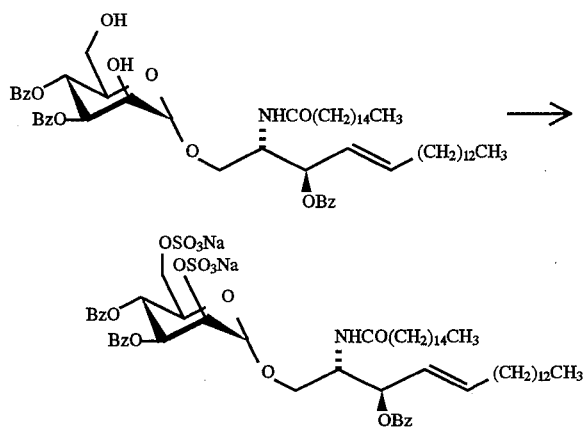

(2S,3R,4E)-2-Hexadecanoylamino-3-benzoyloxy-1-(3,4-di-O-benzoyl-α-D-mannopyranosyloxy)-4-octadecene (0.091 g, 0.09 mmol) was reacted by the general procedure as described in Example 1-L and afforded the title compound (0.089 g, 81%) as a white solid.

IR (CH$_2$Cl$_2$) ν$_{max}$ (cm$^{-1}$): 2920, 2850 (C—H), 1720, 1645 (C=O).

$^1$H NMR 400 MHz (CDCl$_3$) δ(ppm): 0.83–0.86 (6H, m, 2×—CH$_3$), 1.14–1.40 (46H, m, —(CH$_2$)$_{11}$— and —(CH$_2$)$_{12}$—), 1.50 (2H, m, —CH$_2$—), 2.05 (2H, qa, J=6.8 Hz, =CH—CH$_2$—), 2.12 (2H, br t, —NHCOCH$_2$—), 3.56 (1H, dd, J=9.9 and 7.3 Hz, H-6'), 5.79–5.89 (2H, m, H-6' and H-1), 3.87 (1H, dd, J=10.1 and 5.9 Hz, H-1), 4.12 (1H, m, H-5'), 4.40 (1H, m, H-2), 4.62 (1H, br s, H-2'), 5.07 (1H, br, s, H-1'), 5.37–5.44 (2H, m, H-4' and H-3'), 5.52 (1H, dd, J=7.4 and 4.9 Hz, H-3), 5.65 (1H, dd, J=15.3 and 7.4 Hz, H-4), 5.83 (1H, dt, J=15.3 and 6.8 Hz, H-5), 7.40–7.65, 7.81–7.87 and 7.98–7.99 (15H, m, 3 sets of m, 3×—C$_6$H$_5$), 8.08 (1H, d, J=8.7 Hz, —NH—).

What is claimed is:

1. A compound of the formula

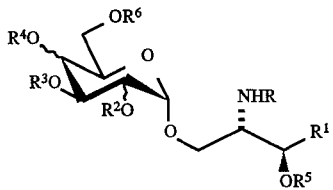

wherein

R is an acyl residue of a fatty acid;

R$^1$ is —(CH=CH)$_m$—(CH$_2$)$_n$—CH$_3$;

R$^2$, R$^3$, R$^4$ and R$^6$ each independently is —SO$_3$H, hydrogen, unsubstituted or substituted alkanoyl, arylalkyl or arylcarbonyl wherein said substituent is selected from the group consisting of halogen, C$_{1-4}$ alkyl, trifluoromethyl, hydroxy and C$_{1-4}$ alkoxy provided that at least two of R$^2$, R$^3$, R$^4$ and R$^6$ are —SO$_3$H;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive; or a non-toxic pharmaceutically acceptable salt, solvate or hydrate thereof.

2. A compound of claim 1 having the formula

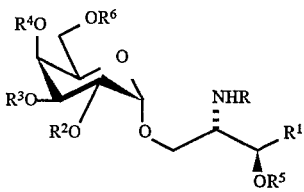

wherein

R is an acyl residue of a fatty acid;

$R^1$ is $—(CH=CH)_m—(CH_2)_n—CH_3$;

$R^2$, $R^3$, $R^4$ and $R^6$ each independently is $—SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that at least two of $R^2$, $R^3$, $R^4$ and $R^6$ are $—SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive; or a non-toxic pharmaceutically acceptable salt, solvate or hydrate thereof.

3. A compound of claim 1 having the formula

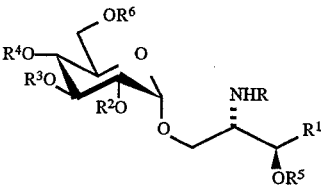

wherein

R is an acyl residue of a fatty acid;

$R^1$ is $—(CH=CH)_m—(CH_2)_n—CH_3$;

$R^2$, $R^3$, $R^4$ and $R^6$ each independently is $—SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that at least two of $R^2$, $R^3$, $R^4$ and $R^6$ are $—SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive; or a non-toxic pharmaceutically acceptable salt, solvate or hydrate thereof.

4. A compound of claim 1 having the formula

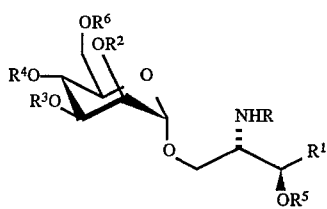

wherein

R is an acyl residue of a fatty acid;

$R^1$ is $—(CH=CH)_m—(CH_2)_n—CH_3$;

$R^2$, $R^3$, $R^4$ and $R^6$ each independently is $—SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that at least two of $R^2$, $R^3$, $R^4$ and $R^6$ are $—SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive; or a non-toxic pharmaceutically acceptable salt, solvate or hydrate thereof.

5. A compound of claim 1 wherein $R^4$ and $R^6$ are $—SO_3H$ and $R^2$, $R^3$ and $R^5$ each are independently hydrogen, unsubstituted or substituted alkanoyl, arylalkyl or arylcarbonyl wherein said substituent is selected from the group consisting of halogen $C_{1-4}$ alkyl, trifluoromethyl, hydroxy and $C_{1-4}$ alkoxy or a non-toxic pharmaceutically acceptable salt, solvate or hydrate thereof.

6. A compound of claim 1 wherein $R^2$ and $R^6$ are $—SO_3H$ and $R^3$, $R^4$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

7. A compound of claim 1 wherein $R^3$ and $R^3$ are $—SO_3H$ and $R^2$, $R^4$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

8. A compound of claim 1 wherein $R^2$ and $R^3$ are $—SO_3H$ and $R^4$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

9. A compound of claim 1 wherein $R^3$ and $R^4$ are $—SO_3H$ and $R^2$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

10. A compound of claim 1 wherein $R^2$ and $R^4$ are $—SO_3H$ and $R^3$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

11. A compound of claim 5 wherein $R^2$, $R^3$ and $R^5$ each are independently hydrogen or benzoyl; or a non-toxic pharmaceutically acceptable salt, solvate or hydrate thereof.

12. A compound of claim 6 wherein $R^3$, $R^4$ and $R^5$ each are independently hydrogen or benzoyl; or a non-toxic pharmaceutically acceptable salt, solvate or hydrate thereof.

13. A compound of claim 7 wherein $R^2$, $R^4$ and $R^5$ each are independently hydrogen or benzoyl; or a non-toxic pharmaceutically acceptable salt, solvate or hydrate thereof.

14. A compound of claim 8 wherein $R^4$, $R^5$ and $R^6$ each are independently hydrogen or benzoyl; or a non-toxic pharmaceutically acceptable salt, solvate or hydrate thereof.

15. A compound of claim 9 wherein $R^2$, $R^5$ and $R^6$ each are independently hydrogen or benzoyl; or a non-toxic pharmaceutically acceptable salt, solvate or hydrate thereof.

16. A compound of claim 10 wherein $R^3$, $R^5$ and $R^6$ each are independently hydrogen or benzoyl; or a non-toxic pharmaceutically acceptable salt, solvate or hydrate thereof.

17. A compound of claim 11 wherein $R^2$, $R^3$ and $R^5$ are benzoyl; or a non-toxic pharmaceutically acceptable salt, solvate or hydrate thereof.

18. A compound of claim 12 wherein $R^3$, $R^4$ and $R^5$ are benzoyl; or a non-toxic pharmaceutically acceptable salt, solvate or hydrate thereof.

19. A compound of claim 13 wherein $R^2$, $R^4$ and $R^5$ are benzoyl; or a non-toxic pharmaceutically acceptable salt, solvate or hydrate thereof.

20. A compound of claim 14 wherein $R^4$, $R^5$ and $R^6$ are benzoyl; or a non-toxic pharmaceutically acceptable salt, solvate or hydrate thereof.

21. A compound of claim 15 wherein $R^2$, $R^5$ and $R^6$ are benzoyl; or a non-toxic pharmaceutically acceptable salt, solvate or hydrate thereof.

22. A compound of claim 16 wherein $R^3$, $R^5$ and $R^6$ are benzoyl; or a non-toxic pharmaceutically acceptable salt, solvate or hydrate thereof.

23. A compound of claim 1 wherein R is the acyl residue of palmitic acid, lignoceric acid, nervonic acid or stearic acid; or a non-toxic pharmaceutically acceptable salt, solvate or hydrate thereof.

24. A compound of claim 17 wherein R is the acyl residue of palmitic acid, lignoceric acid, nervonic acid or stearic acid; or a non-toxic pharmaceutically acceptable salt, solvate or hydrate thereof.

25. A compound of claim 18 wherein R is the acyl residue of palmitic acid, lignoceric acid, nervonic acid or stearic acid; or a non-toxic pharmaceutically acceptable salt, solvate or hydrate thereof.

26. A compound of claim 19 wherein R is the acyl residue of palmitic acid, lignoceric acid, nervonic acid or stearic acid; or a non-toxic pharmaceutically acceptable salt, solvate or hydrate thereof.

27. A compound of claim 20 wherein R is the acyl residue of palmitic acid, lignoceric acid, nervonic acid or stearic acid; or a non-toxic pharmaceutically acceptable salt, solvate or hydrate thereof.

28. A compound of claim 21 wherein R is the acyl residue of palmitic acid, lignoceric acid, nervonic acid or stearic acid; or a non-toxic pharmaceutically acceptable salt, solvate or hydrate thereof.

29. A compound of claim 22 wherein R is the acyl residue of palmitic acid, lignoceric acid, nervonic acid or stearic acid; or a non-toxic pharmaceutically acceptable salt, solvate or hydrate thereof.

30. A compound of claim 1 wherein m is 1 and n is 12; or a non-toxic pharmaceutically acceptable salt, solvate or hydrate thereof.

31. A compound of claim 1 wherein m is 0 and n is 14; or a non-toxic pharmaceutically acceptable salt, solvate or hydrate thereof.

32. A compound of claim 24 wherein R is the acyl residue of nervonic acid; or a non-toxic pharmaceutically acceptable salt, solvate or hydrate thereof.

33. A compound of claim 32 wherein m is 1 and n is 12; or a non-toxic pharmaceutically acceptable salt, solvate or hydrate thereof.

34. A compound of claim 32 wherein m is 0 and n is 14; or a non-toxic pharmaceutically acceptable salt, solvate or hydrate thereof.

35. A compound of claim 1 selected from the group consisting of:
(2S,3R,4E)-3-Benzoyloxy-2-hexadecanoylamino-1-[2,3-di-O-benzoyl-4,6-di-(sodium oxysulfonyl)-α-D-galactopyranosyloxy]-4-octadecene;
(2S,3R,4E)-3-Hydroxy-2-hexadecanoylamino-1-[4,6-di-O-(sodium oxysulfonyl)-α-D-galactopyranosyloxy]-4-octadecene;
(2S,3R,4E)-3-Benzoyloxy-2-(cis-15-tetracosenoylamino)-1-[2,3-di-O-benzoyl-4,6-di-O-(sodium oxysulfonyl]-α-D-galactopyranosyloxy)-4-octadecene;
(2S,3R,4E)-3-Hydroxy-2-(cis-15-tetracosenoylamino)-1-[4,6-di-O-(sodium oxysulfonyl)-α-D-galactopyranosyloxy]-4-octadecene;
(2S,3R)-3-Benzoyloxy-2-hexadecanoylamino-1-[2,3-di-O-benzoyl-4,6-di-O-(sodium oxysulfonyl)-α-D-galactopyranosyloxy]-octadecane;
(2S,3R)-2-Hexadecanoylamino-3-hydroxy-1-(4,6-di-O-sodium oxysulfonyl)-α-D-galactopyranosyloxy)-octadecane;
(2S,3R,4E)-3-Benzoyloxy-2-hexadecanoylamino-1-[2,3-di-O-benzoyl-4,6-di-O-(sodium oxysulfonyl)-α-D-glucopyranosyloxy]-4-octadecene;
(2S,3R,4E)-3-Hydroxy-2-hexadecanoylamino-1-[4,6-di-O-(sodium oxysulfonyl)-α-D-glucopyranosyloxy]-4-octadecene;
(2S,3R,4E)-3-Benzoyloxy-1-[2,3-di-O-benzoyl-4,6-di-O-(sodium oxysulfonyl)-α-D-glucopyranosyloxy)-2-(cis-15-tetracosenoylamino)-4-octadecene;
(2S,3R,4E)-1-[2,3-Di-O-benzoyl-4,6-di-O-(sodium oxysulfonyl)-α-D-galactopyranosyloxy]-3-benzoyloxy-2-hexanoylamino-4-undecene;
(2S,3R,4E)-2-Hexadecanoylamino-3-benzoyloxy-1-[2,3-di-O-benzyl-4,6-di-O-(sodium oxysulfonyl)-α-D-galactopyranosyloxy]-4-octadecene;
(2S,3R,4E)-3-Benzoyloxy-2-(cis-15-tetracosenoylamino)-1-[2,6-di-O-(sodium oxysulfonyl)-α-D-galactopyranosyloxy]-4-octadecene;
(2S,3R,4E)-3-Benzoyloxy-2-(cis-15-tetracosenoylamino)-1-[3,4-di-O-benzoyl-2,6-di-O-(sodium oxysulfonyl)-α-D-galactopyranosyloxy]-4-octadecene;
(2S,3R,4E)-3-Hydroxy-2-(cis-15-tetracosenoylamino)-1-[2,6-di-O-(sodium oxysulfonyl)-α-D-galactopyranosyloxy]-4-octadecene;
(2S,3R,4E)-3-Benzoyloxy-2-hexadecanoylamino-1-[2,6-di-O-(sodium oxysulfonyl)-α-D-galactopyranosyloxy]-4-octadecene;
(2S,3R,4E)-3-Benzoyloxy-2-hexadecanoylamino-1-[3,4-di-O-benzoyl-2,6-di-O-(sodium oxysulfonyl)-α-D-galactopyranosyloxy]-4-octadecene;
(2S,3R,4E)-2-Hexadecanoylamino-3-hydroxy-1-[2,6-di-O-(sodium oxysulfonyl)-α-D-galactopyranosyloxy]-4-octadecene;

(2S,3R,4E)-3-Benzoyloxy-2-hexadecanoylamino-1-[2,3-di-O-benzoyl-4,6-di-O-(sodium oxysulfonyl)-α-D-mannopyranosyloxy]-4-octadecene;

(2S,3R,4E) 1-[2-O-Benzoyl-3,4,6-tri-O-(sodium oxysulfonyl)-α-D-galactopyranosyloxy]-3-benzoyloxy-2-hexadecanoylamino-4-octadecene;

(2S,3R,4E)-2-Hexadecanoylamino-3-hydroxy-1-[3,4,6-tri-O-(sodium oxysulfonyl)-α-D-galactopyranosyloxy]-4-octadecene;

(2S,3R,4E)-3-Benzoyloxy-2-hexadecanoylamino-1-[2-O-(4-methoxybenzyl)-3,4,6-tri-O-(sodium oxysulfonyl)-α-D-galactopyranosyloxy]-4-octadecene;

(2S,3R,4E)-2-Hexadecanoylamino-3-hydroxy-1-[2-O-(4-methoxybenzyl)-3,4,6-tri-O-(sodium oxysulfonyl)-α-D-galactopyranosyloxy]-4-octadecene;

(2S,3R,4E)-3-Benzoyloxy-2-hexadecanoylamino-1-[2,3,4,6-tetra-O-(sodium oxysulfonyl)-α-D-galactopyranosyloxy]-4-octadecene; and (2S,3R,4E)-2-Hexadecanoylamino-3-hydroxy-1-[2,3,4,6-tetra-O-(sodium oxysulfonyl)-α-D-galactopyranosyloxy]-4-octadecene; or a non-toxic pharmaceutically acceptable salt, solvate or hydrate thereof.

36. A pharmaceutical composition for the treatment of diseases characterized by selectin-mediated cellular adhesion comprising a therapeutically effective amount of a compound as defined in claim 1 in association with a pharmaceutically acceptable carrier or diluent.

37. A method for the treatment of diseases characterized by selectin-mediated cellular adhesion in a mammal in need of such treatment, which comprises administering to said mammal a therapeutically effective amount of a compound as defined in claim 1 or a pharmaceutical composition thereof.

38. A method for the treatment of diseases characterized by selectin-mediated cellular adhesion in a mammal in need of such treatment, which comprises administering to said mammal a therapeutically effective amount of a compound as defined in claim 2 or a pharmaceutical composition thereof.

39. A method for the treatment of diseases characterized by selectin-mediated cellular adhesion in a mammal in need of such treatment, which comprises administering to said mammal a therapeutically effective amount of a compound as defined in claim 5 or a pharmaceutical composition thereof.

40. A method for the treatment of inflammatory related diseases in a mammal in need of such treatment, which comprises administering to said mammal a therapeutically effective amount of a compound as defined in claim 1 or a pharmaceutical composition thereof.

41. A method for the treatment of inflammatory related diseases in a mammal in need of such treatment, which comprises administering to said mammal a therapeutically effective amount of a compound as defined in claim 2 or a pharmaceutical composition thereof.

42. A method for the treatment of inflammatory related diseases in a mammal in need of such treatment, which comprises administering to said mammal a therapeutically effective amount of a compound as defined in claim 5 or a pharmaceutical composition thereof.

* * * * *